(12) United States Patent
Chen et al.

(10) Patent No.: US 11,993,800 B2
(45) Date of Patent: *May 28, 2024

(54) USE OF TERMINAL TRANSFERASE ENZYME IN NUCLEIC ACID SYNTHESIS

(71) Applicant: Nuclera, Ltd., Cambridge (GB)

(72) Inventors: Michael Chen, Cambridge (GB); Jiahao Huang, Cambridge (GB); Gordon McInroy, Cambridge (GB)

(73) Assignee: Nuclera Ltd., Cambridge (GB)

( * ) Notice: Subject to any disclaimer, the term of this patent is extended or adjusted under 35 U.S.C. 154(b) by 1076 days.

This patent is subject to a terminal disclaimer.

(21) Appl. No.: 16/616,633

(22) PCT Filed: May 29, 2018

(86) PCT No.: PCT/GB2018/051449
§ 371 (c)(1),
(2) Date: Nov. 25, 2019

(87) PCT Pub. No.: WO2018/215803
PCT Pub. Date: Nov. 29, 2018

(65) Prior Publication Data
US 2021/0164008 A1 Jun. 3, 2021

(30) Foreign Application Priority Data

May 26, 2017 (GB) ..................................... 1708503
May 30, 2017 (GB) ..................................... 1708551

(51) Int. Cl.
*C12P 19/34* (2006.01)
*C12N 9/12* (2006.01)

(52) U.S. Cl.
CPC ............ *C12P 19/34* (2013.01); *C12N 9/1264* (2013.01); *C12Y 207/07031* (2013.01)

(58) Field of Classification Search
CPC .................................................. C12N 9/1264
See application file for complete search history.

(56) References Cited

U.S. PATENT DOCUMENTS 7,494,797 B2  2/2009  Mueller et al.
8,808,989 B1  8/2014  Efcavitch et al.
(Continued)

FOREIGN PATENT DOCUMENTS

FR      3052462 A1 * 12/2017  ............ C12N 15/70
WO     01/64909 A1    9/2001
(Continued)

OTHER PUBLICATIONS

NCBI blast (summary of NCBI blast alignment of SEQ ID 1 of Ybert compared to the claimed species, run at https://blast.ncbi.nlm.nih.gov/Blast.cgi, on May 3, 2023.) (Year: 2023).*
(Continued)

*Primary Examiner* — Robert J Yamasaki
*Assistant Examiner* — Charles Zoltan Constantine
(74) *Attorney, Agent, or Firm* — Morgan, Lewis & Bockius LLP

(57) ABSTRACT

The invention relates to the use of a modified terminal transferase enzyme in a method of adding one or more nucleotides to the 3' end of a nucleic acid. The invention also relates to methods of nucleic acid synthesis and sequencing comprising the use of said modified terminal transferase enzyme, to kits comprising said modified terminal transferase enzyme and to the use of said kits in methods of nucleic acid synthesis and sequencing.

17 Claims, 5 Drawing Sheets

Specification includes a Sequence Listing.

(56) References Cited

U.S. PATENT DOCUMENTS

| | | | |
|---|---|---|---|
| 2004/0043396 A1 | 3/2004 | Mueller et al. | |
| 2014/0363851 A1* | 12/2014 | Efcavitch | C12P 19/34 |
| | | | 435/91.5 |
| 2016/0108382 A1 | 4/2016 | Efcavitch et al. | |
| 2020/0002690 A1* | 1/2020 | Ybert | C12Y 207/07031 |

FOREIGN PATENT DOCUMENTS

| | | |
|---|---|---|
| WO | WO 01/68895 A1 | 9/2001 |
| WO | 2016/128731 A1 | 8/2016 |
| WO | 2016/139477 A1 | 9/2016 |

OTHER PUBLICATIONS

Repasky, et al., "Mutational Analysis of Terminal Deoxynucleotidyltransferase-Mediated N-Nucleotide Addition in V(D) J Recombination," The Journal of Immunology, vol. 172, No. 9, pp. 5478-5488, Apr. 20, 2004.

International Search Report issued in corresponding International Patent Application No. PCT/GB2018/051449 dated Jul. 27, 2018.

Mueller et al., "A comparison of BRCT domains involved in nonhomologous end-joining: Introducing the solution structure of the BRCT domain of polymerase lambda," DNA Repair, 7 (8): 1340-1351 (2008).

Mizushina et al., "Monoacetylcurcumin: a new inhibitor of eukaryotic DNA polymerase lambda and a new ligand for Inhibitor-affinity chromatography," Biochemical and Biophysical Research Communications, 337 (4): 1288-1295 (2005).

\* cited by examiner

USE OF TERMINAL TRANSFERASE ENZYME IN NUCLEIC ACID SYNTHESIS

CROSS-REFERENCE TO RELATED APPLICATIONS

This application claims the benefit of International Application No. PCT/GB2018/051449, filed May 29, 2018, which claims the benefit of GB Patent Application No. 1708503.6 filed May 26, 2017, and GB Patent Application No. 1708551.5 filed May 30, 2017, the entire contents of which are hereby incorporated by reference herein in their entireties.

DESCRIPTION OF THE TEXT FILE SUBMITTED ELECTRONICALLY

This application contains a Sequence Listing in ASCII format submitted electronically herewith via EFS-Web. The ASCII copy, created on Dec. 17, 2022, is named 119744-5016_ST25.txt and is 380,928 bytes in size. The Sequence Listing is incorporated herein by reference in its entirety.

FIELD OF THE INVENTION

The invention relates to the use of a modified terminal transferase enzyme in a method of adding one or more nucleotides to the 3' end of a nucleic acid. The invention also relates to methods of nucleic acid synthesis and sequencing comprising the use of said modified terminal transferase enzyme, to kits comprising said modified terminal transferase enzyme and to the use of said kits in methods of nucleic acid synthesis and sequencing.

BACKGROUND OF THE INVENTION

Nucleic acid synthesis is vital to modern biotechnology. The rapid pace of development in the biotechnology arena has been made possible by the scientific community's ability to artificially synthesize DNA, RNA and proteins.

Artificial DNA synthesis—a £1.8 billion and growing market—allows biotechnology and pharmaceutical companies to develop a range of peptide therapeutics, such as insulin for the treatment of diabetes. It allows researchers to characterise cellular proteins to develop new small molecule therapies for the treatment of diseases our aging population faces today, such as heart disease and cancer. It even paves the way forward to creating life, as the Venter Institute demonstrated in 2010 when they placed an artificially synthesised genome into a bacterial cell.

However, current DNA synthesis technology does not meet the demands of the biotechnology industry. While the benefits of DNA synthesis are numerous, an oft-mentioned problem prevents the further growth of the artificial DNA synthesis industry, and thus the biotechnology field. Despite being a mature technology, it is practically impossible to synthesise a DNA strand greater than 200 nucleotides in length, and most DNA synthesis companies only offer up to 120 nucleotides. In comparison, an average protein-coding gene is of the order of 2000-3000 nucleotides, and an average eukaryotic genome numbers in the billions of nucleotides. Thus, all major gene synthesis companies today rely on variations of a 'synthesise and stitch' technique, where overlapping 40-60-mer fragments are synthesised and stitched together by PCR (see Young, L. et al. (2004) *Nucleic Acid Res.* 32, e59). Current methods offered by the gene synthesis industry generally allow up to 3 kb in length for routine production.

The reason DNA cannot be synthesised beyond 120-200 nucleotides at a time is due to the current methodology for generating DNA, which uses synthetic chemistry (i.e., phosphoramidite technology) to couple a nucleotide one at a time to make DNA. As the efficiency of each nucleotide-coupling step is 95.0-99.0% efficient, it is mathematically impossible to synthesise DNA longer than 200 nucleotides in acceptable yields. The Venter Institute illustrated this laborious process by spending 4 years and 20 million USD to synthesise the relatively small genome of a bacterium (see Gibson, D. G. et al. (2010) *Science* 329, 52-56).

Known methods of DNA sequencing use template-dependent DNA polymerases to add 3'-reversibly terminated nucleotides to a growing double-stranded substrate (see, Bentley, D. R. et al. (2008) *Nature* 456, 53-59). In the 'sequencing-by-synthesis' process, each added nucleotide contains a dye, allowing the user to identify the exact sequence of the template strand. Albeit on double-stranded DNA, this technology is able to produce strands of between 500-1000 bps long. However, this technology is not suitable for de novo nucleic acid synthesis because of the requirement for an existing nucleic acid strand to act as a template.

There is therefore a need to provide improved methods of nucleic acid synthesis and sequencing that is able to overcome the problems associated with currently available methods.

SUMMARY OF THE INVENTION

According to a first aspect of the invention, the use of a modified terminal transferase enzyme in a method of adding one or more nucleotides to the 3' end of a nucleic acid, characterised in that said enzyme comprises a mutated BRCA-1 C-terminal (BRCT) domain.

According to a second aspect of the invention, there is provided a method of nucleic acid synthesis, which comprises the steps of:
(a) providing an initial initiator sequence;
(b) adding a reversibly blocked nucleotide triphosphate to said initiator sequence in the presence of a modified terminal transferase enzyme as defined herein;
(c) removal of all reagents from the initiator sequence;
(d) cleaving the blocking group from the reversibly blocked nucleotide added in step (b) to said initiator sequence; and
(e) removal of the cleaving agent.

According to a further aspect of the invention, there is provided a method of nucleic acid synthesis which is performed in a microfluidic device comprising the steps of:
(a) providing an initial initiator sequence bound to a surface within a microfluidic device;
(b) adding a reversibly blocked nucleotide triphosphate to said initiator sequence in the presence of a modified terminal transferase enzyme as defined herein;
(c) removal of all reagents from the initiator sequence;
(d) cleaving the blocking group from the reversibly blocked nucleotide added in step (b) to said initiator sequence; and
(e) removal of the cleaving agent.

According to a further aspect of the invention, there is provided a kit comprising a modified terminal transferase enzyme as defined herein, optionally in combination with one or more components selected from: an initiator sequence, a microfluidic device or chip, one or more reversibly blocked nucleotide triphosphates, inorganic pyrophosphatase, such as purified, recombinant inorganic pyrophosphatase from *Saccharomyces cerevisiae*, and a cleaving agent; further optionally together with instructions for use of the kit in accordance with the method as defined herein.

According to a further aspect of the invention, there is provided the use of a kit as defined herein in a method of nucleic acid synthesis or nucleic acid sequencing.

Expression was performed in *E. coli* in 3-ml of Terrific Broth overnight at 20° C. following standard induction by IPTG. Lysis was performed using 1× BugBuster in 20 mM HEPES KOH (pH 7.5), 300 mM KCl, 10% glycerol, and 1 mM PMSF. Following lysis, proteins were purified using a HisPur Ni-NTA 96-well spin plate. Proteins were purified to >80% homogeneity as assessed by standard SDS-PAGE. Concentrations and yields were determined using the NanoOrange Protein Quantitation Kit (Thermo Fisher) on the QuantiFluor fluorimeter (Promega). Each expression was performed in triplicate.

Figure 8:
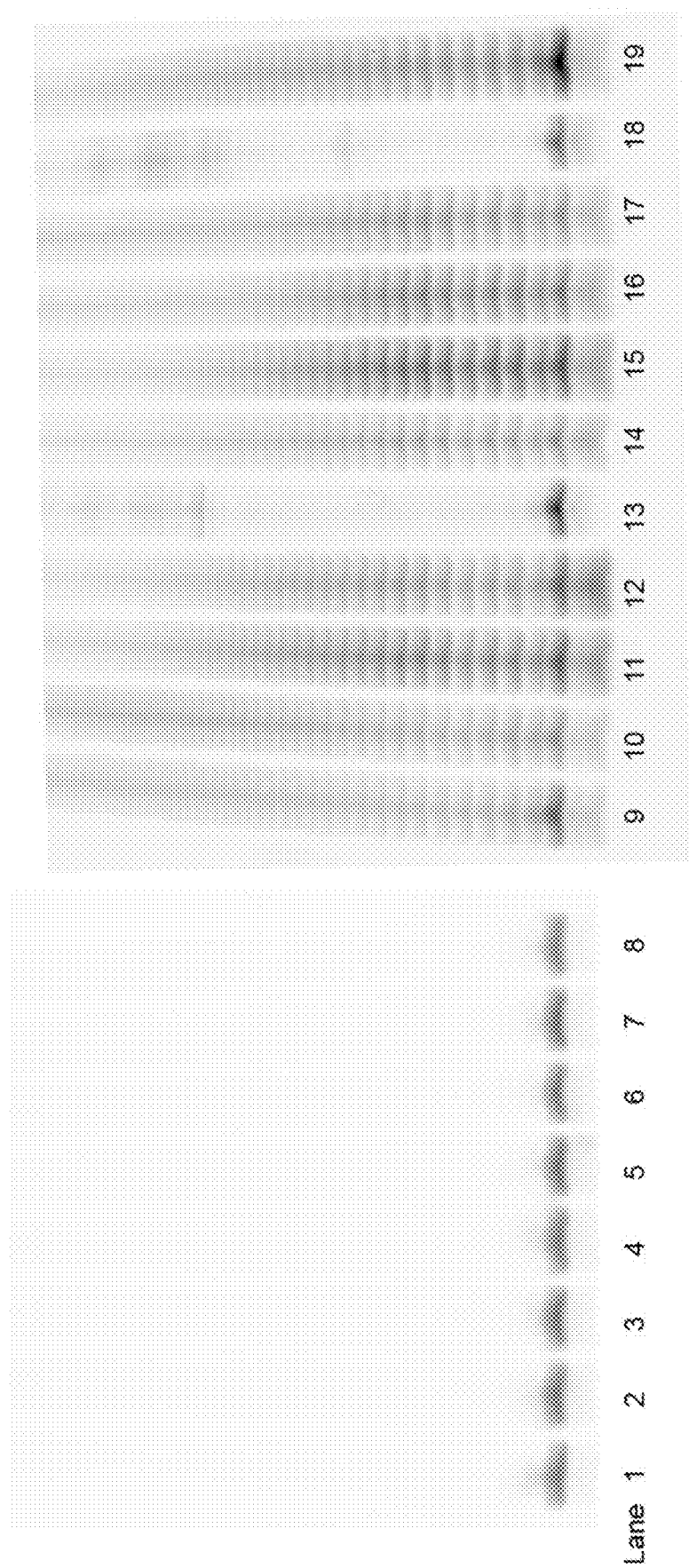

FIG. 8: Surface accessibility tests between wild-type and BRCT-truncated TdT enzymes conclude TdT with BRCT domains increase fouling of DNA-immobilized surfaces preventing terminal transferase activity. In all lanes, TdT orthologs were incubated in a well containing a surface 5-immobilized single-stranded piece of DNA. TdT was incubated in a suitable buffer for proper terminal transferase activity in the well for 1 h at 37° C. Following the 1 h incubation, commercial *B. taurus* TdT, pyrophosphatase, and thymidine 5'-triphosphate (free 3'-OH) was added to the well. The reactions were analyzed by 20% denaturing PAGE (19:1) and imaged by virtue of an internal fluorophore on the single-stranded piece of DNA. Lanes 1-8 contain wild-type TdT orthologs (respectively, *S. harrisii, S. scrofa, O. garnettii, C. lanigera, B. taurus, P. panicus,* and *M. musculus*). Lanes 9-19 contain BRCT-truncated TdT orthologs (respectively, *S. harrisii, S. scrofa, O. garnettii, C. lanigera, B. taurus, D. novemcinctus, M. domestica, P. nyererei, M. brandtii, P. panicus,* and *M. musculus*). Not all wild-type TdT orthologs could be tested due to low expression yield as a result of high insolubility. BRCT truncation surprisingly prevents the surface fouling seen with wild-type TdTs over a wide range of TdT orthologs (up to 39.8% identity). Surface fouling, protein aggregation, and general protein misbehavior prevents efficient multi-cycle addition of nucleotides to surface immobilized DNA. Thus, BRCT truncation is necessary for the de novo, TdT-mediated synthesis of DNA.

DETAILED DESCRIPTION OF THE INVENTION

According to a first aspect of the invention, the use of a modified terminal transferase enzyme in a method of adding one or more nucleotides to the 3' end of a nucleic acid, characterised in that said enzyme comprises a mutated BRCA-1 C-terminal (BRCT) domain.

De novo enzymatic-based nucleic acid synthesis is an alternative method to phosphoramidite DNA synthesis. One method to achieve the former is the use of polymerases that act as terminal transferases (e.g., DNA nucleotidylexotransferase (DNTT/TdT), DNA polymerase mu (POLM or Polµ), DNA polymerase lambda (POLL or Polλ), DNA polymerase theta (POLQ or PolΘ), and prokaryotic polymerases) to add nucleotide triphosphates one at a time in a random or sequence-specific fashion. In order to achieve sequence control, modified nucleotides such as those blocked via the nitrogenous base (as described in GB Patent Application No. 1701396.2) or the sugar moiety (as described in WO 2016/128731 and U.S. Pat. No. 6,232,465), must be used in the synthesis process. Terminal transferase-mediated de novo DNA synthesis in a sequence-controlled fashion thus requires a cyclic process of (1) addition of a modified solution or solid phase nucleotide to the 3'-end of a nucleic acid (N species) to form a blocked N+1 species and (2) deprotection of the added nucleotide to regenerate an active N+1 species. Such a cyclic process requires a well-behaved terminal transferase enzyme that (a) readily releases from the N+1 species, (b) does not greatly foul the areas or surfaces in which the nucleotide addition occurs, and (c) is stable (e.g., not prone to aggregation or inactivation) during the nucleotide addition.

Figure 1:
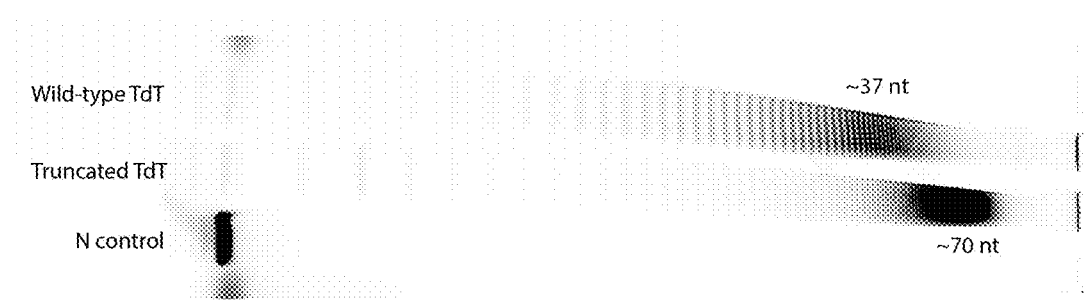
FIG. 1: A terminal transferase, TdT, engineered with N-terminal truncations retains full or better catalytic activity, including full truncations of the N-terminal BRCT domain from TdT, corresponding to approximately 21% of the protein molecular weight. In this experiment, a TdT containing a 21% N-terminal truncation ("Truncated TdT" or ΔNTE-TdT) added more modified 2'-deoxynucleotide triphosphates (biotin-16-dUTP) to the 3'-end of a DNA initiator molecule (N control) when compared to "Wild-type TdT." TdT was incubated with a DNA initiator and biotin-16-dUTP for 5 min at 37° C. The DNA was visualized by a Cy-5 fluorescent dye covalently attached to the 5'-end of the initiator molecule. The reaction products were analyzed by denaturing PAGE. The gel is shown at a 90° angle for space consideration.

The inventors have surprisingly found that TdT appears to not only retain activity, but furthermore gains activity in solution after removing 21% of the wild-type mass of TdT from the N-terminus (ΔNTE-TdT), which corresponds to the deletion of the BRCT domain (see FIG. 1). Previously, it had only been demonstrated that TdT retains catalytic activity in crystalline form when residues are deleted from the N-terminus, but activity was not shown in solution[1,2]. Protein activity, macromolecule conformation, and substrate accessibility are often significantly different between a solution phase macromolecule and the same macromolecule locked in a crystal lattice. According to Mozzarelli and Rossi, "ligand binding, catalysis and allosteric regulation occur in the crystalline environment but intermolecular interactions may hinder function-associated transitions and alter activity with respect to solution[3]." In a well-known example, the first atomic model of duplex DNA was not elucidated in the familiar B-DNA conformation[4], but rather a Z-DNA conformation, the biological function of which has yet to be conclusively determined.

Indeed, in vivo observations of the effect of N-terminal deletions on TdT reinforce the inventors' surprising finding that TdT gains activity upon the N-terminal deletion of 21% of the wild-type TdT mass (ΔNTE-TdT). In a reconstituted V(D)J recombination assay in HEK293T cells, Schatz and colleagues demonstrated that the absence of the BRCT domain on the N-terminus of murine TdT resulted in a consistent reduction of coding joint N-nucleotide addition to levels similar to that of an inactive long isoform of murine TdT (TdTL)[5]. In *Mus musculus*, TdT is alternatively spliced into two isoforms, known as TdTS and TdTL. TdTS was shown to be active at physiological temperatures, while TdTL was shown to be inactive at physiological temperatures[6]. Given that TdT lacking a BRCT domain displays consistently reduced or non-existent activity (similar to that of TdTL) in vivo, it would be expected that recombinant, engineered TdT with N-terminal BRCT domain truncations would result in reduced or non-existent terminal transferase activity. FIG. 1 clearly shows ΔNTE-TdT surprisingly both retains and gains terminal transferase catalytic activity.

The surprising result shown in FIG. 1 can be extended to the highly homologous cousins of TdT, DNA polymerases mu and lambda. Indeed, it is well known in the literature that DNA polymerases mu and lambda are easily converted to highly active terminal transferases following mutations guided by homology to wild-type TdT sequences. For example, Blanco and colleagues demonstrated that a point mutation mimicking TdT (R387K in human DNA polymerase mu) converted DNA polymerase mu from a weak terminal transferase capable of adding tens of nucleotides to a strong terminal transferase capable of adding hundreds of nucleotides[7]. Since we demonstrate novel terminal transferase activity from TdT lacking a BRCT domain, it thus follows that polymerase mu and polymerase lambda carrying TdT-mimicking point mutations are active as terminal transferases even if the BRCT domain is absent.

Figure 7:
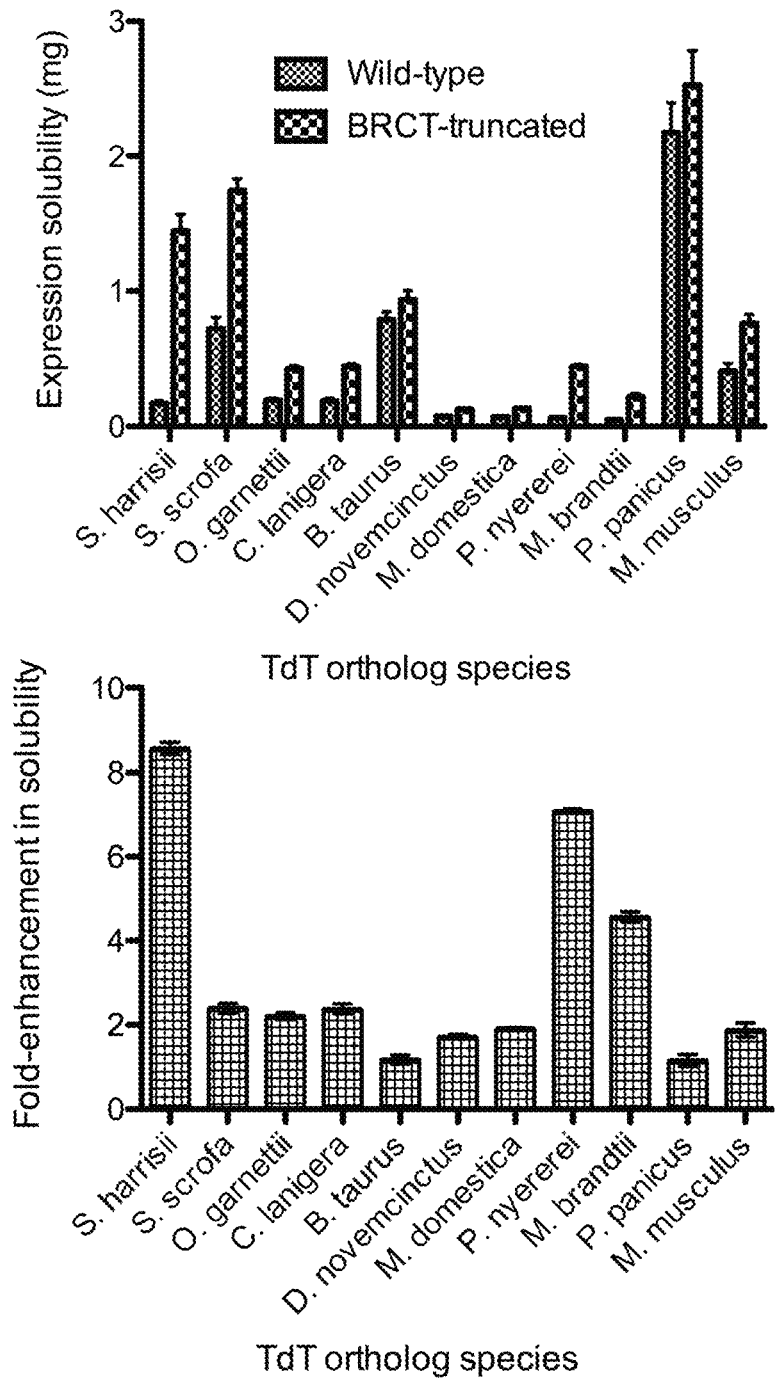
FIG. 7: Eleven orthologs of TdT, with variance up to 41.0% identity of the *L. oculatus* TdT and also with variance up to 39.8% identity of *S. harrisii* TdT, are demonstrably more soluble when the BRCT domain is truncated (top). Expression yields within *E. coli* are a standard measure of the (1) behavior and (2) solubility of a protein. Higher yields generally indicate well-behaved, highly soluble proteins. As a result of the BRCT truncation on a wide range of TdT orthologs covering most ortholog classes within the chordata phylum, TdT solubility increases as evidenced by the consistent >2-fold improvement in solubility (bottom). Truncations were made in the genes of the eleven TdT orthologs by site-directed mutagenesis following standard protocols.

Data is also presented that demonstrates that solubility is increased (see FIG. 7) and surface accessibility to immobilized DNA is increased (see FIG. 8) when the BRCT domain is truncated. These results are observed for TdTs having over 40% sequence identity from each other. Without being bound by theory, it is believed that the data presented herein provides excellent plausibility that all TdTs having BRCT deletions according to the invention find utility in an enhanced method of nucleic acid synthesis.

Thus, in one embodiment the terminal transferase enzyme is from the DNA polymerase X family, such as terminal deoxynucleotidyl transferase (TdT), DNA polymerase λ (Polλ) and DNA polymerase µ (Polµ). In a yet further embodiment, the terminal transferase enzyme is selected from terminal deoxynucleotidyl transferase (TdT).

References herein to "TdT" refer to a terminal deoxynucleotidyl transferase (TdT) enzyme and include references to purified and recombinant forms of said enzyme. TdT is also commonly known as DNTT (DNA nucleotidylexotransferase) and any such terms should be used interchangeably.

References herein to "Polλ" refer to DNA Polymerase λ (also known as POLL or DNA Polymerase Lambda) is a protein found in eukaryotes. In humans, it is encoded by the POLLA gene. Pol A is a member of the X family of DNA polymerases. It is thought to resynthesize missing nucleotides during non-homologous end joining (NHEJ), a pathway of DNA double-strand break (DSB) repair.

References herein to "Polµ" refer to DNA Polymerase µ (also known as POLM or DNA Polymerase Mu) is a polymerase enzyme found in eukaryotes. In humans, this protein is encoded by the POLM gene. Polµ is a member of the X family of DNA polymerases. It participates in resynthesis of damaged or missing nucleotides during the non-homologous end joining (NHEJ) pathway of DNA repair.

References herein to the term "BRCA-1 C-terminal (BRCT) domain" refer to the C-terminal domain of a breast cancer susceptibility protein). This domain is found predominantly in proteins involved in cell cycle checkpoint functions responsive to DNA damage, for example as found in the breast cancer DNA-repair protein BRCA1. The domain is an approximately 100 amino acid tandem repeat, which appears to act as a phospho-protein binding domain. For example, the BRCT domain is present in TdT from amino acid residues 26-130.

References herein to the term "mutated BRCA-1 C-terminal (BRCT) domain" refer to any inactivated form of the BRCT domain. Examples of a mutated BRCT domain include one or more mutations selected from: a deletion, substitution or an insertion.

In one embodiment, said enzyme comprises a truncated BRCT domain, such as an N-terminal truncated BRCT domain (e.g. an N-terminal truncation to approximately 21% of the TdT wild-type molecular weight). This embodiment of the invention is surprisingly crucial to multi-step de novo enzymatic DNA synthesis. N-terminal truncations endow wild-type and engineered TdTs with much higher cycling efficiencies that greatly enhance the industrial utility of TdT-mediated nucleic acid synthesis.

In an alternative embodiment, said BRCT domain is absent.

Figure 3:
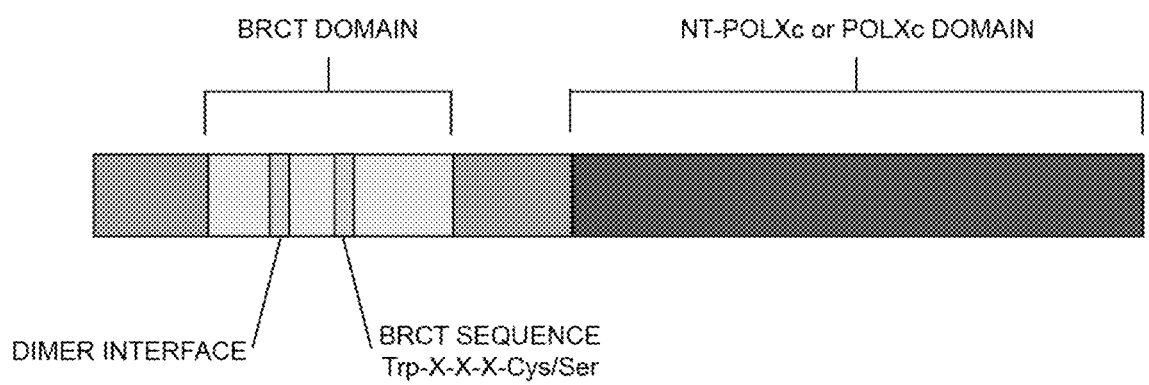
FIG. 3: A schematic of a typical POLX family polymerase with terminal transferase activity. NT-POLXc and POLXc are domain annotations that indicate a DNA Polymerase beta-like domain, which conveys terminal transferase and nucleotidyltransferase activity. N-terminal to the NT-POLXc/POLXc domain is the BRCT domain, which contains a dimer interface motif as well as the signature BRCT sequence consisting of the sequence Trp-X-X-X-Cys/Ser, where X is any amino acid.

The absence or truncation of a BRCT domain in a terminal transferase enzyme is defined as the following:
any amino acid sequences having:
(1) terminal transferase activity; and
(2) containing a domain belonging to the NT-POLXc/POLXc DNA polymerase beta thumb superfamily (cd00141, cl25961, smart00483, pfam14791, COG1796);
and not containing:
(3) a domain belonging to the BRCT superfamily (cl00038, cd00027, smart00292, pfam00533, pfam12738, pfam16589, pfam16759, pfam16770);
as defined by the Conserved Domain Database (CDD)[8] maintained by the US National Center for Biotechnology Information (NCBI) identified via Conserved Domain Searches (CD-Search)[9]. A schematic domain is presented in FIG. 3. A protein domain shall be identified as belonging to either NT-POLXc/POLXc (cd00141) or BRCT (cd00027) if their threshold bit score is greater than 199.344 or 29.2119, respectively. The threshold bit score for each annotated domain is set by the NCBI CDD curators as a conservative measure of whether or not a protein sequence belongs to a specific domain. The bit score of a query sequence is calculated to determine if it is above the threshold set by NCBI curators. A bit score is calculated by first performing an alignment using the position-specific scoring matrix (PSSM) specific for each domain annotation to maximize a raw alignment score, where the cost to open a gap is 11 and the cost to extend a gap by one is 1. The domain-specific PSSMs for the domain annotations given above is provided in Tables 1 and 2 for NT-POLXc/POLXc (cd00141) or BRCT (cd00027), respectively. The raw alignment score is then used to calculate a bit score using the following equation:

$$S' = \frac{\lambda S - \ln(K)}{\ln(2)}$$

where S' is equal to the bit score, S is the raw alignment score, and $\lambda$ and K are normalizing factors obtained as described by Gertz (Gertz, E. M. BLAST scoring parameters. 2005.). The process of calculating a bit score is typically performed through a publicly available algorithm called a reverse-position-specific BLAST (RPS-BLAST) against the CDD database, as described by Marchler-Bauer and colleagues[8-9].

TABLE 1

Position-specific scoring matrix (PSSM) for NT-POLXc (cd00141) domain where a threshold bit score of 199.344 is required to qualify as a member of this family. The PSSM was obtained from the NCBI CDD. In the upper left hand corner table header, P signifies position, C signifies the consensus sequence, and M signifies the master sequence of known structure. In the rest of the table, letters indicate standard amino acid single letter nomenclature.

| P | C | M | A | G | I | L | V | M | F | W | P | C | S | T | Y | N | Q | H | K | R | D | E |
|---|---|---|---|---|---|---|---|---|---|---|---|---|---|---|---|---|---|---|---|---|---|---|
| 1 | | 4-G | 2 | -3 | -2 | -4 | -5 | -4 | -5 | 1 | -5 | -6 | 0 | 0 | 0 | -1 | 4 | 4 | 2 | 2 | -4 | 2 |
| 2 | | 5-G | -1 | -1 | -1 | 0 | -5 | -4 | -1 | 2 | -1 | -1 | -4 | -2 | -5 | -1 | -1 | 2 | 2 | 0 | 3 | 4 |
| 3 | | 6-I | -5 | -7 | 5 | 2 | 3 | 0 | 4 | -5 | -6 | -5 | -5 | -1 | -3 | -3 | -6 | -6 | -6 | -6 | -7 | -6 |
| 4 | | 7-T | 4 | -4 | 4 | -4 | 1 | -3 | -5 | -6 | -5 | 0 | -1 | 4 | -5 | -5 | -2 | -5 | -4 | -5 | -5 | -5 |
| 5 | | 8-D | 1 | -1 | -6 | -4 | -6 | -5 | -6 | 2 | -5 | 2 | -1 | -4 | -5 | 1 | -3 | 2 | 0 | 2 | 4 | 3 |
| 6 | | 9-M | 3 | -5 | 4 | 0 | 2 | 2 | 1 | -6 | -5 | 0 | -4 | -4 | -4 | -5 | -1 | -5 | 1 | -5 | -5 | -1 |
| 7 | | 10-L | -5 | -7 | 0 | 5 | -3 | 1 | 6 | -4 | -7 | -5 | -6 | -5 | -2 | -7 | -6 | -6 | -6 | -6 | -7 | -6 |
| 8 | | 11-T | -4 | -1 | -5 | -5 | -1 | 1 | -5 | -6 | -5 | -6 | 2 | 2 | 1 | 0 | 1 | -4 | 0 | -4 | 1 | 5 |
| 9 | | 12-E | -3 | -5 | 1 | -5 | 0 | -4 | -6 | -6 | -2 | -6 | -1 | 0 | -5 | -4 | 3 | -4 | 1 | 3 | -3 | 5 |
| 10 | | 13-L | -5 | -7 | 4 | 5 | 0 | 5 | -3 | -5 | -6 | -5 | 0 | -5 | -6 | -5 | -6 | -6 | -6 | -6 | -7 | -6 |
| 11 | | 14-A | 6 | 0 | -2 | -1 | -4 | 0 | -5 | -6 | -5 | -4 | -3 | -1 | -5 | -5 | -4 | 0 | -1 | -1 | -5 | -1 |
| 12 | | 15-N | -3 | -5 | -5 | -2 | -3 | -5 | -6 | -6 | -5 | -6 | -3 | 1 | -1 | 2 | -3 | -4 | 3 | -3 | 5 | 3 |
| 13 | | 16-F | 1 | -6 | 1 | 4 | -2 | 0 | 0 | -4 | -6 | 1 | -1 | -4 | 5 | -1 | -4 | 2 | -1 | 0 | -6 | -5 |
| 14 | | 17-E | -3 | -6 | -3 | 3 | -4 | 3 | 0 | -3 | -6 | 1 | -1 | -4 | 6 | -5 | -4 | 0 | -4 | 0 | -2 | 1 |
| 15 | | 18-K | -3 | -3 | -6 | -6 | -6 | -5 | -7 | -6 | -5 | -6 | -1 | 1 | -5 | -3 | 0 | -4 | 2 | 2 | 0 | 6 |
| 16 | | 19-N | 0 | -3 | 4 | 3 | 1 | -3 | 4 | -5 | -6 | -5 | -5 | -4 | -4 | 3 | -5 | -1 | -5 | -2 | -2 | -5 |
| 17 | | 20-V | -2 | -5 | -4 | 1 | 1 | -4 | -5 | -6 | -5 | 0 | -2 | 0 | -5 | 2 | 3 | -4 | 3 | 3 | -4 | 2 |
| 18 | | 21-S | -1 | 5 | -2 | -2 | -2 | -2 | -2 | -2 | -2 | 0 | -1 | -2 | 1 | 0 | -2 | -2 | -2 | 0 | 0 |
| 19 | | 22-Q | -1 | 4 | -7 | -7 | -6 | -6 | -7 | -6 | -5 | -6 | -3 | -4 | -6 | 1 | -1 | 0 | 1 | 1 | 2 | 4 |
| 20 | | 23-A | 0 | -4 | -6 | -6 | -3 | -6 | -7 | -7 | -5 | -6 | -1 | -4 | -6 | 6 | -1 | -4 | -3 | -4 | 5 | 3 |
| 21 | | 24-I | -1 | -5 | 2 | -5 | -4 | -1 | -6 | -6 | 4 | -6 | -1 | 0 | -5 | -4 | 1 | 1 | 3 | 2 | 1 | 1 |
| 22 | | 25-H | -5 | 1 | 0 | -4 | -2 | -4 | 7 | 7 | -7 | -6 | -5 | -5 | 3 | -5 | -5 | 5 | -5 | -2 | -6 | -6 |
| 23 | | 26-K | -4 | -2 | -6 | -6 | -6 | -5 | -2 | -6 | -2 | -7 | -1 | -4 | -5 | -4 | -2 | -4 | 5 | 7 | -5 | -2 |
| 24 | | 27-Y | 1 | -5 | 3 | -2 | 3 | -3 | -4 | -5 | -2 | 4 | 1 | 1 | 3 | -1 | -5 | 0 | -5 | -5 | -5 | -5 |
| 25 | | 28-N | -5 | -3 | -1 | 2 | -2 | -3 | -0 | -6 | -6 | -6 | -2 | -4 | -5 | 3 | 0 | -4 | -1 | 6 | -5 | -4 |
| 26 | | 29-A | 6 | 1 | -5 | -5 | -2 | -4 | -6 | -6 | -4 | -4 | 2 | -2 | -5 | -4 | -1 | -5 | -4 | -5 | -5 | -2 |
| 27 | | 30-Y | -5 | -7 | -5 | -4 | -5 | -4 | 4 | -1 | -7 | -6 | -5 | -5 | 9 | -6 | -5 | -2 | -5 | -5 | -7 | -6 |
| 28 | | 31-R | -2 | -2 | -5 | 0 | -5 | 2 | -5 | -5 | -5 | -6 | 1 | -4 | 1 | -4 | 0 | 0 | -1 | 7 | -5 | -4 |
| 29 | | 32-K | -4 | -5 | -6 | -1 | -5 | 1 | -6 | -6 | -5 | -6 | 0 | -4 | -5 | 2 | 0 | -4 | 5 | 5 | -4 | -2 |
| 30 | | 33-A | 7 | -2 | -4 | -5 | -2 | 1 | -6 | -6 | -4 | -4 | -1 | -3 | -5 | -5 | -4 | -5 | -4 | -5 | -5 | -4 |
| 31 | | 34-A | 5 | -4 | 4 | -2 | -1 | -4 | -5 | -6 | -5 | -4 | 1 | -3 | -5 | -5 | -4 | -5 | -1 | -1 | -5 | -5 |
| 32 | | 35-S | 1 | -2 | -6 | -6 | -5 | -5 | -6 | -6 | -2 | -6 | 3 | -3 | -5 | 2 | 2 | -4 | 0 | 4 | -2 | 2 |
| 33 | | 36-V | 4 | -5 | 1 | -1 | 4 | -3 | -2 | -6 | -5 | -4 | 2 | 1 | -5 | -5 | -5 | -5 | -5 | -5 | -5 | -5 |

TABLE 1-continued

Position-specific scoring matrix (PSSM) for NT-POLXc (cd00141) domain where a threshold bit score of 199.344 is required to qualify as a member of this family. The PSSM was obtained from the NCBI CDD. In the upper left hand corner table header, P signifies position, C signifies the consensus sequence, and M signifies the master sequence of known structure. In the rest of the table, letters indicate standard amino acid single letter nomenclature.

| P | C | M | A | G | I | L | V | M | F | W | P | C | S | T | Y | N | Q | H | K | R | D | E |
|---|---|---|---|---|---|---|---|---|---|---|---|---|---|---|---|---|---|---|---|---|---|---|
| 34 | | 37-I | −5 | −7 | 6 | 4 | 2 | 3 | −3 | −6 | −6 | −5 | −6 | −4 | −5 | −7 | −6 | −6 | −6 | −6 | −7 | −6 |
| 35 | | 38-A | 1 | −3 | −2 | −3 | −5 | −5 | −6 | −6 | −5 | −6 | 0 | −4 | −2 | −4 | 0 | −4 | 4 | 2 | −1 | 4 |
| 36 | | 39-K | 1 | −1 | −6 | −2 | −5 | −5 | −2 | −6 | −5 | −5 | 4 | −3 | −5 | 2 | −1 | 0 | 2 | 1 | 1 | 1 |
| 37 | | 40-Y | −5 | −6 | −3 | 4 | 0 | 0 | 2 | −4 | −6 | 1 | −3 | −2 | 5 | −5 | 1 | 4 | −5 | −5 | −2 | −5 |
| 38 | | 41-P | −4 | −2 | −6 | −6 | −6 | −6 | −7 | −7 | 7 | −6 | −1 | 0 | −5 | 1 | 0 | 3 | −2 | −1 | −2 | −2 |
| 39 | | 42-H | −1 | −5 | −4 | −2 | −1 | −4 | 3 | −5 | −5 | 0 | −1 | 2 | 3 | −4 | −2 | 1 | 2 | 2 | −4 | 3 |
| 40 | | 43-K | −1 | −5 | −6 | −6 | −6 | −5 | −7 | −7 | 6 | −6 | 1 | −4 | −6 | −1 | −1 | −4 | 3 | 1 | 2 | 1 |
| 41 | | 44-I | −1 | −7 | 6 | 2 | 4 | −2 | −4 | −6 | −6 | −4 | −5 | −1 | −5 | −6 | −6 | −7 | −6 | −6 | −7 | −6 |
| 42 | | 45-K | 2 | −5 | −5 | −5 | −5 | −5 | −6 | −6 | 0 | −5 | −1 | 3 | −1 | −4 | 2 | 0 | 1 | 1 | −1 | 3 |
| 43 | | 46-S | −1 | −4 | −5 | −6 | −3 | −5 | −6 | −6 | −4 | 0 | 5 | 3 | −5 | −1 | −1 | −4 | −1 | −2 | 0 | 3 |
| 44 | | 47-G | 0 | 2 | 1 | 3 | 0 | 5 | −3 | −5 | −6 | −1 | −2 | −4 | 3 | −5 | −4 | −5 | −1 | −5 | −6 | −1 |
| 45 | | 48-A | 2 | −5 | −2 | 0 | −1 | −4 | 1 | 3 | −5 | −5 | −1 | −2 | 1 | −4 | 0 | 0 | 2 | −2 | 1 | 3 |
| 46 | | 49-E | 1 | −3 | −6 | −6 | −6 | −5 | −6 | −6 | −5 | −6 | −1 | −4 | −1 | −3 | 4 | −4 | −1 | 1 | 3 | 5 |
| 47 | | 50-A | 4 | −5 | 0 | 1 | −1 | 0 | −5 | −6 | −2 | 0 | −3 | −1 | −5 | −2 | −4 | −5 | −1 | 3 | 0 | 1 |
| 48 | | 51-K | −1 | −2 | −4 | −1 | −2 | 1 | −5 | −5 | −2 | 2 | 1 | 2 | −4 | −4 | 1 | 3 | 3 | 2 | −2 | 1 |
| 49 | | 52-K | 0 | 2 | −2 | −6 | −5 | −5 | −6 | −6 | −5 | −6 | 1 | −4 | −5 | −1 | −3 | 2 | 4 | 2 | 0 | 2 |
| 50 | | 53-L | −5 | −7 | 5 | 5 | −1 | 3 | −3 | −5 | −6 | −5 | −6 | −4 | −5 | −7 | −5 | −6 | −6 | −6 | −7 | −2 |
| 51 | | 54-P | −4 | −5 | −6 | −6 | −6 | −6 | −7 | −7 | 8 | −6 | −2 | −4 | −6 | 1 | −4 | 0 | −2 | 1 | 1 | 4 |
| 52 | | 55-G | −3 | 6 | −7 | −6 | −6 | −6 | −2 | 1 | −6 | 3 | −4 | −1 | −1 | 1 | −5 | 0 | −1 | −5 | −2 | −5 |
| 53 | | 56-V | −4 | −7 | 6 | 1 | 4 | 0 | −1 | −6 | −6 | 3 | −5 | −4 | −5 | −7 | −6 | −7 | −6 | −6 | −7 | −6 |
| 54 | | 57-G | −3 | 8 | −7 | −7 | −7 | −6 | −7 | −6 | −6 | −6 | −1 | −5 | −7 | −4 | −5 | −5 | −5 | −6 | −5 | −5 |
| 55 | | 58-T | −1 | −3 | −6 | −3 | −3 | −5 | −6 | −7 | 1 | −6 | −2 | −3 | −6 | −3 | −1 | −4 | 5 | 0 | 3 | 3 |
| 56 | | 59-K | 2 | 3 | −6 | −6 | −5 | −5 | −6 | −6 | −5 | −6 | 0 | −1 | −5 | −2 | 0 | 3 | 4 | 2 | 0 | −3 |
| 57 | | 60-I | −4 | −7 | 6 | 2 | 0 | 5 | −4 | −6 | −6 | −5 | −3 | 2 | −5 | −6 | −5 | −6 | −5 | −6 | −6 | −6 |
| 58 | | 61-A | 6 | −1 | −2 | −2 | −1 | −4 | −5 | −6 | −5 | −4 | −1 | −2 | −1 | −2 | −4 | −5 | 1 | 0 | −5 | −2 |
| 59 | | 62-E | 0 | 1 | −6 | −2 | −6 | −5 | −6 | −6 | −5 | −6 | 1 | −4 | −5 | −1 | 2 | 2 | 3 | 0 | 3 | 3 |
| 60 | | 63-K | −4 | −5 | −1 | −1 | 1 | −4 | −6 | −6 | −5 | −6 | −4 | −4 | −5 | −1 | −2 | 0 | 7 | 1 | −4 | 1 |
| 61 | | 64-I | −5 | −7 | 8 | 1 | −1 | 2 | −3 | 2 | −6 | −5 | −5 | −1 | 0 | −6 | −6 | −6 | −6 | −6 | −7 | −6 |
| 62 | | 65-D | 0 | −3 | 0 | −3 | −1 | −1 | −6 | 1 | −1 | −6 | 0 | −2 | −5 | −1 | 4 | −4 | 2 | −1 | 2 | 3 |
| 63 | | 66-E | −4 | −3 | −5 | −3 | −1 | −5 | −1 | −6 | −5 | −7 | −4 | −4 | −5 | −4 | 0 | −4 | −3 | −4 | 1 | 7 |
| 64 | | 67-F | −5 | −7 | 6 | 2 | −1 | 0 | 5 | −4 | −7 | −5 | −6 | −5 | 3 | −7 | −6 | −5 | −6 | −6 | −7 | −6 |
| 65 | | 68-L | 1 | −6 | 4 | 4 | 2 | 2 | −1 | −5 | −6 | −5 | −5 | −4 | −4 | −6 | −5 | −6 | −5 | −2 | −7 | −6 |
| 66 | | 69-A | 0 | −5 | −6 | −4 | −3 | −5 | −6 | −5 | −6 | 1 | 2 | −5 | −1 | 2 | −4 | 1 | 3 | 1 | 4 |
| 67 | | 70-T | −3 | −1 | −5 | −2 | −4 | −4 | −1 | −6 | −5 | −5 | 1 | 6 | −5 | −1 | −1 | 0 | −4 | −2 | −2 | 1 |
| 68 | | 71-G | −3 | 7 | −7 | −7 | −7 | −6 | −7 | −6 | −6 | −6 | −4 | −5 | −6 | 0 | −5 | 0 | −5 | −2 | −5 | −5 |
| 69 | | 72-K | −4 | −3 | −5 | −6 | −2 | −5 | −6 | −6 | −5 | −6 | 1 | 2 | −4 | −3 | −3 | 5 | 4 | 3 | −2 | 2 |
| 70 | | 73-L | −4 | −6 | 1 | 5 | 0 | 2 | 0 | −5 | −2 | 4 | 2 | −2 | −4 | −6 | −5 | −6 | −5 | −5 | −6 | −6 |
| 71 | | 74-R | 1 | −2 | −6 | −5 | −3 | −5 | 0 | −6 | 1 | −6 | 1 | −2 | −1 | −4 | 2 | −4 | 2 | 4 | −2 | 2 |
| 72 | | 75-K | −2 | 0 | −2 | −1 | −5 | −4 | −5 | −5 | 0 | −6 | −1 | −2 | 2 | −4 | 0 | −4 | 5 | 1 | −2 | 2 |
| 73 | | 76-L | 1 | −6 | −1 | 5 | 1 | −2 | −3 | 1 | −6 | −5 | −5 | −4 | 3 | −6 | −5 | 4 | −5 | −5 | −6 | −1 |
| 74 | | 77-E | −1 | −3 | −6 | −2 | −6 | −5 | −6 | −6 | −5 | −6 | −3 | −4 | −6 | 1 | 1 | −4 | 1 | −3 | 3 | 6 |
| 75 | | 78-K | −1 | −5 | −6 | −3 | −3 | −5 | −2 | −6 | −5 | −6 | −2 | −2 | 0 | 1 | −1 | 3 | 3 | 1 | 2 | 4 |
| 76 | | 79-I | −1 | −6 | 4 | 4 | 1 | 1 | 1 | −5 | −6 | −5 | −2 | −2 | −4 | −6 | −5 | −6 | −5 | −5 | −2 | 0 |
| 77 | | 80-R | 0 | −3 | −5 | 1 | −1 | 0 | −5 | −6 | −5 | −6 | 1 | −4 | −5 | −1 | 2 | 2 | 1 | 5 | 0 | 1 |
| 78 | | 81-Q | −1 | 1 | −5 | −3 | −5 | −5 | −6 | −6 | −2 | 2 | 0 | 2 | −5 | 2 | 1 | −1 | 2 | 1 | −1 | 3 |
| 79 | | 82-D | −2 | 1 | −4 | −4 | −4 | 0 | −4 | −4 | 0 | −4 | 2 | −3 | −4 | −2 | 1 | −3 | 1 | −1 | 5 | 2 |
| 80 | | 84-T | −1 | −3 | 1 | 1 | 2 | −3 | −2 | −5 | −5 | −5 | 1 | 0 | 2 | −4 | −4 | −4 | 1 | 3 | 0 | −1 |
| 81 | | 85-S | −2 | −5 | −4 | −3 | 1 | −5 | −5 | −5 | 6 | −5 | 1 | 0 | 3 | −2 | −4 | −4 | −4 | −2 | −2 | 1 |
| 82 | | 86-S | 0 | −5 | −2 | −2 | 0 | −4 | −6 | −6 | 4 | −6 | 1 | −2 | −5 | −4 | 2 | −4 | 2 | 2 | −1 | 2 |
| 83 | | 87-S | 2 | 4 | 1 | −5 | 2 | −4 | −6 | −6 | −5 | 0 | 2 | 1 | −5 | −4 | −4 | −1 | −1 | −5 | 0 | −1 |
| 84 | | 88-I | −3 | −7 | 3 | 4 | 3 | 4 | 2 | −5 | −6 | −5 | −5 | 0 | −4 | −6 | −5 | −6 | −6 | −6 | −7 | −6 |
| 85 | | 89-N | −1 | −5 | 0 | 2 | 0 | −3 | −5 | −6 | −5 | −5 | 0 | −2 | −5 | 2 | −1 | −4 | 3 | 2 | −1 | 0 |
| 86 | | 90-F | −1 | −3 | −2 | 3 | −4 | −1 | 1 | −5 | −2 | −5 | −1 | −2 | 3 | −5 | 0 | −4 | −4 | −5 | 0 | 4 |
| 87 | | 91-L | −5 | −7 | 0 | 4 | −2 | 3 | 7 | −4 | −7 | −5 | −6 | −5 | −2 | −7 | −6 | −5 | −6 | −6 | −7 | −6 |
| 88 | | 92-T | −2 | −3 | −3 | 3 | −3 | 2 | −4 | −5 | −5 | −5 | 0 | 4 | 0 | −4 | 0 | 1 | 1 | −4 | −5 | −2 |
| 89 | | 93-R | −1 | 2 | −6 | −6 | −6 | −5 | −6 | −6 | −5 | −6 | 1 | −4 | −5 | 3 | 2 | −4 | 3 | 4 | 0 | 2 |
| 90 | | 94-V | −2 | −7 | 5 | 1 | 5 | −2 | −4 | −6 | −6 | 4 | −5 | −4 | −5 | −7 | −6 | −7 | −6 | −6 | −7 | −6 |
| 91 | | 95-S | −5 | −6 | −5 | −5 | −5 | −5 | 3 | 7 | −4 | −6 | −1 | 0 | 3 | −5 | 0 | 3 | −2 | −1 | −5 | 1 |
| 92 | | 96-G | −3 | 8 | −7 | −7 | −7 | −6 | −7 | −6 | −6 | −6 | −4 | −5 | −7 | −4 | −5 | −5 | −5 | −6 | −1 | −5 |
| 93 | | 97-I | 0 | −6 | 5 | 2 | 5 | 1 | −4 | −6 | −6 | −4 | −5 | −4 | −5 | −6 | −6 | −6 | −6 | −6 | −7 | −6 |
| 94 | | 98-G | −1 | 8 | −7 | −7 | −7 | −6 | −7 | −6 | −6 | −6 | −4 | −5 | −7 | −4 | −5 | −5 | −5 | −6 | −5 | −6 |
| 95 | | 99-P | 1 | −2 | −2 | −2 | 0 | −5 | −6 | −7 | 7 | −6 | −2 | −5 | −4 | −5 | −2 | −1 | −5 | −2 |
| 96 | | 100-S | 1 | −2 | −5 | −5 | −3 | −5 | −1 | −6 | −5 | −6 | 0 | 1 | −5 | 0 | −1 | −4 | 6 | 1 | −4 | −1 |
| 97 | | 101-A | 1 | −5 | −1 | −5 | −4 | 0 | −5 | −6 | −5 | −5 | −3 | 6 | −1 | −4 | −1 | 1 | 3 | 2 | −5 | −4 |
| 98 | | 102-A | 6 | −4 | 2 | −2 | 2 | −4 | −5 | −6 | −5 | −4 | 0 | −3 | −5 | −5 | −5 | −5 | −4 | −5 | −5 | −5 |
| 99 | | 103-R | 2 | −1 | −6 | −3 | −5 | −5 | −6 | −5 | −6 | −1 | 0 | −1 | 0 | 2 | −4 | 3 | 4 | −2 | 1 |
| 100 | | 104-K | −2 | −5 | −1 | 0 | −2 | 2 | −5 | −6 | −5 | −6 | 0 | 1 | −5 | 1 | 0 | 4 | 3 | −4 | 1 |
| 101 | | 105-F | −3 | −7 | 0 | 4 | −2 | −2 | 3 | 10 | −7 | −5 | −6 | −5 | 1 | −7 | −6 | −6 | −6 | −6 | −7 | −6 |
| 102 | | 106-V | −3 | −6 | −2 | −3 | 1 | −4 | 3 | 6 | −6 | −6 | −5 | −5 | 8 | 0 | −5 | 3 | −5 | 0 | −6 | −5 |
| 103 | | 107-D | 1 | −3 | −6 | −1 | −5 | −4 | −2 | −6 | −5 | −6 | −1 | −4 | −5 | 2 | 3 | −4 | 0 | 3 | 1 | 4 |
| 104 | | 108-E | −1 | −6 | −3 | 4 | −3 | 4 | −1 | −5 | −5 | −5 | −4 | −4 | −5 | −5 | 1 | −5 | 2 | −1 | −1 | −1 |

TABLE 1-continued

Position-specific scoring matrix (PSSM) for NT-POLXc (cd00141) domain where a threshold bit score of 199.344 is required to qualify as a member of this family. The PSSM was obtained from the NCBI CDD. In the upper left hand corner table header, P signifies position, C signifies the consensus sequence, and M signifies the master sequence of known structure. In the rest of the table, letters indicate standard amino acid single letter nomenclature.

| P | C | M | A | G | I | L | V | M | F | W | P | C | S | T | Y | N | Q | H | K | R | D | E |
|---|---|---|---|---|---|---|---|---|---|---|---|---|---|---|---|---|---|---|---|---|---|---|
| 105 | | 109-G | -3 | 7 | -7 | -7 | -7 | -6 | -7 | -6 | -6 | -6 | -4 | -5 | -6 | 0 | -2 | -5 | -5 | -5 | -2 | -3 |
| 106 | | 110-I | -2 | -7 | 5 | 0 | 3 | -3 | 4 | 4 | -6 | 0 | -5 | -4 | 2 | -6 | -6 | 0 | -6 | -6 | -7 | -6 |
| 107 | | 111-K | -4 | -3 | -6 | -5 | -3 | -1 | -6 | -6 | -5 | -6 | 2 | 2 | -5 | -3 | -1 | 0 | 2 | 5 | 0 | 2 |
| 108 | | 112-T | -3 | -4 | -5 | -5 | -4 | -5 | -6 | -6 | -5 | 1 | 4 | 6 | -5 | 2 | -4 | -5 | -4 | -4 | 2 | -4 |
| 109 | | 113-L | -2 | -7 | 2 | 5 | 2 | -2 | 1 | -5 | -6 | -5 | -5 | -4 | -4 | -7 | -6 | -6 | -3 | -6 | -7 | -6 |
| 110 | | 114-E | 2 | -2 | -6 | -6 | -3 | -5 | -6 | -7 | -5 | -6 | -2 | -2 | -6 | -3 | 0 | -4 | -3 | -4 | 4 | 6 |
| 111 | | 115-D | 0 | -2 | -6 | -6 | -6 | -6 | -7 | -7 | -5 | -7 | -2 | -4 | -6 | -3 | 2 | -4 | -1 | 0 | 6 | 4 |
| 112 | | 116-L | -5 | -7 | 4 | 5 | 2 | -2 | -1 | -5 | -6 | -5 | -6 | -4 | -4 | -7 | -6 | -6 | -2 | -6 | -7 | -6 |
| 113 | | 117-R | -1 | -5 | 0 | -1 | -2 | -4 | -6 | -6 | -5 | -6 | -4 | -4 | -1 | -4 | -1 | -4 | 4 | 5 | -4 | 4 |
| 114 | | 118-K | 1 | -3 | -6 | -6 | -5 | -5 | -6 | -6 | -1 | -6 | 0 | 2 | -1 | 2 | 1 | 0 | 3 | 2 | 0 | 2 |
| 115 | | 119-N | 4 | -1 | -3 | -2 | -2 | -4 | -5 | -5 | -1 | -5 | -3 | -4 | 0 | 1 | 1 | 3 | 1 | -4 | 0 | 0 |
| 116 | | 120-E | 3 | 0 | 0 | -1 | -1 | -3 | -4 | -4 | 0 | 4 | -1 | -4 | -3 | -3 | -3 | 2 | 0 | -3 | 1 | |
| 117 | | — | -1 | 5 | -3 | -3 | -2 | -2 | -3 | 3 | -2 | -2 | 1 | -1 | -2 | 0 | 0 | -2 | -2 | -2 | -2 | 0 |
| 118 | | 121-D | 2 | -1 | -2 | 0 | -2 | -4 | 1 | 2 | 1 | -5 | -3 | -4 | -4 | -4 | -1 | 2 | 0 | -4 | 3 | 2 |
| 119 | | 122-K | -2 | -3 | -5 | -3 | 0 | -4 | -6 | -6 | -2 | -6 | 1 | 0 | 0 | 0 | -1 | -4 | 6 | 2 | -4 | -3 |
| 120 | | 123-L | -4 | -6 | -3 | 4 | -1 | 3 | 1 | -5 | -5 | -5 | 2 | 2 | -4 | -5 | -4 | 0 | 0 | 0 | -6 | -5 |
| 121 | | 124-N | 2 | -4 | -1 | -5 | -4 | -5 | -6 | -6 | -1 | -5 | 0 | 4 | -5 | 4 | -1 | -4 | -3 | -4 | -1 | 4 |
| 122 | | 125-H | 1 | -5 | -6 | -2 | -5 | -4 | -5 | 6 | 0 | -6 | -3 | 0 | -4 | -1 | 3 | 5 | 2 | 2 | -4 | 1 |
| 123 | | 126-H | 0 | -1 | -5 | -5 | -1 | 4 | -6 | -6 | -5 | -5 | -2 | 2 | -5 | 4 | 3 | 4 | 2 | -2 | -1 | -3 |
| 124 | | 127-Q | -4 | -6 | 6 | 0 | -2 | 1 | -4 | -6 | -5 | -5 | -4 | -4 | -5 | -5 | 7 | -4 | -4 | -4 | -5 | -3 |
| 125 | | 128-R | -2 | -6 | -3 | 5 | -2 | -2 | -4 | -6 | -5 | -5 | -5 | -4 | -5 | -5 | 2 | -5 | 3 | 2 | -5 | -1 |
| 126 | | 129-I | 1 | -5 | 4 | -2 | 1 | -3 | -1 | -6 | -5 | 0 | -4 | -1 | 0 | -1 | 1 | 0 | 2 | 0 | -2 | 1 |
| 127 | | 130-G | 1 | 7 | -7 | -7 | -6 | -6 | -6 | -6 | -5 | -6 | -1 | -4 | -6 | 2 | -5 | -5 | -5 | -5 | -4 | -5 |
| 128 | | 131-L | -3 | -7 | 5 | 4 | 1 | 2 | 1 | 2 | -6 | -5 | -6 | -2 | -4 | -7 | -6 | -6 | -6 | -6 | -7 | -6 |
| 129 | | 132-K | 1 | -1 | -5 | 0 | -1 | -1 | -6 | -6 | -2 | -6 | -1 | -4 | -5 | -4 | 1 | -4 | 3 | 2 | -2 | 4 |
| 130 | | 133-Y | -1 | -6 | -2 | 1 | -2 | 2 | 4 | -3 | -6 | -5 | -3 | -2 | 6 | -5 | -4 | 5 | -5 | 0 | -6 | -2 |
| 131 | | 134-F | 2 | -6 | -2 | -2 | 0 | 0 | 3 | 2 | -6 | -5 | -4 | -5 | 8 | -5 | -5 | 3 | -3 | -5 | -6 | -5 |
| 132 | | 135-G | -4 | -1 | -6 | -6 | -6 | -5 | 0 | -6 | -5 | -7 | -1 | -2 | -5 | -3 | 0 | 0 | 2 | 3 | 4 | 4 |
| 133 | | 136-D | 0 | -5 | -6 | -6 | -6 | -6 | -7 | -7 | -5 | -6 | -1 | -2 | -6 | -1 | -1 | -4 | 1 | 2 | 6 | 2 |
| 134 | | 137-F | 0 | -6 | 2 | 1 | -2 | -3 | 5 | 6 | -3 | -5 | -1 | -4 | 0 | -5 | 1 | -5 | -2 | 2 | -6 | -3 |
| 135 | | 138-E | -1 | -2 | -2 | 0 | -1 | -4 | -5 | -6 | -1 | 1 | 2 | -2 | -5 | 0 | 3 | -4 | 1 | 3 | -2 | 2 |
| 136 | | 139-K | -2 | 2 | -6 | -1 | -5 | -4 | -6 | -6 | -5 | 1 | 1 | 1 | -5 | -4 | 4 | -4 | 2 | 1 | -2 | 3 |
| 137 | | 140-R | -2 | -5 | -6 | -6 | -6 | -5 | -6 | -6 | -2 | 2 | -2 | -1 | -1 | -4 | -2 | 0 | 2 | 7 | -5 | -3 |
| 138 | | 141-I | -4 | 6 | 6 | -2 | 2 | 6 | 3 | -5 | -6 | -5 | -3 | 0 | -4 | -6 | 0 | -5 | -1 | -6 | -5 | |
| 139 | | 142-P | -1 | -5 | -5 | 0 | -5 | -4 | -6 | -6 | 7 | -5 | 2 | -1 | -1 | -2 | -4 | -5 | -2 | 0 | -5 | -4 |
| 140 | | 143-R | -5 | -6 | 2 | 3 | -4 | -3 | -4 | 1 | -6 | -6 | -5 | -5 | 0 | -5 | -3 | -4 | 0 | 6 | -6 | -4 |
| 141 | | 144-E | 2 | 1 | -1 | -6 | -5 | -5 | -2 | 1 | -2 | -5 | 2 | -4 | -5 | 0 | -1 | 0 | -2 | -1 | 2 | 4 |
| 142 | | 145-E | 0 | -5 | -5 | -5 | 0 | -1 | -6 | -6 | -5 | -6 | -3 | -2 | 0 | 4 | 0 | 0 | 0 | -1 | 0 | 6 |
| 143 | | 146-M | 6 | -1 | -2 | -4 | 3 | 3 | -5 | -6 | -5 | 3 | -1 | -1 | -5 | -5 | -4 | -5 | -5 | -5 | -6 | -5 |
| 144 | | 147-L | -2 | -1 | -2 | 2 | -1 | 1 | 0 | -5 | -5 | -6 | -4 | 2 | 2 | -2 | 0 | -4 | 1 | 0 | 0 | 3 |
| 145 | | 148-Q | 2 | -5 | -6 | -3 | -5 | -5 | -6 | -6 | 3 | -6 | -1 | -5 | -4 | 3 | -4 | 1 | 2 | -2 | 3 | |
| 146 | | 149-M | -3 | -6 | 5 | 2 | 2 | 4 | -1 | -5 | -6 | -5 | -5 | 0 | 1 | -5 | -5 | 5 | -5 | -5 | -6 | -1 |
| 147 | | 150-Q | 4 | 1 | -5 | -2 | -1 | -4 | 0 | -5 | -5 | -5 | -1 | -2 | 2 | -4 | 1 | -4 | -4 | -2 | -4 | 3 |
| 148 | | 151-D | 0 | -3 | -6 | -3 | -5 | 1 | -6 | -6 | -5 | 0 | -1 | -2 | -5 | 0 | 3 | -4 | 1 | 2 | 1 | 5 |
| 149 | | 152-I | -2 | -3 | 4 | 1 | 0 | -3 | -5 | -6 | -2 | -5 | -3 | 1 | -5 | -5 | -3 | -1 | 1 | 2 | -4 | 3 |
| 150 | | 153-V | -4 | -7 | 6 | 3 | 4 | 1 | -3 | -6 | -6 | -5 | -6 | -4 | -5 | -7 | -6 | -7 | -6 | -6 | -7 | -6 |
| 151 | | 154-L | -1 | -3 | 1 | 2 | 0 | 0 | -5 | -6 | -5 | -6 | -4 | -4 | -5 | -4 | 2 | -4 | 4 | 2 | -4 | 2 |
| 152 | | 155-N | 2 | 0 | -5 | -2 | -3 | -5 | -6 | -6 | -2 | -6 | 1 | -4 | -5 | 1 | 0 | -4 | 3 | 1 | 0 | 3 |
| 153 | | 156-E | 4 | -3 | -1 | -5 | -2 | -4 | 1 | -5 | -5 | 1 | -3 | -1 | 3 | -4 | -1 | 6 | -3 | 1 | -5 | 1 |
| 154 | | 157-V | 2 | -3 | 1 | 4 | 3 | 4 | 1 | -5 | -6 | -4 | -4 | -2 | -4 | -6 | -5 | -6 | -5 | -6 | -6 | -6 |
| 155 | | 158-K | -2 | -5 | -5 | -2 | -3 | -5 | -6 | 1 | 1 | 0 | -2 | -1 | -5 | 1 | 1 | 3 | 2 | 4 | 0 | 2 |
| 156 | | 159-K | 1 | 0 | -2 | -3 | -3 | -5 | -6 | 1 | -1 | -5 | 1 | 2 | -5 | 0 | 1 | -4 | 1 | -2 | 2 | 2 |
| 157 | | 160-V | -1 | -2 | 3 | 2 | 3 | 0 | 3 | -4 | -5 | 2 | -4 | 1 | -3 | -2 | -2 | 0 | -4 | -4 | -5 | -2 |
| 158 | | 161-D | -1 | 0 | -4 | 0 | -2 | -4 | -4 | -5 | 4 | -4 | -1 | -4 | 1 | -3 | 1 | 0 | -3 | 4 | -1 | |
| 159 | | 162-S | 0 | 3 | -1 | -3 | -2 | -4 | -5 | -5 | 6 | -5 | -1 | -2 | -1 | -4 | -3 | 0 | 0 | -4 | -4 | 1 |
| 160 | | 163-E | 1 | 2 | 0 | -1 | 2 | -4 | -5 | -5 | -5 | -2 | -1 | -1 | 1 | 0 | -4 | 1 | -4 | 2 | 1 | |
| 161 | | 164-Y | 1 | -6 | 2 | 2 | 0 | 2 | 1 | -5 | -5 | 1 | -3 | -4 | 2 | -5 | -2 | -5 | -1 | 1 | -5 | 2 |
| 162 | | 165-I | -2 | -3 | 2 | 0 | -1 | -4 | -2 | 2 | -5 | 1 | 0 | -1 | -5 | 1 | 4 | 0 | 1 | 1 | -2 | 1 |
| 163 | | 166-A | 3 | -4 | 3 | 0 | 4 | 3 | -1 | -6 | -1 | 3 | -1 | -4 | -5 | -6 | -5 | -6 | -5 | -6 | -6 | -5 |
| 164 | | 167-T | 0 | -5 | 0 | -4 | 2 | -1 | -5 | -6 | -5 | 1 | -1 | 4 | -5 | -4 | -1 | 0 | -4 | -4 | -4 | 4 |
| 165 | | 168-V | 0 | -6 | 5 | 2 | 3 | 0 | -4 | 1 | 1 | 0 | -5 | -1 | -1 | -6 | -5 | -6 | -5 | -2 | -6 | -6 |
| 166 | | 169-C | 5 | -2 | -4 | -4 | 0 | 3 | -5 | -6 | -5 | 7 | -3 | 2 | -5 | -5 | -1 | -5 | -5 | -5 | -5 | -5 |
| 167 | | 170-G | -3 | 8 | -7 | -7 | -7 | -6 | -7 | -6 | -6 | -6 | -4 | -5 | -7 | -4 | -5 | -6 | -5 | -6 | -5 | -6 |
| 168 | | 171-S | -2 | 3 | -6 | -6 | -5 | -5 | -6 | -6 | -4 | -5 | 7 | -2 | -5 | -3 | -4 | -4 | -4 | -4 | 0 | -4 |
| 169 | | 172-F | -3 | -7 | 0 | 2 | 0 | -3 | 5 | -2 | -6 | -5 | -5 | -1 | 7 | -6 | -5 | -3 | -6 | -6 | -7 | -6 |
| 170 | | 173-R | -5 | -6 | -7 | -6 | -6 | -5 | -6 | -6 | -7 | -2 | -4 | -5 | -1 | -2 | -4 | -1 | 8 | -5 | -3 | |
| 171 | | 174-R | -5 | -6 | -7 | -6 | -6 | -5 | -6 | -6 | -7 | -4 | -5 | -5 | -4 | -2 | -4 | -1 | 9 | -5 | -3 | |
| 172 | | 175-G | -2 | 6 | -6 | -6 | -6 | 3 | -2 | 3 | -6 | -4 | -5 | -2 | -4 | -2 | -5 | -2 | 1 | -5 | -3 | |
| 173 | | 176-A | 1 | -5 | -6 | -2 | -5 | -4 | -6 | -6 | -5 | -6 | 0 | -2 | 0 | -4 | 0 | -4 | 6 | 4 | -4 | -3 |
| 174 | | 177-E | 2 | -5 | -5 | -2 | -5 | -1 | -6 | -6 | 3 | -6 | 0 | 0 | -5 | -4 | -1 | -4 | 0 | -4 | 0 | 5 |
| 175 | | 178-S | -1 | -5 | -1 | -5 | -1 | -4 | -5 | -6 | -5 | -5 | 1 | 7 | -1 | -3 | 0 | -5 | 0 | -1 | -2 | -4 |

TABLE 1-continued

Position-specific scoring matrix (PSSM) for NT-POLXc (cd00141) domain
where a threshold bit score of 199.344 is required to qualify as a member of this family.
The PSSM was obtained from the NCBI CDD. In the upper left hand corner table header,
P signifies position, C signifies the consensus sequence, and M signifies the master
sequence of known structure. In the rest of the table, letters indicate standard amino
acid single letter nomenclature.

| P | C | M | A | G | I | L | V | M | F | W | P | C | S | T | Y | N | Q | H | K | R | D | E |
|---|---|---|---|---|---|---|---|---|---|---|---|---|---|---|---|---|---|---|---|---|---|---|
| 176 |  | 179-S | −3 | 2 | 1 | −2 | 5 | −4 | −5 | −6 | −6 | 7 | 3 | −3 | −5 | −5 | −5 | −6 | −5 | −6 | −6 | −5 |
| 177 |  | 180-G | −1 | 7 | −7 | −7 | −6 | −6 | −6 | −6 | −5 | −6 | −4 | −5 | −5 | −4 | −4 | 4 | −1 | −1 | −2 | −5 |
| 178 |  | 181-D | −2 | −5 | −7 | −7 | −7 | −6 | −7 | −8 | −5 | −7 | −4 | −4 | −7 | −2 | −4 | −5 | −4 | −5 | 8 | −2 |
| 179 |  | 182-M | −1 | −7 | 5 | 3 | 4 | 3 | −4 | −6 | −6 | −4 | −5 | −4 | −5 | −7 | −6 | −6 | −6 | −6 | −7 | −6 |
| 180 |  | 183-D | −5 | −5 | −7 | −7 | −7 | −7 | −7 | −8 | −5 | −7 | −4 | −4 | −7 | −2 | −3 | −4 | −4 | −5 | 8 | 1 |
| 181 |  | 184-V | −3 | −7 | 6 | 2 | 4 | 2 | 3 | −5 | −6 | −5 | −5 | −4 | 0 | −7 | −6 | −6 | −6 | −6 | −7 | −6 |
| 182 |  | 185-L | −4 | −7 | 1 | 6 | 3 | 1 | −3 | −5 | −6 | −5 | −5 | −1 | −5 | −7 | −6 | −6 | −6 | −6 | −7 | −6 |
| 183 |  | 186-L | 2 | −3 | 4 | 2 | 4 | −2 | 1 | −6 | −6 | −4 | −5 | −4 | −4 | −6 | −6 | −6 | −6 | −6 | −6 | −6 |
| 184 |  | 187-T | 2 | −2 | −4 | −5 | −2 | −4 | −1 | −5 | −5 | 0 | 2 | 6 | 0 | −4 | −4 | 1 | −4 | −5 | −5 | −4 |
| 185 |  | 188-H | 2 | 0 | −5 | −5 | −5 | 2 | −5 | −6 | −1 | 0 | 3 | 0 | −4 | −3 | −3 | 7 | 1 | 2 | −5 | −4 |
| 186 |  | 189-P | −1 | −5 | −6 | −6 | −5 | −5 | −7 | −7 | 6 | 0 | 0 | 0 | −6 | −2 | −2 | −5 | 1 | −1 | 2 | 1 |
| 187 |  | 190-S | −4 | 1 | −5 | −5 | −5 | −5 | −1 | −5 | −4 | 0 | 0 | −1 | −1 | 0 | −3 | 3 | −2 | −1 | 6 | 2 |
| 188 |  | 191-F | 1 | 2 | −1 | −2 | −2 | 1 | −2 | −2 | 3 | −2 | 0 | 2 | −2 | 0 | −2 | 1 | −2 | −1 | 0 |  |
| 189 |  | 192-T | 0 | 0 | −2 | −2 | −2 | −2 | −2 | −2 | −1 | −2 | −1 | 3 | −2 | 2 | 1 | −2 | 1 | −1 | 2 | 0 |
| 190 |  | 193-S | 0 | 0 | −1 | −1 | −2 | −2 | −2 | −2 | −1 | −2 | 3 | −1 | −2 | 1 | 0 | −2 | 0 | −1 | 2 | 0 |
| 191 |  | 199-P | 0 | −2 | −2 | −2 | −1 | −2 | −2 | −2 | 1 | −2 | 0 | 1 | −2 | 0 | 2 | 1 | 1 | 2 | −1 | 1 |
| 192 |  | 200-K | −2 | 3 | −1 | −1 | −2 | −2 | −2 | −2 | 0 | −2 | −1 | 0 | 0 | 0 | 1 | 2 | 0 | 1 | 0 | −1 |
| 193 |  | 201-L | −1 | −1 | −1 | 2 | 1 | 1 | 2 | −2 | −2 | −2 | 0 | −2 | −2 | 0 | 0 | −2 | −2 | −2 | 1 | 1 |
| 194 |  | 202-L | 0 | 1 | −1 | 3 | −1 | 1 | 1 | 1 | 4 | −5 | −4 | −1 | −4 | −5 | −4 | −5 | −1 | 1 | −5 | −5 |
| 195 |  | 203-H | 2 | −1 | −5 | −2 | −3 | −5 | −6 | −6 | 1 | −5 | 1 | 0 | −5 | −1 | −1 | 3 | 3 | −2 | −1 | 3 |
| 196 |  | 204-Q | 3 | −5 | −6 | −3 | −5 | −5 | −6 | −6 | 2 | −6 | 0 | −4 | −5 | −2 | 1 | 2 | 4 | 2 | −1 | 1 |
| 197 |  | 205-V | −2 | −6 | 2 | 4 | 5 | −2 | −1 | −6 | −6 | −5 | −3 | −4 | −4 | −2 | −5 | −6 | −5 | −6 | −1 | −3 |
| 198 |  | 206-V | −4 | −7 | 4 | 2 | 4 | 5 | −4 | −6 | −6 | −5 | −5 | 0 | −5 | −6 | −5 | −1 | −5 | −2 | −3 | −6 |
| 199 |  | 207-E | −2 | −5 | −1 | −1 | −2 | −5 | −6 | −6 | −2 | 0 | −2 | −2 | −5 | −3 | 1 | 3 | 0 | 1 | 5 | 3 |
| 200 |  | 208-Q | 3 | −1 | −5 | −4 | −2 | −4 | −2 | −6 | −5 | 1 | 0 | −1 | −1 | −4 | 1 | 5 | 2 | 3 | −4 | 0 |
| 201 |  | 209-L | −5 | −7 | −1 | 5 | −3 | 0 | 6 | 1 | −7 | −5 | −6 | −5 | −2 | −2 | −6 | −5 | −6 | −1 | −7 | −6 |
| 202 |  | 210-Q | 0 | −6 | −1 | 1 | 3 | −3 | −5 | −6 | −5 | 3 | −4 | 3 | −5 | −4 | 1 | 2 | 2 | −2 | −5 | 0 |
| 203 |  | 211-K | 0 | −1 | −2 | −5 | −5 | 1 | −6 | −6 | 0 | −6 | 1 | 1 | −5 | 1 | 2 | 1 | 1 | 1 | 1 | 2 |
| 204 |  | 212-V | −2 | −6 | 1 | 1 | −1 | 4 | 1 | 1 | −2 | 2 | 1 | −1 | 2 | −5 | 3 | 0 | 1 | −4 | −5 | 0 |
| 205 |  | 213-H | −4 | 4 | −5 | 0 | −3 | −4 | −5 | −6 | 5 | −6 | −4 | −4 | −5 | 1 | −4 | 0 | −1 | −5 | 0 | −1 |
| 206 |  | 214-F | −2 | 2 | −1 | 1 | −1 | −1 | 5 | −4 | −5 | −5 | −4 | −1 | 4 | −1 | 0 | −4 | −4 | −2 | 0 | 1 |
| 207 |  | 215-I | −2 | −6 | 4 | 3 | 5 | −2 | −4 | −6 | −5 | −4 | −5 | −2 | −4 | −6 | −5 | −6 | 0 | −5 | −6 | −2 |
| 208 |  | 216-T | −1 | −4 | −1 | 1 | −2 | −3 | −5 | −4 | −4 | −4 | −1 | 4 | −4 | −1 | −4 | 1 | 1 | 1 | 3 |  |
| 209 |  | 217-D | −2 | −2 | −5 | −5 | −4 | −4 | 0 | −4 | −1 | 4 | 1 | −2 | 3 | −3 | −1 | 2 | −3 | 0 | 4 | 3 |
| 210 |  | 218-T | −2 | 1 | 2 | −2 | 4 | −3 | −4 | −5 | −4 | −4 | −1 | 2 | 0 | −4 | −3 | −4 | −4 | −4 | 1 | 2 |
| 211 |  | 219-L | 1 | −1 | 3 | 3 | 0 | −2 | −3 | 2 | −4 | −4 | 0 | 0 | −1 | −4 | −1 | 1 | −4 | −4 | 0 | −1 |
| 212 |  | 220-S | 2 | −1 | −2 | −2 | 0 | 3 | −1 | −5 | −4 | −4 | 3 | −1 | −4 | 2 | −3 | −4 | −1 | 0 | −0 | −1 |
| 213 |  | 221-K | 0 | 2 | −5 | −3 | −5 | −5 | −6 | −6 | −5 | 1 | 1 | −2 | −5 | −3 | 2 | 2 | 3 | 0 | 3 | 0 |
| 214 |  | 222-G | −2 | 6 | −1 | −1 | −2 | −4 | −5 | −6 | −5 | 0 | −3 | 1 | −5 | 0 | −2 | 3 | −4 | −5 | 1 | −3 |
| 215 |  | 223-E | −4 | 0 | −1 | −2 | −2 | −4 | 3 | −5 | 1 | 0 | 0 | 0 | −4 | −3 | 1 | −4 | −2 | −4 | 4 | 3 |
| 216 |  | 224-T | −2 | 0 | −5 | −5 | −2 | −5 | −6 | −6 | −1 | −5 | −2 | 5 | −5 | 0 | 2 | −4 | 3 | −2 | 0 | 1 |
| 217 |  | 225-K | −4 | −3 | −5 | −5 | −1 | −5 | −6 | −6 | −5 | −6 | −1 | −1 | −5 | −4 | 0 | −4 | 7 | 3 | −4 | −3 |
| 218 |  | 226-F | 2 | −1 | −4 | −2 | 1 | 0 | 3 | 5 | −6 | 5 | 1 | −2 | 5 | −5 | −5 | −4 | −5 | −5 | −6 | −5 |
| 219 |  | 227-M | −3 | −5 | −4 | 0 | −4 | 6 | 4 | −4 | −5 | −5 | 4 | 1 | 2 | −4 | −4 | 0 | 1 | −2 | −5 | −4 |
| 220 |  | 228-G | −1 | 5 | 1 | −1 | 4 | 3 | −1 | −6 | −6 | 0 | −4 | −2 | −5 | −5 | −6 | −5 | −6 | −2 | −6 |  |
| 221 |  | 229-V | −2 | −2 | 5 | 0 | 4 | 1 | −2 | −6 | −6 | 0 | −3 | −4 | −5 | −5 | −5 | −6 | −2 | 3 | 1 | −5 |
| 222 |  | 230-C | −4 | −2 | 1 | 5 | 0 | −2 | −3 | 2 | −6 | 7 | −1 | −4 | 0 | −6 | −6 | −6 | −6 | −6 | −7 | −6 |
| 223 |  | 231-Q | −1 | 0 | −3 | −6 | −5 | −5 | −6 | −6 | −5 | −6 | 1 | −1 | −5 | 0 | 2 | 0 | 4 | 4 | −2 | 1 |
| 224 |  | 232-L | −2 | −1 | −1 | 4 | 1 | −2 | −1 | −5 | −5 | 0 | −1 | 0 | −1 | 1 | −4 | −4 | 0 | −4 | −1 | 1 |
| 225 |  | 233-P | −2 | −1 | 0 | −2 | −2 | −2 | −2 | −2 | 5 | −2 | 0 | −2 | 0 | −2 | 1 | −2 | 1 | −2 | 0 | 1 |
| 226 |  | 234-S | −2 | 1 | −2 | −1 | −2 | −2 | −2 | −2 | 0 | 0 | −1 | −2 | −2 | 1 | 2 | 3 | 1 | −1 | 2 | 1 |
| 227 |  | 240-E | 0 | 2 | −1 | −1 | −2 | −2 | −2 | −2 | 0 | −2 | 1 | 1 | −2 | 1 | 1 | −2 | −1 | −1 | 1 | 0 |
| 228 |  | 241-Y | 0 | −2 | 1 | −2 | −2 | −2 | −2 | 7 | 0 | −2 | 0 | −1 | 1 | 0 | 0 | −2 | 0 | 2 | −2 | 0 |
| 229 |  | 242-P | −2 | −2 | 1 | 0 | −1 | 1 | −2 | 2 | 3 | −2 | −2 | 0 | 3 | −2 | 0 | −2 | 2 | 1 | −2 | −2 |
| 230 |  | 243-H | 1 | 4 | −6 | −6 | −5 | −5 | −2 | 3 | −5 | 4 | −4 | −1 | 0 | −1 | −1 | 6 | −4 | −1 | −2 | −2 |
| 231 |  | 244-R | −4 | −6 | 2 | 0 | 3 | 0 | −2 | −6 | −6 | −5 | −4 | 0 | −5 | −5 | −1 | −5 | −3 | 6 | −6 | −4 |
| 232 |  | 245-R | −2 | −5 | −6 | −6 | −6 | −5 | −6 | −6 | 0 | −7 | −2 | −2 | −5 | −1 | 4 | −4 | −2 | 7 | −2 | −1 |
| 233 |  | 246-I | 1 | −6 | 4 | 2 | 5 | −2 | −4 | −6 | −6 | 2 | −5 | −4 | −5 | −6 | −6 | −6 | −6 | −6 | −7 | −6 |
| 234 |  | 247-D | −5 | −5 | −7 | −7 | −7 | −7 | 7 | −8 | −5 | −7 | −4 | −4 | −7 | −2 | −3 | −4 | −4 | −5 | 8 | 0 |
| 235 |  | 248-I | −5 | −7 | 5 | 5 | −1 | 1 | 4 | −5 | −6 | −5 | −6 | −5 | −3 | −7 | −6 | −6 | −6 | −6 | −7 | −7 |
| 236 |  | 249-R | −2 | −6 | 3 | 1 | 1 | −3 | −1 | −6 | −6 | −6 | −5 | −4 | −5 | −5 | −1 | −5 | 0 | 6 | −6 | −4 |
| 237 |  | 250-L | −1 | −6 | 3 | 3 | 5 | 2 | −1 | −6 | −6 | 5 | −5 | 0 | −5 | −6 | −6 | −6 | −6 | −6 | −7 | −6 |
| 238 |  | 251-I | 0 | −6 | 2 | 0 | 6 | −3 | −2 | −5 | −2 | 4 | −2 | 1 | 1 | −6 | −5 | −6 | −5 | −6 | −6 | −6 |
| 239 |  | 252-P | −2 | −5 | −6 | −6 | −6 | −6 | −7 | −7 | 7 | −6 | 0 | −2 | −6 | −2 | −4 | −5 | 1 | −4 | 0 | 1 |
| 240 |  | 253-K | 0 | −5 | −5 | −5 | −3 | −5 | 0 | 6 | 4 | −6 | −2 | −4 | 5 | −5 | −4 | 2 | 1 | −2 | 0 | 1 |
| 241 |  | 254-D | 1 | −2 | −3 | −6 | −5 | −5 | −6 | −7 | −5 | −6 | 1 | −4 | −5 | −1 | 0 | 0 | −1 | −2 | 4 | 5 |
| 242 |  | 255-Q | 0 | −2 | −2 | −4 | −3 | −4 | −6 | −6 | −5 | 0 | 3 | −1 | 0 | −4 | 4 | −4 | −3 | 0 | −3 | 4 |
| 243 |  | 256-Y | −2 | −6 | 0 | −1 | −4 | −4 | 6 | 5 | −6 | −6 | −5 | −5 | 6 | −6 | −5 | −3 | −2 | 2 | −7 | −6 |
| 244 |  | 257-Y | 1 | 6 | −6 | −6 | −3 | −5 | −2 | −5 | 2 | −6 | −2 | −5 | 2 | −4 | −5 | −1 | −5 | −5 | −5 | −5 |
| 245 |  | 258-C | 5 | −4 | −5 | −5 | −4 | −4 | 2 | −5 | −5 | 7 | 1 | 0 | 2 | −5 | −5 | −5 | −5 | −5 | −5 | −5 |
| 246 |  | 259-G | 6 | 3 | −5 | 0 | −4 | −4 | −5 | −6 | −5 | 1 | −1 | 1 | −5 | −5 | −4 | −5 | −4 | −5 | −5 | −5 |

TABLE 1-continued

Position-specific scoring matrix (PSSM) for NT-POLXc (cd00141) domain
where a threshold bit score of 199.344 is required to qualify as a member of this family.
The PSSM was obtained from the NCBI CDD. In the upper left hand corner table header,
P signifies position, C signifies the consensus sequence, and M signifies the master
sequence of known structure. In the rest of the table, letters indicate standard amino
acid single letter nomenclature.

| P | C | M | A | G | I | L | V | M | F | W | P | C | S | T | Y | N | Q | H | K | R | D | E |
|---|---|---|---|---|---|---|---|---|---|---|---|---|---|---|---|---|---|---|---|---|---|---|
| 247 | | 260-V | −5 | −7 | 1 | 5 | 2 | 2 | −1 | −5 | −6 | −5 | −5 | −2 | −4 | −1 | −5 | −6 | −5 | −1 | −1 | −6 |
| 248 | | 261-L | −5 | −6 | 3 | 4 | 0 | 0 | −4 | −5 | −6 | −5 | −5 | −4 | −4 | −5 | 4 | 6 | −4 | −4 | −6 | −4 |
| 249 | | 262-Y | −3 | 2 | −5 | −2 | −5 | −4 | −1 | −2 | −6 | −6 | −5 | −5 | 8 | −5 | −4 | 5 | −5 | −2 | −6 | −5 |
| 250 | | 263-F | −6 | −6 | −4 | −2 | −5 | −4 | 8 | 8 | −7 | −6 | −3 | −5 | 2 | −6 | −6 | −5 | −6 | −1 | −7 | −6 |
| 251 | | 264-T | −3 | −5 | −1 | −5 | −3 | −4 | −6 | −6 | −4 | −4 | 1 | 8 | −5 | −3 | −4 | −5 | −4 | −5 | −4 | −4 |
| 252 | | 265-G | −3 | 8 | −7 | −7 | −7 | −6 | −7 | −6 | −6 | −6 | −1 | −5 | −7 | −4 | −5 | −5 | −5 | −6 | −5 | −5 |
| 253 | | 266-S | −2 | 0 | −6 | −6 | −5 | −5 | −6 | −6 | −4 | −5 | 6 | −2 | −5 | 3 | −3 | −4 | −1 | −4 | −1 | −1 |
| 254 | | 267-D | −1 | −5 | −2 | −6 | −3 | −5 | −6 | 1 | −5 | −6 | −3 | −1 | −5 | 1 | 2 | 2 | 5 | 2 | 4 | −3 |
| 255 | | 268-I | 1 | −4 | 1 | −1 | −1 | 1 | 1 | −5 | −2 | −5 | −2 | 0 | −4 | 1 | 3 | 4 | −3 | −4 | 1 | 2 |
| 256 | | 269-F | −5 | −6 | −4 | −2 | −5 | −4 | 8 | −3 | −6 | −6 | −5 | −5 | 2 | −4 | −5 | 8 | −5 | −5 | −6 | −5 |
| 257 | | 270-N | −2 | −1 | −6 | −3 | −6 | −5 | −6 | −6 | −5 | −6 | −2 | −2 | −1 | 8 | 0 | 0 | −4 | −4 | −2 | 0 |
| 258 | | 271-K | −2 | −2 | 3 | −4 | 2 | −4 | −5 | −6 | −6 | −6 | −4 | −2 | −5 | −4 | −3 | −5 | 3 | 6 | −5 | −4 |
| 259 | | 272-N | 3 | −4 | −6 | −6 | −5 | −5 | −6 | 2 | −5 | −5 | 2 | −2 | −5 | 0 | 2 | 1 | 2 | 1 | 3 | 0 |
| 260 | | 273-M | −4 | −7 | 2 | 5 | 2 | 7 | −1 | −5 | −6 | 1 | −5 | −4 | −4 | −6 | −5 | −6 | −6 | −6 | −7 | −6 |
| 261 | | 274-R | −5 | −6 | −7 | −6 | −6 | −5 | −6 | −6 | −5 | −7 | −4 | −4 | −5 | −4 | 1 | −4 | 0 | 8 | −5 | −3 |
| 262 | | 275-A | 2 | −3 | 0 | 2 | −4 | −3 | −5 | −6 | −5 | −5 | −3 | 2 | −1 | −2 | 0 | 1 | 0 | 4 | −1 | 0 |
| 263 | | 276-H | −2 | −6 | 3 | 3 | −3 | 1 | 1 | 1 | −6 | −5 | −5 | −5 | 4 | −5 | −4 | 3 | −1 | 4 | −6 | −3 |
| 264 | | 277-A | 7 | −3 | −5 | −5 | −4 | 0 | −6 | −6 | −4 | 1 | −1 | −3 | −5 | −5 | −4 | −5 | −4 | −5 | −5 | −4 |
| 265 | | 278-L | −1 | −5 | 0 | 2 | −2 | −3 | −5 | −6 | −5 | −5 | −1 | 0 | −5 | 2 | 3 | −4 | 4 | 1 | −4 | 0 |
| 266 | | 279-E | 1 | −3 | −6 | −6 | −3 | −5 | −6 | −6 | −5 | −6 | 0 | 0 | −5 | −3 | 3 | 1 | 3 | −1 | 1 | 4 |
| 267 | | 280-K | −3 | −5 | −5 | −1 | −5 | 4 | −6 | −6 | −5 | −6 | −2 | −4 | −5 | 0 | 1 | 2 | 5 | 4 | −4 | −2 |
| 268 | | 281-G | −3 | 7 | −7 | −7 | −6 | −6 | −7 | −6 | −5 | −6 | −1 | −5 | −6 | −2 | 0 | −5 | −1 | −1 | −2 | −5 |
| 269 | | 282-F | −5 | −7 | −1 | −3 | −3 | 7 | 4 | −3 | −6 | −5 | −3 | −5 | 5 | −6 | −5 | −4 | −5 | −5 | −6 | −3 |
| 270 | | 283-T | −4 | −5 | −5 | −3 | −2 | 2 | −6 | 1 | −5 | −5 | 2 | 3 | −5 | −1 | −3 | −4 | 5 | 2 | −2 | −3 |
| 271 | | 284-I | −5 | −7 | 3 | 6 | 1 | 1 | 1 | −5 | −6 | −5 | −6 | −4 | 0 | −7 | −6 | −6 | −6 | −6 | −7 | −6 |
| 272 | | 285-N | −4 | −4 | −6 | −6 | −4 | −5 | −6 | −7 | −5 | −5 | 4 | 1 | −6 | 6 | −3 | −4 | −4 | −4 | 3 | −3 |
| 273 | | 286-E | −1 | −5 | −7 | −6 | −6 | −5 | −7 | −6 | −5 | −6 | 1 | −4 | −5 | 3 | 3 | 1 | −3 | −3 | 1 | 6 |
| 274 | | 287-Y | −5 | −2 | −6 | −5 | −5 | −5 | 0 | −3 | −6 | −6 | −2 | −2 | 7 | −4 | −4 | 8 | −2 | 1 | −1 | −4 |
| 275 | | 288-T | 1 | 7 | −6 | −6 | −6 | −6 | −6 | −6 | −5 | −5 | 0 | 1 | −6 | −4 | −5 | −5 | −5 | −5 | −4 | −2 |
| 276 | | 289-I | −5 | −7 | 4 | 5 | 3 | −2 | −1 | −5 | −6 | −5 | −6 | −4 | −4 | −7 | −6 | −6 | −6 | −6 | −7 | −6 |
| 277 | | 290-R | −1 | −6 | −1 | −4 | −4 | −4 | 6 | −3 | −6 | −6 | 0 | −2 | 5 | −1 | −4 | −3 | −1 | −3 | −5 | −2 |
| 278 | | 291-P | 2 | 1 | 6 | 6 | 6 | 2 | 6 | 7 | 3 | 1 | 1 | 5 | 1 | 3 | 0 | 3 | 4 | 4 | 2 |
| 279 | | 292-L | 1 | 3 | −2 | 1 | 0 | 0 | −5 | −6 | −2 | −5 | −4 | −1 | −5 | 2 | −1 | −5 | 1 | 2 | 0 | −4 |
| 280 | | 293-G | 0 | 2 | −2 | −2 | 3 | −2 | −3 | −3 | −2 | −2 | 0 | 2 | −2 | −2 | 0 | −2 | 0 | −1 | 2 | 0 |
| 281 | | 298-A | 1 | −1 | −3 | −3 | −2 | −3 | −4 | −4 | 1 | −3 | 0 | 1 | −3 | 1 | 1 | −3 | 2 | −1 | 2 | 1 |
| 282 | | 299-G | −4 | 6 | −7 | −7 | −6 | −6 | −7 | −6 | −5 | −6 | −3 | −1 | −6 | 1 | −4 | −5 | 1 | −1 | 2 | 2 |
| 283 | | 300-E | −1 | −5 | −2 | −3 | −1 | −5 | −5 | 2 | −5 | −1 | 0 | −1 | −1 | 1 | 1 | 3 | 0 | 2 | 1 | 4 |
| 284 | | 301-P | −1 | −6 | 1 | 1 | 1 | −3 | 2 | −5 | 3 | 3 | −2 | −2 | −1 | −5 | −4 | −5 | 0 | 4 | −6 | −3 |
| 285 | | 302-L | −2 | −7 | 3 | 5 | 3 | −2 | −1 | −6 | −6 | −5 | −5 | −4 | −4 | −6 | −5 | −6 | −2 | −5 | −2 | −3 |
| 286 | | 303-P | 3 | −1 | −2 | −2 | −5 | −5 | −2 | −6 | 5 | −5 | −2 | 0 | −5 | −4 | −3 | 1 | 0 | −4 | −4 | 3 |
| 287 | | 304-V | 1 | 3 | 0 | −2 | 2 | −4 | 0 | −6 | −5 | 3 | 2 | 1 | −5 | −4 | −5 | −5 | −2 | −5 | 0 | −5 |
| 288 | | 305-D | 1 | −1 | −5 | −5 | −5 | 2 | 0 | −6 | 2 | −6 | −1 | 0 | −4 | 0 | −3 | 3 | −1 | 2 | 0 | 3 |
| 289 | | 306-S | −1 | −5 | −5 | −3 | −4 | −4 | −6 | −6 | −2 | 1 | 3 | 5 | −5 | 1 | −1 | −1 | −4 | −2 | 1 | 0 |
| 290 | | 307-E | −4 | −6 | −7 | −6 | −6 | −5 | −7 | −6 | −5 | −7 | −3 | −4 | −5 | −4 | −1 | −3 | −2 | −3 | −2 | 8 |
| 291 | | 308-K | 1 | −5 | −2 | −5 | −5 | 0 | −5 | −5 | −5 | −6 | −2 | −4 | 2 | −4 | −1 | 0 | 3 | 3 | −1 | 5 |
| 292 | | 309-D | −1 | 0 | −6 | −6 | −2 | −5 | −7 | −7 | −5 | −6 | −2 | −4 | −6 | −1 | −1 | −4 | 0 | 2 | 5 | 5 |
| 293 | | 310-I | −4 | −7 | 6 | −1 | 5 | 0 | 0 | −6 | −6 | −4 | −5 | −4 | −7 | −6 | −7 | −6 | −6 | −6 | −7 | −6 |
| 294 | | 311-F | −5 | −7 | −4 | −1 | −4 | 1 | 8 | −2 | −7 | −6 | −6 | −5 | 7 | −6 | −6 | −3 | −6 | −6 | −7 | −6 |
| 295 | | 312-D | 2 | −5 | −4 | −6 | −5 | −5 | −6 | −6 | −5 | −6 | −2 | −2 | −5 | −3 | 2 | 2 | 1 | 3 | 3 | 4 |
| 296 | | 313-Y | 2 | −1 | 2 | 1 | −2 | 1 | −1 | −5 | −5 | 0 | −2 | −2 | 3 | −5 | 0 | 5 | −1 | −1 | −5 | −2 |
| 297 | | 314-I | −3 | −7 | 3 | 6 | 1 | −1 | 1 | −5 | −6 | −5 | −6 | −4 | −4 | −7 | −6 | −6 | −6 | −6 | −7 | −6 |
| 298 | | 315-Q | −3 | 7 | −7 | −7 | −7 | −6 | −7 | −6 | −1 | −6 | −1 | −5 | −6 | −1 | 0 | −5 | −5 | −5 | −1 | −5 |
| 299 | | 316-W | −2 | −7 | −1 | 5 | 1 | 5 | 2 | 4 | −6 | −5 | −5 | −4 | −4 | −7 | −5 | −6 | −6 | −6 | −7 | −6 |
| 300 | | 317-K | 0 | −5 | −6 | −4 | −6 | −5 | −7 | −7 | 5 | −6 | −1 | −4 | −6 | −4 | 1 | −4 | 2 | 0 | 3 | 3 |
| 301 | | 318-Y | −5 | −6 | −5 | −3 | −5 | −4 | 2 | 9 | −7 | 0 | −5 | −5 | 8 | −5 | −3 | −2 | −1 | −7 | −6 |
| 302 | | 319-R | −2 | −6 | 5 | 1 | 1 | −3 | −4 | 1 | −2 | −5 | −5 | −4 | −5 | −5 | −2 | −5 | 1 | 4 | −6 | −5 |
| 303 | | 320-E | −1 | −5 | −6 | −6 | −6 | −6 | −7 | −7 | 6 | −6 | −2 | −4 | −6 | −4 | −3 | 0 | −1 | −4 | −3 | 6 |
| 304 | | 321-P | −4 | −6 | −6 | −6 | −6 | −6 | −7 | −7 | 9 | −6 | −4 | −4 | −6 | −5 | −5 | −6 | −4 | −6 | −5 | −5 |
| 305 | | 322-K | −3 | −5 | −6 | −6 | −6 | −5 | −6 | 6 | −2 | −6 | −1 | 0 | −4 | −4 | 0 | 4 | 2 | −3 | −3 | 6 |
| 306 | | 323-D | −5 | −6 | 1 | 3 | −4 | 0 | 0 | −6 | −5 | −6 | −4 | −4 | −4 | −4 | 2 | 4 | −4 | −4 | 2 | 4 |
| 307 | | 324-R | −5 | −6 | −7 | −6 | −6 | −5 | −6 | −6 | −6 | −7 | −4 | −5 | −5 | −4 | −2 | −4 | −1 | 8 | −1 | −1 |

TABLE 2

Position-specific scoring matrix (PSSM) for BRCT (cd00027) (SEQ ID NO: 88) domain where a threshold bit score of 29.2119 is required to qualify as a member of this family. The PSSM was obtained from the NCBI CDD. In the upper left hand corner table header, P signifies position, C signifies the consensus sequence, and M signifies the master sequence of known structure. In the rest of the table, letters indicate standard amino acid single letter nomenclature.

| P | C | M | A | G | I | L | V | M | F | W | P | C | S | T | Y | N | Q |
|---|---|---|---|---|---|---|---|---|---|---|---|---|---|---|---|---|---|
| 1 | G | 8-G | -3 | 5 | -5 | -7 | -1 | -10 | -3 | -11 | -5 | -10 | -5 | -4 | -3 | 3 | -1 |
| 2 | L | 9-K | -9 | -11 | 1 | 3 | 2 | 1 | 2 | -10 | -1 | 6 | -2 | -4 | -3 | -5 | -2 |
| 3 | T | 10-H | -1 | -5 | 0 | -2 | 2 | -1 | -9 | 2 | -5 | -10 | 2 | 3 | 0 | -2 | -1 |
| 4 | F | 11-F | -4 | -11 | 5 | -1 | 3 | 3 | 7 | -8 | -11 | -3 | -10 | -9 | 1 | -6 | -10 |
| 5 | V | 12-F | 0 | -5 | -1 | 0 | 3 | -1 | 3 | -8 | -10 | 6 | 0 | -5 | 5 | -10 | -9 |
| 6 | I | 13-L | -4 | -11 | 5 | 3 | 3 | -7 | 4 | -9 | -6 | 3 | -4 | -4 | -1 | -11 | -5 |
| 7 | T | 14-Y | -2 | 0 | -4 | -1 | -1 | 1 | -1 | 0 | -5 | 1 | 3 | 5 | 3 | 0 | -9 |
| 8 | G | 15-G | -2 | 5 | -1 | -6 | -2 | -1 | -3 | -11 | -1 | -2 | 2 | -8 | -10 | 0 | -4 |
| 9 | D | 16-E | -1 | -1 | 0 | 0 | -2 | 0 | 2 | -1 | -1 | 2 | 1 | 0 | 1 | -2 | -2 |
| 10 | L | 17-F | -1 | -4 | -1 | 2 | 0 | -3 | 3 | -8 | -1 | 1 | -1 | 1 | -2 | 0 | -1 |
| 11 | P | 18-P | -1 | -1 | -1 | -2 | -1 | 2 | -1 | -3 | 2 | -1 | -1 | 1 | -1 | 1 | 0 |
| 12 | S | 19-G | -2 | 1 | -1 | -2 | -3 | 0 | -5 | -5 | 2 | 0 | 2 | 0 | -2 | 1 | 2 |
| 13 | E | 20-D | -2 | -4 | 0 | -1 | -2 | 3 | 2 | -10 | 2 | 1 | 1 | 0 | 1 | 2 | 1 |
| 14 | E | 21-E | -2 | -3 | -4 | -1 | -2 | -9 | -2 | -10 | 1 | -2 | 1 | 1 | -2 | 2 | 1 |
| 15 | R | 22-R | -2 | -10 | 0 | -1 | -3 | 2 | -3 | -10 | -10 | -10 | -3 | -3 | 0 | -2 | -2 |
| 16 | D | 23-R | 0 | -2 | -1 | -2 | -5 | -2 | -2 | -1 | -5 | -1 | 2 | 1 | -2 | 0 | 0 |
| 17 | E | 24-K | -2 | -4 | 1 | -2 | -4 | -4 | 0 | -1 | -2 | -10 | -1 | -2 | 0 | 0 | 2 |
| 18 | L | 25-L | 1 | -7 | 3 | 5 | 1 | 3 | -2 | 3 | -10 | -9 | -3 | -2 | 0 | -4 | -9 |
| 19 | K | 26-I | -2 | -5 | 1 | -4 | -2 | 1 | -9 | -10 | -9 | -2 | 0 | 2 | 1 | -5 | 3 |
| 20 | E | 27-R | 0 | -4 | -6 | -5 | -10 | -9 | 0 | -2 | -9 | -11 | -2 | 0 | -4 | 2 | 0 |
| 21 | L | 28-Y | 0 | -10 | 2 | 4 | -2 | 3 | 2 | 1 | -10 | 0 | -2 | -2 | -1 | -5 | 1 |
| 22 | I | 29-V | 2 | -11 | 6 | 2 | 3 | -2 | 2 | -10 | -10 | -3 | -6 | -3 | -3 | -11 | -10 |
| 23 | E | 30-T | -3 | 6 | -1 | -1 | 1 | 1 | -10 | -10 | -4 | -10 | -1 | -1 | -3 | -1 | 2 |
| 24 | K | 31-A | 2 | -4 | -2 | 0 | -6 | 0 | -4 | -1 | -5 | 1 | 0 | -1 | -2 | 1 | 1 |
| 25 | L | 32-F | -1 | -1 | -2 | 4 | -3 | 3 | 3 | -9 | -10 | 2 | -4 | -4 | 1 | 2 | -3 |
| 26 | G | 33-N | -4 | 7 | -11 | -4 | -11 | -10 | 0 | -10 | -10 | -3 | -8 | -9 | -2 | -3 | -9 |
| 27 | G | 34-G | 3 | 6 | -4 | -5 | -4 | -1 | 0 | -2 | -4 | -2 | -8 | -9 | -10 | -5 | -3 |
| 28 | K | 35-E | -1 | -9 | -3 | -4 | -1 | -9 | -10 | -11 | -9 | -3 | 1 | 3 | -2 | 0 | 0 |
| 29 | V | 36-L | -6 | -11 | 4 | 0 | 6 | 0 | 2 | -9 | -4 | 0 | -4 | -4 | 3 | -11 | -10 |
| 30 | T | 37-E | -1 | -3 | -1 | 1 | 2 | 1 | -5 | -10 | -3 | -1 | 1 | 4 | -2 | -3 | -2 |
| 31 | S | 38-D | -2 | 0 | -4 | -6 | -3 | -9 | -1 | 2 | 1 | -2 | 2 | 2 | -2 | 1 | 0 |
| 32 | S | 39-Y | -2 | -5 | -10 | -4 | -3 | -4 | 0 | -10 | -3 | -1 | 3 | 0 | 1 | 0 | 1 |
| 33 | V | 40-M | -1 | -2 | 2 | 2 | 3 | 1 | 2 | 1 | 0 | -1 | -2 | -3 | 1 | -3 | -2 |
| 34 | S | 41-S | -2 | -4 | -3 | -4 | -1 | -2 | -1 | -10 | 1 | -1 | 4 | 2 | -4 | 1 | 1 |
| 35 | K | 42-D | -2 | 0 | -1 | -2 | -2 | -5 | -1 | 1 | 1 | -5 | 1 | 0 | 0 | 1 | -2 |
| 36 | K | 43-R | -3 | -2 | -5 | -4 | -2 | -9 | -10 | -10 | -2 | -2 | 2 | 2 | 0 | 1 | 2 |
| 37 | T | 44-V | 1 | -10 | 1 | -3 | 3 | -2 | -1 | -10 | -10 | 4 | -2 | 4 | -4 | 0 | -2 |
| 38 | T | 45-Q | -4 | -9 | -5 | -6 | -4 | -9 | -2 | -11 | -2 | -2 | 1 | 7 | -9 | -3 | -1 |
| 39 | H | 46-F | -6 | -10 | 1 | -1 | -2 | -8 | 4 | -9 | -11 | 0 | -9 | -9 | 5 | -1 | -8 |
| 40 | V | 47-V | -2 | -11 | 3 | 4 | 5 | -3 | 2 | -10 | -5 | 3 | -4 | -5 | -1 | -11 | -5 |
| 41 | I | 48-I | -4 | -11 | 7 | 0 | 6 | -7 | -2 | -10 | -11 | -9 | -10 | -8 | -9 | -11 | -10 |
| 42 | V | 49-T | 2 | -3 | 1 | 0 | 4 | 1 | 1 | -10 | -10 | 3 | 1 | 1 | 0 | -10 | -9 |
| 43 | G | 50-A | -1 | 3 | -3 | -5 | -2 | -9 | -10 | -2 | 2 | 1 | 1 | -2 | 0 | 1 | 0 |
| 44 | S | 51-Q | -4 | 0 | -4 | -7 | -4 | -9 | -5 | -11 | -1 | -1 | 2 | 3 | -2 | 0 | -1 |
| 45 | D | 52-E | 0 | -3 | -1 | -1 | -3 | -1 | -1 | -10 | 2 | -1 | 0 | 0 | 1 | 3 | -4 |
| 46 | A | 53-W | 2 | 0 | -1 | -2 | -2 | -2 | -1 | -1 | 2 | 0 | 1 | -1 | -1 | 1 | -1 |
| 47 | G | 54-D | -1 | 3 | -5 | -2 | -2 | -3 | -1 | 0 | -1 | -2 | 1 | -2 | 2 | 0 | 0 |
| 48 | P | 55-P | 1 | 1 | -2 | -3 | -5 | -2 | -2 | -7 | 2 | -2 | 1 | 1 | -3 | -3 | 1 |
| 49 | K | 56-S | -3 | -3 | 0 | -1 | 1 | -6 | -1 | -7 | -4 | -2 | 1 | 0 | -2 | -1 | -4 |
| 50 | K | 57-F | -1 | -2 | -2 | 1 | 1 | 0 | 1 | -3 | -1 | 4 | -1 | -1 | 0 | 0 | -2 |
| 51 | L | 59-E | -2 | -6 | -1 | 3 | 1 | 1 | 3 | -5 | -2 | 2 | -3 | -5 | 5 | -6 | -3 |
| 52 | L | 60-A | 1 | -4 | 0 | 2 | -3 | 2 | 1 | 0 | -3 | -2 | -2 | -1 | -4 | 0 | 2 |
| 53 | K | 61-L | 1 | -5 | 0 | 1 | -1 | 0 | 0 | -8 | -3 | 1 | 0 | -2 | -2 | -1 | 0 |
| 54 | A | 62-M | 5 | 0 | 1 | -2 | -1 | -3 | -4 | 4 | -5 | 0 | -1 | -3 | 1 | -5 | -1 |
| 55 | I | 63-D | -2 | -6 | 4 | 0 | 0 | -4 | 0 | -1 | 0 | -3 | 0 | -4 | -9 | -1 | 2 |
| 56 | K | 64-N | 1 | -3 | -1 | -1 | -2 | -2 | 1 | -10 | -2 | 1 | 1 | -2 | -2 | 1 | 1 |
| 57 | L | 65-P | -2 | -3 | -5 | 2 | -2 | -2 | -1 | 3 | 1 | 1 | 1 | -2 | 1 | 2 | -3 |
| 58 | G | 66-S | -3 | 5 | -11 | -6 | -3 | -10 | -4 | -11 | -2 | -10 | -1 | -9 | -4 | 4 | -1 |
| 59 | I | 67-L | -1 | -4 | 5 | 0 | 3 | -8 | -2 | -1 | 0 | 1 | -2 | 1 | -2 | 10 | -5 |
| 60 | P | 68-A | 0 | -6 | 2 | -4 | -1 | -3 | -3 | 5 | 4 | -2 | -4 | -3 | -4 | -3 | 0 |
| 61 | I | 69-F | -3 | -11 | 6 | 1 | 4 | 0 | 2 | -10 | -11 | 4 | -9 | -1 | 0 | -11 | -4 |
| 62 | V | 70-V | -2 | -4 | 3 | 2 | 6 | 4 | -8 | 1 | -10 | -9 | -10 | -8 | -4 | -3 | -10 |
| 63 | T | 71-R | -8 | -3 | -10 | -4 | -10 | 0 | -10 | -11 | -2 | -1 | 2 | 3 | -3 | 3 | -2 |
| 64 | P | 72-P | -1 | -4 | 1 | -7 | 0 | -1 | 0 | -2 | 4 | 0 | -1 | -2 | -3 | -1 | -1 |
| 65 | E | 73-R | -3 | 0 | -1 | -10 | -5 | -3 | -1 | -2 | -9 | -10 | 3 | 0 | -9 | -1 | 3 |
| 66 | W | 74-W | -5 | -5 | -9 | -2 | -3 | -9 | 3 | 12 | -11 | -10 | -10 | -10 | 3 | -11 | -10 |
| 67 | L | 75-I | -5 | -11 | 5 | 4 | 4 | 4 | 2 | -1 | -11 | -9 | -4 | -9 | -8 | -11 | -10 |
| 68 | L | 76-Y | -3 | -4 | 0 | 2 | 0 | -1 | 0 | 4 | -6 | 0 | -4 | 2 | 2 | -1 | 0 |
| 69 | D | 77-S | 2 | -6 | -6 | -1 | -4 | -9 | -1 | -10 | -9 | -10 | 0 | -3 | -1 | -1 | 0 |
| 70 | C | 78-C | -3 | -6 | 1 | 0 | -2 | -1 | -5 | -10 | -10 | 9 | 4 | -3 | -2 | -9 | -9 |
| 71 | L | 79-N | -2 | -5 | 4 | 3 | 1 | 2 | 2 | 2 | -6 | 1 | -9 | -3 | 1 | -3 | -5 |
| 72 | K | 80-E | 0 | -2 | -5 | -5 | -3 | 0 | -10 | -11 | -4 | 1 | 0 | -1 | -2 | -1 | 2 |

TABLE 2-continued

Position-specific scoring matrix (PSSM) for BRCT (cd00027) (SEQ ID NO: 88) domain where a threshold bit score of 29.2119 is required to qualify as a member of this family. The PSSM was obtained from the NCBI CDD. In the upper left hand corner table header, P signifies position, C signifies the consensus sequence, and M signifies the master sequence of known structure. In the rest of the table, letters indicate standard amino acid single letter nomenclature.

| P | C | M | H | K | R | D | E |
|---|---|---|---|---|---|---|---|
| 1 | G | 8-G | −1 | 1 | −2 | 2 | −1 |
| 2 | L | 9-K | 2 | 3 | −4 | −10 | −6 |
| 3 | T | 10-H | 0 | 2 | 2 | −9 | 0 |
| 4 | F | 11-F | −10 | −11 | −11 | −11 | −11 |
| 5 | V | 12-F | 3 | −4 | −3 | −5 | −6 |
| 6 | I | 13-L | −10 | −10 | −10 | −11 | −11 |
| 7 | T | 14-Y | 1 | −5 | −5 | −1 | −9 |
| 8 | G | 15-G | −2 | −3 | 1 | −1 | −1 |
| 9 | D | 16-E | −9 | −1 | −1 | 2 | 0 |
| 10 | L | 17-F | −1 | 1 | −1 | 1 | −2 |
| 11 | P | 18-P | −1 | 1 | 0 | 1 | 1 |
| 12 | S | 19-G | −1 | 1 | −1 | 0 | 0 |
| 13 | E | 20-D | 0 | −1 | −3 | −5 | 2 |
| 14 | E | 21-E | −2 | 0 | 1 | 2 | 3 |
| 15 | R | 22-R | −1 | 3 | 6 | 0 | −3 |
| 16 | D | 23-R | 3 | 2 | −1 | 3 | 2 |
| 17 | E | 24-K | 0 | 1 | 0 | 3 | 3 |
| 18 | L | 25-L | −10 | −3 | −5 | −11 | −6 |
| 19 | K | 26-I | 0 | 4 | 1 | −4 | 2 |
| 20 | E | 27-R | −1 | 3 | 3 | 2 | 4 |
| 21 | L | 28-Y | −3 | 2 | 0 | −5 | −4 |
| 22 | I | 29-V | −2 | −10 | −10 | −11 | −6 |
| 23 | E | 30-T | 0 | 3 | 3 | −8 | 4 |
| 24 | K | 31-A | 0 | 3 | 1 | −1 | 2 |
| 25 | L | 32-F | 4 | 0 | −1 | −5 | −9 |
| 26 | G | 33-N | 0 | −2 | −3 | −1 | −10 |
| 27 | G | 34-G | −10 | 0 | −9 | −9 | −9 |
| 28 | K | 35-E | −1 | 5 | 2 | 0 | 1 |
| 29 | V | 36-L | −2 | −4 | −4 | −11 | −10 |
| 30 | T | 37-E | 2 | −2 | −1 | −5 | 1 |
| 31 | S | 38-D | −4 | 1 | −1 | 1 | 1 |
| 32 | S | 39-Y | −3 | 0 | 0 | 4 | 1 |
| 33 | V | 40-M | −1 | −1 | −6 | −10 | −1 |
| 34 | S | 41-S | −3 | −3 | −2 | 2 | −2 |
| 35 | K | 42-D | 0 | 2 | 2 | 1 | 1 |
| 36 | K | 43-R | −9 | 3 | 0 | 3 | 1 |
| 37 | T | 44-V | 0 | −2 | −2 | −2 | −4 |
| 38 | T | 45-Q | −2 | −6 | −9 | 3 | −4 |
| 39 | H | 46-F | 10 | −9 | −5 | −10 | −9 |
| 40 | V | 47-V | −1 | −10 | −10 | −11 | −10 |
| 41 | I | 48-I | −11 | −10 | −11 | −11 | −11 |
| 42 | V | 49-T | −10 | −9 | −5 | −10 | −10 |
| 43 | G | 50-A | 1 | 2 | −9 | 2 | 0 |
| 44 | S | 51-Q | 1 | 1 | 2 | 2 | 2 |
| 45 | D | 52-E | 1 | −2 | −1 | 3 | 1 |
| 46 | A | 53-W | 0 | −4 | −1 | 0 | 2 |
| 47 | G | 54-D | −8 | −1 | 1 | 2 | −2 |
| 48 | P | 55-P | 0 | 1 | 0 | 0 | 1 |
| 49 | K | 56-S | −1 | 4 | 1 | 0 | 2 |
| 50 | K | 57-F | −3 | 3 | −1 | −1 | −2 |
| 51 | L | 59-E | 1 | 2 | −4 | −6 | −1 |
| 52 | L | 60-A | −6 | 2 | 0 | 0 | 1 |
| 53 | K | 61-L | 1 | 3 | 0 | −1 | −1 |
| 54 | A | 62-M | −8 | 0 | −1 | −8 | −2 |
| 55 | I | 63-D | −1 | 3 | 0 | 0 | 1 |
| 56 | K | 64-N | −1 | 2 | 1 | 0 | 1 |
| 57 | L | 65-P | 3 | −1 | 1 | −3 | −1 |
| 58 | G | 66-S | 2 | 2 | 0 | −1 | −1 |
| 59 | I | 67-L | −3 | 1 | 0 | −3 | −5 |
| 60 | P | 68-A | 3 | 2 | 1 | −1 | −1 |
| 61 | I | 69-F | −3 | −10 | −10 | −11 | −11 |
| 62 | V | 70-V | −11 | −10 | −10 | −11 | −10 |
| 63 | T | 71-R | 3 | 3 | 1 | 2 | −6 |
| 64 | P | 72-P | 3 | −2 | −3 | −1 | 3 |
| 65 | E | 73-R | 0 | −1 | −2 | 3 | 3 |
| 66 | W | 74-W | −2 | −10 | −6 | −5 | −4 |
| 67 | L | 75-I | −3 | −6 | −6 | −11 | −11 |
| 68 | L | 76-Y | 0 | 2 | 0 | −1 | 1 |
| 69 | D | 77-S | −2 | −1 | −1 | 5 | 3 |
| 70 | C | 78-C | −2 | −4 | −6 | −10 | −10 |
| 71 | L | 79-N | −4 | −2 | −2 | −4 | −2 |
| 72 | K | 80-E | 0 | 4 | 2 | 2 | 2 |

Alternatively, the absence or truncation of a BRCT domain in a terminal transferase enzyme is defined as the following:

any modifications, mutations, deletions, or insertions of the two conserved motifs of the wild-type, natural BRCT domain consisting of the "dimer interface" and/or the "BRCT sequence" (with a characteristic sequence of Trp-X-X-X-Cys/Ser) as to make the terminal transferase better behaved and/or dissociate from nucleic acids more rapidly. The dimer interface shall be defined as positions 16, 20, 23, 26, and 28 in the cd00027 PSSM with a consensus sequence of Asp/Glu (16), Glu/Lys (20), Glu/Arg/Lys (23), Gly (26), and Lys/Thr (28). The BRCT sequence shall be defined as positions 66 and 70 in the cd00027 PSSM with a consensus sequence of Trp (66) and Cys/Ser (70). Better behaved can mean less prone to aggregation, greater enzymatic turnover rates, better multi-step cycling efficiencies, and/or maintains longer activity under storage or reaction conditions. Conserved motifs are as annotated by the Conserved Domain Database (CDD).

Alternatively, the absence or truncation of a BRCT domain in a terminal transferase enzyme is defined as the following:

any amino acid sequences that have a 90% or more sequence identity to the terminal transferase sequence list provided in Appendix 1 or a fragment thereof that do not contain a BRCT superfamily annotation (cl00038, cd00027, smart00292, pfam00533, pfam12738, pfam16589, pfam16759, pfam16770) as defined by the Conserved Domain Database (CDD)[8] maintained by the US National Center for Biotechnology Information (NCBI) identified via a Conserved Domain Search (CD-Search)[9].

Alternatively, the absence or truncation of a BRCT domain in a terminal transferase enzyme is defined as the following:

any mutation, modification or truncation of the N-terminal portion (defined as first 200 amino acids). Such a truncation is shown herein to result in greater multi-step cycling efficiency.

In one embodiment, the modified terminal transferase enzyme is immobilised on a solid support. In an alternative embodiment, the modified terminal transferase enzyme is in solution phase. Detailed methodology of providing a terminal transferase enzyme in the solution phase or immobilised on a solid support are provided in GB Patent Application No. 1701396.2, the contents of which are herein incorporated by reference.

Nucleic Acid Synthesis Method

In one embodiment of the invention, there is provided a use according to the first aspect of the invention in a method of nucleic acid synthesis.

According to a second aspect of the invention, there is provided a method of nucleic acid synthesis, which comprises the steps of:

(a) providing an initial initiator sequence;
(b) adding a reversibly blocked nucleotide triphosphate to said initiator sequence in the presence of a modified terminal transferase enzyme as defined herein;
(c) removal of all reagents from the initiator sequence;
(d) cleaving the blocking group from the reversibly blocked nucleotide added in step (b) to said initiator sequence; and
(e) removal of the cleaving agent.

References herein to a 'method of nucleic acid synthesis' include methods of synthesising lengths of DNA (deoxyribonucleic acid) or RNA (ribonucleic acid) wherein a strand of nucleic acid (n) is extended by adding a further nucleotide (n+1). In one embodiment, the nucleic acid is DNA. In an alternative embodiment, the nucleic acid is RNA.

References herein to 'method of DNA synthesis' refer to a method of DNA strand synthesis wherein a DNA strand (n) is extended by adding a further nucleotide (n+1). The method described herein provides a novel use of the terminal deoxynucleotidyl transferases of the invention and nucleotide triphosphate having a 3'-O-azidomethyl substituent to sequentially add nucleotides in de novo DNA strand synthesis which has several advantages over the DNA synthesis methods currently known in the art.

In a further embodiment greater than 1 nucleotide is added by repeating steps (b) to (e).

It will be understood that steps (b) to (e) of the method may be repeated multiple times to produce a DNA or RNA strand of a desired length. Therefore, in one embodiment, greater than 1 nucleotide is added to the initiator sequence, such as greater than 5, 10, 20, 30, 40, 50, 60, 70, 80, 90, 100, 110 or 120 nucleotides are added to the initiator sequence by repeating steps (b) to (e). In a further embodiment, greater than 200 nucleotides are added, such as greater than 300, 400, 500, 600, 700, 800, 900, 1000, 1250, 1500, 1750, 2000, 2250, 2500, 2750, 3000, 4000, 5000, 6000, 7000, 8000, 9000 or 10000 nucleotides.

References herein to 'nucleotide triphosphates' refer to a molecule containing a nucleoside (i.e. a base attached to a deoxyribose or ribose sugar molecule) bound to three phosphate groups. Examples of nucleotide triphosphates that contain deoxyribose are: deoxyadenosine triphosphate (dATP), deoxyguanosine triphosphate (dGTP), deoxycytidine triphosphate (dCTP) or deoxythymidine triphosphate (dTTP). Examples of nucleotide triphosphates that contain ribose are: adenosine triphosphate (ATP), guanosine triphosphate (GTP), cytidine triphosphate (CTP) or uridine triphosphate (UTP). Other types of nucleosides may be bound to three phosphates to form nucleotide triphosphates, such as naturally occurring modified nucleosides and artificial nucleosides.

References herein to 'reversibly blocked' nucleotides include nucleotides containing reversibly terminating moieties at the sugar moiety (3'-blocked nucleotide triphosphates) and the nitrogenous base moiety (base-blocked nucleotide triphosphates). A reversible terminator is a chemical moiety that can be added to the 3'-end of a nucleic acid initiator by a polymerase or terminal transferase and prevents further addition of nucleotides. If and only if the reversible terminator is cleaved by a cleaving agent can the polymerase or terminal transferase add additional nucleotides.

3'-Blocked Nucleotide Triphosphates Therefore, references herein to '3'-blocked nucleotide triphosphates' refer to nucleotide triphosphates (e.g., dATP, dGTP, dCTP or dTTP) which have an additional group on the 3' end which prevents further addition of nucleotides, i.e., by replacing the 3'-OH group with a protecting group.

It will be understood that references herein to '3'-blocked', '3'-blocking group' or '3'-protecting group' refer to the group attached to the 3' end of the nucleotide triphosphate which prevents further nucleotide addition. The present method uses reversible 3'-blocking groups which can be removed by cleavage to allow the addition of further nucleotides. By contrast, irreversible 3'-blocking groups refer to dNTPs where the 3'-OH group can neither be exposed nor uncovered by cleavage.

There exist several documented reversible protecting groups, such as 2-cyanoethyl, azidomethyl, aminoxy, and allyl, which can be applied to the method described herein. Examples of suitable protecting groups are described in Greene's *Protective Groups in Organic Synthesis*, (Wuts, P. G. M. & Greene, T. W. (2012) 4th Ed., John Wiley & Sons).

In one embodiment, the 3'-blocked nucleotide triphosphate is blocked by a reversible protecting group. In an alternative embodiment, the 3'-blocked nucleotide triphosphate is blocked by an irreversible protecting group.

Therefore, in one embodiment, the 3'-blocked nucleotide triphosphate is blocked by either a 3'-O-methyl, 3'-azido, 3'-O-azidomethyl, 3'-aminoxy, 3'-O-(2-cyanoethyl), 3'-O-(2-cyanoethoxy), or 3'-O-allyl group. In a further embodiment, the 3'-blocked nucleotide triphosphate is blocked by either a 3'-O-azidomethyl, 3'-aminoxy, 3'-O-(2-cyanoethyl), 3'-O-(2-cyanoethoxy), or 3'-O-allyl group.

Base-Blocked Nucleotide Triphosphates

Therefore, references herein to base-blocked nucleotide triphosphates' refer to nucleotide triphosphates (e.g., dATP, dGTP, dCTP or dTTP) which have an additional group on the nitrogenous base which prevents further addition of nucleotides. Reversibly terminating moieties located on the nitrogenous base may be any molecular moiety that if and only if cleaved with a cleaving agent allows the addition of subsequent nucleotides. The reversible terminator may be located on guanine at the 7 or 8 position; adenine at the 7, 8, or N6 positions; and the pyrimidines at the 5 position.

There exist several documented reversible protecting groups that can be attached to the nitrogenous base, including photocleavable substituted nitrobenzyl groups, peptides, and other chemical/support moieties mentioned in the alternating-phase section of this patent.

Cleaving Agent

References herein to 'cleaving agent' refer to a substance which is able to cleave the 3'-blocking group from the reversibly blocked nucleotide triphosphate.

The reversible blocking groups described herein may all be quantitatively removed in aqueous solution with documented compounds which may be used as cleaving agents (for example, see: Wuts, P. G. M. & Greene, T. W. (2012) 4th Ed., John Wiley & Sons; Hutter, D. et al. (2010) *Nucleosides Nucleotides Nucleic Acids* 29, 879-895; EP 1560838 and U.S. Pat. No. 7,795,424).

In one embodiment, the cleaving agent is a chemical cleaving agent. In an alternative embodiment, the cleaving agent is an enzymatic cleaving agent. In a further embodiment, the cleaving agent is electromagnetic radiation, for instance ultraviolet or visible light.

It will be understood by the person skilled in the art that the selection of cleaving agent is dependent on the type of reversibly blocked nucleotide used. For instance, tris(2-carboxyethyl)phosphine (TCEP) can be used to cleave a 3'-O-azidomethyl group, palladium complexes can be used to cleave a 3'-O-allyl group, ammonium hydroxide can be used to cleave a 3'-O-(2-cyanoethyl)/3'-O-2-(cyanoethoxy) methyl group, or sodium nitrite can be used to cleave a 3'-aminoxy group. Therefore, in one embodiment, the cleaving agent is selected from: tris(2-carboxyethyl)phosphine (TCEP), a palladium complex or sodium nitrite.

In one embodiment, the cleaving agent is added in the presence of a cleavage solution comprising a denaturant, such as urea, guanidinium chloride, formamide or betaine. The addition of a denaturant has the advantage of being able to disrupt any undesirable secondary structures in the DNA. In a further embodiment, the cleavage solution comprises one or more buffers. It will be understood by the person skilled in the art that the choice of buffer is dependent on the exact cleavage chemistry and cleaving agent required.

Initiator Sequences

References herein to an 'initial initiator sequence' refer to a short oligonucleotide with a free 3'-end which the reversibly blocked nucleotide triphosphate can be attached to for the first addition of a reversibly blocked nucleotide triphosphate by a terminal transferase enzyme. In one embodiment, the initial initiator sequence is a DNA initiator sequence. In an alternative embodiment, the initial initiator sequence is an RNA initiator sequence.

References herein to an 'initiator sequence' refer to an oligonucleotide with a free 3'-end which the reversibly blocked nucleotide triphosphate can be attached to. In one embodiment, the initiator sequence is a DNA initiator sequence. In an alternative embodiment, the initiator sequence is an RNA initiator sequence.

References herein to a 'DNA initiator sequence' refer to a sequence of DNA which the reversibly blocked nucleotide triphosphate can be attached to, i.e. DNA will be synthesised from the end of the DNA initiator sequence.

In one embodiment, the initial initiator sequence is between 5 and 100 nucleotides long, such as between 10 and 90 nucleotides long, in particular between 5 and 20 nucleotides long.

In one embodiment, the initiator sequence is single-stranded. In an alternative embodiment, the initiator sequence is double-stranded. It will be understood by persons skilled in the art that a 3'-overhang (i.e., a free 3'-end) allows for efficient addition.

In one embodiment, the initiator sequence is immobilised on a solid support. This allows the modified terminal transferase enzyme and the cleaving agent to be removed (in steps (c) and (e), respectively) without washing away the synthesised nucleic acid. The initiator sequence may be attached to a solid support stable under aqueous conditions so that the method can be easily performed via a flow setup.

In one embodiment, the initiator sequence is immobilised on a solid support via a reversible interacting moiety, such as a chemically-cleavable linker, an antibody/immunogenic epitope, a biotin/biotin binding protein (such as avidin or streptavidin), or glutathione-GST tag. Therefore, in a further embodiment, the method additionally comprises extracting the resultant nucleic acid by removing the reversible interacting moiety in the initiator sequence, such as by incubating with proteinase K.

In a further embodiment, the initiator sequence is immobilised on a solid support via a chemically-cleavable linker, such as a disulfide, allyl, or azide-masked hemiaminal ether linker. Therefore, in one embodiment, the method additionally comprises extracting the resultant nucleic acid by cleaving the chemical linker through the addition of tris(2-carboxyethyl)phosphine (TCEP) or dithiothreitol (DTT) for a disulfide linker; palladium complexes for an allyl linker; or TCEP for an azide-masked hemiaminal ether linker.

In one embodiment, the resultant nucleic acid is extracted and amplified by polymerase chain reaction using the nucleic acid bound to the solid support as a template. The initiator sequence could therefore contain an appropriate forward primer sequence and an appropriate reverse primer could be synthesised.

In an alternative embodiment, the immobilised initiator sequence contains at least one restriction site. Therefore, in a further embodiment, the method additionally comprises extracting the resultant nucleic acid by using one or more restriction enzymes.

The use of restriction enzymes and restriction sites to cut nucleic acids in a specific location is well known in the art. The choice of restriction site and enzyme can depend on the desired properties, for example whether 'blunt' or 'sticky' ends are required. Examples of restriction enzymes include: AluI, BamHI, EcoRI, EcoRII, EcoRV, HaeII, HgaI, HindIII, HinfI, NotI, PstI, PvuII, SalI, Sau3A, ScaI, SmaI, TaqI and XbaI.

In an alternative embodiment, the initiator sequence contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Buffers

In one embodiment, the modified terminal transferase enzyme of the invention is added in the presence of an extension solution comprising one or more buffers (e.g., Tris or cacodylate), one or more salts (e.g., $Na^+$, $K^+$, $Mg^{2+}$, $Mn^{2+}$, $Cu^{2+}$, $Zn^{2+}$, $Co^{2+}$, etc., all with appropriate counterions, such as $Cl^-$) and inorganic pyrophosphatase (e.g., the *Saccharomyces cerevisiae* homolog). It will be understood that the choice of buffers and salts depends on the optimal enzyme activity and stability.

The use of an inorganic pyrophosphatase helps to reduce the build-up of pyrophosphate due to nucleotide triphosphate hydrolysis by terminal transferase. Therefore, the use of an inorganic pyrophosphatase has the advantage of reducing the rate of (1) backwards reaction and (2) terminal transferase strand dismutation. In one embodiment, the inorganic pyrophosphatase comprises purified, recombinant inorganic pyrophosphatase from *Saccharomyces cerevisiae*.

In one embodiment, step (b) is performed at a pH range between 5 and 10. Therefore, it will be understood that any buffer with a buffering range of pH 5-10 could be used, for example cacodylate, Tris, HEPES or Tricine, in particular cacodylate or Tris.

In one embodiment, step (d) is performed at a temperature less than 99° C., such as less than 95° C., 90° C., 85° C., 80° C., 75° C., 70° C., 65° C., 60° C., 55° C., 50° C., 45° C., 40° C., 35° C., or 30° C. It will be understood that the optimal temperature will depend on the cleavage agent utilised. The temperature used helps to assist cleavage and disrupt any secondary structures formed during nucleotide addition.

In one embodiment, steps (c) and (e) are performed by applying a wash solution. In one embodiment, the wash solution comprises the same buffers and salts as used in the extension solution described herein. This has the advantage of allowing the wash solution to be collected after step (c) and recycled as extension solution in step (b) when the method steps are repeated.

Devices

In one embodiment, the method is performed within a flow instrument, such as a microfluidic or column-based flow instrument. The method described herein can easily be performed in a flow setup which makes the method simple to use. It will be understood that examples of commercially available DNA synthesisers (e.g., MerMade 192E from BioAutomation or H-8 SE from K&A) may be optimised for the required reaction conditions and used to perform the method described herein.

In one embodiment, the method is performed on a plate or microarray setup. For example, nucleotides may be individually addressed through a series of microdispensing nozzles using any applicable jetting technology, including piezo and thermal jets. This highly parallel process may be used to generate hybridization microarrays and is also amenable to DNA fragment assembly through standard molecular biology techniques.

In one embodiment, there is provided a method which is performed in a microfluidic device. Thus, according to a further aspect of the invention, there is provided a method of nucleic acid synthesis which is performed in a microfluidic device comprising the steps of:

(a) providing an initial initiator sequence bound to a surface within a microfluidic device;
(b) adding a reversibly blocked nucleotide triphosphate to said initiator sequence in the presence of a modified terminal transferase enzyme as defined herein;
(c) removal of all reagents from the initiator sequence;
(d) cleaving the blocking group from the reversibly blocked nucleotide added in step (b) to said initiator sequence; and
(e) removal of the cleaving agent.

References herein to microfluidic device include continuous-flow microfluidic devices, droplet-based microfluidic devices, programmable digital microfluidic device, digital microfluidic devices, microarray devices (such as DNA chips), optofluidic devices and acoustic droplet ejection (ADE) devices.

In a further embodiment, greater than 1 nucleotide is added by repeating steps (b) to (e). In a further embodiment, the surface within the microfluidic device in step (a) may be patterned to yield initiators bound at defined locations. Therefore in a further embodiment the microfluidic device may have a reaction chamber or a plurality of reaction chambers, such as greater than 100, 1000 or 10000 reaction chambers.

In one embodiment, the method additionally comprises amplifying the resultant nucleic acid. Methods of DNA/RNA amplification are well known in the art. For example, in a further embodiment, the amplification is performed by polymerase chain reaction (PCR). This step has the advantage of being able to amplify and extract the resultant nucleic acid all in one step.

The template independent nucleic acid synthesis method described herein has the capability to add a nucleic acid sequence of defined composition and length to an initiator sequence. Therefore, it will be understood by persons skilled in the art, that the method described herein may be used as a novel way to introduce adapter sequences to a nucleic acid library.

If the initiator sequence is not one defined sequence, but instead a library of nucleic acid fragments (for example generated by sonication of genomic DNA, or for example messenger RNA) then this method is capable of de novo synthesis of 'adapter sequences' on every fragment. The installation of adapter sequences is an integral part of library preparation for next-generation library nucleic acid sequencing methods, as they contain sequence information allowing hybridisation to a flow cell/solid support and hybridisation of a sequencing primer.

Currently used methods include single-stranded ligation; however, this technique is limited because ligation efficiency decreases strongly with increasing fragment length. Consequently, current methods are unable to attach sequences longer than 100 nucleotides in length. Therefore, the method described herein allows for library preparation in an improved fashion to that which is currently possible.

Therefore, in one embodiment, an adapter sequence is added to the initiator sequence. In a further embodiment, the initiator sequence may be a nucleic acid from a library of nucleic acid fragments.

Alternating-Phase Processes

General Alternating-Phase Process

According to a fifth aspect of the invention, there is provided an alternating-phase polymer synthesis method which comprises the steps of:
- (a) providing a monomer immobilised to a support moiety via a cleavable linker;
- (b) providing a polymer of length (N);
- (c) providing a modified terminal transferase enzyme as defined herein to couple the polymer to the immobilised monomer to create an immobilised, coupled polymer of length (N+1);
- (d) removing any uncoupled polymers; and
- (e) cleaving the immobilised, coupled polymer of length (N+1) from the support moiety.

Full details of the fifth aspect of the invention are provided in GB Patent Application No. 1701396.2, the description and figures of which are herein incorporated by reference.

It will be appreciated that greater than one monomer may be added by providing the product of step (e) to an additional monomer immobilised to a support moiety and then repeating steps (b) and (e) until a polymer of desired length is synthesised.

In one embodiment, the removing in step (d) comprises a washing step. Such a washing step serves the purpose of providing an error correction step by removing all unbound polymers.

In one embodiment, the cleaving in step (e) comprises light, pH, temperature, voltage and the like.

In one embodiment, an isolation or capture step is conducted following step (e).

It will be appreciated that the polymer may either be in solution phase or is itself immobilised to a support moiety via a cleavable linker.

Alternating-Phase Nucleic Acid Synthesis Process

One embodiment of the general alternating-phase process described herein as the fifth aspect of the invention is referred to herein as "Alternating-Phase Nucleic Acid Synthesis Process".

In one embodiment of the fifth aspect of the invention, the monomer is a deoxynucleotide triphosphate (dNTP) or nucleotide triphosphate (NTP) immobilised to a support moiety via a cleavable linker.

In one embodiment of the fifth aspect of the invention, the polymer is an initiator nucleic acid sequence of length (N).

Thus, according to a sixth aspect of the invention, there is provided a nucleic acid synthesis method which comprises the steps of:
- (a) providing a deoxynucleotide triphosphate (dNTP) or nucleotide triphosphate (NTP) immobilised to a support moiety via a cleavable linker;
- (b) providing an initiator nucleic acid sequence of length (N);
- (c) adding a modified terminal transferase enzyme as defined herein to couple the initiator nucleic acid sequence to the immobilised dNTP/NTP to create an immobilised, coupled sequence of length (N+1);
- (d) removing any uncoupled initiator nucleic acid sequences; and
- (e) cleaving the immobilised, coupled polymer of length (N+1) from the support moiety.

Full details of the sixth aspect of the invention are provided in GB Patent Application No. 1701396.2, the description and figures of which are herein incorporated by reference.

It will be appreciated that greater than one dNTP/NTP may be added by providing the product of step (e) to an additional deoxynucleotide triphosphate (dNTP) or nucleotide triphosphate (NTP) immobilised to a support moiety and then repeating steps (b) and (e) until a nucleic acid of desired length is synthesised.

In one embodiment, the removing in step (d) comprises a washing step. Such a washing step serves the purpose of providing an error correction step by removing all unbound initiator nucleic acid sequences.

In one embodiment, the cleaving in step (e) comprises light, pH, temperature, voltage and the like.

In one embodiment, an isolation or capture step is conducted following step (e).

Process Variant 1

One embodiment of the alternating-phase nucleic acid synthesis process described herein as the sixth aspect of the invention is referred to herein as "process variant 1". In general, this variant to the process relates to the inclusion of a trap strand which is immobilised to the same support moiety as the dNTP/NTP.

Therefore, in one embodiment of the sixth aspect of the invention, the method additionally comprises providing a nucleic acid trap strand sequence which is complimentary to, and capable of hybridising to, the initiator nucleic acid sequence, wherein said trap strand is immobilised at the 3'-end to the same support moiety as the dNTP/NTP in step (a).

Thus, according to a seventh aspect of the invention, there is provided a nucleic acid synthesis method which comprises the steps of:
- (a) providing a deoxynucleotide triphosphate (dNTP) or nucleotide triphosphate (NTP) immobilised to a support moiety via a cleavable linker;
- (b) providing an initiator nucleic acid sequence of length (N);
- (c) providing a nucleic acid trap strand sequence which is complimentary to, and capable of hybridising to, the initiator nucleic acid sequence, wherein said trap strand is immobilised at the 3'-end to the same support moiety as the dNTP/NTP in step (a);
- (d) adding a modified terminal transferase enzyme as defined herein to couple the initiator nucleic acid sequence to the immobilised dNTP/NTP to create an immobilised, coupled sequence of length (N+1);
- (e) providing a reaction temperature greater than the melting temperature of any trap strand/initiator sequence duplexes;
- (f) removing any uncoupled initiator nucleic acid sequences;
- (g) providing a reaction temperature lower than the melting temperature of any trap strand/initiator sequence duplexes;
- (h) cleaving the immobilised, coupled sequence of length (N+1) from the support moiety; and
- (i) providing a reaction temperature greater than the melting temperature of any trap strand/initiator sequence duplexes to separate the trap strand/initiator sequence duplexes.

Full details of the seventh aspect of the invention are provided in GB Patent Application No. 1701396.2, the description and figures of which are herein incorporated by reference.

It will be appreciated that greater than one dNTP/NTP may be added by providing the product of step (i) to an additional support moiety having immobilised thereon a required deoxynucleotide triphosphate (dNTP) or nucleotide triphosphate (NTP) and an immobilised trap strand and then repeating steps (d) and (i) until a nucleic acid of desired length is synthesised.

It will also be appreciated that the 5' end of the initiator nucleic acid sequence may hybridize to the trap strand to form a duplex. In one embodiment, the duplex is at least 10, 20 or 30 base pairs in length.

Additionally or alternatively, the modified terminal transferase enzyme in step (d) adds the immobilised dNTP/NTP to the 3' end of the initiator nucleic acid sequence.

In one embodiment, the temperature provided in steps (e) and (i) is selected to prevent the formation of duplexes, such a temperature will suitably be approximately 95° C.

In one embodiment, the removing in step (f) comprises a washing step. Such a washing step serves the purpose of providing an error correction step by removing all unbound initiator nucleic acid sequences. In a further embodiment, step (f) is conducted at the same temperature as step (e).

In one embodiment, the temperature provided in step (g) is selected to allow the formation of duplexes via hybridisation.

In one embodiment, the cleaving in step (h) comprises light, pH, temperature, voltage and the like. In a further embodiment, the cleaving in step (h) comprises a cleavage agent selected from a reducing agent (i.e. TCEP) or a specific pH buffer. Such a cleavage agent cleaves the cleavable linker connecting the 3' end of the coupled sequence of length (N+1) from the support moiety. In one embodiment, the temperature provided in step (h) is any temperature below the melting temperature of any trap strand/initiator sequence duplexes in order to facilitate cleavage.

In one embodiment, following cleavage in step (h), a washing step may be performed in order to remove any leftover cleavage agent.

Process Variant 2

A further embodiment to the alternating-phase nucleic acid synthesis process described herein as the sixth aspect of the invention is referred to herein as "process variant 2". In general, this variant to the process relates to the fact that the dNTP/NTP is immobilized to a mobile phase support moiety and the initiator nucleic acid sequence is immobilised to a solid phase support moiety.

Therefore, in one embodiment of the sixth aspect of the invention, the method additionally comprises providing the dNTP/NTP immobilized to a mobile phase support moiety via a cleavable linker and an initiator nucleic acid sequence of length (N) immobilised to a solid phase support moiety via a cleavable linker.

Thus, according to an eighth aspect of the invention, there is provided a nucleic acid synthesis method which comprises the steps of:
(a) providing a deoxynucleotide triphosphate (dNTP) or nucleotide triphosphate (NTP) immobilised to a mobile phase support moiety via a cleavable linker or a dNTP/NTP containing a reversible terminator or blocking moiety via the nitrogenous base;
(b) providing an initiator nucleic acid sequence of length (N) immobilised to a solid phase support moiety via a cleavable linker;
(c) adding a modified terminal transferase enzyme as defined herein to couple the mobile phase immobilised dNTP/NTP to the solid phase immobilised initiator nucleic acid sequence to create an immobilised, coupled sequence of length (N+1);
(d) removing any uncoupled initiator nucleic acid sequences; and
(e) cleaving the mobile phase support moiety from the immobilised, coupled sequence of length (N+1).

Full details of the eighth aspect of the invention are provided in GB Patent Application No. 1701396.2, the description and figures of which are herein incorporated by reference.

In one embodiment, the solid phase support moiety comprises the base of a reaction well and the mobile phase support moiety comprises a bead in solution phase within said reaction well.

In one embodiment, the 5' end of the initiator nucleic acid sequence is immobilised to the solid phase support moiety and the 3' end is free from the surface.

In one embodiment, following addition of the modified terminal transferase enzyme in step (c), an exonuclease, such as a 3'-5' exonuclease (e.g. exonuclease I from *E. coli*) may be added.

This step provides the advantage of degrading any N species which remain as an error correction step to prevent deletions or mutations.

In one embodiment, the cleaving in step (e) comprises light, pH, temperature, voltage and the like. In a further embodiment, the cleaving in step (h) comprises a cleavage agent selected from a reducing agent (i.e. TCEP), light, heat or a specific pH buffer.

In one embodiment, following the cleaving step (e) a washing step is performed. Such a washing step serves the purpose of removing all solutions used in the previous steps.

dNTP/NTPs

References herein to 'deoxynucleotide triphosphate (dNTP)' refer to a molecule containing a nucleoside (i.e. a base attached to a deoxyribose or ribose sugar molecule) bound to three phosphate groups. Examples of nucleotide triphosphates that contain deoxyribose are: deoxyadenosine triphosphate (dATP), deoxyguanosine triphosphate (dGTP), deoxycytidine triphosphate (dCTP) or deoxythymidine triphosphate (dTTP). Examples of "nucleotide triphosphates (NTPs) that contain ribose are: adenosine triphosphate (ATP), guanosine triphosphate (GTP), cytidine triphosphate (CTP) or uridine triphosphate (UTP). Other types of nucleosides may be bound to three phosphates to form nucleotide triphosphates, such as naturally occurring modified nucleosides and artificial nucleosides.

Support Moieties

It will be appreciated that the support moiety will either comprise a solid phase support moiety or a mobile phase support moiety. It will also be appreciated that the solid phase support moiety or mobile phase support moiety for the dNTP/NTP and/or initiator nucleic acid sequence to be immobilised will be selected from any suitable substrate capable of allowing a dNTP/NTP and/or initiator nucleic acid sequence to be immobilised. Solid phase support moieties typically comprise a surface, material, or particle that remains stationary during the entirety of the synthesis process. Mobile phase support moieties (e.g., particles, beads, nanomaterials, etc.) typically comprise a surface, material, or bead greater than or equal to 1 nm in size, such as 1-1000 nm, in particular 1-100 nm, especially 2 nm, 3 nm, >5 nm or 10 nm, that may be mobile or stationary during different portions of the synthesis process.

Examples of suitable solid/mobile phase support moieties may be selected from: a solid surface, (e.g., glass, silicon, gold, plastic etc.), such as a flat surface in particular a 96/384-well plate or a hydrophobic substrate (such as Teflon); a particle, bead, nanoparticle, and/or nanobead including quantum dots (e.g., CdSeS/ZnS, InP/ZnS, and/or CuInS2ZnS), magnetic particles (e.g., iron oxide), metal/metalloid/metal alloy particles (e.g., gold, silver, and/or selenium), metal oxide particles (e.g., oxides of Al, Mg, Zr, Ce, Ti, Zn, Fe, Sn), silica particles, agarose particles, polystyrene particles, carbon-based, i.e. organic, particles (e.g., graphene and/or graphene oxide, nucleic acids, proteins and carbohydrates); and any aforementioned surface, particle, bead, nanoparticle, and/or nanobead that is functionalized or passivated (e.g., with polyethylene glycol, gold, etc.), each of which may be ≥1 nm, such as 1-1000 nm, in particular 1-100 nm, especially ≥1 nm, ≥2 nm, ≥3 nm, ≥5 nm or ≥10 nm in any dimension.

In one embodiment, the solid phase support moiety is selected from a solid surface (e.g., glass, silicon, gold, plastic etc.), such as a flat surface in particular a 96/384-well plate or a hydrophobic substrate (such as Teflon); a solid phase particle, a polymer, and a membrane.

In one embodiment, the mobile phase support moiety is selected from: a mobile phase particle, nanoparticle, ultrafine particle, nanomaterial, or any other material greater than or equal to 1 nm in size, such as 1-1000 nm, in particular 1-100 nm, especially ≥1 nm, ≥2 nm, ≥3 nm, ≥5 nm or ≥10 nm. When using the terms nanoparticle, ultrafine particle, or nanomaterial, they apply to both soluble and insoluble particles.

Examples of suitable polymers may be selected from: polyethylene glycols and polyethylene oxides of any molecular weight; natural polymers and biopolymers of any molecular weight (e.g., dextran, cellulose, collagen, lignins, polyamino acids, chitosan/chitin, nucleic acids, and/or any other carbohydrate or starches); biodegradable polymers (e.g., polylactide, polyglycolide, polyphosphoesters, caprolactone, etc.); Pi-conjugated polymers (e.g., cyano-polyphenylene vinylene, polyaniline, polyfluorenes, poly(fluorine vinylenes), polypyridines, etc.); hydrophilic polymers (e.g., poly(vinyl alcohol), poly(acrylic acid), polyvinylpyrrolidone, poly(2-oxazoline), etc.); polysiloxane polymers; hydrophobic polymers (e.g., styrenes, olefins, esters, ethers, carbonates, etc.); and any aforementioned polymer that is functionalized with a chemical or biochemical moiety allowing for covalent or noncovalent attachment of molecules.

Examples of suitable membranes may be selected from: a lipid bilayer; a lipid monolayer; a vesicle or micelle; a membrane formed by polymers (e.g., cellulose-based, polyvinylidene fluoride, etc.); and any aforementioned membrane that is functionalized with a chemical or biochemical moiety allowing for covalent or noncovalent attachment of molecules.

In one embodiment, the support moiety (i.e. the mobile phase support moiety) comprises a spherical or globular particle which is ≥1 nm in diameter. In a further embodiment, the support moiety comprises a spherical or globular particle which is 1-1000 nm, such as 1-100 nm, in particular ≥1 nm, ≥2 nm, ≥3 nm, ≥5 nm or ≥10 nm in diameter.

In an alternative embodiment, the support moiety (i.e. the mobile phase support moiety) comprises a rod or rod-like particle which is 1 nm in any dimension. In a further embodiment, the support moiety comprises a rod or rod-like particle which is 1-1000 nm, such as 1-100 nm, in particular ≥1 nm, ≥2 nm, ≥3 nm, ≥5 nm or ≥10 nm in any dimension.

In an alternative embodiment, the support moiety (i.e. the mobile phase support moiety) comprises a flat structure such as a surface which is 1 nm in any dimension. In a further embodiment, the support moiety comprises a flat structure such as a surface which is 1-1000 nm, such as 1-100 nm, in particular ≥1 nm, ≥2 nm, ≥3 nm, ≥5 nm or ≥10 nm in any dimension.

In one embodiment, the support moiety (i.e. the mobile phase support moiety) has a molecular weight >1,000 Da, such as >5,000, in particular, >10,000 Da, especially >25,000 Da.

In one embodiment, the dNTP/NTP is immobilized on a solid phase particle or immobilized by depositing directly onto the surface where nucleic acid synthesis will occur. If the dNTP/NTP is immobilized on a solid phase particle, the solid phase particle will be immobilized onto the surface where nucleic acid synthesis will occur. Alternatively, the solid phase particle may be first immobilized on the surface where nucleic acid synthesis will occur. The dNTP/NTP is then immobilized onto the solid phase particle. In an alternative embodiment, the dNTP/NTP is immobilized on a mobile phase particle. The dNTP/NTP immobilized on a mobile phase particle is subsequently immobilized to a solid phase support moiety following addition to an initiator strand immobilized to a solid phase support moiety as per the process described in process variant 2.

In one embodiment the method of immobilization of solid phase particles is magnetic.

In one embodiment, the dNTP/NTP is immobilized to the solid phase support via the nitrogenous base (i.e. purine or pyrimidine moiety) or the triphosphate moiety or the sugar moiety.

In a further embodiment, the immobilisation comprises an azide-alkyne 1,3-dipolar cycloaddition, a tetrazine/alkene-based cycloaddition, a gold-sulfur bond, a nucleophilic addition of an amine to an epoxide group, a biotin-streptavidin/avidin interaction, the Michael addition of a sulfhydryl group to a Michael acceptor (e.g., maleimide), the oxidation of two sulfhydryl groups to form a disulfide bond, an antibody-antigen interaction (e.g., digoxigenin-anti-digoxigenin), etc.

It will be understood that the immobilization linker contains a cleavable linker. Thus, in one embodiment, immobilization is reversible and/or cleavable.

In one embodiment, the cleavable linker is capable of being cleaved by electromagnetic radiation (e.g., 350 nm light) or a reducing agent or an oxidizing agent or heat or electrochemical or a combination thereof.

In one embodiment, the 5' immobilized strand (i.e., the trap strand) contains a functional group, such as an azido group, capable of linking the strand on the 5'-end to the solid support surface.

Cleavable Linkers

It will be appreciated that a cleavable linker is a broadly stable moiety that connects two or more units. However, upon exposure to the cleavage condition the linker is disrupted, and thus separation of the two units connected by the linker occurs. To offer utility, the cleavage condition must be compatible with the system of interest. There are many chemically cleavable linkers available in the art. Some suitable non-limiting examples include:

A linker comprising an azide masked hemiaminal ether sites (—OCHN$_3$—), which may be cleaved by an azide to amine reduction, triggering a spontaneous breakdown of the revealed hemiaminal ether. Suitable reducing agents include phosphines (e.g., TCEP), thiols (e.g., DTT, EDT) and metal-ligand complexes, including organometallic Ru-, Ir-, Cr-, Rh- and Co-complexes. An example of a suitable metal-ligand complexes is organometallic (Ru(bpy)3 2+) and salts thereof, including Ru(bpy)$_3$Cl$_2$.

Other compositions for protected hemiaminal ethers include allyl or allyl carbamate moieties, which may be cleaved using transition metals complexed with water soluble ligands, e.g., Pd with water soluble phosphine ligands); sulfmoc, which may be cleaved with a mild base, e.g. 1% $Na_2CO_3$; m-chloro-p-acyloxybenzyl carbamate, which may be cleaved with mild base, e.g.: 0.1 M NaOH; and 4-azidobenzyl carbamate, which may be cleaved with reducing agents, e.g.: TCEP, DTT).

A linker comprising a phosphine moiety, which may be cleaved through incubation with azide reagents, for example alkyl or aryl azides. The aza-ylid generated may react with a suitably positioned ester moiety to facilitate cleavage.

A linker comprising a silicon containing site, which may be cleaved in the presence of fluoride ions, such as KF and tetra-n-butylammonium fluoride (TBAF).

A linker comprising a disulfide site, which may be cleaved by reduction with phosphine or thiol reagents.

A linker comprising a cyanoethyl site, which may be cleaved under basic conditions, such as solutions of $NH_3$ or 10% $K_2CO_3$.

A linker comprising a photocleavable site, which may be cleaved by UV light, ideally of a wavelength orthogonal to the system of interest. Suitable photocleavable sites are well known in the art. For example, an orthonitrobenzyl group may be cleaved by UV at 365 nm.

Other suitable cleavage sites are well known in the art.

Immobilised dNTP/NTPs

In one embodiment, the nucleotide is blocked with a compound of formula (I):

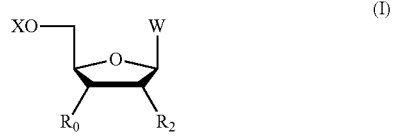

(I)

wherein $R_0$ represents a hydroxyl protecting group;

$R_2$ represents hydrogen, hydroxyl, —$N_3$, alkoxy, alkyl, alkenyl, alkynyl, —O-2-(cyanoethoxy)methyl, —O-(2-cyanoethyl), —O-azidomethyl, -aminoxy, or —O-allyl;

X represents hydrogen or one or more phosphate groups; and

W represents a base.

In an alternative embodiment, the nucleotide is blocked with a compound of formula (II):

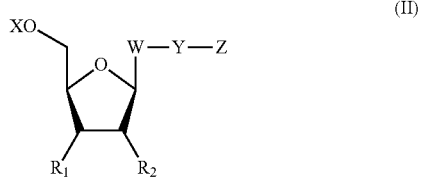

(II)

wherein $R_1$ and $R_2$ independently represent H or OH or a protected derivative thereof;

X represents hydrogen or one or more phosphate groups;

W represents a base;

Y represents a cleavable linker; and

Z represents a blocking group or support moiety.

In one embodiment, X represents a monophosphate, diphosphate, triphosphate or tetraphosphate group.

In one embodiment, W is selected from a nitrogenous base. In a further embodiment, W is selected from a purine or pyrimidine moiety. In a yet further embodiment, the base is selected from adenine, guanine, uracil, thymine or cytosine.

In one embodiment, the support moiety defined as Z is as defined herein.

In a further embodiment, the support moiety additionally comprises a nucleic acid trap strand sequence as defined herein.

Kits

According to a further aspect of the invention, there is provided a kit comprising a modified terminal transferase enzyme as defined herein, optionally in combination with one or more components selected from: an initiator sequence, a microfluidic device or chip, one or more reversibly blocked nucleotide triphosphates, inorganic pyrophosphatase, such as purified, recombinant inorganic pyrophosphatase from *Saccharomyces cerevisiae*, and a cleaving agent; further optionally together with instructions for use of the kit in accordance with the method as defined herein.

Suitably a kit according to the invention may also contain one or more components selected from the group: an extension solution, a wash solution and/or a cleaving solution as defined herein; optionally together with instructions for use of the kit in accordance with any of the methods defined herein.

According to a further aspect of the invention, there is provided the use of a kit as defined herein in a method of nucleic acid synthesis.

Figure 2:
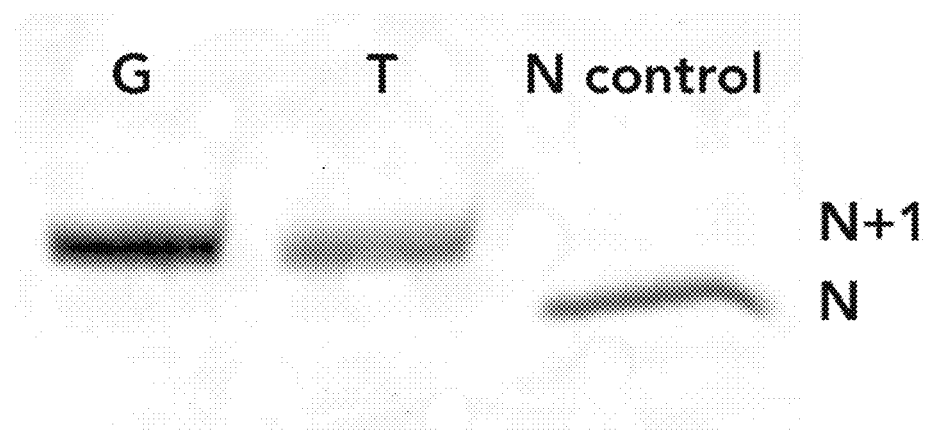
FIG. 2: Single-step incorporation of modified nucleotide triphosphates. An engineered, full length TdT can add 3'-O-modified reversibly terminated nucleotide triphosphates in a quantitative fashion. The full length TdT was able to add a 3'-O-azidomethyl 2'-deoxythymidine triphosphate and a 3'-O-azidomethyl 2'-deoxyguanosine triphosphate quantitatively. Reactions were analysed by denaturing PAGE.
Figure 4:
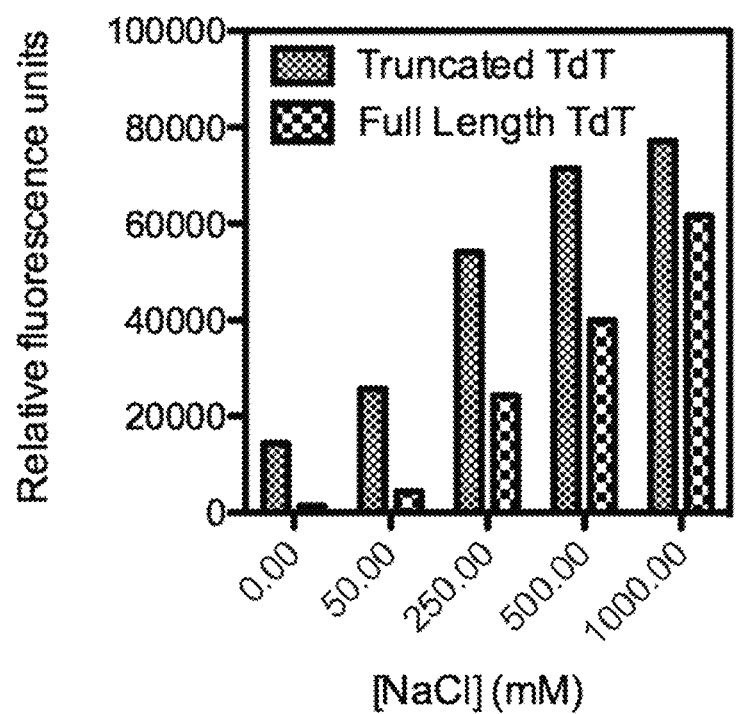
FIG. 4: An N-terminal truncation of TdT ("Truncated TdT") readily dissociates from a 5'-Cy5 labeled oligonucleotide, whereas the full-length version of TdT only shows comparable dissociation at >1 M NaCl concentrations. TdT (5 µM) was incubated with a 5'-Cy5 labeled 2'-deoxyoligonucleotide (1 µM) for 30 min at 37° C. Prior to fluorescence intensity measurements, all samples were brought up to the specified ionic strengths and filtered through a 0.22 micron spin filter. Fluorescence intensity was determined using a fluorescence plate reader.

The following studies and protocols illustrate embodiments of the methods described herein: Full length TdT can be engineered to accept 3'-reversibly blocked nucleotide triphosphates (see WO 2016/128731), which provide a means of sequence control in an enzymatic-based nucleic acid synthesis platform, as evidenced by FIG. 2. However, full length TdT possesses several traits that make it ill suited as an enzyme for use in cyclical processes, which are not observed in single addition assays. Full length TdT is prone to aggregation in solution, rapidly fouls a large variety of surfaces, and strongly associates with DNA as a monomeric species, multimeric species, or an aggregate, as evidenced by FIG. 4. In FIG. 4, the inventors have demonstrated that full-length TdT does not readily dissociate from a DNA initiator molecule whereas truncated TdT does readily dissociate. It follows that the incorporation efficiency of subsequent modified nucleotides may suffer due to the misbehavior of full length TdT. Possible causes include restriction of access to the added 3' reversible terminator, preventing either deprotection by chemical or enzymatic means, or persistent binding of an incompetent enzyme form.

Figure 5:
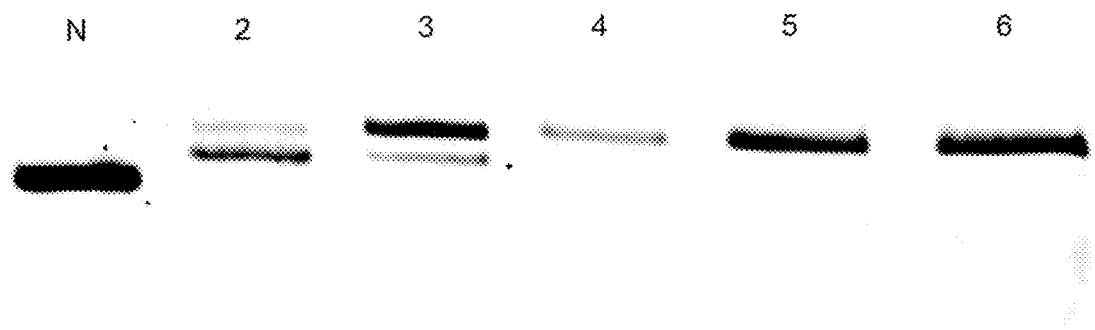
FIG. 5: TdT engineered with N-terminal truncations shows superior performance in a cyclic DNA synthesis process. In this experiment, the cyclic process described in the text was repeated to yield an N+2 product. Lane 1 (N): N control DNA initiator. Lanes 2 and 3: full length engineered TdT variant. Lanes 4-6: N-terminal truncated engineered TdT variant. The DNA was visualized by the Cy-5 fluorescent dye covalently attached to the 5'-end of the initiator molecule. Reactions were analysed by denaturing PAGE.
Figure 6:
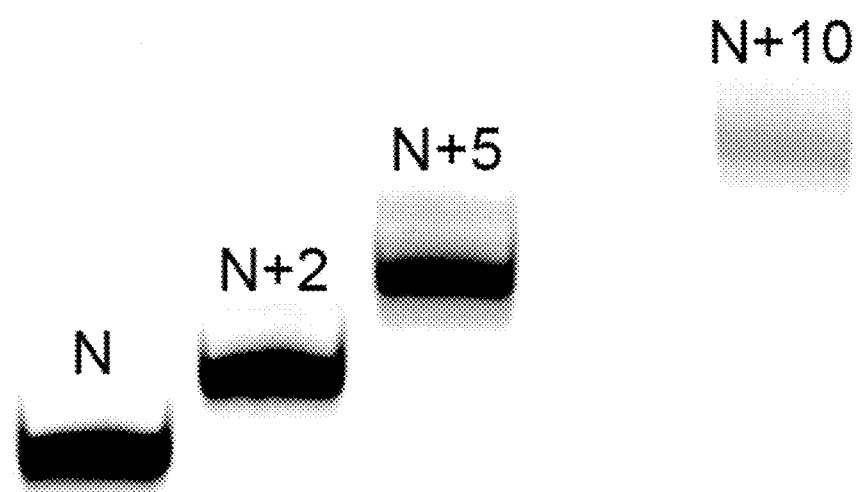
FIG. 6: TdT engineered with N-terminal truncations is capable of catalysing the addition of 2, 5, 10, and more modified nucleotides carrying a reversible terminator. For each cycle, engineered truncated TdT was introduced with a reversibly terminated nucleotide to a DNA initiator. Following addition, the DNA initiator was washed to remove any remaining modified nucleotides. The nucleotide was then "deprotected" and additional wash steps followed to remove any remaining deprotecting agent. This cyclic process was repeated until the indicated number of reversibly terminated nucleotides were added (i.e., N+X, where X is the number of cycles). Reactions were analysed by denaturing PAGE.

Indeed, full length engineered TdTs are generally incapable of adding modified nucleotide triphosphates quantitatively in series, as evidenced by FIGS. 5 and 6. The multi-step cycling assay was performed as follows: the (1) reversibly terminated nucleotide triphosphate is added onto the 3'-end of an immobilized DNA initiator molecule via TdT catalysis, (2) unreacted nucleotide triphosphate and enzyme are washed off, (3) the added reversibly terminated nucleotide is deprotected, (4) the deprotection agent is washed off, and (5) the process repeats from step (1). Due to the cyclic nature of TdT-mediated nucleic acid synthesis, multi-step incorporation efficiency rather than single-step incorporation efficiency must be used to judge the quality of TdT enzyme variants. Thus, the tendency to associate strongly with DNA is the reason for poor multi-step modified nucleotide triphosphate incorporation efficiencies (FIGS. 3-4), despite the quantitative single-step conversion of the same modified nucleotides triphosphates shown in FIG. 2.

As mentioned above, the inventors made a series of truncations to wild-type and engineered variants of TdT as part of our search for a better TdT variant. Surprisingly, the inventors found that an engineered TdT lacking the BRCT domain or a fragment thereof is capable of adding modified nucleotide triphosphates quantitatively in series, whereas the full length engineered TdT enzyme is unable to do such sequential additions. As shown in FIG. 4, truncated TdT does not associate as strongly with DNA, thus resulting in better multi-step incorporation efficiencies. N-terminal mutations and truncations of TdT also reduce the Stokes radius of the enzyme, resulting in less steric issues if the DNA initiator molecule is immobilized to a surface, as well as better penetration of the enzyme into a porous matrix. FIG. 5 shows full-length TdT exhibits poor conversion of an initiator to an N+2 product. In stark contrast, N-terminal mutations of TdT result in drastic increases in cycle incorporation efficiencies, as evidenced by the ability to add more than ten reversibly blocked nucleotides in series to the 3'-end of a DNA initiator molecule, as shown in FIG. 6.

REFERENCES

1. Sukumar, N., Boulé, J. B. & Expert-Bezançon, N. Crystallization of the catalytic domain of murine terminal deoxynucleotidyl transferase . . . . Section D: Biological . . . (2000). doi:10.1107/S090744490001297X
2. Delarue, M. et al. Crystal structures of a template-independent DNA polymerase: murine terminal deoxynucleotidyltransferase. 21, 427-439 (2002).
3. Mozzarelli, A. & Rossi, G. L. Protein function in the crystal. Annual review of biophysics and . . . (1996).
4. Wang, A. H. et al. Molecular structure of a left-handed double helical DNA fragment at atomic resolution. Nature 282, 680-686 (1979).
5. Repasky, J. A. E., Corbett, E., Boboila, C. & Schatz, D. G. Mutational analysis of terminal deoxynucleotidyltransferase-mediated N-nucleotide addition in V(D)J recombination. J. Immunol. 172, 5478-5488 (2004).
6. Thai, T. H., Purugganan, M. M., Roth, D. B. & Kearney, J. F. Distinct and opposite diversifying activities of terminal transferase splice variants. Nature immunology (2002).
7. Andrade, P., Martin, M. J., Juarez, R., López de Saro, F. & Blanco, L. Limited terminal transferase in human DNA polymerase mu defines the required balance between accuracy and efficiency in NHEJ. Proc. Natl. Acad. Sci. U.S.A. 106, 16203-16208 (2009).
8. Marchler-Bauer, A. et al. CDD/SPARCLE: functional classification of proteins via subfamily domain architectures. Nucl. Acids Res. 45, D200-D203 (2017).
9. Marchler-Bauer, A. & Bryant, S. H. CD-Search: protein domain annotations on the fly. Nucleic Acids Res. 32, W327-31 (2004).

APPENDIX 1

Terminal Transferase Enzyme Sequences
>tr|W5MK82|W5MK82_LEPOC Uncharacterized protein OS=Lepisosteus oculatus GN=DNTT PE=4 SV=1; (SEQ ID NO: 1)
>tr|A0A1S3N3Q5|A0A1S3N3Q5_SALSA DNA nucleotidylexotransferase-like OS=Salmo salar GN=LOC106576788 PE=4 SV=1;
>tr|A0A1S3RVH9|A0A1S3RVH9_SALSA DNA nucleotidylexotransferase isoform X1 OS=Salmo salar GN=LOC106605322 PE=4 SV=1;
>tr|A0A1S3RVI4|A0A1S3RVI4_SALSA DNA nucleotidylexotransferase isoform X2 OS=Salmo salar GN=LOC106605322 PE=4 SV=1;
>tr|W5U8U3|W5U8U3_ICTPU DNA nucleotidylexotransferase OS=Ictalurus punctatus GN=dntt PE=2 SV=1;
>sp|Q92089|TDT_ONCMY DNA nucleotidylexotransferase OS=Oncorhynchus mykiss GN=dntt PE=2 SV=1;
>tr|Q6T422|Q6T422_GINCI Terminal deoxynucleotidyl transferase OS=Ginglymostoma cirratum GN=TdT PE=2 SV=1;
>tr|W5L524|W5L524_ASTMX Uncharacterized protein OS=Astyanax mexicanus GN=DNTT PE=4 SV=1;
>tr|A0A1S3FAV4|A0A1S3FAV4_DIPOR DNA nucleotidylexotransferase isoform X1 OS=Dipodomys ordii GN=Dntt PE=4 SV=1;
>tr|Q5EB91|Q5EB91_PAT Deoxynucleotidyltransferase, terminal OS=Rattus norvegicus GN=Dntt PE=2 SV=1;
>tr|E9PT58|E9PT58_PAT DNA nucleotidylexotransferase OS=Rattus norvegicus GN=Dntt PE=4 SV=1;
>tr|H3DI66|H3DI66_TETNG Uncharacterized protein OS=Tetraodon nigroviridis GN=DNTT PE=4 SV=1;
>tr|A0A1S3FA64|A0A1S3FA64_DIPOR DNA nucleotidylexotransferase isoform X2 OS=Dipodomys ordii GN=Dntt PE=4 SV=1;
>tr|G1PDC9|G1PDC9_MYOLU Uncharacterized protein OS=Myotis lucifugus GN=DNTT PE=4 SV=1;
>tr|G3QFE9|G3QFE9_GORGO Uncharacterized protein OS=Gorilla gorilla gorilla GN=DNTT PE=4 SV=1;
>tr|G7PDN0|G7PDN0_MACFA Putative uncharacterized protein OS=Macaca fascicularis GN=EGM_18244 PE=4 SV=1;
>tr|F7A3Y1|F7A3Y1_MACMU DNA nucleotidylexotransferase isoform 1 OS=Macaca mulatta GN=DNTT PE=2 SV=1;
>tr|I3KC46|I3KC46_ORENI Uncharacterized protein OS=Oreochromis niloticus GN=DNTT PE=4 SV=1;
>tr|A0A096P5U2|A0A096P5U2_PAPAN Uncharacterized protein OS=Papio anubis GN=DNTT PE=4 SV=1;
>tr|G1RSJ0|G1RSJ0_NOMLE Uncharacterized protein OS=Nomascus leucogenys GN=DNTT PE=4 SV=1;
>sp|P06526|TDT_BOVIN DNA nucleotidylexotransferase OS=Bos taurus GN=DNTT PE=1 SV=2;
>tr|A0A140T8D0|A0A140T8D0_BOVIN DNA nucleotidylexotransferase OS=Bos taurus GN=DNTT PE=4 SV=1;
>tr|Q3UZ80|Q3UZ80_MOUSE Putative uncharacterized protein OS=Mus musculus GN=Dntt PE=2 SV=1;
>tr|F1SBG2|F1SBG2_PIG Uncharacterized protein OS=Sus scrofa GN=DNTT PE=4 SV=1 (SEQ ID NO: 24);
>sp|P09838-2|TDT_MOUSE Isoform TDT-S of DNA nucleotidylexotransferase OS=Mus musculus GN=Dntt;
>tr|F6V4S9|F6V4S9_HORSE Uncharacterized protein OS=Equus caballus GN=DNTT PE=4 SV=1;
>tr|H2Q2B9|H2Q2B9_PANTR Uncharacterized protein OS=Pan troglodytes GN=DNTT PE=4 SV=1;
>tr|L8|DA9|L8|DA9_9CETA DNA nucleotidylexotransferase (Fragment) OS=Bos mutus GN=M91_12325 PE=4 SV=1;

>tr|H2NB52|H2NB52_PONAB Uncharacterized protein OS=Pongo abelii GN=DNTT PE=4 SV=1;
>tr|D2H5M3|D2H5M3_AILME Putative uncharacterized protein (Fragment) OS=Ailuropoda melanoleuca GN=PANDA_005205 PE=4 SV=1;
>sp|P04053|TDT_HUMAN DNA nucleotidylexotransferase OS=Homo sapiens GN=DNTT PE=1 SV=3;
>tr|F6RGZ5|F6RGZ5_CALJA Uncharacterized protein OS=Callithrix jacchus GN=DNTT PE=4 SV=1;
>tr|A0A1S3AC31|A0A1S3AC31_ERIEU DNA nucleotidylexotransferase isoform X1 OS=Erinaceus europaeus GN=DNTT PE=4 SV=1;
>tr|G3SSH5|G3SSH5_LOXAF Uncharacterized protein OS=Loxodonta africana GN=DNTT PE=4 SV=1;
>tr|M3Z065|M3Z065_MUSPF Uncharacterized protein OS=Mustela putorius furo GN=DNTT PE=4 SV=1;
>tr|A4PCE6|A4PCE6_OTOGA Deoxynucleotidyltransferase, terminal OS=Otolemur garnettii GN=DNTT PE=4 SV=1 (SEQ ID NO: 36);
>tr|G1L0B5|G1L0B5_AILME Uncharacterized protein (Fragment) OS=Ailuropoda melanoleuca GN=DNTT PE=4 SV=1;
>tr|W5PCG3|W5PCG3_SHEEP Uncharacterized protein OS=Ovis aries GN=DNTT PE=4 SV=1;
>tr|F1P657|F1P657_CANLF Uncharacterized protein OS=Canis lupus familiaris GN=DNTT PE=4 SV=2;
>tr|G3VQ55|G3VQ55_SARHA Uncharacterized protein OS=Sarcophilus harrisii GN=DNTT PE=4 SV=1; (SEQ ID NO: 40)
>tr|H0UYE5|H0UYE5_CAVPO Uncharacterized protein OS=Cavia porcellus GN=DNTT PE=4 SV=1;
>tr|U3JZX7|U3JZX7_FICAL Uncharacterized protein OS=Ficedula albicollis GN=DNTT PE=4 SV=1;
>tr|M3W767|M3W767_FELCA Uncharacterized protein OS=Felis catus GN=DNTT PE=4 SV=1;
>sp|P04053-2|TDT_HUMAN Isoform 2 of DNA nucleotidylexotransferase OS=Homo sapiens GN=DNTT;
>tr|K7FHL8|K7FHL8_PELSI Uncharacterized protein OS=Pelodiscus sinensis GN=DNTT PE=4 SV=1;
>tr|A0A1S3ACC1|A0A1S3ACC1_ERIEU DNA nucleotidylexotransferase isoform X2 OS=Erinaceus europaeus GN=DNTT PE=4 SV=1;
>tr|A0A091ECZ8|A0A091ECZ8_CORBR DNA nucleotidylexotransferase OS=Corvus brachyrhynchos GN=N302_13526 PE=4 SV=1;
>tr|G3VQ54|G3VQ54_SARHA Uncharacterized protein OS=Sarcophilus harrisii GN=DNTT PE=4 SV=1 (SEQ ID NO: 48);
>tr|Q6T421|Q6T421_RAJEG Terminal deoxynucleotidyl transferase OS=Raja eglanteria GN=TdT PE=2 SV=1;
>sp|P09838|TDT_MOUSE DNA nucleotidylexotransferase OS=Mus musculus GN=Dntt PE=1 SV=3;
>tr|H2ZX52|H2ZX52_LATCH Uncharacterized protein OS=Latimeria chalumnae GN=DNTT PE=4 SV=1;
>tr|G1SII3|G1SII3_RABIT Uncharacterized protein OS=Oryctolagus cuniculus GN=DNTT PE=4 SV=2;
>tr|A0A087V8F5|A0A087V8F5_BALRE DNA nucleotidylexotransferase OS=Balearica regulorum gibbericeps GN=N312_00864 PE=4 SV=1;
>tr|A0A1L8FJ83|A0A1L8FJ83_XENLA Uncharacterized protein OS=Xenopus laevis GN=XELAEV_18034610 mg PE=4 SV=1;
>sp|P42118|TDT_XENLA DNA nucleotidylexotransferase OS=Xenopus laevis GN=dntt PE=2 SV=1;
>tr|Q75U67|Q75U67_TAKRU Terminal deoxynucleotidyl transferase OS=Takifugu rubripes GN=TdT PE=2 SV=1;
>tr|A0A093EPJ1|A0A093EPJ1_GAVST DNA nucleotidylexotransferase OS=Gavia stellata GN=N328_03245 PE=4 SV=1;
>tr|G5BEU5|G5BEU5_HETGA DNA nucleotidylexotransferase OS=Heterocephalus glaber GN=GW7_11927 PE=4 SV=1;
>tr|A2VDB4|A2VDB4_XENLA Dntt-A protein (Fragment) OS=Xenopus laevis GN=dntt-A PE=2 SV=1;
>tr|A0A087X2V1|A0A087X2V1_POEFO Uncharacterized protein OS=Poecilia formosa GN=DNTT PE=4 SV=2;
>sp|O02789|TDT_MONDO DNA nucleotidylexotransferase OS=Monodelphis domestica GN=DNTT PE=2 SV=1 (SEQ ID NO: 61);
>tr|G3UED4|G3UED4_LOXAF Uncharacterized protein OS=Loxodonta africana GN=DNTT PE=4 SV=1;
>tr|H0ZFJ8|H0ZFJ8_TAEGU Uncharacterized protein OS=Taeniopygia guttata GN=DNTT PE=4 SV=1;
>tr|M3ZZI8|M3ZZI8_XIPMA Uncharacterized protein OS=Xiphophorus maculatus GN=DNTT PE=4 SV=1;
>tr|F6UMV3|F6UMV3_MONDO DNA nucleotidylexotransferase OS=Monodelphis domestica GN=DNTT PE=4 SV=1 (SEQ ID NO: 65);
>tr|A0A091H8B9|A0A091H8B9_BUCRH DNA nucleotidylexotransferase OS=Buceros rhinoceros silvestris GN=N320_10189 PE=4 SV=1;
>tr|A0A091ULI4|A0A091ULI4_NIPNI DNA nucleotidylexotransferase OS=Nipponia nippon GN=Y956_01479 PE=4 SV=1;
>tr|F1P317|F1P317_CHICK DNA nucleotidylexotransferase OS=Gallus gallus GN=DNTT PE=4 SV=1;
>tr|A0A0D9R168|A0A0D9R168_CHLSB Uncharacterized protein OS=Chlorocebus sabaeus GN=DNTT PE=4 SV=1;
>sp|P36195|TDT_CHICK DNA nucleotidylexotransferase OS=Gallus gallus GN=DNTT PE=2 SV=1;
>tr|A0A0A0AT06|A0A0A0AT06_CHAVO DNA nucleotidylexotransferase OS=Charadrius vociferus GN=N301_10607 PE=4 SV=1;
>tr|H2TS88|H2TS88_TAKRU Uncharacterized protein OS=Takifugu rubripes GN=dntt PE=4 SV=1;
>tr|A0A091VHH3|A0A091VHH3_OPIHO DNA nucleotidylexotransferase OS=Opisthocomus hoazin GN=N306_09804 PE=4 SV=1;
>tr|A4PCD8|A4PCD8_LEMCA Deoxynucleotidyltransferase, terminal OS=Lemur catta GN=DNTT PE=4 SV=1;
>tr|A0A091KGW0|A0A091KGW0_9GRUI DNA nucleotidylexotransferase OS=Chlamydotis macqueenii GN=N324_12983 PE=4 SV=1;
>tr|A0A087QZ53|A0A087QZ53_APTFO DNA nucleotidylexotransferase OS=Aptenodytes forsteri GN=AS27_02643 PE=4 SV=1;
>tr|A0A093HUU2|A0A093HUU2_STRCA DNA nucleotidylexotransferase OS=Struthio camelus australis GN=N308_09005 PE=4 SV=1;
>sp|A4PCD4|TDT_EULMA DNA nucleotidylexotransferase OS=Eulemur macaco GN=DNTT PE=3 SV=1;
>tr|A0A093NX62|A0A093NX62_PYGAD DNA nucleotidylexotransferase OS=Pygoscelis adeliae GN=AS28_07241 PE=4 SV=1;
>tr|A0A091TYT5|A0A091TYT5_PHORB DNA nucleotidylexotransferase OS=Phoenicopterus ruber ruber GN=N337_08342 PE=4 SV=1;
>tr|A0A091QDL2|A0A091QDL2_MERNU DNA nucleotidylexotransferase OS=Merops nubicus GN=N331_12273 PE=4 SV=1;

>tr|A0A091QU30|A0A091QU30_LEPDC DNA nucleotidylexotransferase OS=Leptosomus discolor GN=N330_14539 PE=4 SV=1;
>tr|A4PCE2|A4PCE2_MICMU Deoxynucleotidyltransferase, terminal OS=Microcebus murinus GN=DNTT PE=4 SV=1;
>tr|H9GAY7|H9GAY7_ANOCA Uncharacterized protein OS=Anolis carolinensis GN=DNTT PE=4 SV=2;
>tr|A0A091II02|A0A091II02_CALAN DNA nucleotidylexotransferase OS=Calypte anna GN=N300_07464 PE=4 SV=1;
>tr|A0A091FKF8|A0A091FKF8_9AVES DNA nucleotidylexotransferase OS=Cuculus canorus GN=N303_09150 PE=4 SV=1;
>tr|A0A093IEV1|A0A093IEV1_PICPB DNA nucleotidylexotransferase OS=Picoides pubescens GN=N307_06181 PE=4 SV=1;
>tr|F6VL88|F6VL88_ORNAN Uncharacterized protein OS=Ornithorhynchus anatinus GN=DNTT PE=4 SV=1;
>tr|A0A091JFK2|A0A091JFK2_9AVES DNA nucleotidylexotransferase OS=Egretta garzetta GN=Z169_12857 PE=4 SV=1;
>tr|A0A0Q3QZM8|A0A0Q3QZM8_AMAAE DNA nucleotidylexotransferase OS=Amazona aestiva GN=AAES_113066 PE=4 SV=1;
>tr|Q5J2Q9|Q5J2Q9_DANRE Terminal deoxynucleotidyl transferase OS=Danio rerio GN=dntt PE=2 SV=1;
>sp|O57486|TDT_AMBME DNA nucleotidylexotransferase OS=Ambystoma mexicanum GN=DNTT PE=2 SV=2;
>tr|G1NAM2|G1NAM2_MELGA Uncharacterized protein OS=Meleagris gallopavo GN=DNTT PE=4 SV=2;
>tr|G3NEP6|G3NEP6_GASAC Uncharacterized protein OS=Gasterosteus aculeatus GN=DNTT PE=4 SV=1;
>tr|H3DI67|H3DI67_TETNG Uncharacterized protein OS=Tetraodon nigroviridis GN=DNTT PE=4 SV=1;
>tr|G3NEP3|G3NEP3_GASAC Uncharacterized protein OS=Gasterosteus aculeatus GN=DNTT PE=4 SV=1;
>tr|B3DKA1|B3DKA1_DANRE Dntt protein OS=Danio rerio GN=dntt PE=2 SV=1;
>tr|G3NEP2|G3NEP2_GASAC Uncharacterized protein OS=Gasterosteus aculeatus GN=DNTT PE=4 SV=1;
>tr|L9JG14|L9JG14_TUPCH DNA nucleotidylexotransferase OS=Tupaia chinensis GN=TREES_T100012289 PE=4 SV=1;
>tr|A0A093PQ85|A0A093PQ85_9PASS DNA nucleotidylexotransferase OS=Manacus vitellinus GN=N305_05476 PE=4 SV=1;
>tr|A0A091DV02|A0A091DV02_FUKDA DNA nucleotidylexotransferase OS=Fukomys damarensis GN=H920_02650 PE=4 SV=1;
>tr|G3UPN2|G3UPN2_MELGA Uncharacterized protein OS=Meleagris gallopavo GN=DNTT PE=4 SV=1;
>tr|A0A091MNY8|A0A091MNY8_9PASS DNA nucleotidylexotransferase (Fragment) OS=Acanthisitta chloris GN=N310_00875 PE=4 SV=1;
>tr|H2TS93|H2TS93_TAKRU Uncharacterized protein OS=Takifugu rubripes GN=dntt PE=4 SV=1;
>tr|H2TS92|H2TS92_TAKRU Uncharacterized protein OS=Takifugu rubripes GN=dntt PE=4 SV=1;
>tr|H2TS91|H2TS91_TAKRU Uncharacterized protein OS=Takifugu rubripes GN=dntt PE=4 SV=1;
>tr|H2TS90|H2TS90_TAKRU Uncharacterized protein OS=Takifugu rubripes GN=dntt PE=4 SV=1;
>tr|H2TS87|H2TS87_TAKRU Uncharacterized protein OS=Takifugu rubripes GN=dntt PE=4 SV=1;
>tr|L5MBP7|L5MBP7_MYODS DNA nucleotidylexotransferase OS=Myotis davidii GN=MDA_GLEAN10023458 PE=4 SV=1;
>tr|H2TS86|H2TS86_TAKRU Uncharacterized protein OS=Takifugu rubripes GN=dntt PE=4 SV=1;
>tr|A0A099YST9|A0A099YST9_TINGU DNA nucleotidylexotransferase (Fragment) OS=Tinamus guttatus GN=N309_05590 PE=4 SV=1;
>tr|G3GZU6|G3GZU6_CRIGR DNA nucleotidylexotransferase OS=Cricetulus griseus GN=I79_003393 PE=4 SV=1;
>tr|S7NPM4|S7NPM4_MYOBR DNA nucleotidylexotransferase OS=Myotis brandtii GN=D623_10025731 PE=4 SV=1 (SEQ ID NO: 85);
>tr|A0A061IE05|A0A061IE05_CRIGR DNA nucleotidylexotransferase OS=Cricetulus griseus GN=H671_3g9305 PE=4 SV=1;
>tr|A0A151P063|A0A151P063_ALLMI DNA nucleotidylexotransferase OS=Alligator mississippiensis GN=DNTT PE=4 SV=1;
>tr|H2TS89|H2TS89_TAKRU Uncharacterized protein OS=Takifugu rubripes GN=dntt PE=4 SV=1;
>tr|M5B5N0|M5B5N0_PLEWA DNA polymerase mu OS=Pleurodeles waltl GN=polymerase mu PE=2 SV=1;
>tr|A0A1A6H3C9|A0A1A6H3C9_NEOLE Uncharacterized protein OS=Neotoma lepida GN=A6R68_13117 PE=4 SV=1;
>tr|A0A147ABX1|A0A147ABX1_FUNHE DNA nucleotidylexotransferase (Fragment) OS=Fundulus heteroclitus PE=4 SV=1;
>tr|A0A1A7ZQP3|A0A1A7ZQP3_NOTFU Deoxynucleotidyltransferase, terminal OS=Nothobranchius furzeri GN=DNTT PE=4 SV=1;
>tr|L5JPN7|L5JPN7_PTEAL DNA nucleotidylexotransferase OS=Pteropus alecto GN=PAL_GLEAN10018329 PE=4 SV=1;
>tr|I3JZZ4|I3JZZ4_ORENI Uncharacterized protein OS=Oreochromis niloticus PE=4 SV=1;
>tr|V9KWD7|V9KWD7_CALMI Terminal deoxynucleotidyl transferase (Fragment) OS=Callorhinchus milii PE=2 SV=1;
>tr|H2VEE3|H2VEE3_TAKRU Uncharacterized protein OS=Takifugu rubripes GN=polm PE=4 SV=1;
>sp|O57486-2|TDT_AMBME Isoform 2 of DNA nucleotidylexotransferase OS=Ambystoma mexicanum GN=DNTT;
>tr|H2VEE1|H2VEE1_TAKRU Uncharacterized protein OS=Takifugu rubripes GN=polm PE=4 SV=1;
>tr|H3D7S0|H3D7S0_TETNG Uncharacterized protein OS=Tetraodon nigroviridis PE=4 SV=1;
>tr|A0A1A8MSX8|A0A1A8MSX8_9TELE Polymerase (DNA directed), mu OS=Nothobranchius pienaari GN=POLM PE=4 SV=1;
>tr|A0A1A6HWD2|A0A1A6HWD2_NEOLE Uncharacterized protein OS=Neotoma lepida GN=A6R68_23458 PE=4 SV=1;
>tr|Q66HH0|Q66HH0_RAT DNA polymerase mu OS=Rattus norvegicus GN=Polm PE=2 SV=1;
>tr|A0A1S3GI13|A0A1S3GI13_DIPOR DNA-directed DNA/RNA polymerase mu OS=Dipodomys ordii GN=Polm PE=4 SV=1;
>tr|A0A1A8ERH9|A0A1A8ERH9_9TELE Polymerase (DNA directed), mu OS=Nothobranchius korthausae GN=POLM PE=4 SV=1;
>tr|M3ZG06|M3ZG06_XIPMA Uncharacterized protein OS=Xiphophorus maculatus PE=4 SV=1;

\>tr|I3MJQ3|I3MJQ3_ICTTR Uncharacterized protein OS=*Ictidomys tridecemlineatus* GN=DNTT PE=4 SV=1;

\>tr|G3NAV1|G3NAV1_GASAC Uncharacterized protein OS=*Gasterosteus aculeatus* PE=4 SV=1;

\>tr|W5UBD8|W5UBD8_ICTPU DNA-directed DNA/RNA polymerase mu OS=*Ictalurus punctatus* GN=Polm PE=2 SV=1;

\>tr|G3HMA0|G3HMA0_CRIGR DNA polymerase mu OS=*Cricetulus griseus* GN=I79_011851 PE=4 SV=1;

\>tr|A0A146NRB1|A0A146NRB1_FUNHE DNA-directed DNA/RNA polymerase mu OS=*Fundulus heteroclitus* PE=4 SV=1;

\>tr|W5LJC9|W5LJC9_ASTMX Uncharacterized protein OS=*Astyanax mexicanus* PE=4 SV=1;

\>tr|Q7ZUU0|Q7ZUU0_DANRE Polm protein OS=*Danio rerio* GN=polm PE=2 SV=1;

\>tr|A0A060W4U6|A0A060W4U6_ONCMY Uncharacterized protein OS=*Oncorhynchus mykiss* GN=GSONMT00066594001 PE=4 SV=1;

\>tr|Q5IBN3|Q5IBN3_DANRE DNA polymerase mu OS=*Danio rerio* GN=polm PE=1 SV=1;

\>tr|A0A1A8D2K8|A0A1A8D2K8_9TELE Polymerase (DNA directed), mu OS=*Nothobranchius kadleci* GN=POLM PE=4 SV=1;

\>tr|F6SV89|F6SV89_MONDO Uncharacterized protein OS=*Monodelphis domestica* GN=POLM PE=4 SV=1 (SEQ ID NO: 83);

\>tr|I3M0V3|I3M0V3_ICTTR Uncharacterized protein OS=*Ictidomys tridecemlineatus* GN=POLM PE=4 SV=1;

\>tr|A0A091T942|A0A091T942_NESNO DNA nucleotidylexotransferase (Fragment) OS=*Nestor notabilis* GN=N333_11068 PE=4 SV=1;

\>sp|Q9JIW4|DPOLM_MOUSE DNA-directed DNA/RNA polymerase mu OS=*Mus musculus* GN=Polm PE=1 SV=2;

\>tr|A0A1A8UBQ3|A0A1A8UBQ3_NOTFU Polymerase (DNA directed), mu OS=*Nothobranchius furzeri* GN=POLM PE=4 SV=1;

\>tr|A0A091LWE4|A0A091LWE4_CARIC DNA nucleotidylexotransferase (Fragment) OS=*Cariama cristata* GN=N322_09261 PE=4 SV=1;

\>tr|K7GPU0|K7GPU0_PIG Uncharacterized protein OS=*Sus scrofa* GN=DNTT PE=4 SV=1 (SEQ ID NO: 77);

\>tr|A0A096NAR8|A0A096NAR8_PAPAN Uncharacterized protein OS=*Papio anubis* GN=POLM PE=4 SV=1;

\>tr|Q924W4|Q924W4_MOUSE DNA polymerase mu OS=*Mus musculus* GN=DNAPOLmu PE=4 SV=1;

\>sp|Q9NP87|DPOLM_HUMAN DNA-directed DNA/RNA polymerase mu OS=*Homo sapiens* GN=POLM PE=1 SV=1;

\>tr|A0A1A8J9K9|A0A1A8J9K9_NOTKU Polymerase (DNA directed), mu OS=*Nothobranchius kuhntae* GN=POLM PE=4 SV=1;

\>tr|U3DX09|U3DX09_CALJA DNA-directed DNA/RNA polymerase mu OS=*Callithrix jacchus* GN=POLM PE=2 SV=1;

\>tr|Q7TN90|Q7TN90_MOUSE Polymerase (DNA directed), mu OS=*Mus musculus* GN=Polm PE=2 SV=1;

\>tr|G3SE66|G3SE66_GORGO Uncharacterized protein OS=*Gorilla gorilla gorilla* GN=POLM PE=4 SV=1;

\>tr|U3FAC2|U3FAC2_CALJA DNA-directed DNA/RNA polymerase mu OS=*Callithrix jacchus* GN=POLM PE=2 SV=1;

\>tr|K7BGH5|K7BGH5_PANTR Polymerase (DNA directed), mu OS=*Pan troglodytes* GN=POLM PE=2 SV=1;

\>tr|H2QUI0|H2QUI0_PANTR Uncharacterized protein OS=*Pan troglodytes* GN=POLM PE=4 SV=1;

\>tr|A0A096MCQ1|A0A096MCQ1_POEFO Uncharacterized protein OS=*Poecilia formosa* PE=4 SV=1;

\>tr|F7BJ05|F7BJ05_HORSE Uncharacterized protein OS=*Equus caballus* GN=POLM PE=4 SV=1;

\>tr|G1PJG7|G1PJG7_MYOLU Uncharacterized protein OS=*Myotis lucifugus* GN=POLM PE=4 SV=1;

\>tr|A0A0D9RSI4|A0A0D9RSI4_CHLSB Uncharacterized protein OS=*Chlorocebus sabaeus* GN=POLM PE=4 SV=1;

\>tr|H2L4T8|H2L4T8_ORYLA Uncharacterized protein OS=*Oryzias latipes* GN=DNTT PE=4 SV=1;

\>tr|A0A1A7ZHN0|A0A1A7ZHN0_NOTFU Polymerase (DNA directed), mu OS=*Nothobranchius furzeri* GN=POLM PE=4 SV=1;

\>tr|G1TSU6|G1TSU6_RABIT Uncharacterized protein OS=*Oryctolagus cuniculus* GN=POLM PE=4 SV=1;

\>tr|F1SSF6|F1SSF6_PIG Uncharacterized protein OS=*Sus scrofa* GN=POLM PE=4 SV=1 (SEQ ID NO: 78);

\>tr|A0A093PRU9|A0A093PRU9_PHACA DNA nucleotidylexotransferase (Fragment) OS=*Phalacrocorax carbo* GN=N336_06051 PE=4 SV=1;

\>tr|H0WUS0|H0WUS0_OTOGA Uncharacterized protein OS=*Otolemur garnettii* GN=POLM PE=4 SV=1 (SEQ ID NO: 80);

\>tr|A0A094KEU6|A0A094KEU6_ANTCR DNA nucleotidylexotransferase (Fragment) OS=*Antrostomus carolinensis* GN=N321_01336 PE=4 SV=1;

\>tr|H0VRU3|H0VRU3_CAVPO Uncharacterized protein OS=*Cavia porcellus* GN=POLM PE=4 SV=1;

\>tr|A0A091ECM1|A0A091ECM1_FUKDA DNA-directed DNA/RNA polymerase mu OS=*Fukomys damarensis* GN=H920_05682 PE=4 SV=1;

\>tr|G5ASQ9|G5ASQ9_HETGA DNA polymerase mu OS=*Heterocephalus glaber* GN=GW7_14800 PE=4 SV=1;

\>tr|G3VIL2|G3VIL2_SARHA Uncharacterized protein (Fragment) OS=*Sarcophilus harrisii* GN=POLM PE=4 SV=1 (SEQ ID NO: 75);

\>tr|Q0VFA6|Q0VFA6_XENTR Uncharacterized protein (Fragment) OS=*Xenopus tropicalis* PE=2 SV=1;

\>tr|A0A1S2ZTW0|A0A1S2ZTW0_ERIEU DNA-directed DNA/RNA polymerase mu OS=*Erinaceus europaeus* GN=POLM PE=4 SV=1;

\>tr|A0A061IPE9|A0A061IPE9_CRIGR DNA-directed DNA/RNA polymerase mu OS=*Cricetulus griseus* GN=H671_1g1703 PE=4 SV=1;

\>tr|F1MPJ5|F1MPJ5_BOVIN Uncharacterized protein OS=*Bos taurus* GN=POLM PE=4 SV=2;

\>tr|L5KMY1|L5KMY1_PTEAL DNA polymerase mu OS=*Pteropus alecto* GN=PAL_GLEAN10002258 PE=4 SV=1;

\>tr|G3T5I6|G3T5I6_LOXAF Uncharacterized protein (Fragment) OS=*Loxodonta africana* GN=POLM PE=4 SV=1;

\>tr|A0A0R4IL28|A0A0R4IL28_DANRE Polymerase (DNA directed), mu OS=*Danio rerio* GN=polm PE=1 SV=1;

>tr|W5Q5W9|W5Q5W9_SHEEP Uncharacterized protein OS=*Ovis aries* GN=POLM PE=4 SV=1;

>tr|F6YZ98|F6YZ98_XENTR Uncharacterized protein (Fragment) OS=*Xenopus tropicalis* GN=polm PE=4 SV=1;

>tr|A0A1D5QIN2|A0A1D5QIN2_MACMU Uncharacterized protein OS=*Macaca mulatta* GN=POLM PE=4 SV=1;

>tr|A0A1A7XD24|A0A1A7XD24_9TELE Polymerase (DNA directed), mu (Fragment) OS=*Aphyosemion striatum* GN=POLM PE=4 SV=1;

>tr|A0A093F2E3|A0A093F2E3_TYTAL DNA nucleotidylexotransferase (Fragment) OS=*Tyto alba* GN=N341_11661 PE=4 SV=1;

>tr|V8NA58|V8NA58_OPHHA DNA-directed DNA/RNA polymerase mu (Fragment) OS=*Ophiophagus hannah* GN=POLM PE=4 SV=1;

>tr|A0A1A8NJB1|A0A1A8NJB1_9TELE Polymerase (DNA directed), mu OS=*Nothobranchius rachovii* GN=POLM PE=4 SV=1;

>tr|M3X1D8|M3X1D8_FELCA Uncharacterized protein OS=*Felis catus* GN=POLM PE=4 SV=1;

>tr|A0A1A8CS80|A0A1A8CS80_9TELE Polymerase (DNA directed), mu OS=*Nothobranchius kadleci* GN=POLM PE=4 SV=1;

>tr|A0A1A8JAN0|A0A1A8JAN0_NOTKU Polymerase (DNA directed), mu OS=*Nothobranchius kuhntae* GN=POLM PE=4 SV=1;

>tr|F6SUN4|F6SUN4_XENTR Uncharacterized protein (Fragment) OS=*Xenopus tropicalis* GN=polm PE=4 SV=2;

>tr|A0A151NPI6|A0A151NPI6_ALLMI DNA-directed DNA/RNA polymerase mu OS=*Alligator mississippiensis* GN=POLM PE=4 SV=1;

>tr|H2VEE2|H2VEE2_TAKRU Uncharacterized protein OS=*Takifugu rubripes* GN=polm PE=4 SV=1;

>tr|A0A1L8GS64|A0A1L8GS64_XENLA Uncharacterized protein OS=*Xenopus laevis* GN=XELAEV_18020298 mg PE=4 SV=1;

>tr|S7NKX1|S7NKX1_MYOBR DNA-directed DNA/RNA polymerase mu OS=*Myotis brandtii* GN=D623_10014907 PE=4 SV=1 (SEQ ID NO: 86);

>tr|A0A091PH27|A0A091PH27_HALAL DNA nucleotidylexotransferase OS=*Haliaeetus albicilla* GN=N329_12936 PE=4 SV=1;

>tr|Q5NCI3|Q5NCI3_MOUSE DNA-directed DNA/RNA polymerase mu OS=*Mus musculus* GN=Polm PE=1 SV=1;

>tr|A0A091L3R3|A0A091L3R3_CATAU DNA nucleotidylexotransferase OS=*Cathartes aura* GN=N323_12768 PE=4 SV=1;

>tr|V9L4E7|V9L4E7_CALMI DNA-directed DNA/RNA polymerase mu (Fragment) OS=*Callorhinchus milii* PE=2 SV=1;

>tr|A0A093JK89|A0A093JK89_EURHL DNA nucleotidylexotransferase OS=*Eurypyga helias* GN=N326_11527 PE=4 SV=1;

>tr|U3KMM5|U3KMM5_RABIT Uncharacterized protein OS=*Oryctolagus cuniculus* GN=POLM PE=4 SV=1;

>tr|A0A1A8P9J9|A0A1A8P9J9_9TELE Deoxynucleotidyltransferase, terminal (Fragment) OS=*Nothobranchius rachovii* GN=DNTT PE=4 SV=1;

>tr|A0A1A8KA73|A0A1A8KA73_NOTKU Polymerase (DNA directed), mu (Fragment) OS=*Nothobranchius kuhntae* GN=POLM PE=4 SV=1;

>tr|S9XEA8|S9XEA8_CAMFR DNA nucleotidylexotransferase isoform 1-like protein OS=*Camelus ferus* GN=CB1_000155020 PE=4 SV=1;

>tr|L5LFP9|L5LFP9_MYODS DNA-directed DNA/RNA polymerase mu OS=*Myotis davidii* GN=MDA_GLEAN10006449 PE=4 SV=1;

>tr|M3Z3D2|M3Z3D2_MUSPF Uncharacterized protein OS=*Mustela putorius* furo GN=POLM PE=4 SV=1;

>tr|A0A146X6G9|A0A146X6G9_FUNHE DNA nucleotidylexotransferase (Fragment) OS=*Fundulus heteroclitus* PE=4 SV=1;

>tr|S9YVX3|S9YVX3_CAMFR DNA-directed DNA/RNA polymerase mu OS=*Camelus ferus* GN=CB1_000193022 PE=4 SV=1;

>tr|W4Y2P6|W4Y2P6_STRPU Uncharacterized protein OS=*Strongylocentrotus purpuratus* PE=4 SV=1;

>tr|A0A087YLM2|A0A087YLM2_POEFO Uncharacterized protein OS=*Poecilia formosa* PE=4 SV=2;

>tr|G1MGP9|G1MGP9_AILME Uncharacterized protein (Fragment) OS=*Ailuropoda melanoleuca* GN=POLM PE=4 SV=1;

>tr|A0A091K5R0|A0A091K5R0_COLST DNA nucleotidylexotransferase (Fragment) OS=*Colius striatus* GN=N325_07143 PE=4 SV=1;

>tr|B1H1C4|B1H1C4_XENTR Uncharacterized protein OS=*Xenopus tropicalis* GN=polm PE=2 SV=1;

>tr|A0A091T176|A0A091T176_9AVES DNA nucleotidylexotransferase (Fragment) OS=*Pelecanus crispus* GN=N334_13201 PE=4 SV=1;

>tr|ROK6L2|ROK6L2_ANAPL DNA nucleotidylexotransferase (Fragment) OS=*Anas platyrhynchos* GN=LOC101804368 PE=4 SV=1;

>tr|W5NDT9|W5NDT9_LEPOC Uncharacterized protein OS=*Lepisosteus oculatus* PE=4 SV=1; (SEQ ID NO: 72)

>tr|A0A091SF87|A0A091SF87_9GRUI DNA nucleotidylexotransferase (Fragment) OS=*Mesitornis unicolor* GN=N332_10317 PE=4 SV=1;

>sp|Q9NP87-2|DPOLM_HUMAN Isoform 2 of DNA-directed DNA/RNA polymerase mu OS=*Homo sapiens* GN=POLM;

>tr|A0A0P7UAY6|A0A0P7UAY6_9TELE DNA-directed DNA/RNA polymerase mu-like OS=*Scleropages formosus* GN=Z043_116844 PE=4 SV=1;

>tr|H2PM88|H2PM88_PONAB Uncharacterized protein OS=*Pongo abelii* GN=POLM PE=4 SV=1;

>tr|A0A1S3LYF6|A0A1S3LYF6_SALSA DNA-directed DNA/RNA polymerase mu-like OS=*Salmo salar* GN=LOC106569276 PE=4 SV=1;

>tr|L7N3V6|L7N3V6_XENTR Uncharacterized protein OS=*Xenopus tropicalis* GN=polm PE=4 SV=1;

>tr|A0A0F8AHZ5|A0A0F8AHZ5_LARCR DNA nucleotidylexotransferase OS=*Larimichthys crocea* GN=EH28_08861 PE=4 SV=1;

>tr|A0A091ND14|A0A091ND14_APAVI DNA nucleotidylexotransferase (Fragment) OS=*Apaloderma vittatum* GN=N311_03749 PE=4 SV=1;

>tr|A0A1A8HR87|A0A1A8HR87_NOTKU Deoxynucleotidyltransferase, terminal OS=*Nothobranchius kuhntae* GN=DNTT PE=4 SV=1;

>tr|A0A1A8UVJ9|A0A1A8UVJ9_NOTFU Deoxynucleotidyltransferase, terminal OS=*Nothobranchius furzeri* GN=DNTT PE=4 SV=1;

>tr|A0A1A8RA57|A0A1A8RA57_9TELE Polymerase (DNA directed), mu (Fragment) OS=*Nothobranchius pienaari* GN=POLM PE=4 SV=1;

>tr|S4RJG9|S4RJG9_PETMA Uncharacterized protein OS=*Petromyzon marinus* PE=4 SV=1;
>tr|A0A1A7ZHB4|A0A1A7ZHB4_NOTFU Polymerase (DNA directed), mu (Fragment) OS=*Nothobranchius furzeri* GN=POLM PE=4 SV=1;
>tr|Q5FVA7|Q5FVA7_XENTR Poll.2 protein (Fragment) OS=*Xenopus tropicalis* GN=poll.2 PE=2 SV=1;
>tr|H9KX16|H9KX16_CALJA Uncharacterized protein OS=*Callithrix jacchus* PE=4 SV=1;
>tr|C3YIS5|C3YIS5_BRAFL Putative uncharacterized protein OS=*Branchiostoma floridae* GN=BRAFLDRAFT_59678 PE=4 SV=1;
>tr|A0A146XGI0|A0A146XGI0_FUNHE DNA-directed DNA/RNA polymerase mu (Fragment) OS=*Fundulus heteroclitus* PE=4 SV=1;
>tr|G9KHQ3|G9KHQ3_MUSPF Polymerase, mu (Fragment) OS=*Mustela putorius furo* PE=2 SV=1;
>tr|V3ZNY9|V3ZNY9_LOTGI Uncharacterized protein (Fragment) OS=*Lottia gigantea* GN=LOTGIDRAFT_72364 PE=4 SV=1;
>tr|B3S8X2|B3S8X2_TRIAD Putative uncharacterized protein OS=*Trichoplax adhaerens* GN=TRIADDRAFT_60774 PE=4 SV=1;
>tr|H2ZGS8|H2ZGS8_CIOSA Uncharacterized protein OS=*Ciona savignyi* PE=4 SV=1;
>tr|H9GW56|H9GW56_CANLF Uncharacterized protein OS=*Canis lupus familiaris* PE=4 SV=2;
>tr|A0A1A8EON8|A0A1A8EON8_9TELE Polymerase (DNA directed), mu OS=*Nothobranchius kadleci* GN=POLM PE=4 SV=1;
>tr|A0A146RC47|A0A146RC47_FUNHE DNA-directed DNA/RNA polymerase mu OS=*Fundulus heteroclitus* PE=4 SV=1;
>tr|A0A1A8AD54|A0A1A8AD54_NOTFU Polymerase (DNA directed), mu (Fragment) OS=*Nothobranchius furzeri* GN=POLM PE=4 SV=1;
>tr|A0A146N7G7|A0A146N7G7_FUNHE DNA-directed DNA/RNA polymerase mu OS=*Fundulus heteroclitus* PE=4 SV=1;
>tr|A0A0S7LMJ9|A0A0S7LMJ9_9TELE DPOLM (Fragment) OS=*Poeciliopsis prolifica* GN=DPOLM PE=4 SV=1;
>tr|L8|E28|L8|E28_9CETA DNA polymerase mu OS=*Bos mutus* GN=M91_15825 PE=4 SV=1;
>tr|A0A060XXZ4|A0A060XXZ4_ONCMY Uncharacterized protein OS=*Oncorhynchus mykiss* GN=GSONMT00003902001 PE=4 SV=1;
>tr|Q58DV2|Q58DV2_BOVIN Polymerase (DNA directed), mu OS=*Bos taurus* GN=POLM PE=2 SV=1;
>tr|A0A091TVD3|A0A091TVD3_PHALP DNA nucleotidylexotransferase (Fragment) OS=*Phaethon lepturus* GN=N335_13210 PE=4 SV=1;
>tr|Q4S1X0|Q4S1X0_TETNG Chromosome undetermined SCAF14764, whole genome shotgun sequence OS=*Tetraodon nigroviridis* GN=GSTENG00025355001 PE=4 SV=1;
>tr|A0A146X6L6|A0A146X6L6_FUNHE DNA nucleotidylexotransferase OS=*Fundulus heteroclitus* PE=4 SV=1;
>tr|A0A1A8FJT0|A0A1A8FJT0_9TELE Polymerase (DNA directed), mu (Fragment) OS=*Nothobranchius korthausae* GN=POLM PE=4 SV=1;
>tr|K7FEN8|K7FEN8_PELSI Uncharacterized protein OS=*Pelodiscus sinensis* GN=POLM PE=4 SV=1;
>tr|V8NQW9|V8NQW9_OPHHA DNA nucleotidylexotransferase (Fragment) OS=*Ophiophagus hannah* GN=DNTT PE=4 SV=1;
>tr|T1JNH2|T1JNH2_STRMM Uncharacterized protein OS=*Strigamia maritima* PE=4 SV=1;
>tr|K7FEM8|K7FEM8_PELSI Uncharacterized protein OS=*Pelodiscus sinensis* GN=POLM PE=4 SV=1;
>tr|A0A146XH72|A0A146XH72_FUNHE DNA-directed DNA/RNA polymerase mu OS=*Fundulus heteroclitus* PE=4 SV=1;
>tr|Q4RN80|Q4RN80_TETNG Chromosome undetermined SCAF15016, whole genome shotgun sequence (Fragment) OS=*Tetraodon nigroviridis* GN=GSTENG00031681001 PE=4 SV=1;
>tr|M7B2F2|M7B2F2_CHEMY DNA-directed DNA/RNA polymerase mu OS=*Chelonia mydas* GN=UY3_16640 PE=4 SV=1;
>tr|A0A0P7UYV0|A0A0P7UYV0_9TELE Uncharacterized protein (Fragment) OS=*Scleropages formosus* GN=Z043_101012 PE=4 SV=1;
>tr|A0A1A7YQL2|A0A1A7YQL2_9TELE Polymerase (DNA directed), mu (Fragment) OS=*Aphyosemion striatum* GN=POLM PE=4 SV=1;
>tr|H9GJR5|H9GJR5_ANOCA Uncharacterized protein OS=*Anolis carolinensis* PE=4 SV=1;
>tr|K1PM26|K1PM26_CRAGI DNA polymerase mu OS=*Crassostrea gigas* GN=CGI_10007307 PE=4 SV=1;
>tr|C5H604|C5H604_HORSE Terminal deoxynucleotidyltransferase (Fragment) OS=*Equus caballus* GN=DNTT PE=2 SV=1;
>tr|A0A0S7LMI4|A0A0S7LMI4_9TELE DPOLM (Fragment) OS=*Poeciliopsis prolifica* GN=DPOLM PE=4 SV=1;
>tr|I1FU11|I1FU11_AMPQE Uncharacterized protein OS=*Amphimedon queenslandica* PE=4 SV=1;
>tr|H9GS78|H9GS78_ANOCA Uncharacterized protein OS=*Anolis carolinensis* GN=POLM PE=4 SV=2;
>tr|A0A0P5QDN2|A0A0P5QDN2_9CRUS DNA-directed DNA/RNA polymerase mu OS=*Daphnia magna* PE=4 SV=1;
>tr|A0A165AGI8|A0A165AGI8_9CRUS Uncharacterized protein OS=*Daphnia magna* GN=APZ42_016503 PE=4 SV=1;
>tr|A0A0P6JT6|A0A0P6JT6_9CRUS DNA-directed DNA/RNA polymerase mu OS=*Daphnia magna* PE=4 SV=1;
>tr|A0A1S3J3X7|A0A1S3J3X7_LINUN DNA-directed DNA/RNA polymerase mu-like isoform X1 OS=*Lingula unguis* GN=LOC106169975 PE=4 SV=1;
>tr|A0A1S3J3Y6|A0A1S3J3Y6_LINUN DNA-directed DNA/RNA polymerase mu-like isoform X2 OS=*Lingula unguis* GN=LOC106169975 PE=4 SV=1;
>tr|F7CVN4|F7CVN4_CALJA Uncharacterized protein OS=*Callithrix jacchus* PE=4 SV=1;
>tr|E9HD36|E9HD36_DAPPU Putative uncharacterized protein OS=*Daphnia pulex* GN=DAPPUDRAFT_300508 PE=4 SV=1;
>tr|A0A0P6AAE9|A0A0P6AAE9_9CRUS DNA-directed DNA/RNA polymerase mu OS=*Daphnia magna* PE=4 SV=1;
>tr|G7P2A2|G7P2A2_MACFA Putative uncharacterized protein OS=*Macaca fascicularis* GN=EGM_12557 PE=4 SV=1;
>tr|A0A0P5GM38|A0A0P5GM38_9CRUS DNA-directed DNA/RNA polymerase mu OS=*Daphnia magna* PE=4 SV=1;
>tr|G7MLE4|G7MLE4_MACMU Uncharacterized protein OS=*Macaca mulatta* GN=EGK_13738 PE=4 SV=1;

>tr|Q6PIY2|Q6PIY2_HUMAN DNA-directed DNA/RNA polymerase mu OS=*Homo sapiens* GN=POLM PE=1 SV=1;
>tr|U9U3O4|U9U3O4_RHIID Uncharacterized protein OS=*Rhizophagus irregularis* (strain DAOM 181602/DAOM 197198/MUCL 43194) GN=GLOINDRAFT_287 PE=4 SV=1;
>tr|A0A0B6ZDL7|A0A0B6ZDL7_9EUPU Uncharacterized protein (Fragment) OS=*Arion vulgaris* GN=ORF59157 PE=4 SV=1;
>tr|F1QNC9|F1QNC9_DANRE Deoxynucleotidyltransferase, terminal OS=*Danio rerio* GN=dntt PE=4 SV=1;
>tr|A0A0P5PJF6|A0A0P5PJF6_9CRUS DNA-directed DNA/RNA polymerase mu (Fragment) OS=*Daphnia magna* PE=4 SV=1;
>tr|A0A0P5WYI3|A0A0P5WYI3_9CRUS DNA-directed DNA/RNA polymerase mu OS=*Daphnia magna* PE=4 SV=1;
>tr|H9KVL9|H9KVL9_CALJA Uncharacterized protein OS=*Callithrix jacchus* PE=4 SV=1;
>tr|A0A0N7ZWR4|A0A0N7ZWR4_9CRUS DNA-directed DNA/RNA polymerase mu (Fragment) OS=*Daphnia magna* PE=4 SV=1;
>tr|Q9H980|Q9H980_HUMAN DNA-directed DNA/RNA polymerase mu OS=*Homo sapiens* GN=POLM PE=1 SV=1;
>tr|H9KVM0|H9KVM0_CALJA Uncharacterized protein OS=*Callithrix jacchus* PE=4 SV=1;
>tr|H9KW19|H9KW19_CALJA Uncharacterized protein OS=*Callithrix jacchus* PE=4 SV=1;
>tr|A0A075AZ03|A0A075AZ03_9FUNG DNA polymerase family X lyase domain-containing protein OS=*Rozella allomycis* CSF55 GN=09G_000755 PE=4 SV=1;
>tr|A0A1A8BGS3|A0A1A8BGS3_9TELE Deoxynucleotidyltransferase, terminal OS=*Nothobranchius kadleci* GN=DNTT PE=4 SV=1;
>tr|U6CZ52|U6CZ52_NEOVI DNA-directed DNA/RNA polymerase mu (Fragment) OS=*Neovison vison* GN=DPOLM PE=2 SV=1;
>tr|A0A0D2UGV9|A0A0D2UGV9_CAPO3 Uncharacterized protein OS=*Capsaspora owczarzaki* (strain ATCC 30864) GN=CAOG_004995 PE=4 SV=1;
>tr|F6PMA5|F6PMA5_MACMU Uncharacterized protein OS=*Macaca mulatta* GN=POLM PE=4 SV=2;
>sp|Q9NP87-3|DPOLM_HUMAN Isoform 3 of DNA-directed DNA/RNA polymerase mu OS=*Homo sapiens* GN=POLM;
>tr|A0A168R3T5|A0A168R3T5_ABSGL Uncharacterized protein OS=*Absidia glauca* GN=ABSGL_11926.1 scaffold 12357 PE=4 SV=1;
>tr|A0A0C3BGD0|A0A0C3BGD0_9HOMO Uncharacterized protein OS=*Serendipita vermifera* MAFF 305830 GN=M408DRAFT_327483 PE=4 SV=1;
>tr|A0A0C2SZ00|A0A0C2SZ00_AMAMU Uncharacterized protein OS=*Amanita muscaria* Koide BX008 GN=M378DRAFT_8228 PE=4 SV=1;
>tr|A0A0W0FVE5|A0A0W0FVE5_9AGAR Uncharacterized protein OS=*Moniliophthora roreri* GN=WG66_7104 PE=4 SV=1;
>tr|S8DTS4|S8DTS4_FOMPI Uncharacterized protein OS=*Fomitopsis pinicola* (strain FP-58527) GN=FOMPIDRAFT_52938 PE=4 SV=1;
>tr|H2L5F7|H2L5F7_ORYLA Uncharacterized protein OS=*Oryzias latipes* PE=4 sv=1;
>tr|V2XUA2|V2XUA2_MONRO Dna polymerase mu OS=*Moniliophthora roreri* (strain MCA 2997) GN=Moror_17783 PE=4 SV=1;
>tr|G3QPE8|G3QPE8_GORGO Uncharacterized protein OS=*Gorilla gorilla gorilla* GN=POLM PE=4 SV=1;
>tr|H9KW10|H9KW10_CALJA Uncharacterized protein OS=*Callithrix jacchus* PE=4 SV=1;
>tr|A0A061ALJ8|A0A061ALJ8_RHOTO RHTO0S01e16908g1_1 OS=*Rhodosporidium toruloides* GN=RHTO0S_01e16908g PE=4 SV=1;
>tr|A0A0G2KCT4|A0A0G2KCT4_DANRE Uncharacterized protein OS=*Danio rerio* PE=4 SV=1;
>tr|A0A0P5PVU2|A0A0P5PVU2_9CRUS DNA-directed DNA/RNA polymerase mu OS=*Daphnia magna* PE=4 SV=1;
>tr|A0A0P5MXJ7|A0A0P5MXJ7_9CRUS DNA-directed DNA/RNA polymerase mu OS=*Daphnia magna* PE=4 SV=1;
>tr|A0A0P5NMK9|A0A0P5NMK9_9CRUS DNA-directed DNA/RNA polymerase mu OS=*Daphnia magna* PE=4 SV=1;
>tr|A0A060VUK5|A0A060VUK5_ONCMY Uncharacterized protein OS=*Oncorhynchus mykiss* GN=GSONMT00078040001 PE=4 SV=1;
>tr|V8P7H4|V8P7H4_OPHHA DNA polymerase lambda (Fragment) OS=*Ophiophagus hannah* GN=POLL PE=4 SV=1;
>tr|A0A137QJR4|A0A137QJR4_9AGAR DNA-directed DNA/RNA polymerase mu OS=*Leucoagaricus* sp. SymC.cos GN=AN958_08787 PE=4 SV=1;
>tr|A0A164P2X5|A0A164P2X5_9HOMO Nucleotidyltransferase OS=*Sistotremastrum niveocremeum* HHB9708 GN=SISNIDRAFT_446120 PE=4 SV=1;
>tr|F7HXH0|F7HXH0_CALJA Uncharacterized protein OS=*Callithrix jacchus* PE=4 SV=1;
>tr|G1QTM9|G1QTM9_NOMLE Uncharacterized protein OS=*Nomascus leucogenys* GN=POLM PE=4 SV=1;
>tr|Q4RN81|Q4RN81_TETNG Chromosome undetermined SCAF15016, whole genome shotgun sequence (Fragment) OS=*Tetraodon nigroviridis* GN=GSTENG00031680001 PE=4 SV=1;
>tr|A0A167PH29|A0A167PH29_9BASI Nucleotidyltransferase OS=*Calocera viscosa* TUFC12733 GN=CALVIDRAFT_478151 PE=4 SV=1;
>tr|A0A165MRI2|A0A165MRI2_EXIGL Nucleotidyltransferase OS=*Exidia glandulosa* HHB12029 GN=EXIGLDRAFT_724655 PE=4 SV=1;
>tr|A0A068SFG6|A0A068SFG6_9FUNG Dna polymerase mu OS=*Lichtheimia corymbifera* JMRC:FSU:9682 GN=LCOR_11539.1 PE=4 SV=1;
>tr|B0D8M6|B0D8M6_LACBS Predicted protein OS=*Laccaria bicolor* (strain S238N-H82/ATCC MYA-4686) GN=LACBIDRAFT_296372 PE=4 SV=1;
>tr|A0A165JL69|A0A165JL69_9BASI Nucleotidyltransferase OS=*Calocera cornea* HHB12733 GN=CALCODRAFT_514361 PE=4 SV=1;
>tr|M3WN40|M3WN40_FELCA Uncharacterized protein OS=*Felis catus* GN=POLL PE=4 SV=1;
>tr|A0A0P4YRE9|A0A0P4YRE9_9CRUS Putative DNA-directed DNA/RNA polymerase mu OS=*Daphnia magna* PE=4 SV=1;
>tr|M3WQL3|M3WQL3_FELCA Uncharacterized protein OS=*Felis catus* GN=POLL PE=4 SV=1;
>tr|A0A1E1X922|A0A1E1X922_9ACAR Putative dna polymerase lambda OS=*Amblyomma aureolatum* PE=2 SV=1;

>tr|E5FGJ8|E5FGJ8_PLECU DNA polymerase lambda (Fragment) OS=*Plecturocebus cupreus* GN=POLL PE=2 SV=1;
>tr|A0A146IDE1|A0A146IDE1_9AGAR Uncharacterized protein OS=*Mycena chlorophos* GN=MCHLO_14360 PE=4 SV=1;
>tr|A0A0B7G3X1|A0A0B7G3X1_THACB DNA-directed DNA/RNA polymerase mu OS=*Homo sapiens* GN=POLM PE=1 SV=1 OS=*Thanatephorus cucumeris* (strain AG1-IB/isolate 7/3/14) GN=RSOLAG1IB_05578 PE=4 SV=1;
>tr|A0A1B7NDI9|A0A1B7NDI9_9HOMO Nucleotidyltransferase OS=*Rhizopogon vinicolor* AM-OR11-026 GN=K503DRAFT_862764 PE=4 SV=1;
>tr|A0A0C3NTP8|A0A0C3NTP8_PHLGI Uncharacterized protein OS=*Phlebiopsis gigantea* 11061_1 CR5-6 GN=PHLGIDRAFT_29452 PE=4 SV=1;
>tr|A0A165Z2P2|A0A165Z2P2_9HOMO Nucleotidyltransferase OS=*Sistotremastrum suecicum* HHB10207 ss-3 GN=SISSUDRAFT_992585 PE=4 sv=1;
>tr|L5JPX4|L5JPX4_PTEAL DNA polymerase lambda OS=*Pteropus alecto* GN=PAL_GLEAN10018254 PE=4 SV=1;
>tr|A0A077W6Z0|A0A077W6Z0_9FUNG Uncharacterized protein OS=*Lichtheimia ramosa* GN=LRAMOSA00609 PE=4 SV=1;
>tr|I3MHE8|I3MHE8_ICTTR Uncharacterized protein OS=*Ictidomys tridecemlineatus* GN=POLL PE=4 SV=1;
>tr|G1T998|G1T998_RABIT Uncharacterized protein OS=*Oryctolagus cuniculus* GN=POLL PE=4 SV=2;
>tr|U3AR34|U3AR34_CALJA DNA polymerase lambda isoform a OS=*Callithrix jacchus* GN=POLL PE=2 SV=1;
>tr|G4TBJ0|G4TBJ0_SERID Related to DNA polymerase Tdt-N OS=*Serendipita indica* (strain DSM 11827) GN=PIIN_02548 PE=4 SV=1;
>tr|A0A168NYM3|A0A168NYM3_ABSGL Uncharacterized protein OS=*Absidia glauca* GN=ABSGL_07199.1 scaffold 8717 PE=4 SV=1;
>tr|E5FGI5|E5FGI5_HYLAG DNA polymerase lambda (Fragment) OS=*Hylobates agilis* GN=POLL PE=2 SV=1;
>tr|Q5K8N6|Q5K8N6_CRYNJ Beta DNA polymerase, putative OS=*Cryptococcus neoformans* var. *neoformans* serotype D (strain JEC21/ATCC MYA-565) GN=CNL05040 PE=4 SV=2;
>tr|X8JQU6|X8JQU6_9HOMO Finger of DNA polymerase lambda domain protein OS=*Rhizoctonia solani* AG-3 Rhs1AP GN=RSOL_474080 PE=4 SV=1;
>tr|A0A074S8B0|A0A074S8B0_9HOMO Finger of DNA polymerase lambda domain protein OS=*Rhizoctonia solani* 123E GN=V565_004060 PE=4 SV=1;
>tr|G3W992|G3W992_SARHA Uncharacterized protein OS=*Sarcophilus harrisii* GN=POLL PE=4 SV=1 (SEQ ID NO: 76);
>tr|A0A066W4N7|A0A066W4N7_9HOMO Uncharacterized protein (Fragment) OS=*Rhizoctonia solani* AG-8 WAC10335 GN=RSAG8_03653 PE=4 SV=1;
>tr|A0A146SIK4|A0A146SIK4_FUNHE DNA nucleotidylexotransferase-like protein (Fragment) OS=*Fundulus heteroclitus* PE=4 SV=1;
>tr|S7NFH1|S7NFH1_MYOBR DNA polymerase lambda OS=*Myotis brandtii* GN=D623_10025942 PE=4 SV=1 (SEQ ID NO: 70);
>tr|A0A0D0ADW7|A0A0D0ADW7_9HOMO Unplaced genomic scaffold CY34scaffold_406, whole genome shotgun sequence OS=*Suillus luteus* UH-Slu-Lm8-n1 GN=CY34DRAFT_527157 PE=4 SV=1;
>tr|G1P3K8|G1P3K8_MYOLU Uncharacterized protein OS=*Myotis lucifugus* GN=POLL PE=4 SV=1;
>tr|L8J3I7|L8J3I7_9CETA DNA polymerase lambda OS=*Bos mutus* GN=M91_06669 PE=4 SV=1;
>tr|A0A0P5Q569|A0A0P5Q569_9CRUS DNA-directed DNA/RNA polymerase mu OS=*Daphnia magna* PE=4 SV=1;
>tr|A0A0H2S450|A0A0H2S450_9HOMO Nucleotidyltransferase OS=*Schizopora paradoxa* GN=SCHPADRAFT_865782 PE=4 SV=1;
>tr|A0A060XWV6|A0A060XWV6_ONCMY Uncharacterized protein OS=*Oncorhynchus mykiss* GN=GSONMT00003903001 PE=4 SV=1;
>tr|E5FGJ5|E5FGJ5_SYMSY DNA polymerase lambda (Fragment) OS=*Symphalangus syndactylus* GN=POLL PE=2 SV=1;
>tr|A4II30|A4II30_XENTR Poll protein OS=*Xenopus tropicalis* GN=poll PE=2 Sv=1;
>tr|F6S5I4|F6S5I4_XENTR Uncharacterized protein OS=*Xenopus tropicalis* GN=poll PE=4 SV=1;
>tr|A0A1L8FJD6|A0A1L8FJD6_XENLA Uncharacterized protein OS=*Xenopus laevis* GN=XELAEV_18034660 mg PE=4 SV=1;
>tr|F6Q4I4|F6Q4I4_XENTR Uncharacterized protein OS=*Xenopus tropicalis* GN=poll PE=4 SV=1;
>tr|U6DAU0|U6DAU0_NEOVI Polymerase (DNA directed), lambda (Fragment) OS=*Neovison vison* GN=Q5JQP8 PE=2 SV=1;
>tr|M5XMY2|M5XMY2_PRUPE Uncharacterized protein OS=*Prunus persica* GN=PRUPE_ppa018614 mg PE=4 SV=1;
>tr|Q55M33|Q55M33_CRYNB Uncharacterized protein OS=*Cryptococcus neoformans* var. *neoformans* serotype D (strain B-3501A) GN=CNBI1790 PE=4 SV=1;
>tr|E2RBL7|E2RBL7_CANLF Uncharacterized protein OS=*Canis lupus familiaris* GN=POLL PE=4 SV=1;
>tr|A0A151MLI3|A0A151MLI3_ALLMI DNA polymerase lambda OS=*Alligator mississippiensis* GN=POLL PE=4 SV=1;
>tr|A0A077X0T8|A0A077X0T8_9FUNG Uncharacterized protein OS=*Lichtheimia ramosa* GN=LRAMOSA05278 PE=4 SV=1;
>tr|A0A1Q3E079|A0A1Q3E079_LENED Dna polymerase mu OS=*Lentinula edodes* GN=LENED_002089 PE=4 SV=1;
>tr|H0V5L3|H0V5L3_CAVPO Uncharacterized protein OS=*Cavia porcellus* GN=POLL PE=4 SV=1;
>tr|E5FGJ9|E5FGJ9_NOMLE DNA polymerase lambda (Fragment) OS=*Nomascus leucogenys* GN=POLL PE=2 SV=1;
>tr|G1RXX0|G1RXX0_NOMLE Uncharacterized protein OS=*Nomascus leucogenys* GN=POLL PE=4 SV=1;
>tr|E1BHH1|E1BHH1_BOVIN Uncharacterized protein OS=*Bos taurus* GN=POLL PE=4 SV=1;
>tr|G3I577|G3I577_CRIGR DNA polymerase lambda OS=*Cricetulus griseus* GN=I79_018621 PE=4 SV=1;
>tr|A0A168HEP9|A0A168HEP9_MUCCL Uncharacterized protein OS=*Mucor circinelloides* f. *lusitanicus* CBS 277.49 GN=MUCCIDRAFT_167147 PE=4 SV=1;

>tr|A0A0D9QZP5|A0A0D9QZP5_CHLSB Uncharacterized protein OS=*Chlorocebus sabaeus* GN=POLL PE=4 SV=1;
>tr|A0A194SOQ7|A0A194S0Q7_RHOGW Uncharacterized protein OS=*Rhodotorula graminis* (strain WP1) GN=RHOBADRAFT_54045 PE=4 SV=1;
>tr|A0A091EXH7|A0A091EXH7_CORBR DNA polymerase lambda OS=*Corvus brachyrhynchos* GN=N302_13582 PE=4 SV=1;
>tr|E5FGJ6|E5FGJ6_SAISC DNA polymerase lambda (Fragment) OS=*Saimiri sciureus* GN=POLL PE=2 SV=1;
>tr|L5MB70|L5MB70_MYODS DNA polymerase lambda OS=*Myotis davidii* GN=MDA_GLEAN10023378 PE=4 SV=1;
>tr|F7DJM0|F7DJM0_CALJA Uncharacterized protein OS=*Callithrix jacchus* GN=POLL PE=4 SV=1;
>tr|G1NCL9|G1NCL9_MELGA Uncharacterized protein OS=*Meleagris gallopavo* GN=POLL PE=4 SV=1;
>tr|A0A093H2Y1|A0A093H2Y1_STRCA DNA polymerase lambda OS=*Struthio camelus australis* GN=N308_06698 PE=4 SV=1;
>tr|A9TCX5|A9TCX5_PHYPA Predicted protein OS=*Physcomitrella patens* subsp. *patens* GN=PHYPADRAFT_193840 PE=4 SV=1;
>tr|J9VLT9|J9VLT9_CRYNH DNA polymerase mu subunit OS=*Cryptococcus neoformans* var. *grubii* serotype A (strain H99/ATCC 208821/CBS 10515/FGSC 9487) GN=CNAG_05116 PE=4 SV=2;
>tr|A0A1B9I360|A0A1B9I360_9TREE DNA polymerase mu subunit OS=*Kwoniella pini* CBS 10737 GN=I206_04466 PE=4 SV=1;
>tr|A0A1A6GV71|A0A1A6GV71_NEOLE Uncharacterized protein OS=*Neotoma lepida* GN=A6R68_01967 PE=4 SV=1;
>tr|A7SK52|A7SK52_NEMVE Predicted protein OS=*Nematostella vectensis* GN=vlg190712 PE=4 SV=1;
>tr|E5FGJ7|E5FGJ7_MIOTA DNA polymerase lambda (Fragment) OS=*Miopithecus talapoin* GN=POLL PE=2 SV=1;
>tr|E5FGJ2|E5FGJ2_TRAFR DNA polymerase lambda (Fragment) OS=*Trachypithecus francoisi* GN=POLL PE=2 SV=1;
>tr|E5FGJ1|E5FGJ1_ALOSA DNA polymerase lambda (Fragment) OS=*Alouatta sara* GN=POLL PE=2 SV=1;
>tr|E5FGI9|E5FGI9_COLGU DNA polymerase lambda (Fragment) OS=*Colobus guereza* GN=POLL PE=2 SV=1;
>tr|E5FGK0|E5FGK0_CERWO DNA polymerase lambda (Fragment) OS=*Cercopithecus wolfi* GN=POLL PE=2 SV=1;
>tr|A0A0N8C1F3|A0A0N8C1F3_9CRUS DNA-directed DNA/RNA polymerase mu (Fragment) OS=*Daphnia magna* PE=4 SV=1;
>tr|G3T3S9|G3T3S9_LOXAF Uncharacterized protein OS=*Loxodonta africana* GN=POLL PE=4 SV=1;
>tr|W5Q4Y8|W5Q4Y8_SHEEP Uncharacterized protein OS=*Ovis aries* GN=POLL PE=4 SV=1;
>tr|A0A093PQD4|A0A093PQD4_9PASS DNA polymerase lambda OS=*Manacus vitellinus* GN=N305_05530 PE=4 SV=1;
>tr|A0A091EX6|A0A091EX6_CALAN DNA polymerase lambda OS=*Calypte anna* GN=N300_12499 PE=4 SV=1;
>tr|D2GXU6|D2GXU6_AILME Putative uncharacterized protein (Fragment) OS=*Ailuropoda melanoleuca* GN=PANDA_001756 PE=4 SV=1;
>tr|E5FGJ0|E5FGJ0_9PRIM DNA polymerase lambda (Fragment) OS=*Gorilla gorilla* GN=POLL PE=2 SV=1;
>tr|G1MGY1|G1MGY1_AILME Uncharacterized protein OS=*Ailuropoda melanoleuca* GN=POLL PE=4 SV=1;
>tr|G3QQQ5|G3QQQ5_GORGO Uncharacterized protein OS=*Gorilla gorilla gorilla* GN=POLL PE=4 SV=1;
>tr|Q245F6|Q245F6_TETTS Helix hairpin-helix protein OS=*Tetrahymena thermophila* (strain SB210) GN=TTHERM_00732550 PE=4 SV=2;
>tr|W5N189|W5N189_LEPOC Uncharacterized protein OS=*Lepisosteus oculatus* PE=4 SV=1; (SEQ ID NO: 73)
>tr|E5FGI7|E5FGI7_PONPY DNA polymerase lambda (Fragment) OS=*Pongo pygmaeus* GN=POLL PE=2 SV=1;
>tr|E5FGJ4|E5FGJ4_PONAB DNA polymerase lambda (Fragment) OS=*Pongo abelii* GN=POLL PE=2 SV=1;
>tr|H2NBD3|H2NBD3_PONAB Uncharacterized protein OS=*Pongo abelii* GN=POLL PE=4 SV=1;
>tr|H2ZVH2|H2ZVH2_LATCH Uncharacterized protein OS=*Latimeria chalumnae* GN=POLL PE=4 SV=1;
>tr|A0A0C9MT17|A0A0C9MT17_9FUNG DNA polymerase beta OS=*Mucor ambiguus* GN=MAM1_0127d06016 PE=4 SV=1;
>tr|G2HIX0|G2HIX0_PANTR DNA polymerase lambda OS=*Pan troglodytes* PE=2 SV=1;
>tr|E5FGI8|E5FGI8_MACFA DNA polymerase lambda (Fragment) OS=*Macaca fascicularis* GN=POLL PE=2 SV=1;
>tr|F7HD68|F7HD68_MACMU DNA polymerase lambda isoform a OS=*Macaca mulatta* GN=POLL PE=2 SV=1;
>sp|Q4R380|DPOLL_MACFA DNA polymerase lambda OS=*Macaca fascicularis* GN=POLL PE=2 SV=1;
>tr|W5N181|W5N181_LEPOC Uncharacterized protein OS=*Lepisosteus oculatus* PE=4 SV=1; (SEQ ID NO: 74)
>tr|A0A0L8GFS8|A0A0L8GFS8_OCTBM Uncharacterized protein OS=*Octopus bimaculoides* GN=OCBIM_22034122 mg PE=4 SV=1;
>tr|A0A0D0T025|A0A0D0T025_9TREE Unplaced genomic scaffold supercont1.13, whole genome shotgun sequence OS=*Cryptococcus gattii* VGII Ram5 GN=I313_05063 PE=4 SV=1;
>tr|A0A095DD01|A0A095DD01_CRYGR DNA polymerase mu subunit OS=*Cryptococcus gattii* serotype B (strain R265) GN=CNBG_4574 PE=4 SV=1;
>tr|A0A0K3C7E6|A0A0K3C7E6_RHOTO BY PROTMAP: gi|814541105|emb|CEQ41545.1| SPOSA6832_03302, partial [Sporidiobolus *salmonicolor*] OS=*Rhodosporidium toruloides* GN=FGENESH: predicted gene_1.231 PE=4 SV=1;
>tr|A0A091LTQ7|A0A091LTQ7_CATAU DNA polymerase lambda OS=*Cathartes aura* GN=N323_09789 PE=4 SV=1;
>tr|U5G1H1|U5G1H1_POPTR Uncharacterized protein OS=*Populus trichocarpa* GN=POPTR_0010s10490g PE=4 SV=1;
>tr|H9GI65|H9GI65_ANOCA Uncharacterized protein OS=*Anolis carolinensis* GN=POLL PE=4 SV=2;

>tr|E5FGI6|E5FGI6_9PRIM DNA polymerase lambda (Fragment) OS=*Lophocebus albigena* GN=POLL PE=2 SV=1;
>tr|E5FGJ3|E5FGJ3_PAPAN DNA polymerase lambda (Fragment) OS=*Papio anubis* GN=POLL PE=2 SV=1;
>tr|H2R0B4|H2R0B4_PANTR Polymerase (DNA directed), lambda OS=*Pan troglodytes* GN=POLL PE=2 SV=1;
>tr|A0A084QFP3|A0A084QFP3_9HYPO Uncharacterized protein OS=*Stachybotrys chlorohalonata* IBT 40285 GN=S40285_07550 PE=4 SV=1;
>tr|A0A0D6EPK6|A0A0D6EPK6_SPOSA SPOSA6832_03302-mRNA-1:cds (Fragment) OS=*Sporidiobolus salmonicolor* GN=SPOSA6832_03302 PE=4 SV=1;
>tr|G5CAF7|G5CAF7_HETGA DNA polymerase lambda OS=*Heterocephalus glaber* GN=GW7_15886 PE=4 SV=1;
>tr|A0A1S3AEZ4|A0A1S3AEZ4_ERIEU DNA polymerase lambda OS=*Erinaceus europaeus* GN=POLL PE=4 SV=1;
>tr|A0A067NJT6|A0A067NJT6_PLEOS Uncharacterized protein OS=*Pleurotus ostreatus* PC15 GN=PLEOSDRAFT_1041924 PE=4 SV=1;
>tr|A0A091J6I3|A0A091J6I3_9AVES DNA polymerase lambda OS=*Egretta garzetta* GN=Z169_01746 PE=4 SV=1;
>sp|Q5RKI3|DPOLL_RAT DNA polymerase lambda OS=*Rattus norvegicus* GN=Poll PE=2 SV=1;
>sp|Q9QXE2|DPOLL_MOUSE DNA polymerase lambda OS=*Mus musculus* GN=Poll PE=2 SV=1;
>tr|A0A1S3FAT0|A0A1S3FAT0_DIPOR DNA polymerase lambda OS=*Dipodomys ordii* GN=Poll PE=4 SV=1;
>tr|L8Y5V2|L8Y5V2_TUPCH DNA polymerase lambda OS=*Tupaia chinensis* GN=TREES_T100016491 PE=4 SV=1;
>tr|H2MC49|H2MC49_ORYLA Uncharacterized protein OS=*Oryzias latipes* PE=4 SV=1;
>tr|G9KHQ2|G9KHQ2_MUSPF Polymerase, lambda (Fragment) OS=*Mustela putorius* furo PE=2 SV=1;
>tr|A0A0C7BXF2|A0A0C7BXF2_9FUNG Uncharacterized protein OS=*Rhizopus microsporus* GN=RMATCC62417_10444 PE=4 SV=1;
>tr|A0A094KZ04|A0A094KZ04_ANTCR DNA polymerase lambda OS=*Antrostomus carolinensis* GN=N321_07972 PE=4 SV=1;
>tr|A0A091P384|A0A091P384_9PASS DNA polymerase lambda OS=*Acanthisitta chloris* GN=N310_03460 PE=4 SV=1;
>tr|A0A091MSF3|A0A091MSF3_CARIC DNA polymerase lambda OS=*Cariama cristata* GN=N322_09127 PE=4 SV=1;
>tr|A0A093GZ12|A0A093GZ12_PICPB DNA polymerase lambda OS=*Picoides pubescens* GN=N307_08772 PE=4 SV=1;
>tr|A0A091UJR4|A0A091UJR4_NIPNI DNA polymerase lambda OS=*Nipponia nippon* GN=Y956_01422 PE=4 SV=1;
>tr|A0A091TC67|A0A091TC67_PHALP DNA polymerase lambda OS=*Phaethon lepturus* GN=N335_05056 PE=4 SV=1;
>tr|M3YZQ5|M3YZQ5_MUSPF Uncharacterized protein OS=*Mustela putorius* furo GN=POLL PE=4 SV=1;
>tr|A0A091DMJ9|A0A091DMJ9_FUKDA DNA polymerase lambda OS=*Fukomys damarensis* GN=H920_06249 PE=4 SV=1;
>tr|B3S2V4|B3S2V4_TRIAD Putative uncharacterized protein (Fragment) OS=*Trichoplax adhaerens* GN=TRIADDRAFT_28268 PE=4 SV=1;
>tr|Q5JQP8|Q5JQP8_HUMAN DNA polymerase lambda OS=*Homo sapiens* GN=POLL PE=1 SV=1;
>tr|A0A0V0VHR8|A0A0V0VHR8_9BILA DNA polymerase lambda OS=*Trichinella* sp. T9 GN=T09_7096 PE=4 SV=1;
>tr|A0A0C3PWZ5|A0A0C3PWZ5_PISTI Uncharacterized protein OS=*Pisolithus tinctorius* Marx 270 GN=M404DRAFT_943795 PE=4 SV=1;
>tr|F7B5D1|F7B5D1_CHICK Uncharacterized protein OS=*Gallus gallus* GN=POLL PE=4 SV=1;
>tr|R0LAZ3|R0LAZ3_ANAPL DNA polymerase lambda (Fragment) OS=*Anas platyrhynchos* GN=Anapl_11657 PE=4 SV=1;
>tr|U3IRR6|U3IRR6_ANAPL Uncharacterized protein OS=*Anas platyrhynchos* GN=POLL PE=4 SV=1;
>tr|A0A093JIL1|A0A093JIL1_FULGA DNA polymerase lambda OS=*Fulmarus glacialis* GN=N327_08286 PE=4 SV=1;
>tr|A0A091PFQ4|A0A091PFQ4_HALAL DNA polymerase lambda OS=*Haliaeetus albicilla* GN=N329_11480 PE=4 SV=1;
>tr|A0A091NUB5|A0A091NUB5_APAVI DNA polymerase lambda OS=*Apaloderma vittatum* GN=N311_06514 PE=4 SV=1;
>tr|A0A091QAN1|A0A091QAM1_LEPDC DNA polymerase lambda OS=*Leptosomus discolor* GN=N330_07141 PE=4 SV=1;
>tr|C3YJ28|C3YJ28_BRAFL Putative uncharacterized protein (Fragment) OS=*Branchiostoma floridae* GN=BRAFLDRAFT_235602 PE=4 SV=1;
>tr|F1S8U1|F1S8U1_PIG Uncharacterized protein OS=*Sus scrofa* GN=POLL PE=4 SV=1;
>sp|Q9UGP5|DPOLL_HUMAN DNA polymerase lambda OS=*Homo sapiens* GN=POLL PE=1 SV=1;
>tr|A0A0C9ZIQ9|A0A0C9ZIQ9_9HOMO Unplaced genomic scaffold scaffold_56, whole genome shotgun sequence OS=*Pisolithus microcarpus* 441 GN=PISMIDRAFT_680433 PE=4 SV=1;
>tr|A0A093C072|A0A093C072_9AVES DNA polymerase lambda OS=*Pterocles gutturalis* GN=N339_07278 PE=4 SV=1;
>tr|A0A091RPW8|A0A091RPW8_9GRUI DNA polymerase lambda OS=*Mesitornis unicolor* GN=N332_09822 PE=4 SV=1;
>tr|A0A091U380|A0A091U380_PHORB DNA polymerase lambda OS=*Phoenicopterus ruber ruber* GN=N337_08802 PE=4 SV=1;
>tr|A0A0V1I8S4|A0A0V1I8S4_9BILA DNA polymerase lambda OS=*Trichinella zimbabwensis* GN=MRPL30 PE=4 SV=1;
>tr|U3K1T5|U3K1T5_FICAL Uncharacterized protein OS=*Ficedula albicollis* GN=POLL PE=4 SV=1;
>tr|F8PSZ2|F8PSZ2_SERL3 Putative uncharacterized protein OS=*Serpula lacrymans* var. *lacrymans* (strain S7.3) GN=SERLA73DRAFT_50337 PE=4 SV=1;
>tr|A0A091KJF3|A0A091KJF3_9GRUI DNA polymerase lambda OS=*Chlamydotis macqueenii* GN=N324_09478 PE=4 SV=1;
>tr|H9FT36|H9FT36_MACMU DNA polymerase lambda isoform a OS=*Macaca mulatta* GN=POLL PE=2 SV=1;

>tr|R7TPZ3|R7TPZ3_CAPTE Uncharacterized protein OS=*Capitella teleta* GN=CAPTEDRAFT_213338 PE=4 SV=1;
>tr|A0A093FDU6|A0A093FDU6_TYTAL DNA polymerase lambda OS=*Tyto alba* GN=N341_04059 PE=4 SV=1;
>tr|A0A0A0A008|A0A0A0A008_CHAVO DNA polymerase lambda OS=*Charadrius vociferus* GN=N301_14659 PE=4 SV=1;
>tr|M7AL53|M7AL53_CHEMY DNA polymerase lambda OS=*Chelonia mydas* GN=UY3_17041 PE=4 SV=1;
>tr|A0A146S619|A0A146S619_FUNHE DNA nucleotidylexotransferase OS=*Fundulus heteroclitus* PE=4 SV=1;
>tr|B9HVB4|B9HVB4_POPTR DNA polymerase lambda family protein OS=*Populus trichocarpa* GN=POPTR_0010s10490g PE=4 SV=1;
>tr|Q4S1W9|Q4S1W9_TETNG Chromosome undetermined SCAF14764, whole genome shotgun sequence OS=*Tetraodon nigroviridis* GN=GSTENG00025356001 PE=4 SV=1;
>tr|A0A094KN48|A0A094KN48_9AVES DNA polymerase lambda OS=*Podiceps cristatus* GN=N338_07866 PE=4 SV=1;
>tr|A0A060YCF7|A0A060YCF7_ONCMY Uncharacterized protein OS=*Oncorhynchus mykiss* GN=GSONMT00007442001 PE=4 SV=1;
>tr|HOX619|HOX619_OTOGA Uncharacterized protein OS=*Otolemur garnettii* GN=POLL PE=4 SV=1 (SEQ ID NO: 81);
>tr|A0A0S7LXJ4|A0A0S7LXJ4_9TELE DPOLL OS=*Poeciliopsis prolifica* GN=DPOLL PE=4 SV=1;
>tr|A0A091V6S1|A0A091V6S1_OPIHO DNA polymerase lambda OS=*Opisthocomus hoazin* GN=N306_14567 PE=4 SV=1;
>tr|V3ZZB0|V3ZZB0_LOTGI Uncharacterized protein (Fragment) OS=*Lottia gigantea* GN=LOTGIDRAFT_72491 PE=4 SV=1;
>tr|A0A0C3C9Q4|A0A0C3C9Q4_HEBCY Uncharacterized protein OS=*Hebeloma cylindrosporum* h7 GN=M413DRAFT_446505 PE=4 SV=1;
>tr|I3KRF4|I3KRF4_ORENI Uncharacterized protein OS=*Oreochromis niloticus* GN=wbpll PE=4 SV=1;
>tr|A0A093CA12|A0A093CA12_TAUER DNA polymerase lambda OS=*Tauraco erythrolophus* GN=N340_11190 PE=4 SV=1;
>tr|A0A0D2QDZ0|A0A0D2QDZ0_GOSRA Uncharacterized protein OS=*Gossypium raimondii* GN=B456_002G164200 PE=4 SV=1;
>tr|K9J1X8|K9J1X8_DESRO Putative dna polymerase iv family x OS=*Desmodus rotundus* PE=2 SV=1;
>tr|A0A146YFR1|A0A146YFR1_FUNHE DNA polymerase lambda OS=*Fundulus heteroclitus* PE=4 SV=1;
>tr|A0A0V1KGE2|A0A0V1KGE2_TRIPS DNA polymerase lambda OS=*Trichinella pseudospiralis* GN=Mrpl30 PE=4 SV=1;
>tr|S9WVS1|S9WVS1_CAMFR DNA polymerase lambda isoform a OS=*Camelus ferus* GN=CB1_000642026 PE=4 SV=1;
>tr|R7VD68|R7VD68_CAPTE Uncharacterized protein OS=*Capitella teleta* GN=CAPTEDRAFT_169992 PE=4 SV=1;
>tr|D8S132|D8S132_SELML Putative uncharacterized protein (Fragment) OS=*Selaginella moellendorffii* GN=SELMODRAFT_106459 PE=4 SV=1;
>tr|A0A0D2U5A1|A0A0D2U5A1_CAPO3 Uncharacterized protein OS=*Capsaspora owczarzaki* (strain ATCC 30864) GN=CAOG_001654 PE=4 SV=1;
>tr|A0A0N5DI78|A0A0N5DI78_TRIMR Uncharacterized protein OS=*Trichuris muris* PE=4 SV=1;
>tr|A0A0V1EYE1|A0A0V1EYE1_TRIPS DNA polymerase lambda OS=*Trichinella pseudospiralis* GN=POLL PE=4 SV=1;
>tr|A0A146YDH9|A0A146YDH9_FUNHE DNA polymerase lambda OS=*Fundulus heteroclitus* PE=4 SV=1;
>tr|A0A1S3L5G2|A0A1S3L5G2_SALSA DNA polymerase lambda-like OS=*Salmo salar* GN=LOC106564589 PE=4 SV=1;
>tr|Q7SXH7|Q7SXH7_DANRE Poll protein OS=*Danio rerio* GN=poll PE=2 SV=1;
>tr|M3ZCZ7|M3ZCZ7_XIPMA Uncharacterized protein OS=*Xiphophorus maculatus* PE=4 SV=1;
>tr|A0A146YDI0|A0A146YDI0_FUNHE DNA polymerase lambda OS=*Fundulus heteroclitus* PE=4 SV=1;
>tr|D8Q9V7|D8Q9V7_SCHCM Putative uncharacterized protein OS=*Schizophyllum commune* (strain H4-8/FGSC 9210) GN=SCHCODRAFT_57262 PE=4 SV=1;
>tr|Q6POS1|Q6POS1_DANRE Polymerase (DNA directed), lambda OS=*Danio rerio* GN=poll PE=2 SV=1;
>tr|B8JIE9|B8JIE9_DANRE Polymerase (DNA directed), lambda OS=*Danio rerio* GN=poll PE=4 SV=1;
>tr|A0A0V0YDC0|A0A0V0YDC0_TRIPS DNA polymerase lambda OS=*Trichinella pseudospiralis* GN=Mrpl30 PE=4 SV=1;
>tr|A0A146NC85|A0A146NC85_FUNHE DNA polymerase lambda OS=*Fundulus heteroclitus* PE=4 SV=1;
>tr|A0A147AV47|A0A147AV47_FUNHE DNA polymerase lambda OS=*Fundulus heteroclitus* PE=4 SV=1;
>tr|A0A0V1MQR6|A0A0V1MQR6_9BILA DNA polymerase lambda OS=*Trichinella papuae* GN=MRPL30 PE=4 SV=1;
>tr|A0A061E5V2|A0A061E5V2_THECC DNA polymerase lambda (POLL) isoform 5 OS=*Theobroma cacao* GN=TCM_010205 PE=4 SV=1;
>tr|M7WSS0|M7WSS0_RHOT1 Beta dna polymerase OS=*Rhodosporidium toruloides* (strain NP11) GN=RHTO_01992 PE=4 SV=1;
>tr|A0A061APG6|A0A061APG6_RHOTO RHTO0S04e05468g1_1 OS=*Rhodosporidium toruloides* GN=RHTO0S_04e05468g PE=4 SV=1;
>tr|A0A061E5Q9|A0A061E5Q9_THECC DNA polymerase lambda (POLL) isoform 4 OS=*Theobroma cacao* GN=TCM_010205 PE=4 SV=1;
>tr|A0A0V0RKB0|A0A0V0RKB0_9BILA DNA polymerase lambda OS=*Trichinella nelsoni* GN=POLL PE=4 SV=1;
>tr|A0A091G5J5|A0A091G5J5_9AVES DNA polymerase lambda OS=*Cuculus canorus* GN=N303_14197 PE=4 SV=1;
>tr|A0A1A7XC13|A0A1A7XC13_9TELE Polymerase (DNA directed), lambda OS=*Aphyosemion striatum* GN=POLL PE=4 SV=1;
>tr|A0A1A8VFI7|A0A1A8VFI7_NOTFU Polymerase (DNA directed), lambda (Fragment) OS=*Nothobranchius furzeri* GN=POLL PE=4 SV=1;
>tr|A0A1A7YLF9|A0A1A7YLF9_9TELE Polymerase (DNA directed), lambda (Fragment) OS=*Aphyosemion striatum* GN=POLL PE=4 SV=1;

>tr|A0A1A8AAH4|A0A1A8AAH4_NOTFU Polymerase (DNA directed), lambda (Fragment) OS=*Nothobranchius furzeri* GN=POLL PE=4 SV=1;

>tr|D8ROV4|D8ROV4_SELML Putative uncharacterized protein (Fragment) OS=*Selaginella moellendorffii* GN=SELMODRAFT_83116 PE=4 SV=1;

>tr|A0A135TQY6|A0A135TQY6_9PEZI Uncharacterized protein OS=*Colletotrichum nymphaeae* SA-01 GN=CNYM01_13026 PE=4 SV=1;

>tr|A0A0C9TIH7|A0A0C9TIH7_PAXIN Unplaced genomic scaffold PAXINscaffold_14, whole genome shotgun sequence OS=*Paxillus involutus* ATCC 200175 GN=PAXINDRAFT_77120 PE=4 SV=1;

>tr|A0A087VCA5|A0A087VCA5_BALRE DNA polymerase lambda OS=*Balearica regulorum gibbericeps* GN=N312_03659 PE=4 SV=1;

>tr|W5LHN1|W5LHN1_ASTMX Uncharacterized protein OS=*Astyanax mexicanus* PE=4 SV=1;

>tr|A0A0V1MQQ1|A0A0V1MQQ1_9BILA DNA polymerase lambda OS=*Trichinella papuae* GN=MRPL30 PE=4 SV=1;

>tr|A0A0D2NNZ0|A0A0D2NNZ0_GOSRA Uncharacterized protein OS=*Gossypium raimondii* GN=B456_002G164200 PE=4 SV=1;

>tr|A0A0V0ZUW5|A0A0V0ZUW5_9BILA DNA polymerase lambda OS=*Trichinella patagoniensis* GN=POLL PE=4 SV=1;

>tr|A0A1E1MHN8|A0A1E1MHN8_RHYSE Related to DNA polymerase Tdt-N OS=*Rhynchosporium secalis* GN=RSE6_09304 PE=4 SV=1;

>tr|A0A1B9GPF0|A0A1B9GPF0_9TREE DNA polymerase mu subunit OS=*Kwoniella heveanensis* BCC8398 GN=I316_05288 PE=4 SV=1;

>tr|A0A1B9H8T1|A0A1B9H8T1_9TREE DNA polymerase mu subunit OS=*Kwoniella heveanensis* CBS 569 GN=I317_06553 PE=4 SV=1;

>tr|A0A022QLW0|A0A022QLW0_ERYGU Uncharacterized protein OS=*Erythranthe guttata* GN=MIMGU_mgv1a026593 mg PE=4 SV=1;

>tr|A0A074YMR2|A0A074YMR2_9PEZI Uncharacterized protein OS=*Aureobasidium subglaciale* EXF-2481 GN=AUEXF2481DRAFT_217585 PE=4 Sv=1;

>tr|M7WGS7|M7WGS7_RHOT1 Beta dna polymerase OS=*Rhodosporidium toruloides* (strain NP11) GN=RHTO_04182 PE=4 SV=1;

>tr|S9RKH6|S9RKH6_SCHOY DNA polymerase Xfamily OS=*Schizosaccharomyces octosporus* (strain yFS286) GN=SOCG_01968 PE=4 SV=1;

>tr|A0A1S3KIF7|A0A1S3KIF7_LINUN DNA polymerase lambda-like isoform X1 OS=*Lingula unguis* GN=LOC106181965 PE=4 SV=1;

>tr|A0A0V0ZUB3|A0A0V0ZUB3_9BILA DNA polymerase lambda OS=*Trichinella patagoniensis* GN=POLL PE=4 SV=1;

>tr|A0A0P7UXQ3|A0A0P7UXQ3_9TELE Uncharacterized protein (Fragment) OS=*Scleropages formosus* GN=Z043_105872 PE=4 SV=1;

>tr|A0A1A8MRC5|A0A1A8MRC5_9TELE Polymerase (DNA directed), lambda (Fragment) OS=*Nothobranchius pienaari* GN=POLL PE=4 SV=1;

>tr|J3MCS5|J3MCS5_ORYBR Uncharacterized protein OS=*Oryza brachyantha* PE=4 SV=1;

>tr|A0A1A8DI13|A0A1A8DI13_9TELE Polymerase (DNA directed), lambda OS=*Nothobranchius kadleci* GN=POLL PE=4 SV=1;

>tr|H2ULE5|H2ULE5_TAKRU Uncharacterized protein OS=*Takifugu rubripes* GN=poll PE=4 SV=1;

>tr|A0A087XHB2|A0A087XHB2_POEFO Uncharacterized protein OS=*Poecilia formosa* PE=4 SV=1;

>tr|A0A1A8P4I0|A0A1A8P4I0_9TELE Polymerase (DNA directed), lambda OS=*Nothobranchius rachovii* GN=POLL PE=4 SV=1;

>tr|A0A1A8QT58|A0A1A8QT58_9TELE Polymerase (DNA directed), lambda OS=*Nothobranchius rachovii* GN=POLL PE=4 SV=1;

>tr|A0A1A8M358|A0A1A8M358_9TELE Polymerase (DNA directed), lambda OS=*Nothobranchius pienaari* GN=POLL PE=4 SV=1;

>tr|A0A1A8II81|A0A1A8II81_NOTKU Polymerase (DNA directed), lambda OS=*Nothobranchius kuhntae* GN=POLL PE=4 SV=1;

>tr|L8G8G3|L8G8G3_PSED2 Uncharacterized protein OS=*Pseudogymnoascus destructans* (strain ATCC MYA-4855/20631-21) GN=GMDG_03600 PE=4 SV=1;

>tr|A0A177A4J2|A0A177A4J2_9PEZI Uncharacterized protein OS=*Pseudogymnoascus destructans* GN=VC83_05832 PE=4 SV=1;

>tr|A0A010RYY6|A0A010RYY6_9PEZI Uncharacterized protein OS=*Colletotrichum fioriniae* PJ7 GN=CFIO01_13046 PE=4 SV=1;

>tr|A0A1A8KDR9|A0A1A8KDR9_NOTKU Polymerase (DNA directed), lambda (Fragment) OS=*Nothobranchius kuhntae* GN=POLL PE=4 SV=1;

>tr|A0A1A8R1Y2|A0A1A8R1Y2_9TELE Polymerase (DNA directed), lambda OS=*Nothobranchius pienaari* GN=POLL PE=4 SV=1;

>tr|A0A0C3E7J0|A0A0C3E7J0_9HOMO Uncharacterized protein OS=*Scleroderma citrinum* Foug A GN=SCLCIDRAFT_116236 PE=4 SV=1;

>tr|K7FIX4|K7FIX4_PELSI Uncharacterized protein OS=*Pelodiscus sinensis* GN=POLL PE=4 SV=1;

>tr|K7FIW4|K7FIW4_PELSI Uncharacterized protein OS=*Pelodiscus sinensis* GN=POLL PE=4 SV=1;

>tr|A0A0V0VI93|A0A0V0VI93_9BILA DNA polymerase lambda OS=*Trichinella* sp. T9 GN=T09_7096 PE=4 SV=1;

>tr|T1ERD2|T1ERD2_HELRO Uncharacterized protein OS=*Helobdella robusta* GN=HELRODRAFT_161346 PE=4 SV=1;

>tr|A0A1A6A4X0|A0A1A6A4X0_9TREE DNA polymerase mu subunit OS=*Kwoniella dejecticola* CBS 10117 GN=I303_04440 PE=4 SV=1;

>tr|A0A1A8QJY3|A0A1A8QJY3_9TELE Polymerase (DNA directed), lambda OS=*Nothobranchius rachovii* GN=POLL PE=4 SV=1;

>tr|A0A166QWC5|A0A166QWC5_9HOMO Nucleotidyltransferase OS=*Fibulorhizoctonia* sp. CBS 109695 GN=FIBSPDRAFT_853496 PE=4 SV=1;

>tr|A0A135TFZ2|A0A135TFZ2_9PEZI Uncharacterized protein OS=*Colletotrichum simmondsii* GN=CSIM01_09367 PE=4 SV=1;

>sp|Q09693|DPO4_SCHPO DNA polymerase type-X family protein pol4 OS=*Schizosaccharomyces pombe* (strain 972/ATCC 24843) GN=pol4 PE=3 SV=1;

>tr|A0A0V1P3A7|A0A0V1P3A7_9BILA DNA polymerase lambda OS=*Trichinella* sp. T8 GN=POLL PE=4 SV=1;

>tr|A0A0V1LPY1|A0A0V1LPY1_9BILA DNA polymerase lambda OS=*Trichinella nativa* GN=POLL PE=4 SV=1;

>tr|A0A1E1L8R7|A0A1E1L8R7_9HELO Related to DNA polymerase Tdt-N OS=*Rhynchosporium commune* GN=RCO7_07163 PE=4 SV=1;

>tr|A0A1B9G359|A0A1B9G359_9TREE DNA polymerase mu subunit OS=*Kwoniella bestiolae* CBS 10118 GN=I302_05273 PE=4 SV=1;
>tr|A0A1A8GWF2|A0A1A8GWF2_9TELE Polymerase (DNA directed), lambda (Fragment) OS=*Nothobranchius korthausae* GN=POLL PE=4 SV=1;
>tr|A0A0V1P3B3|A0A0V1P3B3_9BILA DNA polymerase lambda OS=*Trichinella* sp. T8 GN=POLL PE=4 SV=1;
>tr|A0A0V1LPY7|A0A0V1LPY7_9BILA DNA polymerase lambda OS=*Trichinella nativa* GN=POLL PE=4 SV=1;
>tr|A0A1A8FGG8|A0A1A8FGG8_9TELE Polymerase (DNA directed), lambda (Fragment) OS=*Nothobranchius korthausae* GN=POLL PE=4 SV=1;
>tr|A0A0V1IBA1|A0A0V1IBA1_9BILA DNA polymerase lambda OS=*Trichinella zimbabwensis* GN=MRPL30 PE=4 SV=1;
>tr|X6MW96|X6MW96_RETFI DNA-directed DNA polymerase lambda (Fragment) OS=*Reticulomyxa filosa* GN=RFI_18997 PE=4 SV=1;
>tr|F6VFI0|F6VFI0_HORSE Uncharacterized protein OS=*Equus caballus* GN=POLL PE=4 SV=1;
>tr|A0A1E1K5W1|A0A1E1K5W1_9HELO Related to DNA polymerase Tdt-N OS=*Rhynchosporium agropyri* GN=RAG0_03773 PE=4 SV=1;
>tr|A0A0D2MBV9|A0A0D2MBV9_GOSRA Uncharacterized protein OS=*Gossypium raimondii* GN=B456_002G164200 PE=4 SV=1;
>tr|A0A1D1UV65|A0A1D1UV65_RAMVA Uncharacterized protein OS=*Ramazzottius varieornatus* GN=RvY_04493-1 PE=4 SV=1;
>tr|M2MR12|M2MR12_BAUCO Uncharacterized protein OS=*Baudoinia compniacensis* (strain UAMH 10762) GN=BAUCODRAFT_85556 PE=4 SV=1;
>tr|A0A0V1D247|A0A0V1D247_TRIBR DNA polymerase lambda OS=*Trichinella britovi* GN=POLL PE=4 SV=1;
>tr|A0A0V0WMC1|A0A0V0WMC1_9BILA DNA polymerase lambda OS=*Trichinella* sp. T6 GN=POLL PE=4 SV=1;
>tr|GOQLY3|GOQLY3_ICHMG DNA-directed polymerase lambda, putative (Fragment) OS=*Ichthyophthirius multifiliis* (strain G5) GN=IMG5_038620 PE=4 SV=1;
>tr|A0A093ZS11|A0A093ZS11_9PEZI Uncharacterized protein OS=*Pseudogymnoascus* sp. VKM F-3775 GN=V491_04165 PE=4 SV=1;
>tr|A0A0P4VZD0|A0A0P4VZD0_9EUCA Uncharacterized protein OS=*Scylla olivacea* PE=4 SV=1;
>tr|G3Q2Q6|G3Q2Q6_GASAC Uncharacterized protein OS=*Gasterosteus aculeatus* PE=4 SV=1;
>tr|A0A1A8Q5T7|A0A1A8Q5T7_9TELE Polymerase (DNA directed), mu (Fragment) OS=*Nothobranchius rachovii* GN=POLM PE=4 SV=1;
>tr|A0A0V1D263|A0A0V1D263_TRIBR DNA polymerase lambda OS=*Trichinella britovi* GN=POLL PE=4 SV=1;
>tr|A0A0V1BLL4|A0A0V1BLL4_TRISP DNA polymerase lambda OS=*Trichinella spiralis* GN=POLL PE=4 SV=1;
>tr|A0A1B8CG84|A0A1B8CG84_9PEZI Uncharacterized protein OS=*Pseudogymnoascus* sp. WSF 3629 GN=VE00_03848 PE=4 SV=1;
>tr|E2LZ52|E2LZ52_MONPE Uncharacterized protein (Fragment) OS=*Moniliophthora perniciosa* (strain FA553/isolate CPO2) GN=MPER_12617 PE=4 SV=1;
>tr|A0A072TY09|A0A072TY09_MEDTR DNA polymerase lambda-like protein OS=*Medicago truncatula* GN=MTR_7g039450 PE=4 SV=1;
>tr|A0A176WNC6|A0A176WNC6_MARPO Uncharacterized protein OS=*Marchantia polymorpha* subsp. *polymorpha* GN=AXG93_1487s1150 PE=4 SV=1;
>tr|A0A194W3X9|A0A194W3X9_9PEZI DNA polymerase type-X family protein pol4 OS=*Valsa mali* GN=VM1G_06647 PE=4 SV=1;
>tr|A0A0V1LPX0|A0A0V1LPX0_9BILA DNA polymerase lambda OS=*Trichinella nativa* GN=POLL PE=4 SV=1;
>tr|A0A0D9WNQ5|A0A0D9WNQ5_90RYZ Uncharacterized protein OS=*Leersia perrieri* PE=4 SV=1;
>tr|A0A0V1BMJ0|A0A0V1BMJ0_TRISP DNA polymerase lambda OS=*Trichinella spiralis* GN=POLL PE=4 SV=1;
>tr|A0A139AY58|A0A139AY58_GONPR Nucleotidyltransferase OS=*Gonapodya prolifera* JEL478 GN=M427DRAFT_276455 PE=4 SV=1;
>tr|A0A1B8FTY4|A0A1B8FTY4_9PEZI Uncharacterized protein OS=*Pseudogymnoascus* sp. 03VT05 GN=VE02_03686 PE=4 SV=1;
>tr|A0A059D505|A0A059D505_EUCGR Uncharacterized protein OS=*Eucalyptus grandis* GN=EUGRSUZ_B02561 PE=4 SV=1;
>tr|H3D3G8|H3D3G8_TETNG Uncharacterized protein OS=*Tetraodon nigroviridis* PE=4 SV=1;
>tr|A0A1S3DX16|A0A1S3DX16_CICAR DNA polymerase beta isoform X2 OS=*Cicer arietinum* GN=LOC101499677 PE=4 SV=1;
>tr|A0A1S2Z862|A0A1S2Z862_CICAR DNA polymerase beta isoform X1 OS=*Cicer arietinum* GN=LOC101499677 PE=4 SV=1;
>tr|A0A0J8BWQ9|A0A0J8BWQ9_BETVU Uncharacterized protein OS=*Beta vulgaris* subsp. *vulgaris* GN=BVRB_8g181170 PE=4 SV=1;
>tr|A0A0B0MKA5|A0A0B0MKA5_GOSAR DNA polymerase lambda OS=*Gossypium arboreum* GN=F383_21525 PE=4 SV=1;
>tr|A0A1B8EAE0|A0A1B8EAE0_9PEZI Uncharacterized protein OS=*Pseudogymnoascus* sp. 23342-1-I1 GN=VE03_02256 PE=4 SV=1;
>tr|A0A194V4W0|A0A194V4W0_9PEZI DNA polymerase type-X family protein pol4 OS=*Valsa mali* var. *pyri* GN=VP1G_06122 PE=4 SV=1;
>sp|Q67VC8|DPOLL_ORYSJ DNA polymerase lambda OS=*Oryza sativa* subsp. *japonica* GN=POLL PE=1 SV=1;
>tr|A0A0S7|WG7|A0A0S7|WG7_9TELE TDT OS=*Poeciliopsis prolifica* GN=TDT PE=4 SV=1;
>tr|A0A1B8F877|A0A1B8F877_9PEZI Uncharacterized protein OS=*Pseudogymnoascus* sp. 05NY08 GN=VF21_01476 PE=4 SV=1;
>tr|S2KCR4|S2KCR4_MUCC1 Uncharacterized protein OS=*Mucor circinelloides* f. *circinelloides* (strain 1006PhL) GN=HMPREF1544_03081 PE=4 SV=1;
>tr|A0A1E1XQK5|A0A1E1XQK5_9ACAR Putative dna polymerase lambda OS=*Amblyomma sculptum* PE=2 SV=1;
>tr|A0A086T1M2|A0A086T1M2_ACRC1 DNA polymerase type-X family protein-like protein OS=*Acremonium chrysogenum* (strain ATCC 11550/

CBS 779.69/DSM 880/JCM 23072/IMI 49137) GN=ACRE_059880 PE=4 SV=1;

>tr|A0A0V0WM43|A0A0V0WM43_9BILA DNA polymerase lambda OS=*Trichinella* sp. T6 GN=POLL PE=4 SV=1;

>tr|B9FSE5|B9FSE5_ORYSJ Uncharacterized protein OS=*Oryza sativa* subsp. *japonica* GN=OsJ_20743 PE=4 SV=1;

>tr|A0A094D6X3|A0A094D6X3_9PEZI Uncharacterized protein OS=*Pseudogymnoascus* sp. VKM F-4281 (FW-2241) GN=V493_01816 PE=4 SV=1;

>tr|A0A0B2NZB6|A0A0B2NZB6_GLYSO DNA polymerase lambda OS=*Glycine soja* GN=glysoja 000287 PE=4 SV=1;

>tr|I1JCZ1|I1JCZ1_SOYBN Uncharacterized protein OS=*Glycine max* GN=LOC100820492 PE=4 SV=2;

>tr|A0A135S367|A0A135S367_9PEZI Uncharacterized protein OS=*Colletotrichum salicis* GN=CSAL01_00528 PE=4 SV=1;

>tr|A0A131XSZ4|A0A131XSZ4_IXORI Putative dna polymerase lambda OS=*Ixodes ricinus* PE=2 SV=1;

>tr|F7HD66|F7HD66_MACMU Uncharacterized protein OS=*Macaca mulatta* GN=POLL PE=4 SV=2;

>tr|A0A0F7SFU3|A0A0F7SFU3_PHARH DNA polymerase IV (Family X) OS=*Phaffia rhodozyma* PE=4 SV=1;

>tr|A0A0V1G2E9|A0A0V1G2E9_TRIPS DNA polymerase lambda OS=*Trichinella pseudospiralis* GN=POLL PE=4 SV=1;

>tr|A0A0V1I9X7|A0A0V1I9X7_9BILA DNA polymerase lambda OS=*Trichinella zimbabwensis* GN=MRPL30 PE=4 SV=1;

>tr|A0A0S3T9T5|A0A0S3T9T5_PHAAN Uncharacterized protein OS=*Vigna angularis* var. *angularis* GN=Vigan.11G102700 PE=4 SV=1;

>tr|A0A1S3V956|A0A1S3V956_VIGRR DNA polymerase beta isoform X2 OS=*Vigna radiata* var. *radiata* GN=LOC106772788 PE=4 SV=1;

>tr|V4VGR5|V4VGR5_9ROSI Uncharacterized protein OS=*Citrus clementina* GN=CICLE_v10031184 mg PE=4 SV=1;

>tr|A0A067H4W7|A0A067H4W7_CITSI Uncharacterized protein OS=*Citrus sinensis* GN=CISIN_1g0093031 mg PE=4 SV=1;

>tr|A0A0V1EY07|A0A0V1EY07_TRIPS DNA polymerase lambda OS=*Trichinella pseudospiralis* GN=POLL PE=4 SV=1;

>tr|A0A1S3V9I3|A0A1S3V9I3_VIGRR DNA polymerase beta isoform X1 OS=*Vigna radiata* var. *radiata* GN=LOC106772788 PE=4 SV=1;

>tr|A0A1G4ATK0|A0A1G4ATK0_9PEZI Uncharacterized protein OS=*Colletotrichum orchidophilum* GN=CORC01_12287 PE=4 SV=1;

>tr|G7KDW6|G7KDW6_MEDTR DNA polymerase lambda-like protein OS=*Medicago truncatula* GN=MTR_5g040170 PE=4 SV=1;

>tr|A0A0V0YEE1|A0A0V0YEE1_TRIPS DNA polymerase lambda OS=*Trichinella pseudospiralis* GN=Mrpl30 PE=4 SV=1;

>tr|D8SG82|D8SG82_SELML Putative uncharacterized protein OS=*Selaginella moellendorffii* GN=SELMODPAFT 155063 PE=4 SV=1;

>tr|A0A0V1BLX4|A0A0V1BLX4_TRISP DNA polymerase lambda OS=*Trichinella spiralis* GN=POLL PE=4 SV=1;

>tr|S8A5W2|S8A5W2_DACHA Uncharacterized protein OS=*Dactylellina haptotyla* (strain CBS 200.50) GN=H072_8085 PE=4 SV=1;

>tr|A0A0V0IDD6|A0A0V0IDD6_SOLCH Putative DNA polymerase lambda-like OS=*Solanum chacoense* PE=4 SV=1;

>tr|M1ER80|M1ER80_MUSPF Deoxynucleotidyltransferase, terminal (Fragment) OS=*Mustela putorius* furo PE=2 SV=1;

>tr|A0A094H117|A0A094H117_9PEZI Uncharacterized protein OS=*Pseudogymnoascus* sp. VKM F-4520 (FW-2644) GN=V502_09208 PE=4 SV=1;

>tr|A0A094G3V5|A0A094G3V5_9PEZI Uncharacterized protein OS=*Pseudogymnoascus* sp. VKM F-4518 (FW-2643) GN=V500_04993 PE=4 SV=1;

>tr|W4GGX8|W4GGX8_9STRA Uncharacterized protein OS=*Aphanomyces astaci* GN=H257_07734 PE=4 SV=1;

>tr|A0A179FSW3|A0A179FSW3_METCM DNA polymerase beta OS=*Pochonia chlamydosporia* 170 GN=VFPPC_04534 PE=4 SV=1;

>tr|A0A1J3FA13|A0A1J3FA13_NOCCA DNA polymerase lambda (Fragment) OS=*Noccaea caerulescens* GN=LC TR10189_c0_g1_i1_g.35893 PE=4 SV=1;

>tr|G2Q7Z8|G2Q7Z8_MYCTT Uncharacterized protein OS=*Myceliophthora thermophila* (strain ATCC 42464/BCRC 31852/DSM 1799) GN=MYCTH_2300738 PE=4 SV=1;

>tr|A0A067JBU8|A0A067JBU8_JATCU Uncharacterized protein OS=*Jatropha curcas* GN=JCGZ_21772 PE=4 SV=1;

>tr|K1VA66|K1VA66_TRIAC Beta DNA polymerase OS=*Trichosporon asahii* var. *asahii* (strain CBS 8904) GN=A1Q2_04783 PE=4 SV=1;

>tr|J5RIV1|J5RIV1_TRIAS Beta DNA polymerase OS=*Trichosporon asahii* var. *asahii* (strain ATCC 90039/CBS 2479/JCM 2466/KCTC 7840/NCYC 2677/UAMH 7654) GN=A1Q1_00793 PE=4 SV=1;

>tr|B8B4F7|B8B4F7_ORYSI Putative uncharacterized protein OS=*Oryza sativa* subsp. *indica* GN=OsI_22314 PE=4 SV=1;

>tr|M3AHI8|M3AHI8_PSEFD Uncharacterized protein OS=*Pseudocercospora fijiensis* (strain CIRAD86) GN=MYCFIDRAFT_162909 PE=4 SV=1;

>tr|A0A132B5Z1|A0A132B5Z1_9HELO Nucleotidyltransferase OS=*Phialocephala scopiformis* GN=LY89DRAFT_602043 PE=4 SV=1;

>tr|F0WG97|F0WG97_9STRA DNA polymerase lambdalike protein putative OS=*Albugo laibachii* Nc14 GN=A1Nc14C89G5627 PE=4 SV=1;

>tr|N1RVS6|N1RVS6_FUSC4 Putative DNA polymerase family X C2F7.06c OS=*Fusarium oxysporum* f. sp. *cubense* (strain race 4) GN=FOC4_g10006769 PE=4 SV=1;

>tr|XOJME1|XOJME1_FUSOX DNA polymerase IV OS=*Fusarium oxysporum* f. sp. *cubense* tropical race 4_54006 GN=FOIG_06662 PE=4 SV=1;

>tr|A0A0V0VHS7|A0A0V0VHS7_9BILA DNA polymerase lambda OS=*Trichinella* sp. T9 GN=T09_7096 PE=4 SV=1;

>tr|A0A0L1HPA7|A0A0L1HPA7_9PLEO Dna polymerase beta-like protein OS=*Stemphylium lycopersici* GN=TW65_05101 PE=4 SV=1;

>tr|A0A094CYS0|A0A094CYS0_9PEZI Uncharacterized protein OS=*Pseudogymnoascus* sp. VKM F-4516 (FW-969) GN=V497_05751 PE=4 SV=1;

>tr|A0A147BMR3|A0A147BMR3_IXORI Putative dna polymerase lambda OS=*Ixodes ricinus* PE=4 SV=1;
>tr|A0A1I8H3S8|A0A1I8H3S8_9PLAT Uncharacterized protein OS=*Macrostomum lignano* PE=4 SV=1;
>tr|A0A1R3FX17|A0A1R3FX17_9ROSI Uncharacterized protein OS=*Corchorus olitorius* GN=COLO4_38096 PE=4 SV=1;
>tr|A0A0L0DBR4|A0A0L0DBR4_THETB PolI protein OS=*Thecamonas trahens* ATCC 50062 GN=AMSG 06060 PE=4 SV=1;
>tr|N1PTU7|N1PTU7_DOTSN Uncharacterized protein OS=*Dothistroma septosporum* (strain NZE10/CBS 128990) GN=DOTSEDRAFT_71509 PE=4 SV=1;
>tr|A0A0V0TT93|A0A0V0TT93_9BILA DNA polymerase lambda OS=*Trichinella murrelli* GN=POLL PE=4 SV=1;
>tr|F8NSL8|F8NSL8_SERL9 Putative uncharacterized protein OS=*Serpula lacrymans* var. *lacrymans* (strain S7.9) GN=SERLADRAFT_447668 PE=4 SV=1;
>tr|A0A0V0TT82|A0A0V0TT82_9BILA DNA polymerase lambda OS=*Trichinella murrelli* GN=POLL PE=4 SV=1;
>tr|A0A093ZF85|A0A093ZF85_9PEZI Uncharacterized protein OS=*Pseudogymnoascus* sp. VKM F-4246 GN=V492_01628 PE=4 SV=1;
>tr|V9KZ36|V9KZ36_CALMI DNA polymerase lambda-like protein OS=*Callorhinchus milii* PE=2 SV=1;
>tr|V4KDK3|V4KDK3_EUTSA Uncharacterized protein OS=*Eutrema salsugineum* GN=EUTSA_v10009477 mg PE=4 SV=1;
>tr|A0A1S3BFG3|A0A1S3BFG3_CUCME DNA polymerase beta isoform X3 OS=*Cucumis melo* GN=LOC103489040 PE=4 SV=1;
>tr|A0A1J3E083|A0A1J3E083_NOCCA DNA polymerase lambda (Fragment) OS=*Noccaea caerulescens* GN=GA TR19700_ci_g1_i1_g.65036 PE=4 SV=1;
>tr|I1Q121|I1Q121_ORYGL Uncharacterized protein OS=*Oryza glaberrima* PE=4 SV=1;
>tr|A0A093Y3X2|A0A093Y3X2_9PEZI Uncharacterized protein OS=*Pseudogymnoascus* sp. VKM F-3557 GN=V490_02785 PE=4 SV=1;
>tr|A0A1B9|ZN9|A0A1B9|ZN9_9TREE DNA polymerase mu subunit OS=*Kwoniella mangroviensis* CBS 10435 GN=L486_00649 PE=4 SV=1;
>tr|A0A0K6FNH4|A0A0K6FNH4_9HOMO Uncharacterized protein OS=*Rhizoctonia solani* GN=dntt PE=4 SV=1;
>tr|F7CJ14|F7CJ14_CALJA Uncharacterized protein OS=*Callithrix jacchus* GN=POLL PE=4 SV=1;
>tr|A0A1S3QOV2|A0A1S3QOV2_SALSA DNA polymerase lambda-like isoform X1 OS=*Salmo salar* GN=LOC106588764 PE=4 SV=1;
>tr|K3XW78|K3XW78_SETIT Uncharacterized protein OS=*Setaria italica* GN=LOC101782419 PE=4 SV=1;
>tr|ROK168|ROK168_SETT2 Uncharacterized protein OS=*Setosphaeria turcica* (strain 28A) GN=SETTUDRAFT_139964 PE=4 SV=1;
>tr|F9F942|F9F942_FUSOF Uncharacterized protein OS=*Fusarium oxysporum* (strain Fo5176) GN=FOXB_02917 PE=4 SV=1;
>tr|X0IJN7|X0IJN7_FUSOX DNA polymerase IV OS=*Fusarium oxysporum* f. sp. *conglutinans* race 2_54008 GN=FOPG_03355 PE=4 SV=1;
>tr|S4R571|S4R571_PETMA Uncharacterized protein OS=*Petromyzon marinus* PE=4 SV=1;
>tr|A0A136J6M4|A0A136J6M4_9PEZI Uncharacterized protein OS=*Microdochium bolleyi* GN=MicbolqcDRAFT_232520 PE=4 SV=1;
>tr|I1GZF6|I1GZF6_BRADI Uncharacterized protein OS=*Brachypodium distachyon* GN=LOC100827137 PE=4 SV=1;
>tr|K5UUC0|K5UUC0_PHACS Uncharacterized protein OS=*Phanerochaete carnosa* (strain HHB-10118-sp) GN=PHACADRAFT_176005 PE=4 SV=1;
>tr|A0A1D6NRF5|A0A1D6NRF5_MAIZE DNA polymerase lambda (POLL) OS=*Zea mays* GN=ZEAMMB73_Zm00001d044780 PE=4 SV=1;
>tr|A0A1Q3DD56|A0A1Q3DD56_CEPFO NTP_transf_2 domain-containing protein/DNA_pol_lambd_f domain-containing protein OS=*Cephalotus follicularis* GN=CFOL_v3_33823 PE=4 SV=1;
>tr|XODAE4|XODAE4_FUSOX DNA polymerase IV OS=*Fusarium oxysporum* f. sp. *raphani* 54005 GN=FOQG_06295 PE=4 SV=1;
>tr|XOL8Y4|XOL8Y4_FUSOX DNA polymerase IV OS=*Fusarium oxysporum* f. sp. *vasinfectum* 25433 GN=FOTG_10014 PE=4 SV=1;
>tr|WPMW0|WPMW0_FUSOX DNA polymerase IV OS=*Fusarium oxysporum* f. sp. *pisi* HDV247 GN=FOVG_08521 PE=4 SV=1;
>tr|N4TUZ3|N4TUZ3_FUSC1 Putative DNA polymerase family X C2F7.06c OS=*Fusarium oxysporum* f. sp. *cubense* (strain race 1) GN=FOC1_g10006650 PE=4 SV=1;
>tr|W9J0J8|W9J0J8_FUSOX DNA polymerase IV OS=*Fusarium oxysporum* FOSC 3-a GN=FOYG_00559 PE=4 SV=1;
>tr|A0A194YIA1|A0A194YIA1_SORBI Uncharacterized protein OS=*Sorghum bicolor* GN=SORBI_010G097500 PE=4 SV=1;
>tr|C7Z1J3|C7Z1J3_NECH7 Putative uncharacterized protein OS=*Nectria haematococca* (strain 77-13-4/ATCC MYA-4622/FGSC 9596/MPVI) GN=NECHADRAFT_50658 PE=4 SV=1;
>tr|A0A177BXP7|A0A177BXP7_9PLEO DNA polymerase beta OS=*Paraphaeosphaeria sporulosa* GN=CC84DRAFT_389629 PE=4 SV=1;
>tr|A0A109FBN5|A0A109FBN5_9BASI Nucleotidyltransferase OS=*Rhodotorula* sp. JG-1b GN=RHOSPDRAFT_36897 PE=4 SV=1;
>tr|Q5JQP4|Q5JQP4_HUMAN DNA polymerase lambda OS=*Homo sapiens* GN=POLL PE=1 SV=1;
>tr|E5SCZ0|E5SCZ0_TRISP DNA polymerase lambda OS=*Trichinella spiralis* GN=Tsp_01603 PE=4 SV=1;
>sp|Q9UGP5-2|DPOLL_HUMAN Isoform 2 of DNA polymerase lambda OS=*Homo sapiens* GN=POLL;
>tr|F4Q5G1|F4Q5G1_DICFS Phosphatase tensin type domain-containing protein OS=*Dictyostelium fasciculatum* (strain SH3) GN=DFA_08207 PE=4 SV=1;
>tr|W9KQZ0|W9KQZ0_FUSOX DNA polymerase IV OS=*Fusarium oxysporum* Fo47 GN=FOZG_02867 PE=4 SV=1;
>tr|A0A0D7BH09|A0A0D7BH09_9HOMO Nucleotidyltransferase OS=*Cylindrobasidium torrendii* FP15055 ss-10 GN=CYLTODRAFT_226281 PE=4 Sv=1;
>tr|A0A1E3QZQ5|A0A1E3QZQ5_9ASCO Uncharacterized protein OS=*Babjeviella inositovora* NRRL Y-12698 GN=BABINDRAFT_159558 PE=4 SV=1;
>tr|A0A063CCJ7|A0A063CCJ7_9HYPO DNA polymerase beta OS=*Ustilaginoidea virens* GN=UV8b_354 PE=4 SV=1;

>tr|A0A0ENFZ0|A0A0E9NFZ0_9ASCO Uncharacterized protein OS=Saitoella complicata NRRL Y-17804 GN=G7K_2923-t1 PE=3 SV=1;
>tr|A0A1S4CC54|A0A1S4CC54_TOBAC DNA polymerase beta-like isoform X3 OS=Nicotiana tabacum GN=LOC107817483 PE=4 SV=1;
>tr|MOSDF3|MOSDF3_MUSAM Uncharacterized protein OS=Musa acuminata subsp. malaccensis PE=4 SV=1;
>tr|J9I2Q5|J9I2Q5_9SPIT Helix-hairpin-helix motif family protein OS=Oxytricha trifallax GN=OXYTRI_11966 PE=4 SV=1;
>tr|A0A1C1WVK1|A0A1C1WVK1_9PEZI DNA polymerase IV OS=Diaporthe helianthi GN=DHEL01_08189 PE=4 SV=1;
>tr|R7TPP6|R7TPP6_CAPTE Uncharacterized protein OS=Capitella teleta GN=CAPTEDRAFT_227708 PE=4 SV=1;
>tr|A0A094H196|A0A094H196_9PEZI Uncharacterized protein OS=Pseudogymnoascus sp. VKM F-4519 (FW-2642) GN=V501_06803 PE=4 SV=1;
>tr|A0A179HAH2|A0A179HAH2_9HYPO DNA polymerase beta OS=Purpureocillium lilacinum GN=VFPBJ_00561 PE=4 SV=1;
>tr|A0A167HMH0|A0A167HMH0_9BASI Nucleotidyltransferase OS=Calocera viscosa TUFC12733 GN=CALVIDRAFT_488572 PE=4 SV=1;
>tr|A0A0D3GEN6|A0A0D3GEN6_9ORYZ Uncharacterized protein OS=Oryza barthii PE=4 SV=1;
>tr|A0A0F8A5P0|A0A0F8A5P0_9HYPO Uncharacterized protein OS=Hirsutella minnesotensis 3608 GN=HIM_04821 PE=4 SV=1;
>tr|E5A138|E5A138_LEPMJ Similar to terminal deoxynucleotidyl transferase OS=Leptosphaeria maculans (strain JN3/isolate v23.1.3/race Av1-4-5-6-7-8) GN=LEMA_P104650.1 PE=4 SV=1;
>tr|E3S5Q0|E3S5Q0_PYRTT Putative uncharacterized protein OS=Pyrenophora teres f. teres (strain 0-1) GN=PTT_17985 PE=4 SV=1;
>tr|T0Q5B0|T0Q5B0_9STRA Uncharacterized protein OS=Saprolegnia diclina VS20 GN=SDRG_09530 PE=4 SV=1;
>tr|B4DEF5|B4DEF5_HUMAN cDNA FLJ55191, highly similar to DNA polymerase lambda (EC 2.7.7.7) OS=Homo sapiens PE=2 SV=1;
>tr|J9|GR6|J9|GR6_9SPIT Helix-hairpin-helix motif family protein OS=Oxytricha trifallax GN=OXYTRI_08498 PE=4 SV=1;
>tr|A0A1S2Z857|A0A1S2Z857_CICAR DNA polymerase beta isoform X3 OS=Cicer arietinum GN=LOC101499677 PE=4 SV=1;
>tr|A0A1S4CCE0|A0A1S4CCE0_TOBAC DNA polymerase beta-like isoform X1 OS=Nicotiana tabacum GN=LOC107817483 PE=4 SV=1;
>tr|A0A0E0PVK3|A0A0E0PVK3_ORYRU Uncharacterized protein OS=Oryza rufipogon PE=4 SV=1;
>tr|A0A0E0HN86|A0A0E0HN86_ORYNI Uncharacterized protein OS=Oryza nivara PE=4 SV=1;
>tr|A0A0E0A7A5|A0A0E0A7A5_9ORYZ Uncharacterized protein OS=Oryza glumipatula PE=4 SV=1;
>tr|A0A061E7L2|A0A061E7L2_THECC DNA polymerase lambda isoform 1 OS=Theobroma cacao GN=TCM_010205 PE=4 SV=1;
>tr|K7V573|K7V573_MAIZE DNA polymerase lambda (POLL) OS=Zea mays GN=ZEAMMB73_Zm00001d044780 PE=4 SV=1;
>tr|Q0U373|Q0U373_PHANO Uncharacterized protein OS=Phaeosphaeria nodorum (strain SN15/ATCC MYA-4574/FGSC 10173) GN=SNOG_13791 PE=4 SV=2;
>tr|A0A074XD59|A0A074XD59_9PEZI Nucleotidyltransferase OS=Aureobasidium namibiae CBS 147.97 GN=M436DRAFT_48818 PE=4 SV=1;
>tr|A0A178W586|A0A178W586_ARATH Pol(lambda) OS=Arabidopsis thaliana GN=AXX17_At1g10600 PE=4 SV=1;
>sp|Q9FNY4|DPOLL_ARATH DNA polymerase lambda OS=Arabidopsis thaliana GN=POLL PE=1 SV=1;
>tr|G7DWL3|G7DWL3_MIXOS Uncharacterized protein OS=Mixia osmundae (strain CBS 9802/IAM 14324/JCM 22182/KY 12970) GN=Mo01628 PE=4 Sv=1;
>tr|A0A1S4A2R6|A0A1S4A2R6_TOBAC DNA polymerase beta-like isoform X2 OS=Nicotiana tabacum GN=LOC107793193 PE=4 SV=1;
>tr|A0A094B2A4|A0A094B2A4_9PEZI Uncharacterized protein OS=Pseudogymnoascus sp. VKM F-4513 (FW-928) GN=V494_05533 PE=4 SV=1;
>tr|D3AVG3|D3AVG3_POLPA Uncharacterized protein OS=Polysphondylium pallidum GN=PPL_00073 PE=4 SV=1;
>tr|K7DF77|K7DF77_PANTR Polymerase (DNA directed), lambda OS=Pan troglodytes GN=POLL PE=2 SV=1;
>tr|A0A0J9URH9|A0A0J9URH9_FUSO4 DNA polymerase IV OS=Fusarium oxysporum f. sp. lycopersici (strain 4287/CBS 123668/FGSC 9935/NRRL 34936) GN=FOXG_04238 PE=4 SV=1;
>tr|W7M835|W7M835_GIBM7 DNA polymerase IV OS=Gibberella moniliformis (strain M3125/FGSC 7600) GN=FVEG_07358 PE=4 SV=1;
>tr|X0AK76|X0AK76_FUSOX DNA polymerase IV OS=Fusarium oxysporum f. sp. melonis 26406 GN=FOMG_02943 PE=4 SV=1;
>tr|A0A1S4CCF8|A0A1S4CCF8_TOBAC DNA polymerase beta-like isoform X2 OS=Nicotiana tabacum GN=LOC107817483 PE=4 SV=1;
>tr|A0A1S4A326|A0A1S4A326_TOBAC DNA polymerase beta-like isoform X1 OS=Nicotiana tabacum GN=LOC107793193 PE=4 SV=1;
>tr|A0A0D2XJX2|A0A0D2XJX2_FUSO4 Uncharacterized protein OS=Fusarium oxysporum f. sp. lycopersici (strain 4287/CBS 123668/FGSC 9935/NRRL 34936) PE=4 SV=1;
>tr|K4BWD9|K4BWD9_SOLLC Uncharacterized protein OS=Solanum lycopersicum PE=4 SV=1;
>tr|B7QK41|B7QK41_IXOSC DNA polymerase lambda, putative OS=Ixodes scapularis GN=IscW_ISCW023259 PE=4 SV=1;
>tr|A0A0C3FSL2|A0A0C3FSL2_9HOMO Uncharacterized protein OS=Piloderma croceum F 1598 GN=PILCRDRAFT_820500 PE=4 SV=1;
>tr|A0A1D6NRF4|A0A1D6NRF4_MAIZE DNA polymerase lambda (POLL) OS=Zea mays GN=ZEAMMB73_Zm00001d044780 PE=4 SV=1;
>tr|A0A061E6T3|A0A061E6T3_THECC DNA polymerase lambda isoform 2 OS=Theobroma cacao GN=TCM_010205 PE=4 SV=1;
>tr|A0A1A8SE80|A0A1A8SE80_9TELE Polymerase (DNA directed), mu (Fragment) OS=Nothobranchius rachovii GN=POLM PE=4 SV=1;

>tr|A0A103YLI5|A0A103YLI5_CYNCS BRCT domain-containing protein OS=*Cynara cardunculus* var. *scolymus* GN=Ccrd_010263 PE=4 SV=1;

>tr|A0A1L7TEU6|A0A1L7TEU6_9HYPO Related to DNA polymerase Tdt-N OS=*Fusarium mangiferae* GN=FMAN_11389 PE=4 SV=1;

>tr|A0A166E9I7|A0A166E9I7_DAUCA Uncharacterized protein OS=*Daucus carota* subsp. *sativus* GN=DCAR_007103 PE=4 SV=1;

>tr|A0A1D6NRF0|A0A1D6NRF0_MAIZE DNA polymerase lambda (POLL) OS=*Zea mays* GN=ZEAMMB73_Zm00001d044780 PE=4 SV=1;

>tr|A0A0C3HYP6|A0A0C3HYP6_9PEZI Uncharacterized protein OS=*Oidiodendron maius* Zn GN=OIDMADRAFT_107688 PE=4 SV=1;

>tr|D7KKS2|D7KKS2_ARALL DNA polymerase lambda OS=*Arabidopsis lyrata* subsp. *lyrata* GN=ARALYDRAFT_312091 PE=4 SV=1;

>tr|A0A1Q8S7P7|A0A1Q8S7P7_9PEZI DNA polymerase type-X family protein pol4 OS=*Colletotrichum chlorophyti* GN=CCHL11_01226 PE=4 SV=1;

>tr|F7WOK8|F7WOK8_SORMK WGS project CABT00000000 data, contig 2.17 OS=*Sordaria macrospora* (strain ATCC MYA-333/DSM 997/K(L3346)/K-hell) GN=SMAC_04011 PE=4 SV=1;

>tr|A0A0P5CMZ8|A0A0P5CMZ8_9CRUS Putative DNA-directed DNA/RNA polymerase mu (Fragment) OS=*Daphnia magna* PE=4 SV=1;

>tr|A0A165G478|A0A165G478_9BASI Nucleotidyltransferase OS=*Calocera cornea* HHB12733 GN=CALCODRAFT_433999 PE=4 SV=1;

>tr|I1JCZ2|I1JCZ2_SOYBN Uncharacterized protein OS=*Glycine max* GN=LOC100820492 PE=4 SV=2;

>tr|D7TNM4|D7TNM4_VITVI Putative uncharacterized protein OS=*Vitis vinifera* GN=VIT_01s0026g00650 PE=4 SV=1;

>tr|A0A1L7TZF3|A0A1L7TZF3_GIBIN Related to DNA polymerase Tdt-N OS=*Gibberella intermedia* GN=FPRN_08252 PE=4 SV=1;

>tr|A0A0V1KG85|A0A0V1KG85_TRIPS DNA polymerase lambda OS=*Trichinella pseudospiralis* GN=Mrpl30 PE=4 SV=1;

>tr|A0A166QBQ4|A0A166QBQ4_9PEZI DNA polymerase beta OS=*Colletotrichum tofieldiae* GN=CT0861_04203 PE=4 SV=1;

>tr|A0A1B8GUD2|A0A1B8GUD2_9PEZI Uncharacterized protein OS=*Pseudogymnoascus verrucosus* GN=VE01_02963 PE=4 SV=1;

>tr|A8K860JA8K860_HUMAN cDNA FLJ77175, highly similar to *Homo sapiens* DNA polymerase lamda2 mRNA OS=*Homo sapiens* PE=2 SV=1;

>tr|B4DE17|B4DE17_HUMAN cDNA FLJ53301, highly similar to DNA polymerase lambda (EC 2.7.7.7) OS=*Homo sapiens* PE=2 SV=1;

>tr|B3KXT3|B3KXT3_HUMAN cDNA FLJ46002 fis, clone SMINT2011509, highly similar to DNA polymerase lambda (EC 2.7.7.7) OS=*Homo sapiens* PE=2 SV=1;

>tr|A0A1L7W175|A0A1L7W175_GIBIN Related to DNA polymerase Tdt-N OS=*Fusarium proliferatum* ET1 GN=FPRO_11862 PE=4 SV=1;

>tr|A0A0D7BNV9|A0A0D7BNV9_9HOMO Nucleotidyltransferase OS=*Cylindrobasidium torrendii* FP15055 ss-10 GN=CYLTODRAFT_368502 PE=4 SV=1;

>tr|A0A0V1EYG3|A0A0V1EYG3_TRIPS DNA polymerase lambda OS=*Trichinella pseudospiralis* GN=POLL PE=4 SV=1;

>tr|B2WHB0|B2WHB0_PYRTR DNA polymerase beta OS=*Pyrenophora tritici-repentis* (strain Pt-1C-BFP) GN=PTRG_09369 PE=4 SV=1;

>tr|W6YYW4|W6YYW4_COCMI Uncharacterized protein OS=*Bipolaris oryzae* ATCC 44560 GN=COCMIDRAFT_41005 PE=4 SV=1;

>tr|F7CWH7|F7CWH7_MONDO Uncharacterized protein OS=*Monodelphis domestica* GN=POLL PE=4 SV=2 (SEQ ID NO: 84);

>tr|W2ZH69|W2ZH69_PHYPR Uncharacterized protein OS=*Phytophthora parasitica* P10297 GN=F442_07139 PE=4 SV=1;

>tr|A0A0W8CA00|A0A0W8CA00_PHYNI DNA polymerase lambda OS=*Phytophthora nicotianae* GN=AM587_10005054 PE=4 SV=1;

>tr|W2X7E5|W2X7E5_PHYPR Uncharacterized protein OS=*Phytophthora parasitica* CJ01A1 GN=F441_07085 PE=4 SV=1;

>tr|A0A081AFN9|A0A081AFN9_PHYPR Uncharacterized protein OS=*Phytophthora parasitica* P1976 GN=F444_07141 PE=4 SV=1;

>tr|W2QFB7|W2QFB7_PHYPN Uncharacterized protein OS=*Phytophthora parasitica* (strain INRA-310) GN=PPTG_10157 PE=4 SV=1;

>tr|V9FC02|V9FC02_PHYPR Uncharacterized protein OS=*Phytophthora parasitica* P1569 GN=F443_07072 PE=4 SV=1;

>tr|W2LF93|W2LF93_PHYPR Uncharacterized protein OS=*Phytophthora parasitica* GN=L914_06888 PE=4 SV=1;

>tr|SOEEQ9|SOEEQ9_GIBF5 Related to DNA polymerase Tdt-N OS=*Gibberella fujikuroi* (strain CBS 195.34/IMI 58289/NRRL A-6831) GN=FFUJ_12212 PE=4 SV=1;

>tr|K3VLK2|K3VLK2_FUSPC Uncharacterized protein OS=*Fusarium pseudograminearum* (strain CS3096) GN=FPSE_05383 PE=4 SV=1;

>tr|I1RE23|I1RE23_GIBZE Uncharacterized protein OS=*Gibberella zeae* (strain PH-1/ATCC MYA-4620/FGSC 9075/NRRL 31084) GN=FG01896.1 PE=4 SV=1;

>tr|A0A165FWW0|A0A165FWW0_9PEZI Terminal deoxynucleotidyl transferas-like protein OS=*Xylona heveae* TC161 GN=L228DRAFT_248190 PE=4 SV=1;

>tr|A0A178AH86|A0A178AH86_9PLEO Nucleotidyltransferase OS=*Stagonospora* sp. SRC1lsM3a GN=IQ06DRAFT_379775 PE=4 SV=1;

>tr|Q5QJV5|Q5QJV5_HUMAN DNA polymerase lamda2 OS=*Homo sapiens* PE=2 SV=1;

>tr|A0A0I9Y516|A0A0I9Y516_GIBFU DNA polymerase Tdt-N OS=*Gibberella fujikuroi* GN=LW93_5943 PE=4 SV=1;

>tr|A0A0K9QPB2|A0A0K9QPB2_SPIOL Uncharacterized protein OS=*Spinacia oleracea* GN=SOVF_161430 PE=4 SV=1;

>tr|A0A1B6DMG4|A0A1B6DMG4_9HEMI Uncharacterized protein OS=*Clastoptera arizonana* GN=g.16118 PE=4 SV=1;

>tr|A0A0G2TCQ4|A0A0G2TCQ4_SINCH DNA-directed DNA/RNA polymerase mu-like protein (Fragment) OS=*Siniperca chuatsi* PE=2 SV=1;

>tr|S3CES3|S3CES3_GLAL2 Nucleotidyltransferase OS=*Glarea lozoyensis* (strain ATCC 20868/MF5171) GN=GLAREA_11578 PE=4 SV=1;

>tr|G1X3Y6|G1X3Y6_ARTOA Uncharacterized protein OS=*Arthrobotrys oligospora* (strain ATCC 24927/CBS 115.81/DSM 1491) GN=AOL_s00043g410 PE=4 SV=1;

>tr|A0A1B8B5I4|A0A1B8B5I4_FUSPO Uncharacterized protein OS=*Fusarium poae* GN=FPOA_01921 PE=4 SV=1;

>tr|K3WBD7|K3WBD7_PYTUL Uncharacterized protein OS=*Pythium ultimum* DAOM BR144 PE=4 SV=1;

>tr|A0A0P1AR42|A0A0P1AR42_9STRA Dna polymerase lambda-like protein OS=*Plasmopara halstedii* PE=4 SV=1;

>tr|I1G678|I1G678_AMPQE Uncharacterized protein OS=*Amphimedon queenslandica* GN=LOC100640740 PE=4 SV=1;

>tr|A0A0V1I9V0|A0A0V1I9V0_9BILA DNA polymerase lambda OS=*Trichinella zimbabwensis* GN=MRPL30 PE=4 SV=1;

>tr|A0A166Y76|A0A166Y76_9HOMO Nucleotidyltransferase OS=*Peniophora* sp. CONT GN=PENSPDRAFT_682328 PE=4 SV=1;

>tr|F9X556|F9X556_ZYMTI DNA polymerase beta-like protein OS=*Zymoseptoria tritici* (strain CBS 115943/IPO323) GN=POLX2 PE=4 SV=1;

>tr|A0A1J7J8L3|A0A1J7J8L3_9PEZI Nucleotidyltransferase OS=*Coniochaeta ligniaria* NRRL 30616 GN=CONLIGDRAFT_643718 PE=4 SV=1;

>tr|M3B059|M3B059_SPHMS Nucleotidyltransferase OS=*Sphaerulina musiva* (strain S02202) GN=SEPMUDRAFT_148552 PE=4 SV=1;

>tr|T0RL69|T0RL69_9STRA Uncharacterized protein OS=*Saprolegnia diclina* VS20 GN=SDRG_09530 PE=4 SV=1;

>tr|R0GTX0|R0GTX0_9BRAS Uncharacterized protein (Fragment) OS=*Capsella rubella* GN=CARUB_v10012462 mg PE=4 SV=1;

>tr|A0A163C683|A0A163C683_DIDRA DNA binding OS=*Didymella rabiei* GN=ST47_g6594 PE=4 SV=1;

>tr|A0A1B6PI3|A0A1B6PI3_9HEMI Uncharacterized protein (Fragment) OS=*Homalodisca liturata* GN=g.26729 PE=4 SV=1;

>tr|G2QRI9|G2QRI9_THITE Uncharacterized protein OS=*Thielavia terrestris* (strain ATCC 38088/NRRL 8126) GN=THITE_2106802 PE=4 SV=1;

>tr|A0A0L0HB69|A0A0L0HB69_SPIPN Uncharacterized protein OS=*Spizellomyces punctatus* DAOM BR117 GN=SPPG_06523 PE=4 SV=1;

>tr|A0CMJ3|A0CMJ3_PARTE Uncharacterized protein OS=*Paramecium tetraurelia* GN=GSPATT00008489001 PE=4 SV=1;

>tr|L7|L19|L7|L19_MAGOY DNA polymerase beta OS=*Magnaporthe oryzae* (strain Y34) GN=OOU_Y34scaffold00140g29 PE=4 SV=1;

>tr|G4MN08|G4MN08_MAGO7 DNA polymerase beta OS=*Magnaporthe oryzae* (strain 70-15/ATCC MYA-4617/FGSC 8958) GN=MGG_06908 PE=4 SV=1;

>tr|L7JI54|L7JI54_MAGOP DNA polymerase beta OS=*Magnaporthe oryzae* (strain P131) GN=OOW_P131scaffold00328g30 PE=4 SV=1;

>tr|V4SV18|V4SV18_9ROSI Uncharacterized protein OS=*Citrus clementina* GN=CICLE_v10031184 mg PE=4 SV=1;

>tr|L7I3D8|L7I3D8_MAGOY DNA polymerase lambda OS=*Magnaporthe oryzae* (strain Y34) GN=OOU_Y34scaffold00619g46 PE=4 SV=1;

>tr|G4MSU5|G4MSU5_MAGO7 Uncharacterized protein OS=*Magnaporthe oryzae* (strain 70-15/ATCC MYA-4617/FGSC 8958) GN=MGG_04577 PE=4 SV=1;

>tr|L7|U60|L7|U60_MAGOP DNA polymerase lambda OS=*Magnaporthe oryzae* (strain P131) GN=OOW_P131scaffold01358g84 PE=4 SV=1;

>tr|A0A178DYJ1|A0A178DYJ1_9PLEO Nucleotidyltransferase OS=*Pyrenochaeta* sp. DS3sAY3a GN=IQ07DRAFT_622852 PE=4 SV=1;

>tr|A0A061EDJ3|A0A061EDJ3_THECC DNA polymerase lambda (POLL) isoform 3 OS=*Theobroma cacao* GN=TCM_010205 PE=4 SV=1;

>tr|A0A0A1V1A1|A0A0A1V1A1_9HYPO DNA polymerase X family protein OS=*Metarhizium robertsii* GN=X797_003415 PE=4 SV=1;

>tr|A0A161W8A7|A0A161W8A7_9PEZI Dna polymerase beta protein OS=*Colletotrichum incanum* GN=CI238_02506 PE=4 SV=1;

>tr|A0A197K957|A0A197K957_9FUNG Nucleotidyltransferase OS=*Mortierella elongata* AG-77 GN=K457DRAFT_69808 PE=4 SV=1;

>tr|A0A1I8HZS6|A0A1I8HZS6_9PLAT Uncharacterized protein OS=*Macrostomum lignano* PE=4 SV=1;

>tr|A0A0D2R796|A0A0D2R796_GOSRA Uncharacterized protein OS=*Gossypium raimondii* GN=B456_002G164200 PE=4 SV=1;

>tr|A0A1I8I2E2|A0A1I8I2E2_9PLAT Uncharacterized protein OS=*Macrostomum lignano* PE=4 SV=1;

>tr|A0A0G2FFQ8|A0A0G2FFQ8_9PEZI Putative dna polymerase beta OS=*Diaporthe ampelina* GN=UCDDA912_g07030 PE=4 SV=1;

>tr|A0A074W8N4|A0A074W8N4_9PEZI DNA polymerase beta-like protein OS=*Aureobasidium melanogenum* CBS 110374 GN=M437DRAFT_39375 PE=4 SV=1;

>tr|A0A1B6LW89|A0A1B6LW89_9HEMI Uncharacterized protein OS=*Graphocephala atropunctata* GN=g.50861 PE=4 SV=1;

>tr|A0A1Q3ES10|A0A1Q3ES10_LENED Dna polymerase lambda OS=*Lentinula edodes* GN=LENED_012117 PE=4 SV=1;

>tr|F8WDE4|F8WDE4_HUMAN DNA-directed DNA/RNA polymerase mu OS=*Homo sapiens* GN=POLM PE=1 SV=1;

>tr|E2AH73|E2AH73_CAMFO DNA polymerase beta (Fragment) OS=*Camponotus floridanus* GN=EAG_09061 PE=4 SV=1;

>tr|C9JF34|C9JF34_HUMAN DNA-directed DNA/RNA polymerase mu (Fragment) OS=*Homo sapiens* GN=POLM PE=1 SV=1;

>tr|M2PG81|M2PG81_CERS8 Uncharacterized protein OS=*Ceriporiopsis subvermispora* (strain B) GN=CERSUDRAFT_157745 PE=4 SV=1;

>tr|R7YS72|R7YS72_CONA1 Uncharacterized protein OS=*Coniosporium apollinis* (strain CBS 100218) GN=W97_03739 PE=4 SV=1;

>tr|V7COP8|V7COP8_PHAVU Uncharacterized protein (Fragment) OS=*Phaseolus vulgaris* GN=PHAVU_004G0710000g PE=4 SV=1;

>tr|A0A0W0FEC6|A0A0W0FEC6_9AGAR Uncharacterized protein OS=*Moniliophthora roreri* GN=WG66_12791 PE=4 SV=1;

>tr|K1PLM1|K1PLM1_CRAGI DNA polymerase lambda OS=Crassostrea gigas GN=CGI_10001943 PE=4 SV=1;

>tr|A0A1D2VPH7|A0A1D2VPH7_9ASCO Nucleotidyltransferase OS=Ascoidea rubescens DSM 1968 GN=ASCRUDRAFT_67555 PE=4 SV=1;

>tr|A0A067C9L0|A0A067C9L0_SAPPC Uncharacterized protein OS=Saprolegnia parasitica (strain CBS 223.65) GN=SPRG_07053 PE=4 SV=1;

>tr|V2YCS0|V2YCS0_MONRO Dna polymerase lambda OS=Moniliophthora roreri (strain MCA 2997) GN=Moror_16092 PE=4 SV=1;

>tr|A0A1J7GWS4|A0A1J7GWS4_LUPAN Uncharacterized protein OS=Lupinus angustifolius GN=TanjilG_25590 PE=4 SV=1;

>tr|A0A0J7KSX3|A0A0J7KSX3_LASNI Metallophosphoesterase 1 OS=Lasius niger GN=RF55_6460 PE=4 SV=1;

>tr|A0A0W7VNN6|A0A0W7VNN6_9HYPO High-affinity nickel transporter OS=Trichoderma gamsii GN=TGAM01_05509 PE=4 SV=1;

>tr|A0A0A1TBX7|A0A0A1TBX7_9HYPO Uncharacterized protein OS=Torrubiella hemipterigena GN=VHEMI10101 PE=4 SV=1;

>tr|A0A0N8H665|A0A0N8H665_9HYPO Uncharacterized protein OS=Neonectria ditissima GN=AK830_g8452 PE=4 SV=1;

>tr|A0A0V1MQQ6|A0A0V1MQQ6_9BILA DNA polymerase lambda OS=Trichinella papuae GN=MRPL30 PE=4 SV=1;

>tr|G2X3I6|G2X3I6_VERDV DNA polymerase lambda OS=Verticillium dahliae (strain VdLs.17/ATCC MYA-4575/FGSC 10137) GN=VDAG_04573 PE=4 SV=1;

>tr|A0A093Y1B2|A0A093Y1B2_9PEZI Uncharacterized protein (Fragment) OS=Pseudogymnoascus sp. VKM F-3808 GN=0988_04227 PE=4 SV=1;

>tr|A0A1C1X2L6|A0A1C1X2L6_9PEZI High-affinity nickel transporter (Fragment) OS=Diaporthe helianthi GN=DHEL01_08081 PE=4 SV=1;

>tr|A0A165D1N9|A0A165D1N9_9APHY Uncharacterized protein OS=Laetiporus sulphureus 93-53 GN=LAESUDRAFT_814364 PE=4 SV=1;

>tr|A0A139ABS3|A0A139ABS3_GONPR Nucleotidyltransferase OS=Gonapodya prolifera JEL478 GN=M427DRAFT_112983 PE=4 SV=1;

>tr|A0A139I956|A0A139I956_9PEZI Uncharacterized protein OS=Pseudocercospora musae GN=AC579_8383 PE=4 SV=1;

>tr|A0A1S4A2W8|A0A1S4A2W8_TOBAC DNA polymerase beta-like isoform X3 OS=Nicotiana tabacum GN=LOC107793193 PE=4 SV=1;

>tr|A0A0F4ZAE6|A0A0F4ZAE6_9PEZI Uncharacterized protein OS=Thielaviopsis punctulata GN=TD95_003167 PE=4 SV=1;

>tr|G3HHH7|G3HHH7_CRIGR DNA polymerase beta OS=Cricetulus griseus GN=I79_010094 PE=4 SV=1;

>tr|A0A0B1PLB7|A0A0B1PLB7_9BILA Uncharacterized protein OS=Trichuris suis GN=D918_06892 PE=4 SV=1;

>tr|A0A026WYD7|A0A026WYD7_CERBI DNA polymerase beta OS=Cerapachys biroi GN=X777_15051 PE=4 SV=1;

>tr|A0A0P5HWD7|A0A0P5HWD7_9CRUS Putative DNA-directed DNA/RNA polymerase mu (Fragment) OS=Daphnia magna PE=4 SV=1;

>tr|A0A085M6E7|A0A085M6E7_9BILA Uncharacterized protein (Fragment) OS=Trichuris suis GN=M513_06284 PE=4 SV=1;

>tr|A0A085NR57|A0A085NR57_9BILA Uncharacterized protein (Fragment) OS=Trichuris suis GN=M514_06284 PE=4 SV=1;

>tr|A0A1D1UJX5|A0A1D1UJX5_RAMVA Uncharacterized protein OS=Ramazzottius varieornatus GN=RvY_02488-1 PE=4 SV=1;

>tr|A0A015KMQ8|A0A015KMQ8_9GLOM Pol4p OS=Rhizophagus irregularis DAOM 197198w GN=RirG_174710 PE=4 SV=1;

>tr|U9UPA5|U9UPA5_RHIID Uncharacterized protein OS=Rhizophagus irregularis (strain DAOM 181602/DAOM 197198/MUCL 43194) GN=GLOINDRAFT_321289 PE=4 SV=1;

>tr|H2XQC3|H2XQC3_CIOIN Uncharacterized protein OS=Ciona intestinalis PE=4 SV=1;

>tr|A0A077ZAV7|A0A077ZAV7_TRITR DNA polymerase lambda OS=Trichuris trichiura GN=TTRE_0000524701 PE=4 SV=1;

>tr|W3XQL7|W3XQL7_9PEZI Uncharacterized protein OS=Pestalotiopsis fici W106-1 GN=PFICI_01384 PE=4 SV=1;

>tr|A0A0M9EXF4|A0A0M9EXF4_9HYPO Dna polymerase iv OS=Fusarium langsethiae GN=FLAG1_05496 PE=4 SV=1;

>tr|A0A0C3L267|A0A0C3L267_9HOMO Uncharacterized protein (Fragment) OS=Tulasnella calospora MUT 4182 GN=M407DRAFT_72655 PE=4 SV=1;

>tr|A0A067H4G2|A0A067H4G2_CITSI Uncharacterized protein (Fragment) OS=Citrus sinensis GN=CISIN_1g0093031 mg PE=4 SV=1;

>tr|G3SQY2|G3SQY2_LOXAF Uncharacterized protein OS=Loxodonta africana GN=POLB PE=4 SV=1;

>tr|A0A067GSH6|A0A067GSH6_CITSI Uncharacterized protein (Fragment) OS=Citrus sinensis GN=CISIN_1g0093031 mg PE=4 SV=1;

>tr|U4LGA6|U4LGA6_PYROM Similar to DNA polymerase lambda acc. no. Q4R380 OS=Pyronema omphalodes (strain CBS 100304) GN=PCON_10034 PE=4 SV=1;

>tr|A0A0C3S642|A0A0C3S642_PHLGI Uncharacterized protein OS=Phlebiopsis gigantea 11061_1 CR5-6 GN=PHLGIDRAFT_480151 PE=4 SV=1;

>tr|E9EUG6|E9EUG6_METRA Nucleotidyltransferase OS=Metarhizium robertsii (strain ARSEF 23/ATCC MYA-3075) GN=MAA 03665 PE=4 SV=2;

>tr|C9J222|C9J222_HUMAN DNA-directed DNA/RNA polymerase mu (Fragment) OS=Homo sapiens GN=POLM PE=1 SV=1;

>tr|C7YGY5|C7YGY5_NECH7 Putative uncharacterized protein OS=Nectria haematococca (strain 77-13-4/ATCC MYA-4622/FGSC 9596/MPVI) GN=NECHADRAFT_74784 PE=4 SV=1;

>tr|H0ZI77|H0ZI77_TAEGU Uncharacterized protein OS=Taeniopygia guttata GN=POLL PE=4 SV=1;

>tr|L9L936|L9L936_TUPCH DNA polymerase beta OS=Tupaia chinensis GN=TREES_T100019179 PE=4 SV=1;

>tr|A0A1R2BTP8|A0A1R2BTP8_9CILI Uncharacterized protein OS=Stentor coeruleus GN=SteCoe_19671 PE=4 SV=1;

>tr|S4RCE7|S4RCE7_PETMA Uncharacterized protein OS=Petromyzon marinus PE=4 SV=1;

>tr|I1RAT5|I1RAT5_GIBZE Uncharacterized protein OS=*Gibberella zeae* (strain PH-1/ATCC MYA-4620/FGSC 9075/NRRL 31084) GN=FG00621.1 PE=4 SV=1;
>tr|A0A136JFC5|A0A136JFC5_9PEZI Uncharacterized protein OS=*Microdochium bolleyi* GN=MicbolqcDRAFT_201184 PE=4 SV=1;
>tr|A0A0B4IB3|A0A0B4IB3_9HYPO DNA-directed DNA polymerase X (Fragment) OS=*Metarhizium majus* ARSEF 297 GN=MAJ_03673 PE=4 SV=1;
>tr|A0A0B4H1V8|A0A0B4H1V8_9HYPO DNA-directed DNA polymerase X OS=*Metarhizium guizhouense* ARSEF 977 GN=MGU_03773 PE=4 SV=1;
>tr|A0A139HWX0|A0A139HWX0_9PEZI Uncharacterized protein OS=*Mycosphaerella eumusae* GN=AC578_7095 PE=4 SV=1;
>tr|A0A0D2A6C0|A0A0D2A6C0_9PEZI Uncharacterized protein OS=*Verruconis gallopava* GN=PVO9_06595 PE=4 SV=1;
>tr|F1PKP7|F1PKP7_CANLF Uncharacterized protein OS=*Canis lupus familiaris* GN=POLB PE=4 SV=1;
>sp|P06766|DPOLB_RAT DNA polymerase beta OS=*Rattus norvegicus* GN=Polb PE=1 SV=4;
>tr|B2B4U9|B2B4U9_PODAN Podospora anserina S mat+genomic DNA chromosome 2, supercontig 2 OS=*Podospora anserina* (strain S/ATCC MYA-4624/DSM 980/FGSC 10383) GN=PODANS_2_2540 PE=4 SV=1;
>tr|A0A0G0A1N0|A0A0G0A1N0_TRIHA Uncharacterized protein OS=*Trichoderma harzianum* GN=THARO2_01643 PE=4 SV=1;
>tr|E0VPG0|E0VPG0_PEDHC DNA polymerase beta, putative OS=*Pediculus humanus* subsp. *corporis* GN=8232106 PE=4 SV=1;
>tr|T1J7P5|T1J7P5_STRMM Uncharacterized protein OS=*Strigamia maritima* PE=4 SV=1;
>tr|L8I911|L8I911_9CETA DNA polymerase beta OS=*Bos mutus* GN=M91_05776 PE=4 SV=1;
>tr|G1SF51|G1SF51_RABIT Uncharacterized protein OS=*Oryctolagus cuniculus* GN=POLB PE=4 SV=1;
>tr|HOXES4|HOXES4_OTOGA Uncharacterized protein OS=*Otolemur garnettii* GN=POLB PE=4 SV=1 (SEQ ID NO: 82);
>sp|Q8K409|DPOLB_MOUSE DNA polymerase beta OS=*Mus musculus* GN=Polb PE=1 SV=3;
>sp|Q27958|DPOLB_BOVIN DNA polymerase beta OS=*Bos taurus* GN=POLB PE=2 SV=3;
>tr|A0PC13|A0PC13_COPCI DNA polymerase lambda OS=*Coprinopsis cinerea* GN=pollambda PE=4 SV=1;
>tr|A0A0D9NN19|A0A0D9NN19_METAN Uncharacterized protein OS=*Metarhizium anisopliae* BRIP 53293 GN=H634G_08840 PE=4 SV=1;
>tr|G9NH38|G9NH38_HYPAI Uncharacterized protein OS=*Hypocrea atroviridis* (strain ATCC 20476/IMI 206040) GN=TRIATDRAFT_51201 PE=4 SV=1;
>tr|G9NDQ2|G9NDQ2_HYPVG Uncharacterized protein OS=*Hypocrea virens* (strain Gv29-8/FGSC 10586) GN=TRIVIDRAFT_51446 PE=4 SV=1;
>tr|G9KHM9|G9KHM9_MUSPF Polymerase, beta (Fragment) OS=*Mustela putorius* furo PE=2 SV=1;
>tr|U6CV23|U6CV23_NEOVI DNA polymerase beta OS=*Neovison vison* GN=DPOLB PE=2 SV=1;
>tr|M3YMQ7|M3YMQ7_MUSPF Uncharacterized protein OS=*Mustela putorius* furo GN=POLB PE=4 SV=1;
>tr|Q9HAJ3|Q9HAJ3_HUMAN cDNA FLJ11538 fis, clone HEMBA1002746, weakly similar to DNA POLYMERASE BETA (EC 2.7.7.7) OS=*Homo sapiens* PE=2 SV=1;
>tr|A0A077ZZ96|A0A077ZZ96_STYLE Helix-hairpin-helix motif family protein OS=*Stylonychia lemnae* GN=Contig18226.g19364 PE=4 SV=1;
>tr|K9ID0|K9ID0_DESRO Putative dna polymerase iv family x OS=*Desmodus rotundus* PE=2 SV=1;
>tr|A0A1A8U639|A0A1A8U639_NOTFU Deoxynucleotidyltransferase, terminal (Fragment) OS=*Nothobranchius furzeri* GN=DNTT PE=4 SV=1;
>tr|A0A026WUA4|A0A026WUA4_CERBI DNA polymerase beta OS=*Cerapachys biroi* GN=X777_16780 PE=4 SV=1;
>tr|A0A178AM56|A0A178AM56_9PLEO Uncharacterized protein OS=*Stagonospora* sp. SRC1lsM3a GN=IQ06DRAFT_278382 PE=4 SV=1;
>tr|L5KAJ8|L5KAJ8_PTEAL DNA polymerase beta OS=*Pteropus alecto* GN=PAL_GLEAN10021536 PE=4 SV=1;
>tr|G1Q072|G1O072_MYOLU Uncharacterized protein OS=*Myotis lucifugus* GN=POLB PE=4 SV=1;
>tr|G1LEW7|G1LEW7_AILME Uncharacterized protein OS=*Ailuropoda melanoleuca* GN=POLB PE=4 SV=1;
>tr|A0A1B6JS91|A0A1B6JS91_9HEMI Uncharacterized protein OS=*Homalodisca liturata* GN=g.26727 PE=4 SV=1;
>tr|R4XCI6|R4XCI6_TAPDE Putative DNA polymerase POL4 OS=*Taphrina deformans* (strain PYCC 5710/ATCC 11124/CBS 356.35/IMI 108563/JCM 9778/NBRC 8474) GN=TAPDE_003785 PE=4 SV=1;
>tr|A0A0C2X4X0|A0A0C2X4X0_AMAMU Uncharacterized protein OS=*Amanita muscaria* Koide BX008 GN=M378DRAFT_163339 PE=4 SV=1;
>tr|G2YW92|G2YW92_BOTF4 Similar to terminal deoxynucleotidyl transferase OS=*Botryotinia fuckeliana* (strain T4) GN=BofuT4_P150220.1 PE=4 SV=1;
>tr|M7USU8|M7USU8_BOTF1 Putative dna polymerase beta protein OS=*Botryotinia fuckeliana* (strain BcDW1) GN=BcDW1_1262 PE=4 SV=1;
>tr|GOSDS2|GOSDS2_CHATD DNA polymerase-like protein OS=*Chaetomium thermophilum* (strain DSM 1495/CBS 144.50/IMI 039719) GN=CTHT_0052790 PE=4 SV=1;
>tr|G9NIX2|G9NIX2_HYPAI Uncharacterized protein (Fragment) OS=*Hypocrea atroviridis* (strain ATCC 20476/IMI 206040) GN=TRIATDRAFT_174080 PE=4 SV=1;
>tr|A0A023GLT6|A0A023GLT6_9ACAR Putative dna polymerase iv family x (Fragment) OS=*Amblyomma triste* PE=2 SV=1;
>tr|T1DLI8|T1DLI8_CROHD DNA polymerase beta-like protein OS=*Crotalus horridus* PE=2 SV=1;
>tr|Q5SBJ1|Q5SBJ1_CANLF DNA polymerase beta (Fragment) OS=*Canis lupus familiaris* PE=2 SV=1;
>tr|H2ZGS9|H2ZGS9_CIOSA Uncharacterized protein OS=*Ciona savignyi* PE=4 SV=1;
>tr|V7COT6|V7COT6_PHAVU Uncharacterized protein (Fragment) OS=*Phaseolus vulgaris* GN=PHAVU_004G0710000g PE=4 SV=1;
>tr|A0A0N8AG30|A0A0N8AG30_9CRUS DNA-directed DNA/RNA polymerase mu (Fragment) OS=*Daphnia magna* PE=4 SV=1;
>tr|A0A0P4W7N0|A0A0P4W7N0_9EUCA Uncharacterized protein OS=*Scylla olivacea* PE=4 SV=1;

>tr|M3XC91|M3XC91_FELCA Uncharacterized protein OS=*Felis catus* GN=POLB PE=4 SV=1;
>tr|F2UQK2|F2UQK2_SALR5 Putative uncharacterized protein OS=*Salpingoeca rosetta* (strain ATCC 50818/BSB-021) GN=PTSG_10190 PE=4 SV=1;
>tr|A0A1Q5UEI8|A0A1Q5UEI8_9EURO DNA polymerase type-X family protein pol4 OS=*Penicillium subrubescens* GN=PENSUB_3710 PE=4 SV=1;
>tr|E9|UZ2|E9|UZ2_SOLIN Putative uncharacterized protein (Fragment) OS=*Solenopsis invicta* GN=SINV_02512 PE=4 SV=1;
>tr|N1Q5N8|N1Q5N8_PSEFD Uncharacterized protein (Fragment) OS=*Pseudocercospora fijiensis* (strain CIRAD86) GN=MYCFIDRAFT_1485 PE=4 SV=1;
>tr|A0A0S6XKL8|A0A0S6XKL8_9FUNG Uncharacterized protein OS=fungal sp. No. 11243 GN=AN011243_043170 PE=4 SV=1;
>tr|A0A0L0S8H4|A0A0L0S8H4_ALLMA Uncharacterized protein OS=*Allomyces macrogynus* ATCC 38327 GN=AMAG_04435 PE=4 SV=1;
>tr|A0A0M9VPF2|A0A0M9VPF2_9BASI Dna polymerase mu OS=*Malassezia pachydermatis* GN=Malapachy_3911 PE=4 SV=1;
>tr|HOEG73|HOEG73_GLAL7 Putative DNA polymerase lambda OS=*Glarea lozoyensis* (strain ATCC 74030/MF5533) GN=M7I_1483 PE=4 SV=1;
>tr|A0A0K9QMR5|A0A0K9QMR5_SPIOL Uncharacterized protein OS=*Spinacia oleracea* GN=SOVF_161430 PE=4 SV=1;
>tr|I3KRF3|I3KRF3_ORENI Uncharacterized protein OS=*Oreochromis niloticus* GN=wbpll PE=4 SV=1;
>tr|A0A178W5U8|A0A178W5U8_ARATH Pol(lambda) OS=*Arabidopsis thaliana* GN=AXX17_Atlgl0600 PE=4 SV=1;
>tr|A0A1P8APE6|A0A1P8APE6_ARATH DNA polymerase lambda (POLL) OS=*Arabidopsis thaliana* GN=Pol{lambda} PE=4 SV=1;
>tr|S3DHN1|S3DHN1_GLAL2 Nucleotidyltransferase OS=*Glarea lozoyensis* (strain ATCC 20868/MF5171) GN=GLAREA_12302 PE=4 SV=1;
>tr|F6TYB0|F6TYB0_CIOIN Uncharacterized protein OS=*Ciona intestinalis* PE=4 SV=2;
>tr|I3M6T3|I3M6T3_ICTTR Uncharacterized protein OS=*Ictidomys tridecemlineatus* GN=POLB PE=4 SV=1;
>tr|G5BT41|G5BT41_HETGA DNA polymerase beta OS=*Heterocephalus glaber* GN=GW7_08532 PE=2 SV=1;
>tr|W5UI78|W5UI78_ICTPU DNA polymerase beta OS=*Ictalurus punctatus* GN=polb PE=2 SV=1;
>tr|W6MJI8|W6MJI8_9ASCO Uncharacterized protein OS=*Kuraishia capsulata* CBS 1993 GN=KUCA_T00002413001 PE=4 SV=1;
>tr|A0A0A2VE68|A0A0A2VE68_BEABA Putative DNA polymerase family X C2F7.06c OS=*Beauveria bassiana* D1-5 GN=BBAD15_g8907 PE=4 SV=1;
>tr|A0A0B7JPX6|A0A0B7JPX6_BIOOC Uncharacterized protein (Fragment) OS=*Bionectria ochroleuca* GN=BN869_000003098_1 PE=4 SV=1;
>tr|A0A069DYM9|A0A069DYM9_9HEMI Putative dna polymerase iv family x OS=*Panstrongylus megistus* PE=2 SV=1;
>tr|A0A060T9I9|A0A060T9I9_BLAAD ARAD1D15576p OS=*Blastobotrys adeninivorans* GN=GNLVRS02_ARAD1D15576g PE=4 SV=1;
>tr|G1RQX7|G1RQX7_NOMLE Uncharacterized protein OS=*Nomascus leucogenys* GN=POLB PE=4 SV=1;
>tr|H2QW35|H2QW35_PANTR Polymerase (DNA directed), beta OS=*Pan troglodytes* GN=POLB PE=2 SV=1;
>sp|P06746|DPOLB_HUMAN DNA polymerase beta OS=*Homo sapiens* GN=POLB PE=1 SV=3;
>tr|Q6C9C2|Q6C9C2_YARLI YALIOD12364p OS=*Yarrowia lipolytica* (strain CLIB 122/E 150) GN=YALI0_D12364g PE=4 SV=1;
>tr|A0A1H6PY30A0A1H6PY30_YARLL YALIA101S12e01794g1_1 OS=*Yarrowia lipolytica* GN=YALIA101_S12E01794G PE=4 SV=1;
>tr|A0A1D8NEA0|A0A1D8NEA0_YARLL Uncharacterized protein OS=*Yarrowia lipolytica* GN=YALI1_D15367g PE=4 SV=1;
>tr|A0A1B8EDN0|A0A1B8EDN0_9PEZI Uncharacterized protein OS=*Pseudogymnoascus* sp. 23342-1-I1 GN=VE03_01116 PE=3 SV=1;
>tr|A0A094BR33|A0A094BR33_9PEZI Uncharacterized protein OS=*Pseudogymnoascus* sp. VKM F-4246 GN=V492_03652 PE=3 SV=1;
>tr|KOKG88|KOKG88_WICCF DNA nucleotidylexotransferase OS=*Wickerhamomyces ciferrii* (strain F-60-10/ATCC 14091/CBS 111/JCM 3599/NBRC 0793/NRRL Y-1031) GN=BN7_3734 PE=4 SV=1;
>tr|K3VGJ0|K3VGJ0_FUSPC Uncharacterized protein OS=*Fusarium pseudograminearum* (strain CS3096) GN=FPSE_06415 PE=4 SV=1;
>tr|F7|KW6|F7|KW6_CALJA DNA polymerase beta OS=*Callithrix jacchus* GN=POLB PE=2 SV=1;
>tr|A0A094FIQ0|A0A094FIQ0_9PEZI Uncharacterized protein OS=*Pseudogymnoascus* sp. VKM F-4516 (FW-969) GN=V497_04262 PE=4 SV=1;
>tr|A0A093XQA1|A0A093XQA1_9PEZI Uncharacterized protein OS=*Pseudogymnoascus* sp. VKM F-3557 GN=V490_05206 PE=4 SV=1;
>tr|A0A0P7BR28|A0A0P7BR28_9HYPO Uncharacterized protein OS=*Neonectria ditissima* GN=AK830_g2708 PE=4 SV=1;
>tr|A0A1D6NRF3|A0A1D6NRF3_MAIZE DNA polymerase lambda (POLL) OS=*Zea mays* GN=ZEAMMB73_Zm00001d044780 PE=4 SV=1;
>tr|A0A0G4|I62|A0A0G4|I62_PLABS Uncharacterized protein OS=*Plasmodiophora brassicae* GN=PBRA_003577 PE=4 SV=1;
>tr|A0A0S6XJT2|A0A0S6XJT2_9FUNG Uncharacterized protein OS=fungal sp. No. 11243 GN=AN011243_041640 PE=4 SV=1;
>tr|F6WYN9|F6WYN9_ORNAN Uncharacterized protein OS=*Ornithorhynchus anatinus* GN=POLL PE=4 SV=2;
>tr|F6WYP8|F6WYP8_ORNAN Uncharacterized protein OS=*Ornithorhynchus anatinus* GN=POLL PE=4 SV=2;
>tr|A0A094GON2|A0A094GON2_9PEZI Uncharacterized protein OS=*Pseudogymnoascus* sp. VKM F-4518 (FW-2643) GN=V500_02402 PE=3 SV=1;
>tr|A0A1B8F8Y4|A0A1B8F8Y4_9PEZI Uncharacterized protein OS=*Pseudogymnoascus* sp. 05NY08 GN=VF21_01182 PE=4 SV=1;
>tr|TOL037|TOL037_COLGC Uncharacterized protein OS=*Colletotrichum gloeosporioides* (strain Cg-14) GN=CGLO_01555 PE=4 SV=1;

>tr|A0A061H8U8|A0A061H8U8_9BASI Uncharacterized protein OS=*Anthracocystis flocculosa* PF-1 GN=PFL1_03308 PE=4 SV=1;

>tr|A0A0L7QQR3|A0A0L7QQR3_9HYME DNA polymerase beta OS=*Habropoda laboriosa* GN=WH47_05677 PE=4 SV=1;

>tr|S7MBS5|S7MBS5_MYOBR DNA polymerase beta (Fragment) OS=*Myotis brandtii* GN=D623_10030529 PE=4 SV=1 (SEQ ID NO: 71);

>tr|A0A093ZRF7|A0A093ZRF7_9PEZI Uncharacterized protein OS=*Pseudogymnoascus* sp. VKM F-3775 GN=V491_06339 PE=3 SV=1;

>tr|A0A094BPD5|A0A094BPD5_9PEZI Uncharacterized protein OS=*Pseudogymnoascus* sp. VKM F-4513 (FW-928) GN=V494_04866 PE=3 SV=1;

>tr|M7T317|M7T317_EUTLA Putative dna polymerase protein OS=*Eutypa lata* (strain UCR-EL1) GN=UCREL1_1708 PE=4 SV=1;

>tr|A0A101M8Z9|A0A101M8Z9_9EURO Uncharacterized protein OS=*Penicillium freii* GN=ACN42_g11030 PE=4 SV=1;

>tr|A0A0U5FQX5|A0A0U5FQX5_9EURO Uncharacterized protein OS=*Aspergillus calidoustus* GN=ASPCAL00639 PE=4 SV=1;

>tr|H2PQ72|H2PQ72_PONAB Uncharacterized protein OS=*Pongo abelii* GN=POLB PE=4 SV=1;

>tr|A0A0D0EBV6|A0A0D0EBV6_9HOMO Unplaced genomic scaffold 77, whole genome shotgun sequence OS=*Paxillus rubicundulus* VeO8.2h10 GN=PAXRUDRAFT_824032 PE=4 SV=1;

>tr|A0A0N0BKH1|A0A0N0BKH1_9HYME DNA polymerase beta OS=*Melipona quadrifasciata* GN=WN51_05442 PE=4 SV=1;

>tr|A0A094H7H0|A0A094H7H0_9PEZI Uncharacterized protein OS=*Pseudogymnoascus* sp. VKM F-4520 (FW-2644) GN=V502_08840 PE=3 SV=1;

>tr|J9HWK2|J9HWK2_9SPIT Helix-hairpin-helix motif family protein OS=*Oxytricha trifallax* GN=OXYTRI_10227 PE=4 SV=1;

>tr|A0A1J8QB20|A0A1J8QB20_9HOMO Uncharacterized protein OS=*Rhizopogon vesiculosus* GN=AZE42_05230 PE=4 SV=1;

>tr|A0A1S3KHL6|A0A1S3KHL6_LINUN DNA polymerase lambda-like isoform X2 OS=*Lingula unguis* GN=LOC106181965 PE=4 SV=1;

>tr|A0A1L9PIQ4|A0A1L9PIQ4_ASPVE Uncharacterized protein OS=*Aspergillus versicolor* CBS 583.65 GN=ASPVEDRAFT_130713 PE=4 SV=1;

>tr|Q53EV2|Q53EV2_HUMAN Polymerase (DNA directed), beta variant (Fragment) OS=*Homo sapiens* PE=2 SV=1;

>tr|A0A1B8CGP1|A0A1B8CGP1_9PEZI Uncharacterized protein OS=*Pseudogymnoascus* sp. WSF 3629 GN=VE00_03720 PE=4 SV=1;

>tr|G2YKX9|G2YKX9_BOTF4 Uncharacterized protein OS=*Botryotinia fuckeliana* (strain T4) GN=BofuT4_P080720.1 PE=4 SV=1;

>tr|G3R1G2|G3R1G2_GORGO Uncharacterized protein OS=*Gorilla gorilla gorilla* GN=POLB PE=4 SV=1;

>tr|G3SIQ7|G3SIQ7_GORGO Uncharacterized protein OS=*Gorilla gorilla gorilla* GN=POLB PE=4 SV=1;

>tr|A0A135M080|A0A135M080_PENPA DNA polymerase family X OS=*Penicillium patulum* GN=PGRI_077250 PE=4 SV=1;

>tr|V5L328|V5L328_9VIRU Putative DNA polymerase family X OS=*Hirudovirus* strain Sangsue GN=HIRUS640 PE=4 SV=1;

>tr|A0A140EOM9|A0A140EOM9_MIMIV DNA polymerase family x protein OS=*Samba virus* PE=4 SV=1;

>tr|A0A165XF78|A0A165XF78_MIMIV Putative DNA polymerase family X OS=*Mimivirus Bombay* PE=4 SV=1;

>tr|A0A0U2SWJ7|A0A0U2SWJ7_9VIRU DNA polymerase family X OS=*Niemeyer virus* PE=4 SV=1;

>tr|G8ED36|G8ED36_9VIRU DNA polymerase family X OS=*Acanthamoeba castellanii mamavirus* GN=MAMA_L395 PE=4 SV=1;

>tr|J3|Z33|J3|Z33_9VIRU DNA polymerase family X OS=*Acanthamoeba polyphaga* lentillevirus GN=L262 PE=4 SV=1;

>tr|E3VZU8|E3VZU8_MIMIV DNA polymerase family X OS=*Acanthamoeba polyphaga* mimivirus GN=L318 PE=4 SV=1;

>tr|A0A1E1EVX4|A0A1E1EVX4_9VIRU Putative DNA polymerase family X OS=*Acanthamoeba castellanii* mimivirus PE=4 SV=1;

>sp|Q7T6Y4|DPOLX_MIMIV Probable DNA polymerase family X OS=*Acanthamoeba polyphaga* mimivirus GN=MIMI_L318 PE=1 SV=2;

>tr|A0A1B8G098|A0A1B8G098_9PEZI Uncharacterized protein OS=*Pseudogymnoascus* sp. 03VT05 GN=VE02_02586 PE=4 SV=1;

>tr|A0A067GS95|A0A067GS95_CITSI Uncharacterized protein (Fragment) OS=*Citrus sinensis* GN=CISIN_1g0093031 mg PE=4 SV=1;

>tr|H6U746|H6U746_9SAUR DNA polymerase beta (Fragment) OS=*Pogona vitticeps* GN=POLB PE=2 SV=1;

>tr|A0A096N1P6|A0A096N1P6_PAPAN Uncharacterized protein OS=*Papio anubis* GN=POLB PE=4 SV=1;

>tr|A0A0D9RRA2|A0A0D9RRA2 CHLSB Uncharacterized protein OS=*Chlorocebus sabaeus* GN=POLB PE=4 SV=1;

>tr|G7PBR6|G7PBR6_MACFA DNA polymerase beta OS=*Macaca fascicularis* GN=EGM_17277 PE=4 SV=1;

>tr|IOFSR3|IOFSR3_MACMU DNA polymerase beta OS=*Macaca mulatta* GN=POLB PE=2 SV=1;

>tr|A0A094GKB1|A0A094GKB1_9PEZI Uncharacterized protein OS=*Pseudogymnoascus* sp. VKM F-103 GN=V499_07542 PE=3 SV=1;

>tr|A0A094CAY7|A0A094CAY7_9PEZI Uncharacterized protein OS=*Pseudogymnoascus* sp. VKM F-4515 (FW-2607) GN=V496_08955 PE=3 SV=1;

>tr|A0A094GUE6|A0A094GUE6_9PEZI Uncharacterized protein OS=*Pseudogymnoascus* sp. VKM F-4517 (FW-2822) GN=V498_00536 PE=3 SV=1;

>tr|A0A1E4RU82|A0A1E4RU82_CYBJA Nucleotidyltransferase OS=*Cyberlindnera jadinii* NRRL Y-1542 GN=CYBJADRAFT_169885 PE=4 SV=1;

>tr|A0A135U6J3|A0A135U6J3_9PEZI Uncharacterized protein OS=*Colletotrichum salicis* GN=CSAL01_12504 PE=4 SV=1;

>tr|Q5JQP2|Q5JQP2_HUMAN DNA polymerase lambda (Fragment) OS=*Homo sapiens* GN=POLL PE=1 SV=1;

>rf 1 5prime-gi|460163 [*Gallus gallus*]-3prime;

>rf 1 5prime-gi|494987 [*Xenopus laevis*]-3prime;

>rf 1 5prime-gi|1354475 [*Oncorhynchus mykiss*]-3prime;

>rf 1 5prime-gi|12802441 [*Mus musculus*]-3prime;

>rf 1 5prime-gi|28852989 [*Ambystoma mexicanum*]-3prime;

>rf 1 5prime-gi|38603668 [*Takifugu rubripes*]-3prime;

>rf 1 5prime-gi|40218593 [*Ginglymostoma cirratum*]-3prime;
>rf 1 5prime-gi|73998101 [*Canis lupus familiaris*]-3prime;
>rf 1 5prime-gi|139001476 [*Lemur catta*]-3prime;
>rf 1 5prime-gi|139001511 [*Otolemur garnettii*]-3prime;
>rf 1 5prime-gi|149704611 [*Equus caballus*]-3prime;
>rf 1 5prime-gi|164451472 [*Bos taurus*]-3prime;
>rf 1 5prime-gi|169642654 [*Xenopus* (Silurana) *tropicalis*]-3prime;
>rf 1 5prime-gi|291394899 [*Oryctolagus cuniculus*]-3prime;
>rf 1 5prime-gi|327280070 [*Anolis carolinensis*]-3prime;
>rf 1 5prime-gi|344274915 [*Loxodonta africana*]-3prime;
>rf 1 5prime-gi|348588114 [*Cavia porcellus*]-3prime;
>rf 1 5prime-gi|351697151 [*Heterocephalus glaber*]-3prime;
>rf 1 5prime-gi|355562663 [*Macaca mulatta*]-3prime;
>rf 1 5prime-gi|395501816 [*Sarcophilus harrisii*]-3prime;
>rf 1 5prime-gi|395508711 [*Sarcophilus harrisii*]-3prime;
>rf 1 5prime-gi|395850042 [*Otolemur garnettii*]-3prime;
>rf 1 5prime-gi|397467153 [*Pan paniscus*]-3prime;
>rf 1 5prime-gi|403278452 [*Saimiri boliviensis boliviensis*]-3prime;
>rf 1 5prime-gi|410903980 [*Takifugu rubripes*]-3prime;
>rf 1 5prime-gi|410975770 [*Felis catus*]-3prime;
>rf 1 5prime-gi|432092624 [*Myotis davidii*]-3prime;
>rf 1 5prime-gi|432113117 [*Myotis davidii*]-3prime;
>rf 1 5prime-gi|444708211 [*Tupaia chinensis*]-3prime;
>rf 1 5prime-gi|460417122 [*Pleurodeles waltl*]-3prime;
>rf 1 5prime-gi|466001476 [*Orcinus orca*]-3prime;
>rf 1 5prime-gi|471358897 [*Trichechus manatus latirostris*]-3prime;
>rf 1 5prime-gi|478528402 [*Ceratotherium simum simum*]-3prime;
>rf 1 5prime-gi|488530524 [*Dasypus novemcinctus*]-3prime;
>rf 1 5prime-gi|499037612 [*Maylandia zebra*]-3prime;
>rf 1 5prime-gi|504135178 [*Ochotona princeps*]-3prime;
>rf 1 5prime-gi|505844004 [*Sorex araneus*]-3prime;
>rf 1 5prime-gi|505845913 [*Sorex araneus*]-3prime;
>rf 1 5prime-gi|507537868 [*Jaculus jaculus*]-3prime;
>rf 1 5prime-gi|507572662 [*Jaculus jaculus*]-3prime;
>rf 1 5prime-gi|507622751 [*Octodon degus*]-3prime;
>rf 1 5prime-gi|507640406 [*Echinops telfairi*]-3prime;
>rf 1 5prime-gi|507669049 [*Echinops telfairi*]-3prime;
>rf 1 5prime-gi|507930719 [*Condylura cristata*]-3prime;
>rf 1 5prime-gi|507940587 [*Condylura cristata*]-3prime;
>rf 1 5prime-gi|511850623 [*Mustela putorius furo*]-3prime;
>rf 1 5prime-gi|512856623 [*Xenopus* (Silurana) *tropicalis*]-3prime;
>rf 1 5prime-gi|512952456 [*Heterocephalus glaber*]-3prime;
>rf 1 5prime-gi|524918754 [*Mesocricetus auratus*]-3prime;
>rf 1 5prime-gi|527251632 [*Melopsittacus undulatus*]-3prime;
>rf 1 5prime-gi|528493137 [*Danio rerio*]-3prime;
>rf 1 5prime-gi|528493139 [*Danio rerio*]-3prime;
>rf 1 5prime-gi|529438486 [*Falco peregrinus*]-3prime;
>rf 1 5prime-gi|530565557 [*Chrysemys picta bellii*]-3prime;
>rf 1 5prime-gi|532017142 [*Microtus ochrogaster*]-3prime;
>rf 1 5prime-gi|532099471 [*Ictidomys tridecemlineatus*]-3prime;
>rf 1 5prime-gi|533166077 [*Chinchilla lanigera*]-3prime;
>rf 1 5prime-gi|533189443 [*Chinchilla lanigera*]-3prime;
>rf 1 5prime-gi|537205041 [*Cricetulus griseus*]-3prime;
>rf 1 5prime-gi|537263119 [*Cricetulus griseus*]-3prime;
>rf 1 5prime-gi|543247043 [*Geospiza fortis*]-3prime;
>rf 1 5prime-gi|543731985 [*Columba livia*]-3prime;
>rf 1 5prime-gi|291404551 [*Oryctolagus cuniculus*]-3prime;
>rf 1 5prime-gi|301763246 [*Ailuropoda melanoleuca*]-3prime;
>rf 1 5prime-gi|478507321 [*Ceratotherium simum simum*]-3prime;
>rf 1 5prime-gi|543351492 [*Pseudopodoces humilis*]-3prime;
>rf 1 5prime-gi|544420267 [*Macaca fascicularis*]-3prime;
>rf 1 5prime-gi|545193630 [*Equus caballus*]-3prime;
>rf 1 5prime-gi|548384565 [*Pundamilia nyererei*]-3prime;
>rf 1 5prime-gi|551487466 [*Xiphophorus maculatus*]-3prime;
>rf 1 5prime-gi|551523268 [*Xiphophorus maculatus*]-3prime;
>rf 1 5prime-gi|554582962 [*Myotis brandtii*]-3prime;
>rf 1 5prime-gi|554588252 [*Myotis brandtii*]-3prime;
>rf 1 5prime-gi|556778822 [*Pantholops hodgsonii*]-3prime;
>rf 1 5prime-gi|556990133 [*Latimeria chalumnae*]-3prime;
>rf 1 5prime-gi|557297894 [*Alligator sinensis*]-3prime;
>rf 1 5prime-gi|558116760 [*Pelodiscus sinensis*]-3prime;
>rf 1 5prime-gi|558207237 [*Myotis lucifugus*]-3prime;
>rf 1 5prime-gi|560895997 [*Camelus ferus*]-3prime;
>rf 1 5prime-gi|560897502 [*Camelus ferus*]-3prime;
>rf 1 5prime-gi|562857949 [*Tupaia chinensis*]-3prime;
>rf 1 5prime-gi|562876575 [*Tupaia chinensis*]-3prime;
>rf 1 5prime-gi|564229057 [*Alligator mississippiensis*]-3prime;
>rf 1 5prime-gi|564236372 [*Alligator mississippiensis*]-3prime;
>rf 1 5prime-gi|564384286 [*Rattus norvegicus*]-3prime;
>rf 1 5prime-gi|573884994 [*Lepisosteus oculatus*]-3prime;
>rf 1 5prime-gi|2149634 [*Monodelphis domestica*]-3prime (pD441-NH);
>rf 1 5prime-gi|40037389 [*Raja eglanteria*]-3prime (pD441-NH);
>rf 1 5prime-gi|46369889 [*Danio rerio*]-3prime (pD441-NH);
>rf 1 5prime-gi|139001490 [*Microcebus murinus*]-3prime (pD441-NH);
>rf 1 5prime-gi|148708614 [*Mus musculus*]-3prime (pD441-NH);
>rf 1 5prime-gi|149040157 [*Rattus norvegicus*]-3prime (pD441-NH);
>rf 1 5prime-gi|311271684 [*Sus scrofa*]-3prime (pD441-NH);
>rf 1 5prime-gi|334313404 [*Monodelphis domestica*]-3prime (pD441-NH);
>rf 1 5prime-gi|345330196 [*Ornithorhynchus anatinus*]-3prime (pD441-NH).

What is claimed is:

1. A method of nucleic acid synthesis, which comprises the steps of:
   (a) providing an initial initiator sequence;
   (b) adding a reversibly blocked nucleotide triphosphate to said initiator sequence in the presence of a modified terminal transferase enzyme, which comprises a truncated BRCA-1 C-terminal (BRCT) domain, such that the BRCT domain is absent, wherein the modified terminal transferase enzyme is derived from a wild type terminal transferase enzyme from *L. oculatus, S. harrisii, S. scrofa, O. garnetti, C. lanigera, D. novemcinctus, M. domestica, P. nyererei,* or *M. brandtii;*
   (c) removing of all reagents from the initiator sequence including said modified terminal transferase enzyme;
   (d) cleaving the blocking group from the reversibly blocked nucleotide added in step (b) to said initiator sequence; and
   (e) removing of the cleaving agent,
   wherein greater than 1 nucleotide is added by repeating steps (b) to (e).

2. The method as defined in claim 1, wherein the reversibly blocked nucleotide triphosphate comprises a compound of formula (I):

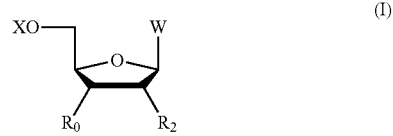

wherein $R_0$ represents a hydroxyl protecting group;
$R_2$ represents hydrogen, hydroxyl, —$N_3$, alkoxy, alkyl, alkenyl, alkynyl, —O-2-(cyanoethoxy)methyl, —O-(2-cyanoethyl), —O-azidomethyl, -aminoxy, or —O-allyl;
X represents triphosphate; and
W represents a base.

3. The method as defined in claim 1, wherein the reversibly blocked nucleotide triphosphate is blocked at the 3' position of the nucleotide sugar moiety by either a 3-O-2-

(cyanoethoxy)methyl, 3'-O-(2-cyanoethyl), 3'-O-azidomethyl, 3'-aminoxy, or 3-O-allyl group.

4. The method as defined in claim 1, wherein the reversibly blocked nucleotide comprises a compound of formula (II):

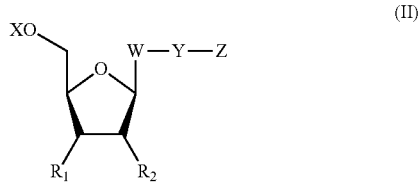

Wherein $R_1$ and $R_2$ independently represent H or OH or a protected derivative thereof;
X represents triphosphate;
W represents a base;
Y represents a cleavable linker; and
Z represents a blocking group or support moiety.

5. The method as defined in claim 1, wherein the initial initiator sequence is between 5 and 100 nucleotides long; or 10 and 90 nucleotides long; or 5 and 20 nucleotides long.

6. The method as defined in claim 1, which is performed in a microfluidic device.

7. A kit comprising a modified terminal transferase enzyme, derived from a wild type terminal transferase enzyme from *L. oculatus, S. harrisii, S. scrofa, O. garnetti, C. lanigera, D. novemcinctus, M. domestica, P. nyererei*, or *M. brandtii* which comprises a truncated BRCA-1 C-terminal (BRCT) domain, such that the BRCT domain is absent, an immobilized initiator sequence, and one or more reversibly blocked nucleoside triphosphates, optionally in combination with one or more components selected from: a microfluidic device or chip, inorganic pyrophosphatase, and a cleaving agent; further optionally together with instructions for use of the kit in accordance with the method as defined in claim 1.

8. The method as defined in claim 1, wherein said enzyme comprises an N-terminal truncated BRCT domain removing approximately 21% of the protein molecular weight.

9. The method as defined in claim 1, wherein the modified terminal transferase enzyme is derived from the wild type terminal transferase enzyme of *L. oculatus*.

10. The method as defined in claim 1, wherein the modified terminal transferase enzyme is derived from the wild type terminal transferase enzyme of *S. harrisii*.

11. The method as defined in claim 1, wherein the modified terminal transferase enzyme is derived from the wild type terminal transferase enzyme of *S. scrofa*.

12. The method as defined in claim 1, wherein the modified terminal transferase enzyme is derived from the wild type terminal transferase enzyme of *O. garnetti*.

13. The method as defined in claim 1, wherein the modified terminal transferase enzyme is derived from the wild type terminal transferase enzyme of *C. lanigera*.

14. The method as defined in claim 1, wherein the modified terminal transferase enzyme is derived from the wild type terminal transferase enzyme of *D. novemcinctus*.

15. The method as defined in claim 1, wherein the modified terminal transferase enzyme is derived from the wild type terminal transferase enzyme of *M. domestica*.

16. The method as defined in claim 1, wherein the modified terminal transferase enzyme is derived from the wild type terminal transferase enzyme of *P. nyererei*.

17. The method as defined in claim 1, wherein the modified terminal transferase enzyme is derived from the wild type terminal transferase enzyme of *M. brandtii*.

* * * * *

SEQUENCE LISTING

<160> NUMBER OF SEQ ID NOS: 88

<210> SEQ ID NO 1
<211> LENGTH: 494
<212> TYPE: PRT
<213> ORGANISM: Lepisosteus oculatus

<400> SEQUENCE: 1

```
Met Leu His Ile Pro Ile Phe Pro Pro Ile Lys Lys Arg Gln Lys Leu
1               5                   10                  15

Pro Glu Ser Arg Asn Ser Cys Lys Tyr Glu Val Lys Phe Ser Glu Val
            20                  25                  30

Ala Ile Phe Leu Val Glu Arg Lys Met Gly Ser Ser Arg Arg Lys Phe
        35                  40                  45

Leu Thr Asn Leu Ala Arg Ser Lys Gly Phe Arg Ile Glu Asp Val Leu
    50                  55                  60

Ser Asp Ala Val Thr His Val Ala Glu Asp Asn Ser Ala Asp Glu
65                  70                  75                  80

Leu Trp Gln Trp Leu Gln Asn Ser Ser Leu Gly Asp Leu Ser Lys Ile
                85                  90                  95

Glu Val Leu Asp Ile Ser Trp Phe Thr Glu Cys Met Gly Ala Gly Lys
            100                 105                 110

Pro Val Gln Val Glu Ala Arg His Cys Leu Val Lys Ser Cys Pro Val
        115                 120                 125

Ile Asp Gln Tyr Leu Glu Pro Ser Thr Val Thr Val Ser Gln Tyr
    130                 135                 140

Ala Cys Gln Arg Arg Thr Thr Met Glu Asn His Asn Gln Ile Phe Thr
145                 150                 155                 160

Asp Ala Phe Ala Ile Leu Ala Glu Asn Ala Glu Phe Asn Glu Ser Glu
                165                 170                 175

Gly Pro Cys Leu Ala Phe Met Arg Ala Ala Ser Leu Leu Lys Ser Leu
            180                 185                 190

Pro His Ala Ile Ser Ser Ser Lys Asp Leu Glu Gly Leu Pro Cys Leu
        195                 200                 205

Gly Asp Gln Thr Lys Ala Val Ile Glu Asp Ile Leu Glu Tyr Gly Gln
    210                 215                 220

Cys Ser Lys Val Gln Asp Val Leu Cys Asp Asp Arg Tyr Gln Thr Ile
225                 230                 235                 240

Lys Leu Phe Thr Ser Val Phe Gly Val Gly Leu Lys Thr Ala Glu Lys
                245                 250                 255

Trp Tyr Arg Lys Gly Phe His Ser Leu Glu Glu Val Gln Ala Asp Asn
            260                 265                 270

Ala Ile His Phe Thr Lys Met Gln Lys Ala Gly Phe Leu Tyr Tyr Asp
        275                 280                 285

Asp Ile Ser Ala Ala Val Cys Lys Ala Glu Ala Gln Ala Ile Gly Gln
    290                 295                 300

Ile Val Glu Glu Thr Val Arg Leu Ile Ala Pro Asp Ala Ile Val Thr
305                 310                 315                 320

Leu Thr Gly Gly Phe Arg Arg Gly Lys Glu Cys Gly His Asp Val Asp
                325                 330                 335

Phe Leu Ile Thr Thr Pro Glu Met Gly Lys Glu Val Trp Leu Leu Asn
            340                 345                 350

Arg Leu Ile Asn Arg Leu Gln Asn Gln Gly Ile Leu Leu Tyr Tyr Asp
        355                 360                 365
```

-continued

```
Ile Val Glu Ser Thr Phe Asp Lys Thr Arg Leu Pro Cys Arg Lys Phe
370                 375                 380

Glu Ala Met Asp His Phe Gln Lys Cys Phe Ala Ile Ile Lys Leu Lys
385                 390                 395                 400

Lys Glu Leu Ala Ala Gly Arg Val Gln Lys Asp Trp Lys Ala Ile Arg
                405                 410                 415

Val Asp Phe Val Ala Pro Pro Val Asp Asn Phe Ala Phe Ala Leu Leu
                420                 425                 430

Gly Trp Thr Gly Ser Arg Gln Phe Glu Arg Asp Leu Arg Phe Ala
                435                 440                 445

Arg His Glu Arg Lys Met Leu Leu Asp Asn His Ala Leu Tyr Asp Lys
450                 455                 460

Thr Lys Lys Tyr Leu Lys Lys Thr Thr Asn Asn Tyr Leu Ala Leu
465                 470                 475                 480

Asn Asp Val Cys Ser Asp Leu Ser Glu Trp His Tyr Lys Gly
                485                 490

<210> SEQ ID NO 2
<211> LENGTH: 502
<212> TYPE: PRT
<213> ORGANISM: Salmo salar

<400> SEQUENCE: 2

Met Ile His Ala Ser Met Leu Pro Arg Val Lys Lys Arg Pro Arg Pro
1               5                   10                  15

Val Glu Ala Gly Ala Arg Gly Gln Glu Glu Val Lys Phe Asn Glu Val
                20                  25                  30

Thr Val Tyr Leu Val Glu Arg Lys Met Gly Ser Ser Arg Arg Ser Phe
            35                  40                  45

Leu Thr Ser Leu Ala Arg Ser Lys Gly Phe Arg Val Glu Tyr Val Leu
    50                  55                  60

Ser Asp Glu Val Thr His Val Ala Glu Asp Asn Arg Ala Gly Ala
65                  70                  75                  80

Leu Trp Ala Trp Leu Arg Gly Ser Gly Leu Arg Asp Val Ser Arg Leu
                85                  90                  95

Gln Val Leu Asp Ile Ser Trp Phe Thr Asp Ser Met Arg Glu Gly Arg
                100                 105                 110

Pro Val Thr Val Glu Thr Arg His Cys Ile Pro Asp Thr Ser Ser Thr
            115                 120                 125

Val Pro Glu Cys Ser Pro Pro Ile Ala Ala Asn Val Ser Gln Tyr
130                 135                 140

Ala Cys Leu Arg Arg Thr Thr Thr Glu Asn His Asn Lys Ile Phe Thr
145                 150                 155                 160

Asp Val Leu Glu Glu Leu Ala Glu Asn Ser Glu Phe Asn Glu Ser Lys
                165                 170                 175

Gly Pro Cys Leu Ala Phe Arg Arg Ala Ala Ser Val Leu Lys Ser Leu
                180                 185                 190

Pro Ser Ala Val His Cys Leu Gly Ala Ile Gln Gly Leu Pro Cys Leu
            195                 200                 205

Gly Glu His Thr Lys Ala Val Met Glu Glu Ile Leu Ile Phe Gly Arg
210                 215                 220

Ser Phe Lys Val Glu Glu Val Gln Ser Asp Glu Arg Tyr Gln Ala Leu
225                 230                 235                 240

Lys Leu Phe Thr Ser Val Phe Gly Val Gly Pro Lys Thr Ala Glu Lys
                245                 250                 255
```

Trp Tyr Arg Arg Gly Leu Arg Ser Leu Lys Glu Ile Leu Ala Glu Pro
            260                 265                 270

Asn Ile Gln Leu Asn Arg Met Gln Arg Ala Gly Phe Leu Tyr Tyr Arg
            275                 280                 285

Asp Ile Ser Lys Ala Val Ser Lys Ala Glu Ala Lys Ala Leu Arg Ser
290                 295                 300

Ile Ile Glu Glu Thr Ala His Trp Ile Ala Pro Asp Ser Ile Leu Ala
305                 310                 315                 320

Leu Thr Gly Gly Phe Arg Gly Lys Glu Tyr Gly His Asp Val Asp
            325                 330                 335

Phe Leu Leu Thr Met Pro Val Met Gly Lys Glu Gly Leu Leu Leu
            340                 345                 350

Arg Val Ile Asp Arg Leu Arg Asp Gln Gly Ile Leu Leu Tyr Cys Glu
            355                 360                 365

His Gln Gly Ser Thr Phe Asp Met Ser Lys Leu Pro Ser Arg Arg Phe
            370                 375                 380

Glu Ala Met Asp His Phe Glu Lys Cys Phe Leu Ile Leu Arg Leu Glu
385                 390                 395                 400

Glu Gly Gln Val Glu Gly Asp Gly Leu Gln Lys Asp Pro Gly Glu
            405                 410                 415

Ser Arg Gly Trp Arg Ala Val Arg Val Asp Leu Val Ala Pro Pro Val
            420                 425                 430

Asp Arg Tyr Ala Phe Ala Leu Leu Gly Trp Thr Gly Ser Arg Gln Phe
            435                 440                 445

Glu Arg Asp Leu Arg Arg Phe Ala Ser Lys Glu Arg Gly Met Cys Leu
            450                 455                 460

Asp Asn His Ala Leu Tyr Asp Lys Thr Lys Lys Leu Phe Leu Pro Ala
465                 470                 475                 480

Thr Ser Glu Glu Asp Ile Phe Ala His Leu Gly Leu Glu Tyr Val Glu
            485                 490                 495

Pro Trp Gln Arg Asn Ala
            500

<210> SEQ ID NO 3
<211> LENGTH: 501
<212> TYPE: PRT
<213> ORGANISM: Salmo salar

<400> SEQUENCE: 3

Met Asn His Ala Gly Met Leu Ala Arg Val Lys Lys Arg Lys Arg Pro
1               5                   10                  15

Val Glu Ala Gly Ala Gln Gly Gln Val Glu Val Lys Phe Lys Glu Val
            20                  25                  30

Thr Leu Tyr Leu Val Glu Arg Lys Met Gly Ser Ser Arg Arg Asn Phe
            35                  40                  45

Leu Thr Ser Leu Ala Arg Ser Lys Gly Phe Arg Val Glu Asp Val Leu
            50                  55                  60

Ser Asp Val Thr His Val Ala Glu Asp Asn Gln Ala Glu Val
65                  70                  75                  80

Leu Trp Ala Trp Leu Met Gly His Gly Leu Arg Asp Val Ser Arg Leu
            85                  90                  95

Ala Val Leu Asp Ile Ser Trp Phe Thr Asp Ser Met Arg Glu Gly Arg
            100                 105                 110

Pro Val Arg Val Glu Thr Arg His Arg Ile Gln Asn Thr Pro Thr Val

```
                        115                 120                 125
        Thr Asp Cys Ser Pro Thr Ala Val Ala Asn Val Ser Gln Tyr Ala
        130                 135                 140
        Cys Gln Arg Arg Thr Thr Thr Glu Asn His Asn Lys Ile Phe Thr Asp
    145                 150                 155                 160
        Val Met Glu Glu Leu Ala Glu Ser Ser Glu Phe Asn Glu Ser Lys Gly
                        165                 170                 175
        Pro Cys Leu Ala Phe Arg Gln Ala Ala Ser Val Leu Lys Ser Leu Pro
                    180                 185                 190
        Ser Ala Val Gln Cys Leu Glu Ala Ile Gln Gly Leu Pro Cys Leu Gly
                195                 200                 205
        Glu His Thr Lys Ala Val Met Glu Glu Ile Leu Thr Phe Gly Arg Ser
            210                 215                 220
        Phe Lys Val Glu Glu Leu Arg Cys Asp Glu Arg Tyr Gln Ala Leu Lys
    225                 230                 235                 240
        Leu Phe Thr Ser Val Phe Gly Val Gly Pro Lys Thr Ala Glu Lys Trp
                        245                 250                 255
        Tyr Arg Arg Gly Leu Arg Ser Leu Lys Glu Ile Leu Thr Glu Pro Ser
                    260                 265                 270
        Ile Gln Leu Asn Arg Met Gln Arg Ala Gly Phe Leu Tyr Tyr Ser Asp
                275                 280                 285
        Ile Ser Lys Ala Val Ser Lys Ala Glu Ala Glu Ala Leu Gly Cys Ile
            290                 295                 300
        Ile Glu Glu Thr Val His Trp Ile Ala Pro Asp Ala Val Leu Ala Leu
    305                 310                 315                 320
        Thr Gly Gly Phe Arg Arg Gly Lys Glu Tyr Gly His Asp Val Asp Phe
                        325                 330                 335
        Leu Leu Thr Met Pro Glu Met Gly Lys Glu Gly Leu Leu Leu His
                    340                 345                 350
        Val Ile Asp Arg Leu Arg Asp Gln Gly Ile Leu Leu Tyr Cys Glu Tyr
                355                 360                 365
        Gln Gly Ser Thr Phe Asp Val Ser Lys Leu Pro Ser Cys Arg Phe Glu
            370                 375                 380
        Asp Met Asp His Phe Gln Lys Cys Phe Leu Ile Leu Arg Leu Glu Gln
    385                 390                 395                 400
        Gly Gln Val Glu Gly Arg Gly Gln Gln Arg Asp Pro Gly Asp Ser
                        405                 410                 415
        Arg Gly Trp Arg Ala Val Arg Val Asp Leu Val Ala Pro Pro Val Asp
                    420                 425                 430
        Arg Tyr Ala Phe Ala Leu Leu Gly Trp Thr Gly Ser Arg Gln Phe Gly
                435                 440                 445
        Arg Asp Leu Arg Ala Phe Ala Gln Lys Glu Arg Gln Met Leu Leu Asp
            450                 455                 460
        Asn His Ala Leu Tyr Asp Lys Thr Lys Gln Leu Phe Leu Pro Val Thr
    465                 470                 475                 480
        Thr Glu Glu Asp Ile Phe Ala His Leu Gly Leu Glu Tyr Val Glu Pro
                        485                 490                 495
        Trp Gln Arg Asn Ala
                    500

<210> SEQ ID NO 4
<211> LENGTH: 500
<212> TYPE: PRT
<213> ORGANISM: Salmo salar
```

<400> SEQUENCE: 4

| | | | | | | | | | | | | | | |
|---|---|---|---|---|---|---|---|---|---|---|---|---|---|---|
|Met|Asn|His|Ala|Gly|Met|Leu|Ala|Arg|Val|Lys|Lys|Arg|Lys|Pro|
|1| | | |5| | | | |10| | | | |15|
|Val|Glu|Ala|Gly|Ala|Gln|Gly|Gln|Val|Glu|Val|Lys|Phe|Lys|Glu|Val|
| | | |20| | | | |25| | | | |30| | |
|Thr|Leu|Tyr|Leu|Val|Glu|Arg|Lys|Met|Gly|Ser|Ser|Arg|Arg|Asn|Phe|
| | | |35| | | | |40| | | | |45| | |
|Leu|Thr|Ser|Leu|Ala|Arg|Ser|Lys|Gly|Phe|Arg|Val|Glu|Asp|Val|Leu|
| |50| | | | |55| | | | |60| | | | |
|Ser|Asp|Asp|Val|Thr|His|Val|Ala|Glu|Asp|Asn|Gln|Ala|Glu|Val|
|65| | | | |70| | | | |75| | | | |80|
|Leu|Trp|Ala|Trp|Leu|Met|Gly|His|Gly|Leu|Arg|Asp|Val|Ser|Arg|Leu|
| | | | |85| | | | |90| | | | |95| |
|Ala|Val|Leu|Asp|Ile|Ser|Trp|Phe|Thr|Asp|Ser|Met|Arg|Glu|Gly|Arg|
| | | |100| | | | |105| | | | |110| | |
|Pro|Val|Arg|Val|Glu|Thr|Arg|His|Arg|Ile|Gln|Asn|Thr|Pro|Thr|Val|
| | | |115| | | | |120| | | | |125| | |
|Thr|Asp|Cys|Ser|Pro|Pro|Thr|Ala|Val|Ala|Asn|Val|Ser|Gln|Tyr|Ala|
| |130| | | | |135| | | | |140| | | | |
|Cys|Gln|Arg|Arg|Thr|Thr|Thr|Glu|Asn|His|Asn|Lys|Ile|Phe|Thr|Asp|
|145| | | | |150| | | | |155| | | | |160|
|Val|Met|Glu|Glu|Leu|Ala|Glu|Ser|Ser|Glu|Phe|Asn|Glu|Ser|Lys|Gly|
| | | | |165| | | | |170| | | | |175| |
|Pro|Cys|Leu|Ala|Phe|Arg|Gln|Ala|Ala|Ser|Val|Leu|Lys|Ser|Leu|Pro|
| | | |180| | | | |185| | | | |190| | |
|Ser|Ala|Val|Gln|Cys|Leu|Glu|Ala|Ile|Gln|Gly|Leu|Pro|Cys|Leu|Gly|
| | | |195| | | | |200| | | | |205| | |
|Glu|His|Thr|Lys|Ala|Val|Met|Glu|Glu|Ile|Leu|Thr|Phe|Gly|Arg|Ser|
| | | |210| | | | |215| | | | |220| | |
|Phe|Lys|Val|Glu|Glu|Leu|Arg|Cys|Asp|Glu|Arg|Tyr|Gln|Ala|Leu|Lys|
|225| | | | |230| | | | |235| | | | |240|
|Leu|Phe|Thr|Ser|Val|Phe|Gly|Val|Gly|Pro|Lys|Thr|Ala|Glu|Lys|Trp|
| | | | |245| | | | |250| | | | |255| |
|Tyr|Arg|Arg|Gly|Leu|Arg|Ser|Leu|Lys|Glu|Ile|Leu|Thr|Glu|Pro|Ser|
| | | |260| | | | |265| | | | |270| | |
|Ile|Gln|Leu|Asn|Arg|Met|Gln|Arg|Ala|Gly|Phe|Leu|Tyr|Tyr|Ser|Asp|
| | | |275| | | | |280| | | | |285| | |
|Ile|Ser|Lys|Ala|Val|Ser|Lys|Ala|Glu|Ala|Glu|Ala|Leu|Gly|Cys|Ile|
| | | |290| | | | |295| | | | |300| | |
|Ile|Glu|Glu|Thr|Val|His|Trp|Ile|Ala|Pro|Asp|Ala|Val|Leu|Ala|Leu|
|305| | | | |310| | | | |315| | | | |320|
|Thr|Gly|Gly|Phe|Arg|Arg|Gly|Lys|Glu|Tyr|Gly|His|Asp|Val|Asp|Phe|
| | | | |325| | | | |330| | | | |335| |
|Leu|Leu|Thr|Met|Pro|Glu|Met|Gly|Lys|Glu|Gly|Leu|Leu|Leu|His|
| | | |340| | | | |345| | | | |350| | |
|Val|Ile|Asp|Arg|Leu|Arg|Asp|Gln|Gly|Ile|Leu|Leu|Tyr|Cys|Glu|Tyr|
| | | |355| | | | |360| | | | |365| | |
|Gln|Gly|Ser|Thr|Phe|Asp|Val|Ser|Lys|Leu|Pro|Ser|Cys|Arg|Phe|Glu|
| | | |370| | | | |375| | | | |380| | |
|Asp|Met|Asp|His|Phe|Gln|Lys|Cys|Phe|Leu|Ile|Leu|Arg|Leu|Glu|Gln|
|385| | | | |390| | | | |395| | | | |400|
|Gly|Gln|Val|Glu|Gly|Glu|Arg|Gly|Gln|Gln|Arg|Asp|Pro|Gly|Asp|Ser|

```
                    405                 410                 415
Arg Gly Trp Arg Ala Val Arg Val Asp Leu Val Ala Pro Pro Val Asp
            420                 425                 430

Arg Tyr Ala Phe Ala Leu Leu Gly Trp Thr Gly Ser Arg Phe Gly Arg
            435                 440                 445

Asp Leu Arg Ala Phe Ala Gln Lys Glu Arg Gln Met Leu Leu Asp Asn
            450                 455                 460

His Ala Leu Tyr Asp Lys Thr Lys Gln Leu Phe Leu Pro Val Thr Thr
465                 470                 475                 480

Glu Glu Asp Ile Phe Ala His Leu Gly Leu Glu Tyr Val Glu Pro Trp
                    485                 490                 495

Gln Arg Asn Ala
            500

<210> SEQ ID NO 5
<211> LENGTH: 501
<212> TYPE: PRT
<213> ORGANISM: Ictalurus punctatus

<400> SEQUENCE: 5

Met Phe Gln Thr Thr Leu Ser Thr Phe Leu Arg Lys Arg Arg Gln Pro
1               5                   10                  15

Glu Leu Thr Cys Ala Gln Pro Gln Lys Glu Met Lys Phe Arg Glu Val
            20                  25                  30

Thr Val Tyr Leu Val Glu Arg Met Gly Lys Ser Arg Arg Asn Phe
        35                  40                  45

Leu Thr Ser Leu Ala Arg Ser Lys Gly Phe Ser Val Asp Asn Thr Leu
    50                  55                  60

Ser Ser Lys Val Thr His Ile Val Ala Glu Asp Asn Pro Ala His Glu
65                  70                  75                  80

Leu Trp Pro Trp Leu Gln Glu Gln Gly Ile Ala Asp Leu Gly Lys Met
                85                  90                  95

Asn Val Leu Asp Ile Ala Trp Phe Thr Gln Ser Met Lys Ala Gly Arg
            100                 105                 110

Pro Ile Pro Val Glu Ala Gln His Arg Ile Gln Lys Pro Ser Val Gln
        115                 120                 125

Pro Lys Pro Glu Ala Gly Pro Pro Asn Ser Pro Trp Leu Thr Val Ser
    130                 135                 140

Gln Tyr Ala Cys Gln Arg Arg Thr Thr Leu Tyr Asn His Asn Lys Ile
145                 150                 155                 160

Leu Thr Asp Ala Leu Glu Val Leu Ala Glu Asn Tyr Glu Phe Ile Glu
                165                 170                 175

Ser Ile Gly Pro Cys Leu Gly Phe Arg Arg Ala Ala Ser Met Leu Lys
            180                 185                 190

Ser Leu Pro Ala Pro Leu Arg Asn Ile Asn Asp Thr Glu Gly Leu Pro
        195                 200                 205

Cys Leu Gly Pro Glu Thr Lys Ala Val Ile Gln Asp Ile Phe Glu Cys
    210                 215                 220

Gly Ser Ser Lys Val Glu Glu Val Leu Thr Asp Glu Arg Tyr Arg
225                 230                 235                 240

Thr Leu Lys Ile Phe Thr Ser Val Phe Gly Val Gly Pro Lys Thr Ala
                245                 250                 255

Glu Lys Trp Tyr Arg Lys Gly Leu Arg Ser Leu Glu Gln Ile Ala Ser
            260                 265                 270
```

Asp Ser Ser Ile His Leu Asn Lys Met Gln Ile Ala Gly Phe Gln Tyr
            275                 280                 285

Tyr Glu Asp Ile Ser Lys Pro Val Ser Lys Ala Glu Ala Glu Ala Val
        290                 295                 300

Gly His Ile Ile Lys Glu Ile Ala Gly Cys Phe Ser Pro Asp Val Thr
305                 310                 315                 320

Met Thr Leu Thr Gly Gly Phe Arg Arg Gly Lys Glu Phe Gly His Asp
                325                 330                 335

Val Asp Phe Leu Leu Thr Val Pro Arg Pro Gly Lys Glu Asp Gly Leu
            340                 345                 350

Leu Pro Ala Val Ile Asn Gln Leu Arg Thr Gln Gly Leu Leu Leu Tyr
        355                 360                 365

Ser Asp Phe Gln Glu Ser Thr Phe Asp Leu Ser Ser Leu Pro Asn Arg
370                 375                 380

Arg Phe Glu Ala Met Asp His Phe Gln Lys Cys Phe Leu Ile Val Lys
385                 390                 395                 400

Leu Lys Lys Asp Gln Val Val Gly Gln Gln Ala Glu Gln Arg Cys Gly
                405                 410                 415

Arg Asp Trp Lys Ala Val Arg Val Asp Leu Val Ala Pro Pro Ala Glu
            420                 425                 430

Arg Tyr Ala Phe Ala Leu Leu Gly Trp Ser Gly Ser Thr Gln Phe Glu
        435                 440                 445

Arg Asp Leu Arg Arg Phe Ser Arg Leu Glu Arg Asn Met Leu Leu Asp
    450                 455                 460

Asn His Ala Leu Phe Asp Lys Thr Thr Asn Thr Phe Leu Gln Ala Lys
465                 470                 475                 480

Thr Glu Glu Asp Ile Phe Thr His Leu Gly Leu Asp Tyr Ile Glu Pro
                485                 490                 495

Trp Gln Arg Asn Ala
                500

<210> SEQ ID NO 6
<211> LENGTH: 501
<212> TYPE: PRT
<213> ORGANISM: Oncorhynchus mykiss

<400> SEQUENCE: 6

Met Asn His Ala Gly Met Leu Ala Leu Val Lys Lys Arg Lys Arg Pro
1               5                   10                  15

Val Glu Ala Gly Ala Gln Gly Gln Val Glu Val Lys Phe Lys Glu Val
            20                  25                  30

Thr Leu Glu Leu Val Glu Arg Lys Met Gly Ser Ser Arg Arg Asn Phe
        35                  40                  45

Leu Thr Arg Leu Ala Arg Ser Lys Gly Phe Arg Val Glu Asp Val Leu
    50                  55                  60

Ser Asp Asp Val Thr His Val Val Ala Glu Asp Asn Gln Ala Glu Val
65                  70                  75                  80

Leu Trp Ala Trp Leu Met Gly His Gly Leu Arg Asp Val Ser Arg Leu
                85                  90                  95

Ala Leu Leu Asp Ile Ser Trp Phe Thr Asp Ser Met Arg Glu Gly Arg
            100                 105                 110

Pro Val Arg Val Glu Thr Arg His Ser Ile Gln Asn Thr Pro Thr Gly
        115                 120                 125

Thr Asp Cys Ser Pro Pro Thr Ala Val Ala Asn Val Ser Gln Tyr Ala
    130                 135                 140

```
Cys Gln Arg Arg Thr Thr Thr Glu Asn His Asn Asn Lys Ile Phe Thr
145                 150                 155                 160

Asp Val Met Glu Glu Leu Ala Glu Ser Ser Glu Phe Asn Glu Ser Lys
            165                 170                 175

Gly Pro Cys Leu Ala Phe Arg Gln Ala Ala Ser Val Leu Lys Ser Leu
            180                 185                 190

Pro Ser Ala Val His Cys Leu Lys Ala Ile Gln Gly Leu Pro Cys Leu
            195                 200                 205

Gly Glu His Thr Lys Ala Val Met Glu Glu Ile Leu Thr Phe Gly Arg
            210                 215                 220

Ser Phe Lys Val Glu Glu Ile Arg Cys Asp Glu Arg Tyr Gln Ala Leu
225                 230                 235                 240

Lys Leu Phe Thr Ser Val Phe Gly Val Gly Pro Lys Thr Ala Glu Lys
            245                 250                 255

Trp Tyr Arg Arg Gly Leu Arg Ser Leu Gln Glu Ile Leu Thr Glu Pro
            260                 265                 270

Asn Ile Gln Leu Asn Arg Met Gln Arg Ala Gly Phe Leu Tyr Tyr Ser
            275                 280                 285

Asp Ile Ser Lys Ala Val Ser Lys Ala Glu Ala Lys Ala Val Gly Cys
290                 295                 300

Ile Ile Glu Asp Thr Phe His Trp Ile Ala Pro Asp Ala Ile Leu Ala
305                 310                 315                 320

Leu Thr Gly Gly Phe Arg Arg Gly Lys Glu Tyr Gly His Asp Val Asp
            325                 330                 335

Phe Leu Leu Thr Met Pro Glu Ile Gly Lys Asp Glu Gly Leu Leu Leu
            340                 345                 350

His Val Ile Asp Arg Leu Lys Asp Gln Gly Ile Leu Leu Tyr Cys Asp
            355                 360                 365

Tyr Gln Gly Ser Thr Phe Asp Val Ser Lys Leu Pro Ser Cys Arg Phe
            370                 375                 380

Glu Asp Met Asp Cys Phe Gln Lys Cys Phe Leu Ile Leu Arg Leu Glu
385                 390                 395                 400

Gln Gly Gln Val Glu Gly Glu Arg Gly Leu Gln Arg Asp Pro Gly Asp
            405                 410                 415

Ser Arg Gly Trp Arg Ala Val Arg Val Asp Leu Val Ala Pro Pro Val
            420                 425                 430

Asp Arg Tyr Ala Phe Ala Leu Leu Gly Trp Thr Gly Ser Arg Phe Gly
            435                 440                 445

Arg Asp Leu Arg Thr Phe Ala Gln Lys Glu Arg Gln Met Leu Leu Asp
450                 455                 460

Asn His Ala Leu Tyr Asp Lys Thr Lys Lys Leu Cys Leu Leu Ala Thr
465                 470                 475                 480

Thr Glu Glu Asp Ile Phe Thr His Leu Gly Leu Glu Tyr Val Glu Pro
            485                 490                 495

Trp Gln Arg Asn Ala
            500
```

<210> SEQ ID NO 7
<211> LENGTH: 522
<212> TYPE: PRT
<213> ORGANISM: Ginglymostoma cirratum

<400> SEQUENCE: 7

Met Ser Leu Ala Gly Ser Leu Gly Gly Met Gly Ile Ile Pro Lys Arg

```
1               5                    10                   15
Lys Arg Gln Lys Val Thr Glu Val Cys Ser Ser Gln Ser Lys His Gln
                20                  25                  30

Val Arg Phe Gln Asp Leu Thr Ile Phe Ile Val Glu Arg Lys Met Gly
                35                  40                  45

Ser Ser Arg Arg Ser Phe Leu Met Asp Leu Ala Arg Lys Lys Gly Phe
            50                  55                  60

Arg Val Glu Asp Val Met Ser Asp Ser Val Thr His Ile Val Thr Glu
65                  70                  75                  80

Asn Asn Ser Trp Asp Glu Ile Trp Asp Trp Ile Gln Asn Leu Lys Leu
                85                  90                  95

Leu Asn Ala Asp Lys Leu Lys Met Leu Asn Ile Ser Trp Phe Thr Asp
                100                 105                 110

Ser Met Ala Ala Gly Lys Pro Val Glu Ile Glu Arg His Lys Leu
                115                 120                 125

Gln Val Gln Lys Met Leu Gln Ser Asn Ser Pro Leu Pro Pro Val
            130                 135                 140

Val Thr Ile Ser Gln Tyr Ala Cys Gln Arg Arg Ser Thr Leu Asn Asn
145                 150                 155                 160

Arg Asn Lys Ile Phe Thr Asp Ala Leu Glu Ile Leu Ala Glu Asn Phe
                165                 170                 175

Glu Phe Asn Glu Asn Glu Ser Ala Tyr Val Ala Phe Ala Arg Ala Thr
                180                 185                 190

Ser Leu Leu Lys Ser Leu Pro Tyr Thr Ile Ser Lys Met Ala Ala Leu
            195                 200                 205

Asp Gly Leu Pro Cys Phe Gly Asp Gln Thr Arg Ala Ile Ile Glu Glu
            210                 215                 220

Ile Leu Glu Asp Gly Val Ser Ser Lys Val Asp Asp Leu Leu Cys Asp
225                 230                 235                 240

Glu Lys Tyr Lys Ala Arg Lys Leu Phe Thr Ser Val Phe Gly Val Gly
                245                 250                 255

Leu Lys Thr Ala Asp Lys Trp Tyr Gly Gln Gly Phe Arg Thr Leu Glu
                260                 265                 270

Ala Val Lys Ala Ser Lys Asp Leu Lys Phe Thr Lys Met Gln Lys Ala
            275                 280                 285

Gly Phe Leu Tyr Tyr Glu Asp Ile Asn Asn Ala Val Thr Arg Pro Glu
            290                 295                 300

Ala Glu Ala Val Ala Gln Ile Ile Glu Thr Ile Val His Asn Tyr Ala
305                 310                 315                 320

Pro Asp Ala Ile Val Thr Leu Thr Gly Gly Phe Arg Arg Gly Lys Glu
                325                 330                 335

Thr Gly His Asp Val Asp Phe Leu Ile Ser Cys Pro Glu Thr Met Asp
                340                 345                 350

Glu Asn Phe Leu Arg Lys Ile Val Asn Lys Leu Asp Phe Arg Gly Leu
            355                 360                 365

Leu Leu Tyr Tyr Asp Met Val Glu Ala Thr Phe Glu Lys Arg Lys Leu
    370                 375                 380

Ser Ser Gln Lys Tyr Asp Ala Met Asp His Phe Gln Lys Cys Phe Leu
385                 390                 395                 400

Ile Leu Lys Leu Asn Lys Ala Leu Val Lys Asn Arg Val Leu Ser Met
                405                 410                 415

Ser Ser Val Ser Ala Ala Arg Pro Thr Asp Glu Gly Ala Glu Pro Glu
            420                 425                 430
```

```
Val Lys Thr Gln Ile Lys Asp Trp Lys Ala Ile Arg Val Asp Leu Val
        435                 440                 445

Ile Val Pro Thr Gln Gln Phe Ala Tyr Ala Leu Leu Gly Trp Thr Gly
        450                 455                 460

Ser Arg Gln Phe Glu Arg Asp Leu Arg Arg Tyr Thr Asn His Glu Lys
465                 470                 475                 480

Ser Met Ile Leu Asp Asn His Gly Leu Tyr Asp Arg Lys Lys Lys Ile
                485                 490                 495

Phe Leu Asn Ala Lys Thr Glu Glu Ile Phe Ala His Leu Asp Leu
                500                 505                 510

Glu Tyr Ile Glu Pro Trp Glu Arg Asn Ala
        515                 520

<210> SEQ ID NO 8
<211> LENGTH: 509
<212> TYPE: PRT
<213> ORGANISM: Astyanax mexicanus

<400> SEQUENCE: 8

Cys Glu Val Met Phe Gln Thr Ala Leu Ser Thr Leu Leu Arg Lys Arg
1               5                   10                  15

Arg Arg Pro Glu Ser Thr Pro Ala Leu Pro Gln Gln Gly Lys Lys Phe
            20                  25                  30

Gly Glu Val Met Val Tyr Leu Val Glu Arg Met Gly Lys Ser Arg
        35                  40                  45

Arg Asn Phe Leu Thr Ser Leu Ala Arg Ser Lys Gly Phe Cys Val Asp
50                  55                  60

Asn Thr Leu Ser Asp Lys Val Thr His Ile Val Ala Glu Gly Ile Ser
65                  70                  75                  80

Ala Asn Glu Leu Trp Pro Trp Leu Glu Glu Gln Asn Leu Pro Gln Leu
                85                  90                  95

Asp Lys Thr Asn Val Leu Asp Ile Thr Trp Phe Thr Glu Ser Met Arg
            100                 105                 110

Ala Asp Arg Pro Val Pro Val Glu Glu Gln His Arg Ile Gln Cys Arg
        115                 120                 125

Cys Val Pro Val Pro Val Cys Pro Glu Gly Tyr Asp Pro Val Ser
    130                 135                 140

Asp Ser Pro Val Pro Thr Val Ser Gln Tyr Ala Cys Gln Arg Arg Thr
145                 150                 155                 160

Thr Leu Asp Asn Pro Asn Lys Val Leu Thr Asp Ala Leu Glu Val Leu
                165                 170                 175

Val Glu Asn Cys Glu Phe Asn Asp Ser Met Gly Pro Cys Ser Gly Phe
            180                 185                 190

Arg Arg Ala Ala Ser Val Leu Lys Ser Leu Thr Thr Ala Leu Ser Cys
        195                 200                 205

Leu Gln Asp Thr Ala Gly Leu Pro Cys Leu Gly Glu Ser Lys Thr
    210                 215                 220

Ile Ile Glu Glu Ile Ile Asp Cys Gly Ser Ser Ser Arg Val Glu Asp
225                 230                 235                 240

Ile Leu Ser Asp Glu Arg Tyr Gln Thr Leu Lys Leu Phe Thr Ser Val
                245                 250                 255

Phe Gly Val Gly Pro Lys Thr Ala Glu Lys Trp Tyr Arg Arg Gly Leu
            260                 265                 270

Arg Ser Leu Glu Gln Val Tyr Ser Asp Ser Ser Leu His Phe Asn Arg
```

```
                275                 280                 285
Met Gln Thr Ala Gly Phe Ile Tyr Tyr Glu Asp Ile Ser Lys Pro Val
    290                 295                 300

Thr Val Ala Glu Ala Arg Ala Val Gly Cys Ile Ile Glu Glu Thr Ala
305                 310                 315                 320

Ser Tyr Tyr Ser Ser Gly Val Ser Ile Ser Leu Thr Gly Gly Phe Arg
                325                 330                 335

Arg Gly Lys Gln Phe Gly His Asp Val Asp Phe Ile Leu Thr Val Pro
                340                 345                 350

Glu Pro Gly Lys Glu Asp Gly Leu Leu Pro Ala Val Ile Asp Thr Leu
                355                 360                 365

Arg Ser Gln Gly Ile Leu Leu Tyr Ser Asp Phe Gln Glu Ser Thr Phe
                370                 375                 380

Asp Leu Asn Lys Leu Pro Ser Arg Arg Phe Glu Ala Met Asp His Phe
385                 390                 395                 400

Gln Lys Cys Phe Leu Ile Leu Lys Leu Arg Ala Gly Leu Val Glu Gly
                405                 410                 415

Gln Gln Val Asp Pro Gly Cys Arg Arg Asp Trp Arg Ala Val Arg Val
                420                 425                 430

Asp Leu Val Ala Pro Pro Ala Glu Arg Tyr Ala Phe Cys Leu Leu Gly
                435                 440                 445

Trp Ser Gly Ser Thr Gln Phe Glu Arg Asp Leu Arg Arg Phe Ala Arg
    450                 455                 460

Leu Glu Arg Gly Met Leu Leu Asp Asn His Ala Leu Tyr Asp Lys Thr
465                 470                 475                 480

Thr Asn Thr Phe Leu Gln Ala Lys Thr Glu Glu Asp Ile Phe Ala His
                485                 490                 495

Leu Gly Leu Asp Tyr Ile Glu Pro Trp Gln Arg Asn Ala
                500                 505

<210> SEQ ID NO 9
<211> LENGTH: 510
<212> TYPE: PRT
<213> ORGANISM: Dipodomys ordii

<400> SEQUENCE: 9

Met Asp Pro Leu Pro Thr Ala His Ser Gly Pro Arg Lys Lys Arg Pro
1               5                   10                  15

Arg Gln Met Gly Ala Leu Met Ser Ser Thr Pro Gln Asp Val Lys Phe
                20                  25                  30

Arg Asp Leu Val Leu Phe Ile Leu Glu Lys Lys Met Gly Thr Ser Arg
            35                  40                  45

Arg Ala Phe Leu Met Glu Leu Ala Arg Ser Lys Gly Phe Arg Val Glu
        50                  55                  60

Asn Glu Leu Ser Asp Ser Val Thr His Ile Val Ala Glu Asn Asn Ser
65              70                  75                  80

Gly Ser Asp Val Leu Glu Trp Leu Gln Val Gln Asn Ile Lys Ala Ser
                85                  90                  95

Ser Gln Leu Glu Phe Leu Asp Ile Ser Trp Leu Val Glu Cys Met Gly
            100                 105                 110

Ala Gly Lys Pro Val Gln Thr Thr Gly Lys His Gln Leu Val Val Arg
        115                 120                 125

Arg Asp His Pro Pro Ser Ser Asn Pro Gly Leu Gln Asn Thr Leu Pro
    130                 135                 140
```

```
Gln Thr Ala Gln Lys Ile Ser Gln Tyr Ala Cys Glu Arg Arg Thr Thr
145                 150                 155                 160

Leu Asn Asn Trp Asn His Val Phe Thr Asp Ala Leu Asp Ile Leu Ala
            165                 170                 175

Glu Asn Ser Glu Phe Arg Glu Asn Glu Ser Cys Cys Leu Ala Phe Met
            180                 185                 190

Arg Ala Ser Ser Val Leu Lys Ser Leu Pro Phe Thr Val Ser Ser Met
        195                 200                 205

Lys Asp Thr Glu Gly Ile Pro Cys Leu Gly Asp Lys Val Lys Cys Ile
    210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Gln Met Gly Phe Arg
            260                 265                 270

Thr Leu Ser Lys Val Arg Ser Asp Lys Ser Leu Lys Phe Thr Arg Met
        275                 280                 285

Gln Lys Ala Gly Phe Leu Tyr Tyr Glu Asp Leu Val Ser Ser Val Thr
    290                 295                 300

Lys Ala Glu Ala Glu Ala Val Ser Met Leu Val Lys Glu Ala Val Arg
305                 310                 315                 320

Thr Phe Leu Pro Ser Ala Leu Val Thr Leu Thr Gly Gly Phe Arg Arg
                325                 330                 335

Gly Lys Lys Ile Gly His Asp Val Asp Phe Leu Ile Thr Ser Pro Glu
            340                 345                 350

Val Thr Glu Glu Lys Glu Gln Gln Leu Leu His Gln Val Thr Asn Leu
        355                 360                 365

Trp Glu Lys Lys Gly Leu Leu Leu Tyr Cys Asp His Val Glu Ser Thr
    370                 375                 380

Phe Glu Lys Leu Lys Leu Pro Ser Arg Lys Val Asp Ala Leu Asp His
385                 390                 395                 400

Phe Gln Lys Cys Phe Leu Ile Leu Lys Leu Asp His Gln Arg Val Asn
                405                 410                 415

Ser Asp Gln Ser Ser Gln Gln Glu Gly Lys Thr Trp Lys Ala Ile Arg
            420                 425                 430

Val Asp Leu Val Met Cys Pro Tyr Glu Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Lys
465                 470                 475                 480

Ala Lys Arg Ile Phe Leu Lys Ala Glu Ser Glu Glu Ile Phe Ala
                485                 490                 495

His Leu Gly Leu Asp Tyr Ile Glu Pro Trp Glu Arg Asn Ala
            500                 505                 510

<210> SEQ ID NO 10
<211> LENGTH: 510
<212> TYPE: PRT
<213> ORGANISM: Rattus norvegicus

<400> SEQUENCE: 10

Met Asp Pro Leu Gln Ala Val His Leu Gly Pro Arg Lys Lys Arg Pro
1               5                   10                  15
```

```
Arg Gln Thr Gly Ala Ser Gly Ala Ser Thr Pro His Asp Ile Arg Phe
            20                  25                  30

Arg Asp Leu Val Leu Phe Ile Leu Glu Lys Lys Met Gly Thr Thr Arg
            35                  40                  45

Arg Ala Phe Leu Met Glu Leu Ala Arg Arg Lys Gly Phe Arg Val Glu
50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Phe Glu Leu Leu Asp Ile Ser Trp Leu Ile Glu Cys Met Gly
            100                 105                 110

Ala Gly Lys Pro Val Glu Met Ala Gly Arg His Gln Leu Val Val Arg
            115                 120                 125

Arg Asn Pro Ser Leu Ser Pro Val Pro Gly Ser Gln Thr Val Pro Pro
130                 135                 140

Pro Leu Met Gln Lys Ile Ser Gln Tyr Ala Cys Gln Arg Arg Thr Thr
145                 150                 155                 160

Leu Asn Asn His Asn Gln Leu Phe Thr Asp Ala Phe Asp Ile Leu Ala
                165                 170                 175

Glu Asn Tyr Glu Phe Arg Glu Asn Glu Val Ser Cys Leu Pro Phe Met
            180                 185                 190

Arg Ala Ala Ser Val Leu Lys Ser Leu Ser Phe Pro Ile Val Ser Met
            195                 200                 205

Lys Asp Ile Glu Gly Ile Pro Cys Leu Gly Asp Lys Val Lys Cys Val
            210                 215                 220

Ile Glu Gly Ile Ile Glu Asp Gly Glu Ser Ser Glu Val Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Lys Ser Asp Lys Ser Leu Arg Phe Thr His Met
            275                 280                 285

Gln Lys Ala Gly Phe Leu Tyr Tyr Glu Asp Leu Val Ser Cys Val Asn
290                 295                 300

Arg Ala Glu Ala Glu Ala Val Ser Met Leu Val Lys Glu Ala Val Val
305                 310                 315                 320

Ala Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Glu Glu Gln Gln Leu Leu His Lys Val Thr Asn Phe
            355                 360                 365

Trp Arg Gln Gln Gly Leu Leu Leu Tyr Cys Asp Ile Ile Glu Ser Thr
            370                 375                 380

Phe Glu Lys Phe Lys Leu Pro Ser Arg Lys Val Asp Ala Leu Asp His
385                 390                 395                 400

Phe Gln Lys Cys Phe Leu Ile Leu Lys Leu His Arg Gly Leu Val Arg
                405                 410                 415

Ser Glu Glu Ser Gly Gln Gln Glu Gly Lys Asp Trp Lys Ala Ile Arg
            420                 425                 430
```

Val Asp Leu Val Met Cys Pro Tyr Glu Arg Arg Ala Phe Ala Leu Leu
            435                 440                 445

Gly Trp Thr Gly Ser Arg Gln Phe Glu Arg Asp Leu Arg Arg Tyr Ala
450                 455                 460

Thr His Glu Arg Lys Met Met Leu Asp Asn His Ala Leu Tyr Asp Lys
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
            500                 505                 510

<210> SEQ ID NO 11
<211> LENGTH: 510
<212> TYPE: PRT
<213> ORGANISM: Rattus norvegicus

<400> SEQUENCE: 11

Met Asp Pro Leu Gln Ala Val His Leu Gly Pro Arg Lys Lys Arg Pro
1               5                   10                  15

Arg Gln Thr Gly Ala Ser Gly Ala Ser Thr Pro His Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Phe Glu Leu Leu Asp Ile Ser Trp Leu Ile Glu Cys Met Gly
            100                 105                 110

Ala Gly Lys Pro Val Glu Met Ala Gly Arg His Gln Leu Val Val Arg
        115                 120                 125

Arg Asn Pro Ser Leu Ser Pro Val Pro Gly Ser Gln Thr Val Pro Pro
    130                 135                 140

Pro Pro Met Gln Lys Ile Ser Gln Tyr Ala Cys Gln Arg Arg Thr Thr
145                 150                 155                 160

Leu Asn Asn His Asn Gln Leu Phe Thr Asp Ala Phe Asp Ile Leu Ala
                165                 170                 175

Glu Asn Tyr Glu Phe Arg Glu Asn Glu Val Ser Cys Leu Pro Phe Met
            180                 185                 190

Arg Ala Ala Ser Val Leu Lys Ser Leu Ser Phe Pro Ile Val Ser Met
        195                 200                 205

Lys Asp Ile Glu Gly Ile Pro Cys Leu Gly Asp Lys Val Lys Cys Val
    210                 215                 220

Ile Glu Gly Ile Ile Glu Asp Gly Glu Ser Ser Glu Val Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Lys Ser Asp Lys Ser Leu Arg Phe Thr His Met
        275                 280                 285

Gln Lys Ala Gly Phe Leu Tyr Tyr Glu Asp Leu Val Ser Cys Val Asn
    290                 295                 300

```
Arg Ala Glu Ala Glu Ala Val Ser Met Leu Val Lys Glu Ala Val Val
305                 310                 315                 320

Ala Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Glu Glu Gln Gln Leu Leu His Lys Val Thr Asn Phe
        355                 360                 365

Trp Arg Gln Gln Gly Leu Leu Leu Tyr Cys Asp Ile Ile Glu Ser Thr
    370                 375                 380

Phe Glu Lys Phe Lys Leu Pro Ser Arg Lys Val Asp Ala Leu Asp His
385                 390                 395                 400

Phe Gln Lys Cys Phe Leu Ile Leu Lys Leu His Arg Gly Leu Val Arg
                405                 410                 415

Ser Glu Glu Ser Gly Gln Gln Glu Gly Lys Asp Trp Lys Ala Ile Arg
            420                 425                 430

Val Asp Leu Val Met Cys Pro Tyr Glu Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Lys
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
            500                 505                 510

<210> SEQ ID NO 12
<211> LENGTH: 501
<212> TYPE: PRT
<213> ORGANISM: Tetraodon nigroviridis

<400> SEQUENCE: 12

Met Phe His Thr Pro Ile Leu Pro Arg Thr Lys Arg Ser Arg Ala
1               5                   10                  15

Glu Gln Glu Val Ala Arg Pro Gly Arg Glu Val Lys Phe Val Asn
                20                  25                  30

Val Arg Leu Tyr Leu Val Glu Met Lys Met Gly His Ser Arg Arg Ser
            35                  40                  45

Phe Leu Thr Gln Leu Ala Arg Ser Lys Gly Phe Met Val Glu Asp Asp
        50                  55                  60

Leu Ser Asp Ser Val Thr His Val Val Ser Glu Asn Ser Gln Ala Ser
65                  70                  75                  80

Val Leu Trp Ala Trp Leu Lys Asp Ser Gly Pro Ala Asn Leu Pro Ser
                85                  90                  95

Met His Val Val Asn Ile Thr Trp Phe Thr Asp Ser Met Lys Glu Arg
            100                 105                 110

Arg Pro Val Ala Val Glu Thr Arg His Leu Ile Gln Asp Thr Leu Pro
        115                 120                 125

Met Leu Pro Glu Gly Arg Lys Val Val Ala Val Ala Thr Val Ser Gln
    130                 135                 140

Tyr Ala Cys Gln Arg Arg Thr Thr Thr Asn His Asn Ala Val Phe
145                 150                 155                 160

Thr Asp Ala Phe Glu Val Leu Ala Glu Cys Tyr Glu Phe Asn Gln Met
```

```
            165                 170                 175
Glu Gly Arg Cys Leu Ala Phe Arg Arg Ala Ala Ser Val Leu Lys Ser
            180                 185                 190

Leu Pro Arg Val Leu Ser Ser Leu Glu Asp Thr His His Leu Pro Cys
        195                 200                 205

Leu Gly Asp His Ala Lys Ala Ile Ile Asp Glu Leu Leu Gln His Gly
    210                 215                 220

Arg Ala Phe Asp Val Gln Lys Val Leu Ser Asp Glu Arg Tyr Gln Thr
225                 230                 235                 240

Leu Lys Leu Phe Thr Ser Val Phe Gly Val Gly Pro Lys Thr Ala Glu
                245                 250                 255

Lys Trp Tyr Arg Thr Gly Leu Arg Ala Phe Glu His Ile Leu Ala Asp
            260                 265                 270

Arg Ser Ile His Leu Asn His Met Gln Gln Asn Gly Phe Leu His Tyr
        275                 280                 285

Glu Asp Ile Ser Arg Ala Val Ser Lys Ala Glu Ala Arg Ala Leu Thr
    290                 295                 300

Lys Val Ile Asp Glu Val Val His Ala Ile Thr Pro Asp Ala Ile Val
305                 310                 315                 320

Ala Leu Thr Gly Gly Phe Arg Arg Gly Lys Glu Phe Gly His Asp Val
                325                 330                 335

Asp Ile Ile Phe Thr Thr Leu Glu Val Gly Lys Glu Gly Asn Leu Leu
            340                 345                 350

Leu Asp Val Ile Lys Ser Leu Glu Asn Gln Gly Val Leu Leu Tyr Cys
        355                 360                 365

Asp Tyr Gln Ala Ala Thr Phe Asp Thr Ala Lys Leu Pro Ala His Ser
    370                 375                 380

Phe Glu Ala Met Asp His Phe Ala Lys Cys Phe Leu Ile Leu Arg Leu
385                 390                 395                 400

Glu Ala Ser Gln Val Glu Gly Gly Leu Asn Ser Gly Glu Glu Asp Ser
                405                 410                 415

Arg Gly Trp Arg Ala Val Arg Val Asp Leu Val Ser Pro Pro Met Asn
            420                 425                 430

Arg Tyr Ala Phe Ala Leu Leu Gly Trp Thr Gly Ser Arg Gln Phe Glu
        435                 440                 445

Arg Asp Met Arg Arg Phe Ala Arg Lys Glu Arg Met Leu Leu Asp
    450                 455                 460

Asn His Gly Leu Phe Asp Lys Asn Lys Glu Phe Leu Ala Ala Thr
465                 470                 475                 480

Thr Glu Lys Asp Ile Phe Asp His Leu Gly Leu Glu Tyr Met Glu Pro
                485                 490                 495

Trp Gln Arg Asn Ala
            500

<210> SEQ ID NO 13
<211> LENGTH: 509
<212> TYPE: PRT
<213> ORGANISM: Dipodomys ordii

<400> SEQUENCE: 13

Met Asp Pro Leu Pro Thr Ala His Ser Gly Pro Arg Lys Lys Arg Pro
1               5                   10                  15

Arg Gln Met Gly Ala Leu Met Ser Ser Thr Pro Gln Asp Val Lys Phe
            20                  25                  30
```

-continued

```
Arg Asp Leu Val Leu Phe Ile Leu Glu Lys Lys Met Gly Thr Ser Arg
         35                  40                  45

Arg Ala Phe Leu Met Glu Leu Ala Arg Ser Lys Gly Phe Arg Val Glu
 50                  55                  60

Asn Glu Leu Ser Asp Ser Val Thr His Ile Val Ala Glu Asn Asn Ser
 65                  70                  75                  80

Gly Ser Asp Val Leu Glu Trp Leu Gln Val Gln Asn Ile Lys Ala Ser
                 85                  90                  95

Ser Gln Leu Glu Phe Leu Asp Ile Ser Trp Leu Val Glu Cys Met Gly
            100                 105                 110

Ala Gly Lys Pro Val Gln Thr Thr Gly Lys His Gln Leu Val Val Arg
            115                 120                 125

Arg Asp His Pro Pro Ser Ser Asn Pro Gly Leu Gln Asn Thr Leu Pro
            130                 135                 140

Gln Thr Ala Gln Lys Ile Ser Gln Tyr Ala Cys Glu Arg Arg Thr Thr
145                 150                 155                 160

Leu Asn Asn Trp Asn His Val Phe Thr Asp Ala Leu Asp Ile Leu Ala
                165                 170                 175

Glu Asn Ser Glu Phe Arg Glu Asn Glu Ser Cys Cys Leu Ala Phe Met
            180                 185                 190

Arg Ala Ser Ser Val Leu Lys Ser Leu Pro Phe Thr Val Ser Ser Met
            195                 200                 205

Lys Asp Thr Glu Gly Ile Pro Cys Leu Gly Asp Lys Val Lys Cys Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Gln Met Gly Phe Arg
            260                 265                 270

Thr Leu Ser Lys Val Arg Ser Asp Lys Ser Leu Lys Phe Thr Arg Met
            275                 280                 285

Gln Lys Ala Gly Phe Leu Tyr Tyr Glu Asp Leu Val Ser Ser Val Thr
290                 295                 300

Lys Ala Glu Ala Glu Ala Val Ser Met Leu Val Lys Glu Ala Val Arg
305                 310                 315                 320

Thr Phe Leu Pro Ser Ala Leu Val Thr Leu Thr Gly Gly Phe Arg Arg
                325                 330                 335

Gly Lys Lys Ile Gly His Asp Val Asp Phe Leu Ile Thr Ser Pro Glu
            340                 345                 350

Val Thr Glu Glu Lys Glu Gln Gln Leu Leu His Gln Val Thr Asn Leu
            355                 360                 365

Trp Glu Lys Lys Gly Leu Leu Leu Tyr Cys Asp His Val Glu Ser Thr
            370                 375                 380

Phe Glu Lys Leu Lys Leu Pro Ser Arg Lys Val Asp Ala Leu Asp His
385                 390                 395                 400

Phe Gln Lys Cys Phe Leu Ile Leu Lys Leu Asp His Gln Arg Val Asn
                405                 410                 415

Ser Asp Gln Ser Gln Gln Glu Gly Lys Thr Trp Lys Ala Ile Arg
            420                 425                 430

Val Asp Leu Val Met Cys Pro Tyr Glu Arg Arg Ala Phe Ala Leu Leu
            435                 440                 445

Gly Trp Thr Gly Ser Arg Phe Glu Arg Asp Leu Arg Arg Tyr Ala Thr
```

```
              450                 455                 460
His Glu Arg Lys Met Met Leu Asp Asn His Ala Leu Tyr Asp Lys Ala
465                 470                 475                 480

Lys Arg Ile Phe Leu Lys Ala Glu Ser Glu Glu Ile Phe Ala His
                485                 490                 495

Leu Gly Leu Asp Tyr Ile Glu Pro Trp Glu Arg Asn Ala
                500                 505

<210> SEQ ID NO 14
<211> LENGTH: 502
<212> TYPE: PRT
<213> ORGANISM: Myotis lucifugus

<400> SEQUENCE: 14

Met Asp Ser Leu Gln Met Ala His Ser Gly Pro Arg Lys Lys Arg Pro
1               5                   10                  15

Arg Gln Met Gly Ala Ser Met Ala Ser Pro Pro Gln Asp Ile Lys Phe
                20                  25                  30

Arg Asp Leu Val Leu Phe Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Val Arg Ala Arg
                85                  90                  95

Ser Gln Pro Glu Leu Leu Asp Val Ser Trp Leu Ile Glu Cys Met Ser
                100                 105                 110

Ala Gly Lys Pro Val Ala Thr Thr Gly Gln His Gln Leu Val Val Ser
            115                 120                 125

Val Leu Val Val Ile Ser Thr Val Arg Gly Leu Ile Lys Ile Ser Pro
        130                 135                 140

Tyr Ala Cys Gln Arg Arg Thr Thr Leu Asn Asn Arg Asn His Ile Phe
145                 150                 155                 160

Thr Asp Ala Phe Glu Ile Leu Ala Glu Asn Cys Glu Phe Arg Glu Asn
                165                 170                 175

Glu Gly Ser Cys Leu Ala Phe Met Arg Ala Ala Ser Val Leu Lys Ser
            180                 185                 190

Leu Pro Phe Thr Ile Ile Ser Met Lys Asp Thr Glu Gly Ile Pro Cys
        195                 200                 205

Leu Gly Asp Lys Val Lys Ser Ile Ile Glu Glu Ile Glu Asp Gly
        210                 215                 220

Glu Ser Ser Glu Val Lys Ala Val Leu Asn Asp Glu Arg Tyr Gln Ser
225                 230                 235                 240

Phe Lys Leu Phe Thr Ser Val Phe Gly Val Gly Leu Lys Thr Ser Glu
                245                 250                 255

Lys Trp Phe Arg Met Gly Phe Arg Thr Leu Ser Lys Ile Arg Ser Asp
            260                 265                 270

Lys Thr Leu Lys Phe Thr Arg Met Gln Lys Ala Gly Phe Phe Tyr Tyr
        275                 280                 285

Glu Asp Leu Val Ser Cys Val Thr Lys Ala Glu Ala Glu Ala Val Gly
        290                 295                 300

Val Leu Val Lys Glu Ala Val Trp Ala Phe Leu Pro Asp Ala Phe Val
305                 310                 315                 320
```

```
Thr Val Thr Gly Gly Phe Arg Arg Gly Lys Ile Gly His Asp Val
            325                 330                 335

Asp Phe Leu Ile Thr Ser Pro Gly Ser Thr Glu Glu Glu Gln Gln
            340                 345                 350

Leu Leu Pro Lys Val Ile Asn Leu Trp Glu Arg Lys Gly Leu Leu Leu
            355                 360                 365

Tyr Tyr Asp Leu Val Glu Ser Thr Phe Glu Lys Phe Lys Leu Pro Ser
            370                 375                 380

Arg Lys Val Asp Ala Leu Asp His Phe Gln Lys Cys Phe Leu Ile Leu
385                 390                 395                 400

Lys Leu His His Gln Arg Val Asp Gly Gly Lys Ser Ser Gln Gln Glu
            405                 410                 415

Gly Lys Thr Trp Lys Ala Ile Arg Val Asp Leu Val Met Cys Pro Tyr
            420                 425                 430

Glu Arg Arg Ala Phe Ala Leu Leu Gly Trp Thr Gly Ser Arg Gln Phe
            435                 440                 445

Glu Arg Asp Leu Arg Arg Tyr Ala Thr His Glu Arg Lys Met Met Leu
            450                 455                 460

Asp Asn His Ala Leu Tyr Asp Lys Thr Lys Arg Ile Val Leu Glu Ala
465                 470                 475                 480

Glu Ser Glu Glu Asp Ile Phe Ala His Leu Gly Leu Asp Tyr Ile Asp
            485                 490                 495

Pro Trp Glu Arg Asn Ala
            500

<210> SEQ ID NO 15
<211> LENGTH: 509
<212> TYPE: PRT
<213> ORGANISM: Gorilla gorilla gorilla

<400> SEQUENCE: 15

Met Asp Pro Pro Arg Ala Ser His Leu Ser Pro Arg Lys Lys Arg Pro
1               5                   10                  15

Arg Gln Thr Gly Ala Ser Met Ala Ser Ser Pro Gln Asp Ile Lys Phe
            20                  25                  30

Gln Asp Leu Val Val Phe Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65              70                  75                  80

Gly Ser Asp Val Leu Glu Trp Leu Gln Val Gln Lys Ile Gln Val Ser
            85                  90                  95

Ser Gln Pro Glu Leu Leu Asp Val Ser Trp Leu Ile Glu Cys Ile Gly
            100                 105                 110

Ala Gly Lys Pro Val Glu Met Thr Gly Lys His Gln Leu Val Val Arg
            115                 120                 125

Arg Asp Tyr Ser Asp Ser Thr Asn Pro Gly Pro Pro Lys Thr Pro Pro
        130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190
```

```
Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
    210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Ser Asp Lys Ser Leu Lys Phe Thr Arg Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Ser Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu Trp
        355                 360                 365

Glu Asn Lys Gly Leu Leu Leu Tyr Tyr Asp Leu Val Glu Ser Thr Phe
    370                 375                 380

Glu Lys Leu Arg Leu Pro Ser Arg Lys Val Asp Ala Leu Asp His Phe
385                 390                 395                 400

Gln Lys Cys Phe Leu Ile Phe Lys Leu Pro Arg Gln Arg Val Asp Ser
                405                 410                 415

Asp Gln Ser Ser Trp Gln Glu Gly Lys Thr Trp Lys Ala Ile Arg Val
            420                 425                 430

Asp Leu Val Leu Cys Pro Tyr Glu Arg Arg Ala Phe Ala Leu Leu Gly
        435                 440                 445

Trp Thr Gly Ser Arg Gln Phe Glu Arg Asp Leu Arg Arg Tyr Ala Thr
    450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505

<210> SEQ ID NO 16
<211> LENGTH: 510
<212> TYPE: PRT
<213> ORGANISM: Macaca fascicularis

<400> SEQUENCE: 16

Met Asp Pro Pro Gln Thr Ser Pro Leu Ser Pro Arg Lys Lys Arg Pro
1               5                   10                  15

Arg Gln Met Gly Ala Leu Met Ala Ser Ser Pro Gln Asp Ile Lys Phe
            20                  25                  30

Gln Asp Leu Val Val Phe Ile Leu Glu Lys Lys Met Gly Thr Thr Arg
        35                  40                  45

Arg Ala Phe Leu Met Glu Leu Ala Arg Arg Lys Gly Phe Arg Val Glu
```

```
            50                  55                  60
Asn Glu Leu Ser Asp Ser Val Thr His Ile Val Ala Glu Asn Asn Ser
 65                  70                  75                  80

Gly Ser Asp Val Leu Glu Trp Leu Gln Val Gln Lys Ile Gln Val Ser
                 85                  90                  95

Ser Gln Pro Glu Leu Leu Asp Val Ser Trp Leu Ile Glu Cys Ile Gly
                100                 105                 110

Ala Gly Lys Pro Val Glu Met Thr Gly Lys His Gln Leu Val Val Arg
                115                 120                 125

Arg Asp Tyr Ser Asp Ser Thr Asn Pro Gly Pro Lys Thr Leu Pro
            130                 135                 140

Thr Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
                180                 185                 190

Arg Ala Ala Ser Val Leu Lys Ser Leu Pro Phe Thr Ile Ile Ser Met
            195                 200                 205

Lys Asp Thr Glu Gly Ile Pro Cys Leu Gly Ser Lys Val Lys Cys Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
                260                 265                 270

Thr Leu Ser Lys Val Arg Ser Asp Glu Ser Leu Lys Phe Thr Arg Met
            275                 280                 285

Gln Arg Ala Gly Phe Leu Tyr Tyr Glu Asp Leu Val Ser Cys Val Thr
            290                 295                 300

Arg Ala Glu Ala Glu Ala Val Ser Val Leu Val Lys Glu Ala Val Gln
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
                340                 345                 350

Ser Thr Glu Asp Glu Glu Gln Gln Leu Leu Gln Lys Val Met Asn Leu
            355                 360                 365

Trp Glu Lys Lys Gly Leu Leu Leu Tyr Tyr Asp Leu Val Glu Ser Thr
370                 375                 380

Phe Glu Lys Leu Arg Leu Pro Ser Arg Lys Val Asp Ala Leu Asp His
385                 390                 395                 400

Phe Gln Lys Cys Phe Leu Ile Phe Lys Leu Pro Leu Gln Arg Val Asp
                405                 410                 415

Ser Asp Gln Ser Ser Trp Gln Glu Gly Lys Thr Trp Lys Ala Ile Arg
            420                 425                 430

Val Asp Leu Val Met Cys Pro Tyr Glu Arg Arg Ala Phe Ala Leu Leu
            435                 440                 445

Gly Trp Thr Gly Ser Arg Gln Phe Glu Arg Asp Leu Arg Arg Tyr Ala
            450                 455                 460

Thr His Glu Arg Lys Met Ile Leu Asp Asn His Ala Leu Tyr Asp Lys
465                 470                 475                 480
```

```
Thr Lys Arg Ile Phe Leu Lys Ala Glu Ser Glu Glu Ile Phe Ala
                485                 490                 495

His Leu Gly Leu Asp Tyr Ile Glu Pro Trp Glu Arg Asn Ala
                500                 505                 510

<210> SEQ ID NO 17
<211> LENGTH: 510
<212> TYPE: PRT
<213> ORGANISM: Macaca mulatta

<400> SEQUENCE: 17

Met Asp Pro Pro Gln Thr Ser Pro Leu Ser Pro Arg Lys Lys Arg Pro
1               5                   10                  15

Arg Gln Thr Gly Ala Leu Met Ala Ser Ser Pro Gln Asp Ile Lys Phe
                20                  25                  30

Gln Asp Leu Val Val Phe Ile Leu Glu Lys Lys Met Gly Thr Thr Arg
                35                  40                  45

Arg Ala Phe Leu Met Glu Leu Ala Arg Arg Lys Gly Phe Arg Val Glu
                50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Ile Gln Val Ser
                85                  90                  95

Ser Gln Pro Glu Leu Leu Asp Val Ser Trp Leu Ile Glu Cys Ile Gly
                100                 105                 110

Ala Gly Lys Pro Val Glu Met Thr Gly Lys His Gln Leu Val Val Arg
                115                 120                 125

Arg Asp Tyr Ser Asp Ser Thr Asn Pro Gly Pro Pro Lys Thr Leu Pro
                130                 135                 140

Thr Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
                180                 185                 190

Arg Ala Ala Ser Val Leu Lys Ser Leu Pro Phe Thr Ile Ile Ser Met
                195                 200                 205

Lys Asp Thr Glu Gly Ile Pro Cys Leu Gly Ser Lys Val Lys Cys Ile
                210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
                260                 265                 270

Thr Leu Ser Lys Val Arg Ser Asp Glu Ser Leu Lys Phe Thr Arg Met
                275                 280                 285

Gln Arg Ala Gly Phe Leu Tyr Tyr Glu Asp Leu Val Ser Cys Val Thr
                290                 295                 300

Arg Ala Glu Ala Glu Ala Val Ser Val Leu Lys Glu Ala Val Gln
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
```

```
                    340                 345                 350
Ser Thr Glu Asp Glu Glu Gln Gln Leu Leu Gln Lys Val Met Asn Leu
            355                 360                 365

Trp Glu Lys Lys Gly Leu Leu Leu Tyr Tyr Asp Leu Val Glu Ser Thr
    370                 375                 380

Phe Glu Lys Leu Arg Leu Pro Ser Arg Lys Val Asp Ala Leu Asp His
385                 390                 395                 400

Phe Gln Lys Cys Phe Leu Ile Phe Lys Leu Pro Leu Gln Arg Val Asp
                405                 410                 415

Ser Asp Gln Ser Ser Trp Gln Glu Gly Lys Thr Trp Lys Ala Ile Arg
            420                 425                 430

Val Asp Leu Val Met Cys Pro Tyr Glu Arg Arg Ala Phe Ala Leu Leu
        435                 440                 445

Gly Trp Thr Gly Ser Arg Gln Phe Glu Arg Asp Leu Arg Tyr Ala
    450                 455                 460

Thr His Glu Arg Lys Met Ile Leu Asp Asn His Ala Leu Tyr Asp Lys
465                 470                 475                 480

Thr Lys Arg Ile Phe Leu Lys Ala Glu Ser Glu Glu Ile Phe Ala
                485                 490                 495

His Leu Gly Leu Asp Tyr Ile Glu Pro Trp Glu Arg Asn Ala
            500                 505                 510

<210> SEQ ID NO 18
<211> LENGTH: 500
<212> TYPE: PRT
<213> ORGANISM: Oreochromis niloticus

<400> SEQUENCE: 18

Met Phe His Ala Pro Ile Val Pro Arg Ala Arg Lys Arg Ser Arg Pro
1               5                   10                  15

Ala Glu Ala Ser Ala Pro Arg Arg Glu Gly Val Lys Phe Glu Asp Val
            20                  25                  30

Arg Leu Tyr Leu Val Glu Arg Lys Met Gly Arg Ser Arg Arg Ser Phe
        35                  40                  45

Leu Thr Glu Leu Ala Arg Ser Lys Gly Phe Ile Val Glu Asp Val Leu
    50                  55                  60

Ser Asp Val Val Thr His Val Val Ser Glu Asp Ser Gln Ala Ser Ser
65                  70                  75                  80

Leu Trp Ala Trp Leu Lys Gly Gly Ser Val Lys Asn Leu Pro Val Met
                85                  90                  95

His Val Leu Asp Ile Ser Trp Phe Thr Asp Ser Met Arg Glu Gly Lys
            100                 105                 110

Pro Val Ala Val Glu Thr Arg His Leu Ile Gln Glu Thr Leu Pro Ala
        115                 120                 125

Ser Pro Glu Ala Thr Thr Pro Thr Pro Val Ser Thr Val Ser Gln Tyr
    130                 135                 140

Ala Cys Gln Arg Arg Thr Thr Thr Gln Asn Asn Asn Lys Ile Phe Thr
145                 150                 155                 160

Asp Ala Phe Glu Val Leu Ala Glu Ser His Glu Phe Asn Asp Met Glu
                165                 170                 175

Gly Pro Cys Leu Ala Phe Arg Arg Ala Ala Ser Val Leu Lys Ser Leu
            180                 185                 190

Pro Trp Thr Val Gln Asn Leu Arg Val Thr Glu Asp Leu Pro Cys Leu
        195                 200                 205
```

Gly Glu His Ser Met Cys Val Ile Glu Glu Ile Leu Gln His Gly Arg
            210                 215                 220

Ser Phe Glu Val Glu Lys Ile Leu Ser Asp Glu Arg Tyr Gln Ile Leu
225                 230                 235                 240

Lys Leu Phe Thr Ser Val Phe Gly Val Gly Pro Lys Thr Ala Glu Lys
                245                 250                 255

Trp Tyr Arg Arg Gly Leu Arg Ser Phe Ser Asp Val Leu Ala Glu Pro
            260                 265                 270

Ser Ile His Leu Asn Arg Met Gln Gln Ser Gly Phe Leu His Tyr Gly
        275                 280                 285

Asp Ile Ser Arg Ala Val Ser Lys Ala Glu Ala Gln Ala Leu Gly Asn
    290                 295                 300

Ile Ile Asp Glu Ala Val His Ala Ile Thr Pro Asp Ala Ile Leu Thr
305                 310                 315                 320

Leu Thr Gly Gly Phe Arg Arg Gly Lys Asp Phe Gly His Asp Val Asp
                325                 330                 335

Phe Ile Val Thr Thr Pro Gln Leu Gly Lys Glu Glu Arg Leu Leu Thr
            340                 345                 350

Ser Val Ile Asp Arg Leu Lys His Gln Gly Ile Leu Leu Tyr Cys Glu
        355                 360                 365

Tyr Gln Ala Ser Thr Phe Asp Glu Ser Lys Leu Pro Ser His Arg Phe
    370                 375                 380

Glu Ala Met Asp His Phe Ala Lys Cys Phe Leu Ile Leu Arg Leu Glu
385                 390                 395                 400

Asp Ser Gln Val Asp Gly Gly Leu Gln Thr Ala Glu Glu Asp Arg Arg
                405                 410                 415

Gly Trp Arg Ala Val Arg Val Asp Leu Val Ser Pro Pro Val Asp Arg
            420                 425                 430

Tyr Ala Phe Thr Leu Leu Gly Trp Ser Gly Ser Arg Gln Phe Glu Arg
        435                 440                 445

Asp Leu Arg Arg Phe Ala Arg Met Glu Arg Arg Met Leu Leu Asp Asn
    450                 455                 460

His Ala Leu Tyr Asp Lys Thr Lys Lys Ser Lys Val Lys Arg Phe Val
465                 470                 475                 480

Ser His Ser Leu Ala Phe Gln Asn Leu Cys Arg Glu Trp Ser Pro Trp
                485                 490                 495

Arg Thr Ser Ala
            500

<210> SEQ ID NO 19
<211> LENGTH: 510
<212> TYPE: PRT
<213> ORGANISM: Papio anubis

<400> SEQUENCE: 19

Met Asp Pro Pro Gln Thr Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Val Phe Ile Leu Glu Lys Lys Met Gly Thr Thr Arg
        35                  40                  45

Arg Thr Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

-continued

```
Gly Ser Asp Val Leu Glu Trp Leu Gln Val Gln Lys Ile Gln Val Ser
                85                  90                  95

Ser Gln Pro Glu Leu Leu Asp Val Ser Trp Leu Ile Glu Cys Ile Gly
            100                 105                 110

Ala Gly Lys Pro Val Glu Met Thr Gly Lys His Gln Leu Val Val Arg
        115                 120                 125

Arg Asp Tyr Ser Asp Ser Thr Ser Pro Gly Pro Lys Thr Leu Pro
    130                 135                 140

Thr Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Cys Ile
    210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Ser Asp Glu Ser Leu Lys Phe Thr Arg Met
        275                 280                 285

Gln Arg Ala Gly Phe Leu Tyr Tyr Glu Asp Leu Val Ser Cys Val Thr
    290                 295                 300

Arg Ala Glu Ala Glu Ala Val Ser Val Leu Val Lys Glu Ala Val Arg
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Gln Leu Leu Gln Lys Val Met Asn Leu
        355                 360                 365

Trp Glu Lys Lys Gly Leu Leu Leu Tyr Tyr Asp Leu Val Glu Ser Thr
    370                 375                 380

Phe Glu Lys Leu Arg Leu Pro Ser Arg Lys Val Asp Ala Leu Asp His
385                 390                 395                 400

Phe Gln Lys Cys Phe Leu Ile Phe Lys Leu Pro Leu Gln Arg Val Asp
                405                 410                 415

Ser His Gln Ser Ser Trp Gln Glu Gly Lys Thr Trp Lys Ala Ile Arg
            420                 425                 430

Val Asp Leu Val Met Cys Pro Tyr Glu Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Ile Leu Asp Asn His Ala Leu Tyr Asp Lys
465                 470                 475                 480

Thr Lys Arg Ile Phe Leu Lys Ala Glu Ser Glu Glu Ile Phe Ala
                485                 490                 495
```

His Leu Gly Leu Asp Tyr Ile Glu Pro Trp Glu Arg Asn Ala
            500                 505                 510

<210> SEQ ID NO 20
<211> LENGTH: 509
<212> TYPE: PRT
<213> ORGANISM: Nomascus leucogenys

<400> SEQUENCE: 20

Met Asp Pro Pro Gln Ala Ser His Leu Ser Pro Arg Lys Lys Arg Pro
1               5                   10                  15

Arg Gln Thr Gly Ala Leu Met Ala Ser Ser Pro Glu Asp Ile Lys Phe
            20                  25                  30

Gln Asp Leu Val Val Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Ile Gln Val Ser
                85                  90                  95

Ser Gln Pro Glu Leu Leu Asp Val Ser Trp Leu Ile Glu Cys Ile Gly
            100                 105                 110

Ala Gly Lys Pro Val Glu Met Thr Gly Lys His Gln Leu Val Val Arg
        115                 120                 125

Arg Asp Tyr Ser Asp Ser Thr Asn Pro Gly Pro Pro Lys Thr Pro Pro
    130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Ala Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Glu Lys Gly Ile
    210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Ser Asp Lys Ser Leu Lys Phe Thr Gln Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Ser Val Leu Val Lys Glu Ala Val Trp
305                 310                 315                 320

Ala Phe Leu Pro Asp Ala Ser Ile Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu Trp
        355                 360                 365

```
Glu Lys Lys Gly Leu Leu Leu Tyr Tyr Asp Leu Val Glu Ser Thr Phe
            370                 375                 380

Glu Lys Leu Arg Leu Pro Ser Arg Lys Val Asp Ala Leu Asp His Phe
385                 390                 395                 400

Gln Lys Cys Phe Leu Ile Phe Lys Leu Pro Arg Gln Arg Val Asp Gly
            405                 410                 415

Asp Gln Ser Ser Trp Gln Glu Gly Lys Thr Trp Lys Ala Ile Arg Val
            420                 425                 430

Asp Leu Val Leu Cys Pro Tyr Glu Arg Arg Ala Phe Ala Leu Leu Gly
            435                 440                 445

Trp Thr Gly Ser Arg Gln Phe Glu Arg Asp Leu Arg Arg Tyr Ala Thr
            450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Ile Phe Ala His
            485                 490                 495

Leu Gly Leu Asp Tyr Ile Glu Pro Trp Glu Arg Asn Ala
            500                 505

<210> SEQ ID NO 21
<211> LENGTH: 509
<212> TYPE: PRT
<213> ORGANISM: Bos taurus

<400> SEQUENCE: 21

Met Asp Pro Leu Cys Thr Ala Ser Ser Gly Pro Arg Lys Lys Arg Pro
1               5                   10                  15

Arg Gln Val Gly Ala Ser Met Ala Ser Pro Pro His Asp Ile Lys Phe
            20                  25                  30

Gln Asn Leu Val Leu Phe Ile Leu Glu Lys Lys Met Gly Thr Thr Arg
            35                  40                  45

Arg Asn Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Ser Glu Val Leu Glu Trp Leu Gln Val Gln Asn Ile Arg Ala Ser
            85                  90                  95

Ser Gln Leu Glu Leu Leu Asp Val Ser Trp Leu Ile Glu Ser Met Gly
            100                 105                 110

Ala Gly Lys Pro Val Glu Ile Thr Gly Lys His Gln Leu Val Val Arg
            115                 120                 125

Thr Asp Tyr Ser Ala Thr Pro Asn Pro Gly Phe Gln Lys Thr Pro Pro
        130                 135                 140

Leu Ala Val Lys Lys Ile Ser Gln Tyr Ala Cys Gln Arg Lys Thr Thr
145                 150                 155                 160

Leu Asn Asn Tyr Asn His Ile Phe Thr Asp Ala Phe Glu Ile Leu Ala
            165                 170                 175

Glu Asn Ser Glu Phe Lys Glu Asn Glu Val Ser Tyr Val Thr Phe Met
            180                 185                 190

Arg Ala Ala Ser Val Leu Lys Ser Leu Pro Phe Thr Ile Ile Ser Met
            195                 200                 205

Lys Asp Thr Glu Gly Ile Pro Cys Leu Gly Asp Lys Val Lys Cys Ile
        210                 215                 220

Ile Glu Glu Ile Ile Glu Asp Gly Glu Ser Ser Glu Val Lys Ala Val
```

```
                225                 230                 235                 240
Leu Asn Asp Glu Arg Tyr Gln Ser Phe Lys Leu Phe Thr Ser Val Phe
                    245                 250                 255
Gly Val Gly Leu Lys Thr Ser Glu Lys Trp Phe Arg Met Gly Phe Arg
                    260                 265                 270
Ser Leu Ser Lys Ile Met Ser Asp Lys Thr Leu Lys Phe Thr Lys Met
                    275                 280                 285
Gln Lys Ala Gly Phe Leu Tyr Tyr Glu Asp Leu Val Ser Cys Val Thr
                    290                 295                 300
Arg Ala Glu Ala Glu Ala Val Gly Val Leu Val Lys Glu Ala Val Trp
305                 310                 315                 320
Ala Phe Leu Pro Asp Ala Phe Val Thr Met Thr Gly Gly Phe Arg Arg
                    325                 330                 335
Gly Lys Lys Ile Gly His Asp Val Asp Phe Leu Ile Thr Ser Pro Gly
                    340                 345                 350
Ser Ala Glu Asp Glu Glu Gln Leu Leu Pro Lys Val Ile Asn Leu Trp
                    355                 360                 365
Glu Lys Lys Gly Leu Leu Leu Tyr Tyr Asp Leu Val Glu Ser Thr Phe
                    370                 375                 380
Glu Lys Phe Lys Leu Pro Ser Arg Gln Val Asp Thr Leu Asp His Phe
385                 390                 395                 400
Gln Lys Cys Phe Leu Ile Leu Lys Leu His His Gln Arg Val Asp Ser
                    405                 410                 415
Ser Lys Ser Asn Gln Gln Glu Gly Lys Thr Trp Lys Ala Ile Arg Val
                    420                 425                 430
Asp Leu Val Met Cys Pro Tyr Glu Asn Arg Ala Phe Ala Leu Leu Gly
                    435                 440                 445
Trp Thr Gly Ser Arg Gln Phe Glu Arg Asp Ile Arg Arg Tyr Ala Thr
                    450                 455                 460
His Glu Arg Lys Met Met Leu Asp Asn His Ala Leu Tyr Asp Lys Thr
465                 470                 475                 480
Lys Arg Val Phe Leu Lys Ala Glu Ser Glu Glu Ile Phe Ala His
                    485                 490                 495
Leu Gly Leu Asp Tyr Ile Glu Pro Trp Glu Arg Asn Ala
                    500                 505

<210> SEQ ID NO 22
<211> LENGTH: 520
<212> TYPE: PRT
<213> ORGANISM: Bos taurus

<400> SEQUENCE: 22

Met Ala Gln Gln Arg Gln His Gln Arg Leu Pro Met Asp Pro Leu Cys
1               5                   10                  15
Thr Ala Ser Ser Gly Pro Arg Lys Lys Arg Pro Arg Gln Val Gly Ala
                20                  25                  30
Ser Met Ala Ser Pro Pro His Asp Ile Lys Phe Gln Asn Leu Val Leu
                35                  40                  45
Phe Ile Leu Glu Lys Lys Met Gly Thr Thr Arg Arg Asn Phe Leu Met
                50                  55                  60
Glu Leu Ala Arg Arg Lys Gly Phe Arg Val Glu Asn Glu Leu Ser Asp
65                  70                  75                  80
Ser Val Thr His Ile Val Ala Glu Asn Asn Ser Gly Ser Glu Val Leu
                85                  90                  95
```

```
Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
        115                 120                 125

Glu Ile Thr Gly Lys His Gln Leu Val Val Arg Thr Asp Tyr Ser Ala
    130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
        195                 200                 205

Leu Lys Ser Leu Pro Phe Thr Ile Ile Ser Met Lys Asp Thr Glu Gly
    210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
                245                 250                 255

Tyr Gln Ser Phe Lys Leu Phe Thr Ser Val Phe Gly Val Gly Leu Lys
            260                 265                 270

Thr Ser Glu Lys Trp Phe Arg Met Gly Phe Arg Ser Leu Ser Lys Ile
        275                 280                 285

Met Ser Asp Lys Thr Leu Lys Phe Thr Lys Met Gln Lys Ala Gly Phe
    290                 295                 300

Leu Tyr Tyr Glu Asp Leu Val Ser Cys Val Thr Arg Ala Glu Ala Glu
305                 310                 315                 320

Ala Val Gly Val Leu Val Lys Glu Ala Val Trp Ala Phe Leu Pro Asp
                325                 330                 335

Ala Phe Val Thr Met Thr Gly Gly Phe Arg Arg Gly Lys Lys Ile Gly
            340                 345                 350

His Asp Val Asp Phe Leu Ile Thr Ser Pro Gly Ser Ala Glu Asp Glu
        355                 360                 365

Glu Gln Leu Leu Pro Lys Val Ile Asn Leu Trp Glu Lys Lys Gly Leu
    370                 375                 380

Leu Leu Tyr Tyr Asp Leu Val Glu Ser Thr Phe Glu Lys Phe Lys Leu
385                 390                 395                 400

Pro Ser Arg Gln Val Asp Thr Leu Asp His Phe Gln Lys Cys Phe Leu
                405                 410                 415

Ile Leu Lys Leu His His Gln Arg Val Asp Ser Ser Lys Ser Asn Gln
            420                 425                 430

Gln Glu Gly Lys Thr Trp Lys Ala Ile Arg Val Asp Leu Val Met Cys
        435                 440                 445

Pro Tyr Glu Asn Arg Ala Phe Ala Leu Leu Gly Trp Thr Gly Ser Arg
    450                 455                 460

Gln Phe Glu Arg Asp Ile Arg Arg Tyr Ala Thr His Glu Arg Lys Met
465                 470                 475                 480

Met Leu Asp Asn His Ala Leu Tyr Asp Lys Thr Lys Arg Val Phe Leu
                485                 490                 495

Lys Ala Glu Ser Glu Glu Glu Ile Phe Ala His Leu Gly Leu Asp Tyr
            500                 505                 510

Ile Glu Pro Trp Glu Arg Asn Ala
```

<210> SEQ ID NO 23
<211> LENGTH: 510
<212> TYPE: PRT
<213> ORGANISM: Mus musculus

<400> SEQUENCE: 23

```
Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365
```

```
Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
                420                 425                 430

Val Asp Leu Val Met Cys Pro Tyr Asp Arg Arg Ala Phe Ala Leu Leu
                435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
                500                 505                 510

<210> SEQ ID NO 24
<211> LENGTH: 510
<212> TYPE: PRT
<213> ORGANISM: Sus scrofa

<400> SEQUENCE: 24

Met Asp Pro Pro Gln Thr Val Pro Ser Pro Arg Lys Lys Arg Pro
1               5                   10                  15

Arg Gln Val Gly Ala Ser Met Ala Ser Pro Ala His Asn Ile Lys Phe
                20                  25                  30

Arg Glu Leu Val Leu Phe Ile Leu Glu Lys Lys Met Gly Thr Thr Arg
                35                  40                  45

Arg Thr Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Glu Val Leu Glu Trp Leu Gln Ala Gln Lys Ile Arg Ala Ser
                85                  90                  95

Ser Gln Leu Thr Leu Leu Asp Val Ser Trp Leu Ile Glu Ser Met Gly
                100                 105                 110

Ala Gly Lys Pro Val Glu Met Thr Gly Lys His Gln Leu Val Val Arg
                115                 120                 125

Thr Asp Cys Ser Ala Ser Pro Ser Pro Gly Ser Gln Asn Thr Leu Pro
    130                 135                 140

Pro Ala Val Lys Lys Ile Ser Gln Tyr Ala Cys Gln Arg Arg Thr Thr
145                 150                 155                 160

Leu Asn Asn Cys Asn His Ile Phe Thr Asp Ala Phe Glu Val Leu Ala
                165                 170                 175

Glu Asn Tyr Glu Phe Arg Glu Asn Glu Thr Phe Cys Leu Ala Phe Met
                180                 185                 190

Arg Ala Ala Ser Val Leu Lys Ser Leu Pro Phe Thr Ile Ile Ser Met
                195                 200                 205

Lys Asp Thr Glu Gly Ile Pro Cys Leu Gly Asp Lys Val Lys Cys Val
    210                 215                 220

Ile Glu Glu Ile Ile Glu Asp Gly Glu Ser Ser Glu Val Lys Ala Val
225                 230                 235                 240
```

```
Leu Asn Asp Glu Arg Tyr Gln Ser Phe Lys Leu Phe Thr Ser Val Phe
                245                 250                 255

Gly Val Gly Leu Lys Thr Ser Glu Arg Trp Phe Arg Met Gly Phe Arg
            260                 265                 270

Ser Leu Ser Lys Ile Arg Ser Asp Lys Thr Leu Lys Phe Thr Arg Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Gly Val Leu Val Lys Glu Ala Val Gln
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Asp Asp Glu Glu Gln Gln Leu Leu Pro Lys Val Val Asn Leu
        355                 360                 365

Trp Glu Arg Glu Gly Leu Leu Leu Tyr Cys Asp Leu Val Glu Ser Thr
    370                 375                 380

Leu Glu Lys Ser Lys Leu Pro Ser Arg Asn Val Asp Ala Leu Asp His
385                 390                 395                 400

Phe Gln Lys Cys Phe Leu Ile Leu Lys Leu His His Gln Arg Val Asp
                405                 410                 415

Ser Gly Met Ser Ser Gln Gln Glu Gly Lys Thr Trp Lys Ala Ile Arg
            420                 425                 430

Val Asp Leu Val Met Cys Pro Tyr Glu Leu Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Ile Leu Asp Asn His Ala Leu Tyr Asp Lys
465                 470                 475                 480

Thr Lys Arg Ile Phe Leu Lys Ala Glu Ser Glu Glu Ile Phe Ala
                485                 490                 495

His Leu Gly Leu Asp Tyr Leu Glu Pro Trp Glu Arg Asn Ala
            500                 505                 510

<210> SEQ ID NO 25
<211> LENGTH: 510
<212> TYPE: PRT
<213> ORGANISM: Mus musculus

<400> SEQUENCE: 25

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
```

```
            100                 105                 110
Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Glu Ile Phe Ala
                485                 490                 495

His Leu Gly Leu Asp Tyr Ile Glu Pro Trp Glu Arg Asn Ala
            500                 505                 510

<210> SEQ ID NO 26
```

```
<211> LENGTH: 509
<212> TYPE: PRT
<213> ORGANISM: Equus caballus

<400> SEQUENCE: 26

Met Asp Pro Phe Gln Met Ala His Ser Ser Pro Arg Lys Lys Arg Pro
1               5                   10                  15

Arg Gln Met Ser Thr Ser Met Ala Ser Pro Pro His Asp Ile Lys Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Asn Ile Lys Ala Gly
                85                  90                  95

Ser Gln Pro Glu Leu Leu Asp Val Ser Trp Leu Ile Glu Cys Met Arg
            100                 105                 110

Ala Gly Lys Pro Val Glu Met Thr Gly Lys His Gln Leu Val Val Arg
        115                 120                 125

Arg Asp Asp Ser Ala Gly Pro Asn Pro Gly Pro Gln Glu Thr Pro Pro
    130                 135                 140

Leu Val Lys Lys Ile Ser Pro Tyr Ala Cys Gln Arg Arg Thr Thr Leu
145                 150                 155                 160

Asp Asn Cys Asn Gln Val Phe Thr Asp Ala Phe Asp Val Leu Ala Glu
                165                 170                 175

Asn Tyr Glu Phe Arg Glu Asn Glu Ser Ser Cys Leu Thr Phe Met Arg
            180                 185                 190

Ala Ala Ser Val Leu Lys Ser Leu Pro Phe Thr Ile Ile Ser Met Lys
        195                 200                 205

Asp Ile Glu Gly Ile Pro Cys Leu Glu Asp Lys Ala Lys Cys Val Ile
    210                 215                 220

Glu Glu Ile Ile Glu Asp Gly Glu Ser Ser Glu Val Lys Thr Val Leu
225                 230                 235                 240

Asn Asp Glu Arg Tyr Gln Ser Phe Lys Leu Phe Thr Ser Val Phe Gly
                245                 250                 255

Val Gly Leu Lys Thr Ser Glu Lys Trp Phe Arg Met Gly Phe Arg Thr
            260                 265                 270

Leu Ser Lys Ile Arg Ser Asp Lys Thr Leu Lys Phe Thr Lys Met Gln
        275                 280                 285

Lys Ala Gly Phe Leu Tyr Tyr Glu Asp Leu Val Ser Cys Val Thr Arg
    290                 295                 300

Pro Glu Ala Glu Ala Val Ser Val Leu Val Lys Glu Ala Val Trp Ala
305                 310                 315                 320

Phe Leu Pro Asp Ala Phe Val Thr Met Thr Gly Gly Phe Arg Arg Gly
                325                 330                 335

Lys Lys Ile Gly His Asp Val Asp Phe Leu Ile Thr Ser Pro Gly Ser
            340                 345                 350

Thr Glu Glu Glu Gln Glu Leu Leu Ser Lys Val Ile Asn Leu Trp
        355                 360                 365

Glu Arg Lys Glu Leu Leu Leu Tyr Tyr Asp Leu Val Glu Ser Thr Phe
    370                 375                 380

Glu Lys Ser Lys Leu Pro Ser Arg Lys Val Asp Ala Leu Asp His Phe
```

```
                385                 390                 395                 400
Gln Lys Cys Phe Leu Ile Leu Lys Leu His His Gln Arg Val Asp Ser
                    405                 410                 415

Gly Lys Ser Ser Gln Gln Glu Gly Lys Thr Trp Lys Ala Ile Arg Val
                420                 425                 430

Asp Leu Val Val Cys Pro Tyr Glu Asn His Ala Phe Ala Leu Leu Gly
            435                 440                 445

Trp Thr Gly Ser Arg Gln Phe Glu Arg Asp Leu Arg Arg Tyr Ala Thr
        450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Ile Phe Ala His
                    485                 490                 495

Leu Gly Leu Asp Tyr Ile Glu Pro Trp Glu Arg Asn Ala
                500                 505

<210> SEQ ID NO 27
<211> LENGTH: 509
<212> TYPE: PRT
<213> ORGANISM: Pan troglodytes

<400> SEQUENCE: 27

Met Asp Pro Pro Arg Ala Ser His Leu Ser Pro Arg Lys Lys Arg Pro
1               5                   10                  15

Arg Gln Thr Gly Ala Leu Met Ala Ser Ser Pro Gln Asp Ile Lys Phe
                20                  25                  30

Gln Asp Leu Val Val Phe Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Ile Gln Val Ser
                85                  90                  95

Ser Gln Pro Glu Leu Leu Asp Val Ser Trp Leu Ile Glu Cys Ile Gly
            100                 105                 110

Ala Gly Lys Pro Val Glu Met Thr Gly Lys His Gln Leu Val Val Arg
        115                 120                 125

Arg Asp Tyr Ser Asp Ser Thr Asn Pro Gly Pro Pro Lys Thr Pro Pro
130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255
```

```
Gly Val Gly Leu Lys Thr Ser Glu Lys Trp Phe Arg Met Gly Phe Arg
            260                 265                 270

Thr Leu Ser Lys Val Arg Ser Asp Lys Ser Leu Lys Phe Thr Arg Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Ser Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu Trp
        355                 360                 365

Glu Lys Lys Gly Leu Leu Leu Tyr Tyr Asp Leu Val Glu Ser Thr Phe
    370                 375                 380

Glu Lys Leu Arg Leu Pro Ser Arg Lys Val Asp Ala Leu Asp His Phe
385                 390                 395                 400

Gln Lys Cys Phe Leu Ile Phe Lys Leu Pro Arg Gln Arg Val Asp Ser
                405                 410                 415

Asp Gln Ser Ser Trp Gln Gly Lys Thr Trp Lys Ala Ile Arg Val
            420                 425                 430

Asp Leu Val Leu Cys Pro Tyr Glu Arg Arg Ala Phe Ala Leu Leu Gly
        435                 440                 445

Trp Thr Gly Ser Arg Gln Phe Glu Arg Asp Leu Arg Arg Tyr Ala Thr
    450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505

<210> SEQ ID NO 28
<211> LENGTH: 517
<212> TYPE: PRT
<213> ORGANISM: Bos mutus

<400> SEQUENCE: 28

Gln Arg Gln His Gln Arg Leu Pro Met Asp Pro Leu Cys Thr Ala Ser
1               5                   10                  15

Ser Gly Pro Arg Lys Lys Arg Pro Arg Gln Val Gly Ala Ser Met Ala
            20                  25                  30

Ser Pro Pro His Asp Ile Lys Phe Gln Asn Leu Ala Leu Phe Ile Leu
        35                  40                  45

Glu Lys Lys Met Gly Thr Thr Arg Arg Asn Phe Leu Met Glu Leu Ala
    50                  55                  60

Arg Arg Lys Gly Phe Arg Val Glu Asn Glu Leu Ser Asp Ser Val Thr
65                  70                  75                  80

His Ile Val Ala Glu Asn Asn Ser Gly Ser Glu Val Leu Glu Trp Leu
                85                  90                  95

Gln Val Gln Asn Ile Arg Ala Ser Ser Gln Leu Glu Leu Leu Asp Val
            100                 105                 110

Ser Trp Leu Ile Glu Ser Met Gly Ala Gly Lys Pro Val Glu Ile Thr
        115                 120                 125
```

```
Gly Lys His Gln Leu Val Val Arg Thr Asp Tyr Ser Ala Thr Pro Asn
            130                 135                 140

Pro Gly Phe Gln Lys Thr Pro Pro Leu Ala Val Lys Lys Ile Ser Gln
145                 150                 155                 160

Tyr Ala Cys Gln Arg Lys Thr Thr Leu Asn Asn Gln Asn His Ile Phe
                165                 170                 175

Thr Asp Ala Phe Glu Ile Leu Ala Glu Asn Ser Glu Phe Lys Glu Asn
            180                 185                 190

Glu Val Ser Tyr Val Thr Phe Met Arg Ala Ala Ser Val Leu Lys Ser
                195                 200                 205

Leu Pro Phe Thr Ile Ile Ser Met Lys Asp Thr Glu Gly Ile Pro Cys
210                 215                 220

Leu Gly Asp Lys Val Lys Cys Ile Ile Glu Glu Ile Glu Asp Gly
225                 230                 235                 240

Glu Ser Ser Glu Val Lys Ala Val Leu Asn Asp Glu Gln Tyr Gln Ser
                245                 250                 255

Phe Lys Leu Phe Thr Ser Val Phe Gly Val Gly Leu Lys Thr Ser Glu
            260                 265                 270

Lys Trp Phe Arg Met Gly Phe Arg Ser Leu Ser Lys Ile Met Ser Asp
            275                 280                 285

Lys Thr Leu Lys Phe Thr Lys Met Gln Lys Ala Gly Phe Leu Tyr Tyr
            290                 295                 300

Glu Asp Leu Val Ser Cys Val Thr Arg Ala Glu Ala Glu Ala Val Gly
305                 310                 315                 320

Val Leu Val Lys Glu Ala Val Trp Ala Phe Leu Pro Asp Ala Phe Val
                325                 330                 335

Thr Met Thr Gly Gly Phe Arg Arg Gly Lys Lys Ile Gly His Asp Val
            340                 345                 350

Asp Phe Leu Ile Thr Ser Pro Gly Ser Ala Glu Asp Glu Glu Gln Leu
            355                 360                 365

Leu Pro Lys Val Ile Asn Leu Trp Glu Lys Lys Gly Leu Leu Leu Tyr
            370                 375                 380

Tyr Asp Leu Val Glu Ser Thr Phe Glu Lys Phe Lys Leu Pro Ser Arg
385                 390                 395                 400

Gln Val Asp Thr Leu Asp His Phe Gln Lys Cys Phe Leu Ile Leu Lys
                405                 410                 415

Leu His His Gln Arg Val Asp Ser Ser Lys Ser Asn Gln Gln Glu Gly
            420                 425                 430

Lys Thr Trp Lys Ala Ile Arg Val Asp Leu Val Met Cys Pro Tyr Glu
            435                 440                 445

Asn Arg Ala Phe Ala Leu Leu Gly Trp Thr Gly Ser Arg Gln Phe Glu
450                 455                 460

Arg Asp Ile Arg Arg Tyr Ala Thr His Glu Arg Lys Met Met Leu Asp
465                 470                 475                 480

Asn His Ala Leu Tyr Asp Lys Thr Lys Arg Val Phe Leu Lys Ala Glu
                485                 490                 495

Ser Glu Glu Glu Ile Phe Ala His Leu Gly Leu Asp Tyr Ile Glu Pro
            500                 505                 510

Trp Glu Arg Asn Ala
            515

<210> SEQ ID NO 29
<211> LENGTH: 509
```

<212> TYPE: PRT
<213> ORGANISM: Pongo abelii

<400> SEQUENCE: 29

```
Met Asp Pro Pro Arg Ala Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Ile Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Ile Gln Val Ser
                85                  90                  95

Ser Gln Pro Glu Leu Leu Asp Ile Ser Trp Leu Ile Glu Cys Ile Gly
            100                 105                 110

Ala Gly Lys Pro Val Glu Met Thr Gly Lys His Gln Leu Val Val Arg
        115                 120                 125

Arg Asp Tyr Ser Asp Ser Thr Asn Pro Gly Pro Lys Thr Pro Pro
    130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
    210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Leu Asp Lys Ser Leu Lys Phe Thr Arg Met
        275                 280                 285

Gln Lys Ala Gly Phe Leu Tyr Tyr Glu Asp Leu Val Ser Cys Val Thr
    290                 295                 300

Arg Ala Glu Ala Glu Val Ser Val Leu Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu Trp
        355                 360                 365

Glu Lys Lys Gly Leu Leu Leu Tyr Tyr Asp Leu Val Glu Ser Thr Phe
    370                 375                 380

Glu Lys Leu Arg Leu Pro Ser Arg Lys Val Asp Ala Leu Asp His Phe
385                 390                 395                 400
```

-continued

```
Gln Lys Cys Phe Leu Ile Phe Lys Leu Pro Arg Gln Arg Val Asp Ser
            405                 410                 415

Asp Gln Ser Ser Trp Gln Glu Gly Lys Thr Trp Lys Ala Ile Arg Val
        420                 425                 430

Asp Leu Val Leu Cys Pro Tyr Glu Cys Arg Ala Phe Ala Leu Leu Gly
        435                 440                 445

Trp Thr Gly Ser Arg Gln Phe Glu Arg Asp Leu Arg Arg Tyr Ala Thr
    450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505
```

<210> SEQ ID NO 30
<211> LENGTH: 509
<212> TYPE: PRT
<213> ORGANISM: Ailuropoda melanoleuca

<400> SEQUENCE: 30

```
Met Asp Pro Leu Gln Met Val His Ser Gly Pro Arg Lys Lys Arg Pro
1               5                   10                  15

Arg Gln Met Gly Thr Ser Met Val Ser Pro His Asp Ile Lys Phe
            20                  25                  30

Gln Asp Leu Val Leu Tyr Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Ile Thr His Ile Val Ala Glu Asn Asn Ser
65                  70                  75                  80

Gly Ser Glu Val Leu Glu Trp Leu Gln Val Gln Asn Ile Lys Ala Ser
                85                  90                  95

Ser Gln Leu Glu Leu Leu Asp Val Ser Trp Leu Ile Glu Ser Met Gly
            100                 105                 110

Ala Gly Lys Pro Val Glu Met Thr Gly Lys His Gln Leu Val Arg Arg
        115                 120                 125

Asp Tyr Ser Ala Ser Pro Asn Pro Glu Leu Gln Lys Thr Pro Pro Leu
    130                 135                 140

Ala Val Lys Lys Ile Ser Gln Tyr Ala Cys Gln Arg Arg Thr Thr Leu
145                 150                 155                 160

Asn Asn Cys Asn His Ile Phe Thr Asp Ala Phe Glu Val Leu Ala Glu
                165                 170                 175

Asn Tyr Glu Phe Arg Glu Asn Glu Val Phe Cys Leu Ala Phe Met Arg
            180                 185                 190

Ala Ala Ser Val Leu Lys Ser Leu Pro Phe Thr Ile Ile Ser Met Lys
        195                 200                 205

Asp Thr Glu Gly Ile Pro Cys Leu Gly Asp Lys Val Lys Cys Val Ile
    210                 215                 220

Glu Glu Ile Ile Glu Asp Gly Glu Ser Ser Val Lys Ala Val Leu
225                 230                 235                 240

Asn Asp Glu Arg Tyr Gln Ser Phe Lys Leu Phe Thr Ser Val Phe Gly
                245                 250                 255

Val Gly Leu Lys Thr Ser Glu Lys Trp Phe Arg Met Gly Phe Arg Thr
```

```
            260                 265                 270
Leu Ser Lys Ile Lys Ser Asp Lys Thr Leu Lys Phe Thr Pro Met Gln
            275                 280                 285

Lys Ala Gly Phe Leu Tyr Tyr Glu Asp Leu Val Ser Cys Val Thr Arg
            290                 295                 300

Ala Glu Ala Glu Ala Val Gly Val Leu Val Lys Glu Ala Val Trp Ala
305                 310                 315                 320

Phe Leu Pro Asp Ala Phe Val Thr Met Thr Gly Gly Phe Arg Arg Gly
                    325                 330                 335

Lys Lys Ile Gly His Asp Val Asp Phe Leu Ile Thr Ser Pro Gly Ser
                340                 345                 350

Thr Asp Glu Asp Glu Glu Gln Leu Leu Pro Lys Val Ile Asn Leu Trp
            355                 360                 365

Glu Arg Lys Gly Leu Leu Leu Tyr Cys Asp Phe Val Glu Ser Thr Phe
            370                 375                 380

Glu Lys Leu Lys Thr Pro Ser Arg Lys Val Asp Ala Leu Asp His Phe
385                 390                 395                 400

Gln Lys Cys Phe Leu Ile Leu Lys Leu His His Gln Arg Val Asp Ser
                    405                 410                 415

Gly Lys Cys Ser Gln Gln Asp Gly Lys Thr Trp Lys Ala Ile Arg Val
                420                 425                 430

Asp Leu Val Met Cys Pro Tyr Glu Arg Arg Ala Phe Ala Leu Leu Gly
            435                 440                 445

Trp Thr Gly Ser Arg Gln Phe Glu Arg Asp Leu Arg Arg Tyr Ala Thr
450                 455                 460

His Glu Arg Lys Met Met Leu Asp Asn His Ala Leu Tyr Asp Lys Thr
465                 470                 475                 480

Lys Lys Ile Phe Leu Lys Ala Glu Ser Glu Glu Glu Ile Phe Ala His
                    485                 490                 495

Leu Gly Leu Asp Tyr Ile Glu Pro Trp Glu Arg Asn Ala
                500                 505

<210> SEQ ID NO 31
<211> LENGTH: 509
<212> TYPE: PRT
<213> ORGANISM: Homo sapiens

<400> SEQUENCE: 31

Met Asp Pro Pro Arg Ala Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Val Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Ala Gln Lys Val Gln Val Ser
                85                  90                  95

Ser Gln Pro Glu Leu Leu Asp Val Ser Trp Leu Ile Glu Cys Ile Arg
            100                 105                 110

Ala Gly Lys Pro Val Glu Met Thr Gly Lys His Gln Leu Val Val Arg
        115                 120                 125
```

```
Arg Asp Tyr Ser Asp Ser Thr Asn Pro Gly Pro Pro Lys Thr Pro Pro
    130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Ser Asp Lys Ser Leu Lys Phe Thr Arg Met
        275                 280                 285

Gln Lys Ala Gly Phe Leu Tyr Tyr Glu Asp Leu Val Ser Cys Val Thr
290                 295                 300

Arg Ala Glu Ala Glu Ala Val Ser Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu Trp
        355                 360                 365

Glu Lys Lys Gly Leu Leu Leu Tyr Tyr Asp Leu Val Glu Ser Thr Phe
370                 375                 380

Glu Lys Leu Arg Leu Pro Ser Arg Lys Val Asp Ala Leu Asp His Phe
385                 390                 395                 400

Gln Lys Cys Phe Leu Ile Phe Lys Leu Pro Arg Gln Arg Val Asp Ser
                405                 410                 415

Asp Gln Ser Ser Trp Gln Glu Gly Lys Thr Trp Lys Ala Ile Arg Val
            420                 425                 430

Asp Leu Val Leu Cys Pro Tyr Glu Arg Arg Ala Phe Ala Leu Leu Gly
        435                 440                 445

Trp Thr Gly Ser Arg Gln Phe Glu Arg Asp Leu Arg Arg Tyr Ala Thr
450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505

<210> SEQ ID NO 32
<211> LENGTH: 510
<212> TYPE: PRT
<213> ORGANISM: Callithrix jacchus

<400> SEQUENCE: 32
```

-continued

```
Met Asp Pro Pro Arg Thr Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Ile Phe Ile Leu Glu Lys Lys Met Gly Thr Thr Arg
            35                  40                  45

Arg Ala Phe Leu Thr Glu Leu Ala Arg Arg Lys Gly Phe Arg Val Glu
        50                  55                  60

Asn Glu Leu Ser Asn Ser Val Thr His Ile Val Ala Glu Asn Asn Ser
65                  70                  75                  80

Gly Ser Asp Val Leu Glu Trp Leu Gln Val Gln Lys Ile Gln Ala Ser
                85                  90                  95

Ser Arg Pro Glu Leu Leu Asp Val Ser Trp Leu Ile Glu Cys Ile Gly
            100                 105                 110

Ala Gly Lys Pro Val Glu Met Thr Gly Lys His Gln Leu Val Val Gly
            115                 120                 125

Arg Asp Tyr Ser Asp Ser Thr Asn Pro Gly Leu Leu Lys Thr Pro Pro
        130                 135                 140

Ile Ala Val Gln Lys Ile Ser Gln Tyr Ala Cys Gln Arg Arg Thr Thr
145                 150                 155                 160

Leu Asn Asn Phe Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Ser Glu Lys Ser Leu Thr Phe Thr Arg Met
        275                 280                 285

Gln Arg Ala Gly Phe Leu Tyr Tyr Glu Asp Leu Val Ser Cys Val Thr
        290                 295                 300

Arg Ala Glu Ala Glu Ala Val Ser Val Leu Val Lys Glu Ala Val Trp
305                 310                 315                 320

Ala Phe Leu Pro Asp Ala Phe Ile Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu
        355                 360                 365

Trp Glu Lys Lys Gly Leu Leu Leu Tyr Tyr Asp Leu Val Glu Ser Thr
    370                 375                 380

Phe Glu Lys Leu Arg Leu Pro Ser Arg Lys Val Asp Ala Leu Asp His
385                 390                 395                 400

Phe Gln Lys Cys Phe Leu Ile Phe Lys Leu Pro Arg Gln Arg Leu Asp
                405                 410                 415
```

```
Ser Asp Gln Pro Ser Trp Gln Glu Gly Lys Thr Trp Lys Ala Ile Arg
            420                 425                 430

Val Asp Leu Val Met Cys Pro Tyr Glu Arg Arg Ala Phe Ala Leu Leu
            435                 440                 445

Gly Trp Thr Gly Ser Arg Gln Phe Glu Arg Asp Leu Arg Arg Tyr Ala
        450                 455                 460

Thr His Glu Arg Lys Met Ile Leu Asp Asn His Ala Leu Tyr Asp Lys
465                 470                 475                 480

Thr Lys Arg Ile Phe Leu Lys Ala Glu Ser Glu Glu Ile Phe Thr
                485                 490                 495

His Leu Gly Leu Asp Tyr Ile Glu Pro Trp Glu Arg Asn Ala
            500                 505                 510

<210> SEQ ID NO 33
<211> LENGTH: 516
<212> TYPE: PRT
<213> ORGANISM: Erinaceus europaeus

<400> SEQUENCE: 33

Met Asp Ala Leu Pro Val Val His Ser Ser Pro Arg Lys Lys Arg Ser
1               5                   10                  15

Arg Leu Met Gly Ala Ser Val Ala Tyr Pro Pro Tyr Asp Ile Lys Phe
            20                  25                  30

His Asn Leu Val Leu Phe Ile Leu Glu Lys Lys Met Gly Ser Ser Arg
        35                  40                  45

Arg Ala Phe Leu Met Glu Leu Ala Arg Arg Lys Gly Phe Arg Val Glu
    50                  55                  60

Asp Glu Leu Ser Asp Ser Ile Thr His Ile Val Ala Glu Asn Asn Thr
65                  70                  75                  80

Gly Ser Glu Val Leu Glu Trp Leu Gln Val Gln Asp Ile Lys Ile Ser
                85                  90                  95

Ser Gln Leu Glu Leu Leu Asp Val Ser Trp Leu Val Glu Cys Met Arg
            100                 105                 110

Ala Gly Asn Pro Val Val Ile Thr Gly Lys His Gln Leu Val Ser Tyr
        115                 120                 125

Thr Val Lys Ser Asp Ala Ser Phe Gly Ser Asn Pro Gly Ser Gln Asn
    130                 135                 140

Thr Pro Pro Leu Ala Ile Lys Lys Ile Ser Gln Tyr Ala Cys Gln Arg
145                 150                 155                 160

Arg Thr Ser Leu Asn Asn Cys Asn His Ile Phe Thr Asp Ala Leu Asp
                165                 170                 175

Ile Leu Ala Glu Asn His Glu Phe Arg Glu Asn Glu Val Ser Cys Val
            180                 185                 190

Ala Phe Met Arg Ala Ala Ser Val Leu Lys Ser Leu Pro Phe Thr Ile
        195                 200                 205

Ile Ser Met Lys Asp Thr Lys Gly Ile Pro Cys Leu Gly Asp Lys Ala
    210                 215                 220

Lys Cys Val Ile Glu Glu Ile Ile Glu Asp Gly Glu Ser Ser Glu Val
225                 230                 235                 240

Lys Ala Ile Leu Asn Asp Glu Arg Tyr Gln Ser Phe Lys Leu Phe Thr
                245                 250                 255

Ser Val Phe Gly Val Gly Leu Lys Thr Ser Glu Lys Trp Phe Arg Met
            260                 265                 270

Gly Phe Arg Thr Leu Asn Lys Ile Met Ser Asp Lys Thr Leu Lys Leu
        275                 280                 285
```

```
Thr Arg Met Gln Lys Ala Gly Phe Leu Tyr Tyr Glu Asp Leu Val Ser
290                 295                 300

Cys Val Ala Lys Ala Glu Ala Asp Ala Val Ser Val Leu Val Gln Glu
305                 310                 315                 320

Ala Val Trp Ala Phe Leu Pro Asp Ala Met Val Thr Met Thr Gly Gly
                325                 330                 335

Phe Arg Arg Gly Lys Lys Leu Gly His Asp Val Asp Phe Leu Ile Thr
                340                 345                 350

Ser Pro Gly Ala Thr Glu Glu Glu Gln Gln Leu Leu Pro Lys Val
            355                 360                 365

Ile Asn Phe Trp Glu Arg Lys Gly Leu Leu Leu Tyr His Asp Leu Val
370                 375                 380

Glu Ser Thr Phe Glu Lys Leu Lys Leu Pro Ser Arg Lys Val Asp Ala
385                 390                 395                 400

Leu Asp His Phe Gln Lys Cys Phe Leu Ile Leu Lys Leu His Leu Gln
                405                 410                 415

His Val Asn Gly Val Gly Asn Ser Lys Thr Gly Gln Gln Glu Gly Lys
                420                 425                 430

Asn Trp Lys Ala Ile Arg Val Asp Leu Val Met Cys Pro Tyr Glu Arg
                435                 440                 445

Arg Ala Phe Ala Leu Leu Gly Trp Thr Gly Ser Arg Gln Phe Glu Arg
450                 455                 460

Asp Leu Arg Arg Phe Ala Thr His Glu Arg Lys Met Met Leu Asp Asn
465                 470                 475                 480

His Ala Leu Tyr Asp Lys Thr Lys Arg Ile Phe Leu Lys Ala Glu Ser
                485                 490                 495

Glu Glu Glu Ile Phe Ala His Leu Gly Leu Asp Tyr Ile Asp Pro Trp
            500                 505                 510

Glu Arg Asn Ala
        515

<210> SEQ ID NO 34
<211> LENGTH: 510
<212> TYPE: PRT
<213> ORGANISM: Loxodonta africana

<400> SEQUENCE: 34

Met Asp Pro Leu Gln Met Ala His Thr Gly Pro Arg Lys Lys Arg Ala
1               5                   10                  15

Arg Pro Met Gly Ala Ser Met Ala Thr Thr Pro Gln Asp Ile Lys Phe
                20                  25                  30

Gln Asp Leu Val Leu Phe Ile Leu Glu Lys Lys Met Gly Thr Ser Arg
            35                  40                  45

Arg Ala Phe Leu Met Glu Leu Ala Arg Arg Lys Gly Phe Arg Val Glu
50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Ile Lys Ala Ser
                85                  90                  95

Ser Gln Leu Glu Leu Leu Asp Val Ser Trp Leu Ile Glu Cys Met Gly
                100                 105                 110

Ala Gly Lys Pro Val Glu Met Thr Gly Lys His Gln Leu Val Val Arg
            115                 120                 125

Gly Asp Tyr Ser Ala Ser Ser Asn Pro Ser Pro Gln Lys Thr Pro Pro
```

```
                130             135             140
Pro Ala Val Lys Lys Ile Ser Gln Tyr Ala Cys Gln Arg Arg Thr Thr
145                 150                 155                 160

Leu Asn Asn His Asn Asn Ile Phe Thr Asp Ala Phe Glu Ile Leu Ala
                165                 170                 175

Glu Asn Cys Glu Phe Arg Glu Asn Glu Gly Ser Tyr Val Val Phe Met
            180                 185                 190

Arg Ala Ala Ser Val Leu Lys Ser Leu Pro Phe Thr Ile Ile Ser Met
            195                 200                 205

Lys Asp Thr Gln Gly Ile Pro Cys Leu Glu Asp Lys Ala Lys Cys Val
210                 215                 220

Ile Glu Asp Ile Ile Glu Asp Gly Glu Ser Ser Glu Val Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Ser Leu Ser Lys Ile Arg Thr Asp Lys Thr Leu Lys Phe Thr Glu Met
            275                 280                 285

Gln Glu Ala Gly Phe Leu Tyr Tyr Glu Asp Leu Val Ser Cys Val Thr
290                 295                 300

Lys Ala Glu Ala Asp Ala Val Ser Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Val Gly His Asp Val Asp Phe Leu Ile Thr Ser Gln Gly
            340                 345                 350

Ser Thr Glu Glu Glu Gln Gln Leu Leu His Lys Val Leu Asn Leu
            355                 360                 365

Trp Lys Lys Glu Gly Leu Leu Leu Tyr Ser Asp Leu Ile Glu Ser Thr
370                 375                 380

Phe Glu Lys Leu Lys Leu Pro Ser Arg Lys Val Asp Ala Leu Asp His
385                 390                 395                 400

Phe Gln Lys Cys Phe Leu Ile Leu Lys Leu His His Gln Arg Ile Asp
                405                 410                 415

Asn Ser Lys Ser Ser Gln Leu Gln Gly Lys Thr Trp Lys Ala Ile Arg
            420                 425                 430

Val Asp Leu Val Met Cys Pro Tyr Glu Cys His Ala Phe Ala Leu Leu
            435                 440                 445

Gly Trp Thr Gly Ser Arg Gln Phe Glu Arg Asp Ile Arg Arg Tyr Ala
450                 455                 460

Ser His Glu Arg Lys Met Ile Leu Asp Asn His Ala Leu Tyr Asp Lys
465                 470                 475                 480

Thr Lys Arg Ile Phe Leu Lys Ala Gly Ser Glu Glu Glu Ile Phe Ala
                485                 490                 495

His Leu Gly Leu Asp Tyr Ile Glu Pro Trp Glu Arg Asn Ala
            500                 505                 510

<210> SEQ ID NO 35
<211> LENGTH: 513
<212> TYPE: PRT
<213> ORGANISM: Mustela putorius furo

<400> SEQUENCE: 35
```

-continued

```
Met Pro Leu Pro Thr Asn Pro Leu Gln Met Val His Leu Gly Pro Arg
1               5                   10                  15

Lys Lys Lys Pro Arg Gln Met Gly Ala Ser Met Val Cys Pro Ser His
            20                  25                  30

Asp Ile Lys Phe Gln Asp Leu Val Leu Tyr Ile Leu Glu Lys Lys Met
            35                  40                  45

Gly Thr Thr Arg Arg Ala Phe Leu Met Glu Leu Ala Arg Arg Lys Gly
            50                  55                  60

Phe Arg Val Glu Asp Glu Leu Ser Asp Ser Ile Thr His Ile Val Ala
65                  70                  75                  80

Glu Asn Asn Ser Gly Ser Glu Val Leu Glu Trp Leu Gln Gly Gln Asn
                85                  90                  95

His Lys Val Ser Ser Gln Leu Glu Leu Leu Asp Val Ser Trp Leu Ile
            100                 105                 110

Glu Ser Met Ala Ala Gly Thr Pro Val Glu Thr Thr Gly Lys His Gln
            115                 120                 125

Leu Val Lys Arg Asp Tyr Ser Ala Asn Pro Asn Pro Glu Leu Gln Lys
    130                 135                 140

Thr Pro Pro Leu Val Ile Lys Lys Ile Ser Gln Tyr Ala Cys Gln Arg
145                 150                 155                 160

Arg Thr Thr Leu Asn Asn Tyr Asn Gln Ile Phe Thr Asp Ala Phe Glu
                165                 170                 175

Val Leu Ala Glu Asn Tyr Glu Phe Arg Glu Asn Glu Val Phe Cys Leu
            180                 185                 190

Ala Phe Met Arg Ala Ala Ser Val Leu Lys Ser Leu Pro Phe Thr Ile
            195                 200                 205

Ile Ser Met Lys Asp Thr Glu Gly Ile Pro Cys Leu Glu Asp Lys Val
    210                 215                 220

Lys Cys Val Ile Glu Glu Ile Ile Glu Asp Gly Glu Ser Ser Glu Val
225                 230                 235                 240

Lys Ala Val Leu Asn Asp Glu Arg Tyr Gln Ser Phe Lys Leu Phe Thr
                245                 250                 255

Ser Val Phe Gly Val Gly Leu Lys Thr Ser Glu Lys Trp Phe Arg Met
            260                 265                 270

Gly Tyr Arg Thr Leu Asn Lys Ile Lys Leu Asp Lys Thr Leu Lys Phe
            275                 280                 285

Thr Pro Met Gln Lys Ala Gly Phe Leu Tyr Tyr Glu Asp Leu Val Ser
    290                 295                 300

Cys Val Thr Arg Ala Glu Ala Glu Ala Val Gly Met Leu Val Lys Glu
305                 310                 315                 320

Ala Val Trp Ala Phe Leu Pro Glu Ala Phe Val Thr Met Thr Gly Gly
                325                 330                 335

Phe Arg Arg Gly Lys Lys Ile Gly His Asp Val Asp Phe Leu Ile Thr
            340                 345                 350

Ser Pro Gly Ser Thr Asp Glu Asp Glu Glu Gln Leu Leu Pro Lys Val
            355                 360                 365

Ile Asn Leu Trp Glu Arg Lys Gly Leu Leu Leu Tyr Cys Asp Leu Val
    370                 375                 380

Glu Ser Thr Phe Glu Lys Leu Lys Leu Pro Ser Arg Lys Val Asp Ala
385                 390                 395                 400

Leu Asp His Phe Gln Lys Cys Phe Leu Ile Leu Lys Leu His His Gln
                405                 410                 415

Arg Val Asp Ser Gly Lys Cys Ser Gln Gln Glu Gly Lys Thr Trp Lys
```

```
                    420                 425                 430
Ala Ile Arg Val Asp Leu Val Met Cys Pro Tyr Glu Arg Arg Ala Phe
            435                 440                 445

Ala Leu Leu Gly Trp Thr Gly Ser Arg Gln Phe Glu Arg Asp Leu Arg
        450                 455                 460

Arg Tyr Ala Thr His Glu Arg Lys Met Ile Leu Asp Asn His Ala Leu
465                 470                 475                 480

Tyr Asp Lys Thr Lys Lys Ile Phe Leu Lys Ala Glu Ser Glu Glu Glu
                485                 490                 495

Ile Phe Ala His Leu Gly Leu Asp Tyr Ile Glu Pro Trp Glu Arg Asn
            500                 505                 510

Ala

<210> SEQ ID NO 36
<211> LENGTH: 511
<212> TYPE: PRT
<213> ORGANISM: Otolemur garnettii

<400> SEQUENCE: 36

Met Asp Pro Leu His Met Ala His Ser Gly Pro Arg Lys Lys Arg Pro
1               5                   10                  15

Arg Gln Thr Ala Ala Ser Met Val Ser Thr Pro Gln Asp Ile Lys Phe
                20                  25                  30

Arg Asp Leu Val Leu Phe Ile Leu Glu Lys Lys Met Gly Thr Thr Arg
            35                  40                  45

Arg Thr Phe Leu Met Glu Leu Ala Arg Thr Lys Gly Phe Arg Val Glu
        50                  55                  60

Asn Glu Phe Ser Asp Ser Val Thr His Ile Ile Ala Glu Asn Asn Ser
65                  70                  75                  80

Gly Ser Asp Val Leu Glu Trp Ile Gln Val Gln Lys Ile Lys Ala Gly
                85                  90                  95

Ser Gln Met Glu Val Leu Asp Val Ser Trp Leu Ile Glu Cys Met Arg
                100                 105                 110

Ala Gly Lys Pro Val Glu Met Thr Gly Lys His Gln Leu Val Val Arg
            115                 120                 125

Gly Asp Tyr Ser Pro Ser Pro Asn Pro Ala Pro Gln Lys Thr Pro Pro
        130                 135                 140

Leu Ala Val Gln Lys Ile Ser Gln Tyr Ala Cys Gln Arg Arg Thr Thr
145                 150                 155                 160

Leu Asn Asn Cys Asn His Ile Phe Thr Asp Ala Phe Glu Ile Met Ala
                165                 170                 175

Glu Asn Tyr Glu Phe Arg Glu Asn Glu Gly Tyr Ser Ala Ala Phe Met
                180                 185                 190

Arg Ala Ala Ser Val Leu Lys Ser Leu Pro Phe Thr Ile Ile Ser Met
            195                 200                 205

Lys Asp Thr Glu Gly Val Pro Cys Leu Gly Asp Asn Val Lys Cys Ile
210                 215                 220

Ile Glu Glu Ile Ile Glu Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Ile Arg Ser Asp Lys Ser Leu Arg Phe Thr Arg Met
```

```
                275                 280                 285
Gln Gln Ala Gly Phe Leu Tyr Tyr Glu Asp Leu Val Ser Cys Val Thr
290                 295                 300

Arg Ala Glu Ala Glu Ala Val Gly Val Leu Val Lys Glu Ala Val Arg
305                 310                 315                 320

Ala Phe Leu Pro Asp Ala Phe Val Thr Met Thr Gly Gly Phe Arg Arg
                325                 330                 335

Gly Lys Asn Ile Gly His Asp Val Asp Phe Leu Ile Thr Ser Pro Gly
            340                 345                 350

Ser Thr Glu Glu Glu Gln Gln Leu Leu His Lys Ile Met Asp Leu
        355                 360                 365

Trp Glu Lys Lys Gly Leu Leu Leu Tyr Cys Asp Leu Val Glu Ser Thr
370                 375                 380

Phe Glu Lys Leu Lys Leu Pro Ser Arg Lys Val Asp Ala Leu Asp His
385                 390                 395                 400

Phe Gln Lys Cys Phe Leu Ile Phe Lys Leu His His Gln Arg Val Val
                405                 410                 415

Asp Ser Glu Gln Ser Asn Gln Gln Glu Gly Lys Thr Trp Lys Ala Ile
            420                 425                 430

Arg Val Asp Leu Val Met Cys Pro Tyr Glu Arg Arg Ala Tyr Ala Leu
        435                 440                 445

Leu Gly Trp Thr Gly Ser Arg Gln Phe Glu Arg Asp Leu Arg Arg Tyr
450                 455                 460

Ala Thr His Glu Arg Lys Met Ile Leu Asp Asn His Gly Leu Trp Asp
465                 470                 475                 480

Lys Thr Lys Arg Ile Phe Leu Lys Ala Glu Ser Glu Glu Ile Phe
                485                 490                 495

Ala His Leu Gly Leu Asp Tyr Ile Glu Pro Trp Glu Arg Asn Ala
            500                 505                 510

<210> SEQ ID NO 37
<211> LENGTH: 512
<212> TYPE: PRT
<213> ORGANISM: Ailuropoda melanoleuca

<400> SEQUENCE: 37

Pro Met Asp Pro Leu Gln Met Val His Ser Gly Pro Arg Lys Lys Arg
1               5                   10                  15

Pro Arg Gln Met Gly Thr Ser Met Val Ser Pro His Asp Ile Lys
            20                  25                  30

Phe Gln Asp Leu Val Leu Tyr Ile Leu Glu Lys Lys Met Gly Thr Thr
        35                  40                  45

Arg Arg Ala Phe Leu Met Glu Leu Ala Arg Arg Lys Gly Phe Arg Val
50                  55                  60

Glu Asn Glu Leu Ser Asp Ser Ile Thr His Ile Val Ala Glu Asn Asn
65                  70                  75                  80

Ser Gly Ser Glu Val Leu Glu Trp Leu Gln Val Gln Asn Ile Lys Ala
                85                  90                  95

Ser Ser Gln Leu Glu Leu Leu Asp Val Ser Trp Leu Ile Glu Ser Met
            100                 105                 110

Gly Ala Gly Lys Pro Val Glu Met Thr Gly Lys His Gln Leu Val Arg
        115                 120                 125

Arg Asp Tyr Ser Ala Ser Pro Asn Pro Glu Leu Gln Lys Thr Pro Pro
130                 135                 140
```

| | | | | | | | | | | | | | | |
|---|---|---|---|---|---|---|---|---|---|---|---|---|---|---|
|Leu|Ala|Val|Lys|Lys|Ile|Ser|Gln|Tyr|Ala|Cys|Gln|Arg|Arg|Thr|Thr|
| |145| | | |150| | | |155| | | |160|

Leu Asn Asn Cys Asn His Ile Phe Thr Asp Ala Phe Glu Val Leu Ala
            165                 170                 175

Glu Asn Tyr Glu Phe Arg Glu Asn Glu Val Phe Cys Leu Ala Phe Met
        180                 185                 190

Arg Ala Ala Ser Val Leu Lys Ser Leu Pro Phe Thr Ile Ile Ser Met
    195                 200                 205

Lys Asp Thr Glu Gly Ile Pro Cys Leu Gly Asp Lys Val Lys Cys Val
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Ile Lys Ser Asp Lys Thr Leu Lys Phe Thr Pro Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Gly Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Ile Arg Gly Lys Lys Ile Gly His Asp Val Asp Phe Leu Ile Thr Ser
            340                 345                 350

Pro Gly Ser Thr Asp Glu Asp Glu Glu Gln Leu Leu Pro Lys Val Ile
        355                 360                 365

Asn Leu Trp Glu Arg Lys Gly Leu Leu Leu Tyr Cys Asp Phe Val Glu
    370                 375                 380

Ser Thr Phe Glu Lys Leu Lys Thr Pro Ser Arg Lys Val Asp Ala Leu
385                 390                 395                 400

Asp His Phe Gln Lys Cys Phe Leu Ile Leu Lys Leu His His Gln Arg
                405                 410                 415

Val Asp Ser Gly Lys Cys Ser Gln Gln Asp Gly Lys Thr Trp Lys Ala
            420                 425                 430

Ile Arg Val Asp Leu Val Met Cys Pro Tyr Glu Arg Arg Ala Phe Ala
        435                 440                 445

Leu Leu Gly Trp Thr Gly Ser Arg Gln Phe Glu Arg Asp Leu Arg Arg
    450                 455                 460

Tyr Ala Thr His Glu Arg Lys Met Met Leu Asp Asn His Ala Leu Tyr
465                 470                 475                 480

Asp Lys Thr Lys Lys Ile Phe Leu Lys Ala Glu Ser Glu Glu Glu Ile
                485                 490                 495

Phe Ala His Leu Gly Leu Asp Tyr Ile Glu Pro Trp Glu Arg Asn Ala
            500                 505                 510

<210> SEQ ID NO 38
<211> LENGTH: 514
<212> TYPE: PRT
<213> ORGANISM: Ovis aries

<400> SEQUENCE: 38

Met Ala Gln Pro Glu Ala Ala Ser Ala Ser Pro Met Asp Pro Leu Cys
1               5                   10                  15

```
       Thr Ala Ser Ser Gly Pro Arg Lys Lys Arg Pro Arg Gln Val Gly Ala
                        20                  25                  30

Ser Met Ala Ser Pro Pro His Asp Ile Lys Phe Gln Asn Leu Val Leu
                    35                  40                  45

Phe Ile Leu Glu Lys Lys Met Gly Thr Thr Arg Arg Asn Phe Leu Met
                50                  55                  60

Glu Leu Ala Arg Arg Lys Gly Phe Arg Val Glu Asn Glu Leu Ser Asp
        65                  70                  75                  80

Ser Val Thr His Ile Val Ala Glu Asn Asn Ser Gly Ser Glu Val Leu
                        85                  90                  95

Glu Trp Leu Gln Val Gln Asn Ile Arg Ala Ser Ser Leu Glu Leu
                    100                 105                 110

Leu Asp Val Ser Trp Leu Ile Glu Ser Met Gly Ala Gly Lys Pro Val
                    115                 120                 125

Glu Ile Thr Gly Lys His Gln Leu Val Val Arg Thr Asp Tyr Ser Ala
                    130                 135                 140

Thr Pro Asn Pro Gly Phe Gln Lys Ile Ser Gln Tyr Ala Cys Gln Arg
       145                 150                 155                 160

Lys Thr Thr Leu Asn Asn Tyr Asn His Ile Phe Thr Asp Ala Phe Glu
                    165                 170                 175

Ile Leu Ala Glu Asn Ser Glu Phe Lys Glu Asn Glu Val Ser Tyr Val
                    180                 185                 190

Thr Phe Met Arg Ala Ala Ser Val Leu Lys Ser Leu Pro Phe Thr Ile
                    195                 200                 205

Ile Ser Met Arg Asp Thr Glu Gly Ile Pro Cys Leu Gly Asp Lys Val
                    210                 215                 220

Lys Cys Ile Ile Glu Glu Ile Ile Glu Asp Gly Glu Ser Ser Glu Val
       225                 230                 235                 240

Lys Ala Val Leu Asn Asp Glu Arg Tyr Gln Ser Phe Lys Leu Phe Thr
                        245                 250                 255

Ser Val Phe Gly Val Gly Leu Lys Thr Ser Glu Lys Trp Phe Arg Met
                    260                 265                 270

Gly Phe Arg Ser Leu Asn Lys Ile Met Ser Asp Lys Thr Leu Lys Phe
                    275                 280                 285

Thr Lys Met Gln Lys Ala Gly Phe Leu Tyr Tyr Glu Asp Leu Val Ser
                    290                 295                 300

Cys Val Thr Arg Ala Glu Ala Glu Ala Val Gly Val Leu Val Lys Glu
       305                 310                 315                 320

Ala Val Trp Ala Phe Leu Pro Asp Ala Phe Val Thr Met Thr Gly Gly
                        325                 330                 335

Phe Arg Arg Ile Arg Gly Lys Lys Ile Gly His Asp Val Asp Phe Leu
                    340                 345                 350

Ile Thr Ser Pro Gly Ser Ala Glu Asp Glu Glu Gln Leu Leu Pro Lys
                    355                 360                 365

Val Ile Asn Phe Trp Glu Lys Lys Gly Leu Leu Leu Tyr Tyr Asp Leu
                    370                 375                 380

Val Glu Ser Thr Phe Glu Lys Phe Lys Leu Pro Ser Arg Gln Val Asp
       385                 390                 395                 400

Thr Leu Asp His Phe Gln Lys Cys Phe Leu Ile Leu Lys Leu His His
                        405                 410                 415

Gln Arg Val Asp Ser Gly Lys Ser Asn Gln Gln Glu Gly Lys Thr Trp
                    420                 425                 430
```

Lys Ala Ile Arg Val Asp Leu Val Met Cys Pro Tyr Glu Asn His Ala
            435                 440                 445

Phe Ala Leu Leu Gly Trp Thr Gly Ser Arg Gln Phe Glu Arg Asp Ile
450                 455                 460

Arg Arg Tyr Ala Thr His Glu Arg Lys Met Met Leu Asp Asn His Ala
465                 470                 475                 480

Leu Tyr Asp Lys Thr Lys Arg Met Phe Leu Lys Ala Glu Ser Glu Glu
                485                 490                 495

Glu Ile Phe Ala His Leu Gly Leu Asp Tyr Ile Glu Pro Trp Glu Arg
                500                 505                 510

Asn Ala

<210> SEQ ID NO 39
<211> LENGTH: 509
<212> TYPE: PRT
<213> ORGANISM: Canis lupus familiaris

<400> SEQUENCE: 39

Met Asp Pro Leu Gln Met Ala His Ser Gly Pro Arg Lys Lys Arg Pro
1               5                   10                  15

Arg Gln Met Gly Ala Pro Met Val Ser Pro Pro His Asn Ile Lys Phe
            20                  25                  30

Gln Asp Leu Val Leu Tyr Ile Leu Glu Lys Lys Met Gly Thr Thr Arg
        35                  40                  45

Arg Ala Phe Leu Met Glu Leu Ala Arg Arg Lys Gly Phe Arg Val Asp
    50                  55                  60

Asn Glu Phe Ser Asp Ser Ile Thr His Ile Val Ala Glu Asn Asn Ser
65                  70                  75                  80

Gly Ser Asp Val Leu Glu Trp Leu Gln Val Gln Asn Ile Lys Ala Ser
                85                  90                  95

Ser Gln Leu Glu Leu Leu Asp Ile Ser Trp Leu Ile Glu Ser Met Gly
            100                 105                 110

Ala Gly Lys Pro Val Glu Met Thr Gly Lys His Gln Leu Met Arg Arg
        115                 120                 125

Asp Tyr Thr Ala Ser Pro Asn Pro Glu Leu Gln Lys Thr Leu Pro Val
    130                 135                 140

Ala Val Lys Lys Ile Ser Gln Tyr Ala Cys Gln Arg Arg Thr Thr Leu
145                 150                 155                 160

Asn Asn Tyr Asn Asn Val Phe Thr Asp Ala Phe Glu Val Leu Ala Glu
                165                 170                 175

Asn Tyr Glu Phe Arg Glu Asn Glu Val Phe Ser Leu Thr Phe Met Arg
            180                 185                 190

Ala Ala Ser Val Leu Lys Ser Leu Pro Phe Thr Ile Ile Ser Met Lys
        195                 200                 205

Asp Thr Glu Gly Ile Pro Cys Leu Gly Asp Gln Val Lys Cys Ile Ile
    210                 215                 220

Glu Glu Ile Ile Glu Asp Gly Glu Ser Ser Glu Val Lys Ala Val Leu
225                 230                 235                 240

Asn Asp Glu Arg Tyr Gln Ser Phe Lys Leu Phe Thr Ser Val Phe Gly
                245                 250                 255

Val Gly Leu Lys Thr Ser Glu Lys Trp Phe Arg Met Gly Phe Arg Thr
            260                 265                 270

Leu Ser Lys Ile Lys Ser Asp Lys Ser Leu Lys Phe Thr Pro Met Gln
        275                 280                 285

```
Lys Ala Gly Phe Leu Tyr Tyr Glu Asp Leu Val Ser Cys Val Thr Arg
    290                 295                 300

Ala Glu Ala Glu Ala Val Gly Val Leu Val Lys Glu Ala Val Gly Ala
305                 310                 315                 320

Phe Leu Pro Asp Ala Phe Val Thr Met Thr Gly Gly Phe Arg Arg Gly
                325                 330                 335

Lys Lys Met Gly His Asp Val Asp Phe Leu Ile Thr Ser Pro Gly Ser
                340                 345                 350

Thr Asp Glu Asp Glu Glu Gln Leu Leu Pro Lys Val Ile Asn Leu Trp
                355                 360                 365

Glu Arg Lys Gly Leu Leu Leu Tyr Cys Asp Leu Val Glu Ser Thr Phe
    370                 375                 380

Glu Lys Leu Lys Leu Pro Ser Arg Lys Val Asp Ala Leu Asp His Phe
385                 390                 395                 400

Gln Lys Cys Phe Leu Ile Leu Lys Leu His His Gln Arg Val Asp Gly
                405                 410                 415

Gly Lys Cys Ser Gln Gln Glu Gly Lys Thr Trp Lys Ala Ile Arg Val
                420                 425                 430

Asp Leu Val Met Cys Pro Tyr Glu Arg Arg Ala Phe Ala Leu Leu Gly
                435                 440                 445

Trp Thr Gly Ser Arg Gln Phe Glu Arg Asp Leu Arg Arg Tyr Ala Ser
    450                 455                 460

His Glu Arg Lys Met Ile Leu Asp Asn His Ala Leu Tyr Asp Lys Thr
465                 470                 475                 480

Lys Lys Ile Phe Leu Lys Ala Glu Ser Glu Glu Glu Ile Phe Ala His
                485                 490                 495

Leu Gly Leu Asp Tyr Ile Glu Pro Trp Glu Arg Asn Ala
                500                 505

<210> SEQ ID NO 40
<211> LENGTH: 517
<212> TYPE: PRT
<213> ORGANISM: Sarcophilus harrisii

<400> SEQUENCE: 40

Met His Arg Ile Arg Thr Thr Asp Ser Asp His Gly Lys Lys Arg Gln
1               5                   10                  15

Lys Lys Met Asp Ala Ile Ser Ser Lys Leu Tyr Glu Ile Lys Phe His
                20                  25                  30

Glu Phe Val Leu Phe Ile Leu Glu Lys Lys Met Gly Ala Thr Arg Arg
            35                  40                  45

Thr Phe Leu Met Asp Leu Ala Arg Lys Lys Gly Phe Arg Val Glu Ser
    50                  55                  60

Glu Leu Ser Asn Ser Val Thr His Ile Val Ala Glu Asn Asn Ser Gly
65                  70                  75                  80

Ser Asp Val Leu Ala Trp Leu Glu Ala His Lys Leu Glu Thr Thr Ala
                85                  90                  95

His Phe Glu Leu Leu Asp Val Ser Trp Leu Ile Glu Cys Met Lys Val
            100                 105                 110

Gly Lys Pro Val Asp Thr Lys Gly Lys Tyr Gln Leu Val Glu Ser Ser
        115                 120                 125

Ile Ala Ser Ala Asn Pro Asp Pro Asn Glu Gly Met Leu Lys Ile Gln
    130                 135                 140

Ser Pro Ala Met Asn Ala Ile Ser Pro Tyr Ala Cys Gln Arg Arg Thr
145                 150                 155                 160
```

```
Thr Leu Asn Asn His Asn Gln Arg Phe Thr Asp Ala Phe Glu Ile Leu
            165                 170                 175

Ala Lys Asn Tyr Glu Phe Arg Glu Asn His Gly His Cys Leu Thr Phe
        180                 185                 190

Leu Arg Ala Thr Ser Val Leu Lys Cys Leu Pro Phe Ala Ile Val Ser
    195                 200                 205

Met Lys Asp Ala Glu Gly Leu Pro Trp Ile Gly Asp Glu Val Lys Gly
210                 215                 220

Ile Met Glu Glu Ile Ile Glu Asp Gly Gln Ser Leu Glu Val Gln Ala
225                 230                 235                 240

Val Leu Asn Asp Glu Arg Tyr Gln Ala Phe Lys Leu Phe Thr Ser Val
                245                 250                 255

Phe Gly Val Gly Leu Lys Thr Ala Glu Lys Trp Tyr Arg Met Gly Phe
            260                 265                 270

Arg Thr Leu Ser Lys Ile Gln Ser Asp Lys Ser Leu Lys Phe Thr Lys
        275                 280                 285

Met Gln Lys Ala Gly Phe Leu Tyr Tyr Glu Asp Leu Ile Ser Cys Val
    290                 295                 300

Ser Lys Ala Glu Ala Asp Ala Val Ser Leu Ile Val Lys Glu Ala Val
305                 310                 315                 320

Trp Thr Phe Leu Pro Asp Ala Leu Ile Thr Ile Thr Gly Gly Phe Arg
                325                 330                 335

Arg Gly Lys Glu Phe Gly His Asp Val Asp Phe Leu Ile Thr Ser Pro
            340                 345                 350

Gly Gly Glu Lys Glu Gln Val Asp Gln Leu Leu Gln Lys Val Thr Asn
        355                 360                 365

Leu Trp Glu Lys Gln Gly Leu Leu Leu Tyr Tyr Asp Leu Met Glu Ser
    370                 375                 380

Thr Phe Glu Asp Leu Lys Leu Pro Ser Arg Lys Val Asp Ala Leu Asp
385                 390                 395                 400

His Phe Gln Lys Cys Phe Leu Ile Leu Lys Leu Tyr Cys Gln Arg Gly
                405                 410                 415

Asp Arg Ser Lys Trp Glu Gly Pro Glu Gly Ser Asn Gly Leu Gln Thr
            420                 425                 430

Lys Asn Trp Lys Ala Ile Arg Val Asp Leu Val Val Cys Pro Tyr Asp
        435                 440                 445

Arg Tyr Ala Tyr Ala Leu Leu Gly Trp Ser Gly Ser Arg Gln Phe Glu
    450                 455                 460

Arg Asp Leu Arg Arg Tyr Ala Thr His Glu Lys Lys Met Met Leu Asp
465                 470                 475                 480

Asn His Ala Leu Tyr Asp Lys Thr Lys Arg Thr Phe Leu Lys Ala Glu
                485                 490                 495

Ser Glu Glu Glu Ile Phe Ser His Leu Gly Leu Glu Tyr Ile Glu Pro
            500                 505                 510

Trp Glu Arg Asn Ala
        515

<210> SEQ ID NO 41
<211> LENGTH: 512
<212> TYPE: PRT
<213> ORGANISM: Cavia porcellus

<400> SEQUENCE: 41

Met Asp Leu Leu Gln Ala Pro His Ser Gly Pro Arg Lys Lys Arg Pro
```

-continued

```
1               5                   10                  15
Arg Lys Ala Gly Ala Leu Met Val Ser Gly Ala His Glu Val Arg Phe
                20                  25                  30

Gly Asp Leu Val Leu Phe Ile Leu Glu Lys Lys Met Gly Ser Thr Arg
                35                  40                  45

Arg Ala Phe Leu Met Asp Leu Ala Arg Ser Lys Gly Phe Arg Val Glu
50                  55                  60

Asp Glu Leu Arg Asp Leu Met Leu Leu Pro His Leu Val Ala Glu Asn
65                  70                  75                  80

Asn Ser Gly Asn Asp Val Leu Glu Trp Leu Gln Val Gln Asn Ile Gln
                85                  90                  95

Ala Ser Ser Arg Leu Glu Leu Leu Asp Val Ser Trp Leu Ile Glu Cys
                100                 105                 110

Met Gly Ala Gly Lys Pro Val Glu Met Thr Arg Lys His Gln Leu Val
                115                 120                 125

Val Arg Arg Gly Ser Pro Ala Ser Pro Asn Pro Asp Ala Gln Lys Thr
                130                 135                 140

Pro Ser Arg Ser Val Gln Arg Ile Ser Glu Tyr Ala Cys Gln Arg Arg
145                 150                 155                 160

Thr Thr Leu Asn Asn Cys Asn Tyr Ala Phe Thr Asn Ala Phe Glu Ile
                165                 170                 175

Leu Ala Glu Asn Cys Glu Phe Lys Glu Asn Glu Asp Ser Tyr Val Thr
                180                 185                 190

Tyr Ile Arg Ala Ala Ser Val Leu Lys Ser Leu Pro Phe Thr Ile Ile
                195                 200                 205

Ser Met Lys Asp Thr Glu Gly Ile Pro Cys Leu Gly Asp Arg Val Lys
                210                 215                 220

Cys Ile Ile Glu Glu Ile Ile Glu Asp Gly Glu Ser Ser Glu Val Asn
225                 230                 235                 240

Ala Val Leu Asn Asp Glu Arg Tyr Lys Ser Phe Lys Leu Phe Thr Ser
                245                 250                 255

Val Phe Gly Val Gly Leu Lys Thr Ser Glu Lys Trp Phe Arg Met Gly
                260                 265                 270

Phe Arg Ser Leu Asn Lys Ile Lys Ser Asp Lys Ser Leu Lys Phe Thr
                275                 280                 285

Arg Met Gln Lys Ala Gly Phe Leu Tyr Tyr Glu Asp Leu Val Ser Cys
                290                 295                 300

Val Thr Arg Ala Glu Ala Glu Ala Val Ser Thr Leu Val Lys Glu Ala
305                 310                 315                 320

Val Trp Ala Phe Leu Pro Gly Ala Phe Ile Ser Met Thr Gly Gly Phe
                325                 330                 335

Arg Arg Gly Lys Glu Ile Gly His Asp Val Asp Phe Leu Ile Thr Ser
                340                 345                 350

Pro Glu Ile Thr Glu Asp Glu Glu Gln Gln Val Leu His Lys Val Ile
                355                 360                 365

Asn Leu Trp Glu Asn Lys Gly Leu Leu Leu Tyr Ser Asp Leu Val Glu
                370                 375                 380

Ser Thr Phe Glu Lys Leu Lys Leu Pro Ser Arg Lys Val Asp Ala Leu
385                 390                 395                 400

Asp His Phe Gln Lys Cys Phe Leu Ile Leu Lys Leu His His Gln Arg
                405                 410                 415

Glu Asp Asn Glu Lys Ser Ser Gln Gln Glu Glu Lys Thr Trp Lys Ala
                420                 425                 430
```

```
Ile Arg Val Asp Leu Val Met Cys Pro Tyr Glu Arg Arg Ala Phe Ala
        435                 440                 445

Leu Leu Gly Trp Thr Gly Ser Arg Gln Phe Glu Arg Asp Leu Arg Arg
    450                 455                 460

Tyr Ala Thr His Glu Arg Lys Met Met Leu Asp Asn His Ala Leu Tyr
465                 470                 475                 480

Asp Lys Thr Lys Arg Ile Phe Leu Lys Ala Glu Ser Glu Glu Glu Ile
                485                 490                 495

Phe Ala His Leu Gly Leu Asp Tyr Ile Glu Pro Trp Glu Arg Asn Ala
                500                 505                 510

<210> SEQ ID NO 42
<211> LENGTH: 534
<212> TYPE: PRT
<213> ORGANISM: Ficedula albicollis

<400> SEQUENCE: 42

Met Asp Arg Phe Lys Ala Pro Thr Val Thr Ser Met Arg Lys Arg Gln
1               5                   10                  15

Lys Gly Leu His Ser Pro Lys Leu Ser Cys Ser Tyr Glu Ile Lys Phe
            20                  25                  30

Ser Ser Phe Val Ile Phe Ile Met Gln Arg Lys Met Gly Met Thr Arg
        35                  40                  45

Arg Ser Phe Leu Met Glu Leu Gly Arg Arg Lys Gly Phe Arg Val Glu
    50                  55                  60

Ser Glu Leu Ser Asp Ser Val Thr His Ile Val Ala Glu Asn Asn Ser
65                  70                  75                  80

Tyr Leu Glu Val Leu Asp Trp Leu Lys Gly Gln Ala Val Gly Asp Ser
                85                  90                  95

Ser Arg Phe Glu Leu Leu Asp Ile Ser Trp Phe Thr Ala Cys Met Glu
            100                 105                 110

Ala Gly Arg Pro Val Asp Ser Glu Met Lys Tyr Arg Leu Val Glu Gln
        115                 120                 125

Cys Gln Ser Pro Pro Leu Ser Thr Pro Glu Leu Glu Met Pro Ala Phe
    130                 135                 140

Ile Ala Thr Lys Val Ser Gln Tyr Ser Cys Gln Arg Lys Thr Thr Leu
145                 150                 155                 160

Asp Asn Tyr Asn Lys Lys Phe Thr Asp Ala Phe Glu Val Met Ala Glu
                165                 170                 175

Asn Tyr Glu Phe Lys Glu Asn Glu Ile Phe Cys Leu Glu Phe Leu Arg
            180                 185                 190

Ala Ala Ser Leu Leu Lys Ser Leu Pro Phe Ser Val Thr Arg Met Lys
        195                 200                 205

Asp Ile Gln Gly Leu Pro Cys Met Gly Asp Gln Val Arg Asp Ile Ile
    210                 215                 220

Glu Glu Ile Ile Glu Glu Gly Glu Ser Ser Arg Val Lys Glu Val Leu
225                 230                 235                 240

Asn Asp Glu Arg Tyr Lys Ala Phe Lys Gln Phe Thr Ser Val Phe Gly
                245                 250                 255

Val Gly Val Lys Thr Ser Glu Lys Trp Tyr Arg Met Gly Leu Arg Thr
            260                 265                 270

Val Glu Glu Val Lys Ala Asp Lys Thr Leu Lys Leu Ser Lys Met Gln
        275                 280                 285

Lys Ala Gly Phe Leu Tyr Tyr Glu Asp Leu Val Ser Cys Val Ser Lys
```

-continued

```
            290                 295                 300
Ala Glu Ala Asp Ala Val Ser Leu Ile Val Lys Asn Thr Val Cys Ser
305                 310                 315                 320

Phe Leu Pro Asp Ala Leu Val Thr Ile Thr Gly Gly Phe Arg Arg Gly
                325                 330                 335

Lys Asn Ile Gly His Asp Ile Asp Phe Leu Ile Thr Asn Pro Gly Pro
                340                 345                 350

Arg Glu Asp Asp Glu Leu Leu His Lys Val Ile Asp Leu Trp Lys Lys
            355                 360                 365

Gln Gly Leu Leu Leu Tyr Cys Asp Ile Ile Glu Ser Thr Phe Val Lys
        370                 375                 380

Glu Gln Leu Pro Ser Arg Lys Val Asp Ala Met Asp His Phe Gln Lys
385                 390                 395                 400

Cys Phe Ala Ile Leu Lys Leu Tyr Gln Pro Arg Val Asp Asn Ser Thr
                405                 410                 415

Cys Asn Thr Ser Lys Lys Leu Gly Met Ala Glu Val Lys Asp Trp Lys
                420                 425                 430

Ala Ile Arg Val Asp Leu Val Ile Thr Pro Phe Glu Gln Tyr Ala Tyr
            435                 440                 445

Ala Leu Leu Gly Trp Thr Gly Ser Arg Gln Phe Gly Arg Asp Leu Arg
        450                 455                 460

Arg Tyr Ala Ala His Glu Arg Lys Met Ile Leu Asp Asn His Ala Leu
465                 470                 475                 480

Tyr Asp Arg Arg Lys Gly Met Thr Leu Lys Met Lys Ser Leu Cys Ile
                485                 490                 495

Asn Ile Gly Lys Leu Lys Lys Gly Leu Glu Arg Ile Phe Leu Lys Ser
                500                 505                 510

Gly Ser Glu Glu Glu Ile Phe Ala His Leu Gly Leu Asp Tyr Val Gln
            515                 520                 525

Pro Trp Glu Arg Asn Ala
    530

<210> SEQ ID NO 43
<211> LENGTH: 509
<212> TYPE: PRT
<213> ORGANISM: Felis catus

<400> SEQUENCE: 43

Met Asp Pro Leu Gln Met Ala His Ser Gly Pro Arg Lys Lys Arg Pro
1               5                   10                  15

Arg Gln Met Gly Ala Ser Met Val Ser Pro Pro His Asp Ile Lys Phe
                20                  25                  30

Arg Asp Leu Val Leu Tyr Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Asn Val Lys Ala Ser
                85                  90                  95

Ser Gln Leu Glu Leu Leu Asp Ile Ser Trp Leu Ile Glu Ser Met Gly
                100                 105                 110

Ala Gly Glu Pro Val Glu Val Thr Arg Lys His Gln Leu Val Arg Arg
            115                 120                 125
```

Asp Tyr Ser Ala Ser Pro Asn Pro Glu Leu Gln Glu Thr Pro Pro Leu
    130                 135                 140

Val Val Lys Lys Ile Pro Leu Tyr Ala Cys Gln Arg Arg Thr Thr Leu
145                 150                 155                 160

Asn Asn Phe Asn His Ile Phe Thr Asp Ala Phe Glu Val Leu Ala Glu
                165                 170                 175

Asn Tyr Glu Phe Lys Glu Asn Glu Ile Ser Ser Ala Thr Phe Met Arg
            180                 185                 190

Ala Ala Ser Val Leu Lys Ser Leu Pro Phe Thr Ile Ile Ser Met Lys
        195                 200                 205

Asp Thr Glu Gly Ile Pro Cys Leu Gly Asp Lys Val Lys Cys Val Ile
    210                 215                 220

Glu Glu Ile Ile Glu Asp Gly Glu Ser Ser Glu Val Lys Ala Val Leu
225                 230                 235                 240

Asn Asp Glu Arg Tyr Gln Ser Phe Lys Leu Phe Thr Ser Val Phe Gly
                245                 250                 255

Val Gly Leu Lys Thr Ser Glu Lys Trp Phe Arg Met Gly Phe Arg Thr
            260                 265                 270

Leu Ser Lys Ile Lys Ser Asp Lys Thr Leu Lys Phe Thr Gln Met Gln
        275                 280                 285

Lys Ala Gly Phe Leu Tyr Tyr Glu Asp Leu Val Ser Cys Val Thr Arg
    290                 295                 300

Ala Glu Ala Glu Ala Val Gly Val Leu Val Lys Glu Ala Val Trp Ala
305                 310                 315                 320

Phe Leu Pro Asp Ala Phe Val Thr Met Thr Gly Gly Phe Arg Arg Gly
                325                 330                 335

Lys Lys Ile Gly His Asp Val Asp Phe Leu Ile Thr Ile Pro Gly Ser
            340                 345                 350

Thr Asp Glu Glu Glu Gln Leu Leu Pro Lys Val Ile Asn Leu Trp
        355                 360                 365

Gln Arg Lys Glu Leu Leu Leu Tyr Tyr Asp Leu Val Glu Ser Thr Phe
    370                 375                 380

Glu Lys Leu Lys Leu Pro Ser Arg Lys Val Asp Ala Leu Asp His Phe
385                 390                 395                 400

Gln Lys Cys Phe Leu Ile Leu Lys Leu His His Gln Arg Val Asp Ser
                405                 410                 415

Gly Lys Cys Ser Gln Gln Glu Gly Lys Thr Trp Lys Ala Ile Arg Val
            420                 425                 430

Asp Leu Val Met Cys Pro Tyr Glu Arg Arg Ala Phe Ala Leu Leu Gly
        435                 440                 445

Trp Thr Gly Ser Arg Gln Phe Glu Arg Asp Leu Arg Arg Tyr Ala Thr
    450                 455                 460

His Glu Arg Lys Met Ile Leu Asp Asn His Ala Leu Tyr Asp Lys Thr
465                 470                 475                 480

Lys Lys Ile Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505

<210> SEQ ID NO 44
<211> LENGTH: 508
<212> TYPE: PRT
<213> ORGANISM: Homo sapiens

<400> SEQUENCE: 44

```
Met Asp Pro Pro Arg Ala Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Val Phe Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Ala Gln Lys Val Gln Val Ser
                85                  90                  95

Ser Gln Pro Glu Leu Leu Asp Val Ser Trp Leu Ile Glu Cys Ile Arg
            100                 105                 110

Ala Gly Lys Pro Val Glu Met Thr Gly Lys His Gln Leu Val Val Arg
        115                 120                 125

Arg Asp Tyr Ser Asp Ser Thr Asn Pro Gly Pro Lys Thr Pro Pro
130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
            245                 250                 255

Gly Val Gly Leu Lys Thr Ser Glu Lys Trp Phe Arg Met Gly Phe Arg
        260                 265                 270

Thr Leu Ser Lys Val Arg Ser Asp Lys Ser Leu Lys Phe Thr Arg Met
        275                 280                 285

Gln Lys Ala Gly Phe Leu Tyr Tyr Glu Asp Leu Val Ser Cys Val Thr
        290                 295                 300

Arg Ala Glu Ala Glu Ala Val Ser Val Leu Val Lys Glu Ala Val Trp
305                 310                 315                 320

Ala Phe Leu Pro Asp Ala Phe Val Thr Met Thr Gly Gly Phe Arg Arg
            325                 330                 335

Gly Lys Lys Met Gly His Asp Val Asp Phe Leu Ile Thr Ser Pro Gly
        340                 345                 350

Ser Thr Glu Asp Glu Glu Gln Leu Leu Gln Lys Val Met Asn Leu Trp
        355                 360                 365

Glu Lys Lys Gly Leu Leu Leu Tyr Tyr Asp Leu Val Glu Ser Thr Phe
        370                 375                 380

Glu Lys Leu Arg Leu Pro Ser Arg Lys Val Asp Ala Leu Asp His Phe
385                 390                 395                 400

Gln Lys Cys Phe Leu Ile Phe Lys Leu Pro Arg Gln Arg Val Asp Ser
            405                 410                 415
```

```
Asp Gln Ser Ser Trp Gln Glu Gly Lys Thr Trp Lys Ala Ile Arg Val
            420                 425                 430

Asp Leu Val Leu Cys Pro Tyr Glu Arg Arg Ala Phe Ala Leu Leu Gly
            435                 440                 445

Trp Thr Gly Ser Arg Phe Glu Arg Asp Leu Arg Arg Tyr Ala Thr His
        450                 455                 460

Glu Arg Lys Met Ile Leu Asp Asn His Ala Leu Tyr Asp Lys Thr Lys
465                 470                 475                 480

Arg Ile Phe Leu Lys Ala Glu Ser Glu Glu Ile Phe Ala His Leu
                485                 490                 495

Gly Leu Asp Tyr Ile Glu Pro Trp Glu Arg Asn Ala
            500                 505

<210> SEQ ID NO 45
<211> LENGTH: 506
<212> TYPE: PRT
<213> ORGANISM: Pelodiscus sinensis

<400> SEQUENCE: 45

Met Asp Lys Thr Arg Thr Pro Ser Leu Phe Pro Gln Arg Lys Lys Gln
1               5                   10                  15

Lys Gly Met His Pro Ala Val Ser Leu Ser Ser Cys Lys Val Lys Phe
            20                  25                  30

Asn Glu Leu Val Ile Phe Ile Met Glu Arg Lys Met Gly Val Thr Arg
        35                  40                  45

Arg Thr Phe Leu Thr Gln Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Tyr Ala Glu Val Leu Glu Trp Leu Arg Gly His Lys Met Arg Asp Ser
                85                  90                  95

Ser Arg Phe Lys Leu Leu Asp Ile Ser Trp Phe Thr Ala Cys Met Glu
            100                 105                 110

Ala Gly Lys Pro Val Asp Ser Glu Lys Lys Tyr Gln Leu Ile Val Gln
        115                 120                 125

Gln Thr Tyr Pro Ala Thr Ser Tyr Thr Pro Glu Leu Glu Thr Ser Ser
    130                 135                 140

Phe Val Ala Gly Arg Val Ser Gln Tyr Ala Cys Gln Arg Arg Thr Thr
145                 150                 155                 160

Leu Asn Asn Cys Asn Lys Lys Phe Thr Asp Ala Phe Glu Ile Leu Ala
                165                 170                 175

Gly Asn Tyr Glu Phe Lys Glu Asn Ala Val Leu Cys Leu Ala Phe Met
            180                 185                 190

Arg Ala Ala Ser Val Leu Lys Ser Leu Pro Phe Thr Ile Leu Arg Met
        195                 200                 205

His Asp Leu Glu Gly Leu Pro Cys Met Gly Asp Glu Ile Arg Ala Val
    210                 215                 220

Ile Glu Glu Ile Ile Asp Glu Gly Glu Ser Ser Arg Val Lys Asp Val
225                 230                 235                 240

Leu Thr Asp Gly Arg Tyr Gln Ser Phe Lys Glu Phe Ser Val Phe
                245                 250                 255

Gly Val Gly Leu Lys Thr Ser Glu Lys Trp Tyr Arg Met Gly Phe Arg
            260                 265                 270

Thr Leu Glu Asp Val Lys Ala Asp Lys Thr Leu Lys Leu Ser Arg Met
        275                 280                 285
```

Gln Lys Ala Gly Phe Leu His Tyr Glu Asp Leu Ile Ser Tyr Val Ser
            290                 295                 300

Lys Val Glu Ala Asp Ala Val Ser Val Ile Val Glu Asp Ala Val Arg
305                 310                 315                 320

Thr Phe Leu Pro Asp Ala Leu Val Thr Ile Thr Gly Gly Phe Arg Arg
                325                 330                 335

Gly Lys Lys Ile Gly His Asp Val Asp Phe Leu Ile Thr Ser Pro Glu
            340                 345                 350

Leu Arg Glu Glu Glu Val Leu His Arg Gly Val Leu Leu Tyr Tyr
            355                 360                 365

Asp Leu Val Glu Ser Thr Phe Glu Gln Ala Lys Leu Pro Ser Arg Lys
        370                 375                 380

Val Asp Ala Phe Asp His Tyr Gln Lys Cys Phe Ala Ile Leu Lys Cys
385                 390                 395                 400

Pro Gln Gln Arg Val Asp Thr Ser Asn Cys Asp Thr Ser Lys Glu Ser
                405                 410                 415

Glu Lys Ala Lys Ala Lys Ala Trp Lys Ala Ile Arg Val Asp Leu Val
            420                 425                 430

Val Ser Pro Phe Glu Gln Tyr Ala Tyr Ala Leu Leu Gly Trp Thr Gly
        435                 440                 445

Ser Arg Gln Phe Glu Arg Asp Leu Arg Arg Tyr Ala Thr His Glu Arg
    450                 455                 460

Lys Met Met Leu Asp Asn His Ala Leu Tyr Asp Lys Thr Lys Arg Ile
465                 470                 475                 480

Phe Leu Lys Ala Lys Ser Glu Asp Glu Ile Phe Ala Tyr Leu Gly Leu
                485                 490                 495

Asp Tyr Leu Glu Pro Trp Glu Arg Asn Ala
            500                 505

<210> SEQ ID NO 46
<211> LENGTH: 515
<212> TYPE: PRT
<213> ORGANISM: Erinaceus europaeus

<400> SEQUENCE: 46

Met Asp Ala Leu Pro Val Val His Ser Ser Pro Arg Lys Lys Arg Ser
1               5                   10                  15

Arg Leu Met Gly Ala Ser Val Ala Tyr Pro Pro Tyr Asp Ile Lys Phe
            20                  25                  30

His Asn Leu Val Leu Phe Ile Leu Glu Lys Lys Met Gly Ser Ser Arg
        35                  40                  45

Arg Ala Phe Leu Met Glu Leu Ala Arg Arg Lys Gly Phe Arg Val Glu
    50                  55                  60

Asp Glu Leu Ser Asp Ser Ile Thr His Ile Val Ala Glu Asn Asn Thr
65                  70                  75                  80

Gly Ser Glu Val Leu Glu Trp Leu Gln Val Gln Asp Ile Lys Ile Ser
            85                  90                  95

Ser Gln Leu Glu Leu Leu Asp Val Ser Trp Leu Val Glu Cys Met Arg
        100                 105                 110

Ala Gly Asn Pro Val Val Ile Thr Gly Lys His Gln Leu Val Ser Tyr
    115                 120                 125

Thr Val Lys Ser Asp Ala Ser Phe Gly Ser Asn Pro Gly Ser Gln Asn
130                 135                 140

Thr Pro Pro Leu Ala Ile Lys Lys Ile Ser Gln Tyr Ala Cys Gln Arg

```
145                 150                 155                 160
Arg Thr Ser Leu Asn Asn Cys Asn His Ile Phe Thr Asp Ala Leu Asp
                165                 170                 175
Ile Leu Ala Glu Asn His Glu Phe Arg Glu Asn Glu Val Ser Cys Val
                180                 185                 190
Ala Phe Met Arg Ala Ala Ser Val Leu Lys Ser Leu Pro Phe Thr Ile
                195                 200                 205
Ile Ser Met Lys Asp Thr Lys Gly Ile Pro Cys Leu Gly Asp Lys Ala
                210                 215                 220
Lys Cys Val Ile Glu Glu Ile Glu Asp Gly Glu Ser Ser Glu Val
225                 230                 235                 240
Lys Ala Ile Leu Asn Asp Glu Arg Tyr Gln Ser Phe Lys Leu Phe Thr
                245                 250                 255
Ser Val Phe Gly Val Gly Leu Lys Thr Ser Glu Lys Trp Phe Arg Met
                260                 265                 270
Gly Phe Arg Thr Leu Asn Lys Ile Met Ser Asp Lys Thr Leu Lys Leu
                275                 280                 285
Thr Arg Met Gln Lys Ala Gly Phe Leu Tyr Tyr Glu Asp Leu Val Ser
                290                 295                 300
Cys Val Ala Lys Ala Glu Ala Asp Ala Val Ser Val Leu Val Gln Glu
305                 310                 315                 320
Ala Val Trp Ala Phe Leu Pro Asp Ala Met Val Thr Met Thr Gly Gly
                325                 330                 335
Phe Arg Arg Gly Lys Lys Leu Gly His Asp Val Asp Phe Leu Ile Thr
                340                 345                 350
Ser Pro Gly Ala Thr Glu Glu Glu Gln Gln Leu Leu Pro Lys Val
                355                 360                 365
Ile Asn Phe Trp Glu Arg Lys Gly Leu Leu Leu Tyr His Asp Leu Val
                370                 375                 380
Glu Ser Thr Phe Glu Lys Leu Lys Leu Pro Ser Arg Lys Val Asp Ala
385                 390                 395                 400
Leu Asp His Phe Gln Lys Cys Phe Leu Ile Leu Lys Leu His Leu Gln
                405                 410                 415
His Val Asn Gly Val Gly Asn Ser Lys Thr Gly Gln Gln Glu Gly Lys
                420                 425                 430
Asn Trp Lys Ala Ile Arg Val Asp Leu Val Met Cys Pro Tyr Glu Arg
                435                 440                 445
Arg Ala Phe Ala Leu Leu Gly Trp Thr Gly Ser Arg Phe Glu Arg Asp
                450                 455                 460
Leu Arg Arg Phe Ala Thr His Glu Arg Lys Met Met Leu Asp Asn His
465                 470                 475                 480
Ala Leu Tyr Asp Lys Thr Lys Arg Ile Phe Leu Lys Ala Glu Ser Glu
                485                 490                 495
Glu Glu Ile Phe Ala His Leu Gly Leu Asp Tyr Ile Asp Pro Trp Glu
                500                 505                 510
Arg Asn Ala
        515

<210> SEQ ID NO 47
<211> LENGTH: 505
<212> TYPE: PRT
<213> ORGANISM: Corvus brachyrhynchos

<400> SEQUENCE: 47
```

-continued

```
Met Asp Arg Phe Lys Ala Pro Ala Val Ile Ser Gln Arg Lys Arg Gln
1               5                   10                  15

Lys Glu Leu His Ser Pro Lys Leu Ser Cys Ser Tyr Glu Ile Lys Phe
            20                  25                  30

Ser Asn Phe Val Ile Phe Ile Met Gln Arg Lys Met Gly Lys Thr Arg
        35                  40                  45

Arg Met Phe Leu Met Glu Leu Gly Arg Arg Lys Gly Phe Arg Val Glu
    50                  55                  60

Ser Glu Leu Ser Asp Ser Val Thr His Ile Val Ala Glu Asn Asn Ser
65                  70                  75                  80

Tyr Leu Glu Val Leu Asp Trp Leu Lys Gly Gln Ala Val Gly Asp Ser
                85                  90                  95

Ser Arg Phe Glu Leu Leu Asp Ile Ser Trp Phe Thr Ala Cys Met Glu
            100                 105                 110

Ala Gly Arg Pro Val Asp Ser Glu Leu Lys Tyr His Leu Met Glu Gln
        115                 120                 125

Arg Gln Ser Pro Pro Leu Asn Val Pro Glu Leu Glu Met Pro Ala Phe
    130                 135                 140

Thr Ala Thr Lys Val Ser Gln Tyr Ser Cys Gln Arg Lys Thr Thr Leu
145                 150                 155                 160

Asn Asn Tyr Asn Lys Lys Phe Thr Asp Ala Phe Glu Val Met Ala Glu
                165                 170                 175

Asn Tyr Glu Phe Lys Glu Ser Glu Ile Phe Cys Leu Glu Phe Leu Arg
            180                 185                 190

Ala Ala Ser Leu Leu Lys Ser Leu Pro Phe Pro Val Thr Arg Met Lys
        195                 200                 205

Asp Ile Gln Gly Leu Pro Cys Met Gly Asp Gln Val Arg Asp Ile Ile
    210                 215                 220

Glu Glu Ile Ile Glu Glu Gly Glu Ser Ser Arg Val Arg Glu Val Leu
225                 230                 235                 240

Asn Asp Glu Arg Tyr Lys Ala Phe Lys Gln Phe Thr Ser Val Phe Gly
                245                 250                 255

Val Gly Val Lys Thr Ser Glu Lys Trp Tyr Arg Met Gly Leu Arg Thr
            260                 265                 270

Val Glu Glu Val Lys Ala Asp Lys Thr Leu Lys Leu Ser Lys Met Gln
        275                 280                 285

Lys Ala Gly Phe Leu Tyr Tyr Glu Asp Leu Val Ser Cys Val Ser Lys
    290                 295                 300

Ala Glu Ala Asp Ala Val Ser Leu Ile Val Lys Asn Ala Val Cys Thr
305                 310                 315                 320

Phe Leu Pro Asp Ala Leu Val Thr Ile Thr Gly Gly Phe Arg Arg Gly
                325                 330                 335

Lys Lys Ile Gly His Asp Ile Asp Phe Leu Ile Thr Ser Pro Gly Pro
            340                 345                 350

Gly Glu Asp Asp Glu Leu Leu His Lys Gly Leu Leu Leu Tyr Cys Asp
        355                 360                 365

Ile Ile Glu Ser Thr Phe Val Lys Glu Gln Leu Pro Ser Arg Lys Val
    370                 375                 380

Asp Ala Met Asp His Phe Gln Lys Cys Phe Ala Ile Leu Lys Leu Cys
385                 390                 395                 400

Gln Pro Arg Val Asp Asn Ser Thr Cys Asn Thr Ser Lys Lys Leu Glu
                405                 410                 415

Met Ala Glu Val Lys Asp Trp Lys Ala Ile Arg Val Asp Leu Val Ile
```

```
                420                 425                 430
Thr Pro Phe Glu Gln Tyr Ala Tyr Ala Leu Leu Gly Trp Thr Gly Ser
        435                 440                 445

Arg Gln Phe Gly Arg Asp Leu Arg Arg Tyr Ala Ser His Glu Arg Lys
    450                 455                 460

Met Val Leu Asp Asn His Ala Leu Tyr Asp Arg Lys Arg Ile Phe
465                 470                 475                 480

Leu Lys Ala Gly Ser Glu Glu Ile Phe Ala His Leu Gly Leu Asp
            485                 490                 495

Tyr Val Glu Pro Trp Glu Arg Asn Ala
            500                 505

<210> SEQ ID NO 48
<211> LENGTH: 519
<212> TYPE: PRT
<213> ORGANISM: Sarcophilus harrisii

<400> SEQUENCE: 48

Met His Arg Ile Arg Thr Thr Asp Ser Asp His Gly Lys Lys Arg Gln
1               5                   10                  15

Lys Lys Met Asp Ala Ile Ser Ser Lys Leu Tyr Glu Ile Lys Phe His
            20                  25                  30

Glu Phe Val Leu Phe Ile Leu Glu Lys Lys Met Gly Ala Thr Arg Arg
        35                  40                  45

Thr Phe Leu Met Asp Leu Ala Arg Lys Lys Gly Phe Arg Val Glu Ser
    50                  55                  60

Glu Leu Ser Asn Ser Val Thr His Ile Val Ala Glu Asn Asn Ser Gly
65                  70                  75                  80

Ser Asp Val Leu Ala Trp Leu Glu Ala His Lys Leu Glu Thr Thr Ala
                85                  90                  95

His Phe Glu Leu Leu Asp Val Ser Trp Leu Ile Glu Cys Met Lys Val
            100                 105                 110

Gly Lys Pro Val Asp Thr Lys Gly Lys Tyr Gln Leu Val Val Ile Leu
        115                 120                 125

Val Gln Arg Gln Glu Ala Asn Pro Asp Pro Asn Glu Gly Met Leu Lys
    130                 135                 140

Ile Gln Ser Pro Ala Met Asn Ala Ile Ser Pro Tyr Ala Cys Gln Arg
145                 150                 155                 160

Arg Thr Thr Leu Asn Asn His Asn Gln Arg Phe Thr Asp Ala Phe Glu
                165                 170                 175

Ile Leu Ala Lys Asn Tyr Glu Phe Arg Glu Asn His Gly His Cys Leu
            180                 185                 190

Thr Phe Leu Arg Ala Thr Ser Val Leu Lys Cys Leu Pro Phe Ala Ile
        195                 200                 205

Val Ser Met Lys Asp Ala Glu Gly Leu Pro Trp Ile Gly Asp Glu Val
    210                 215                 220

Lys Gly Ile Met Glu Glu Ile Ile Glu Asp Gly Gln Ser Leu Glu Val
225                 230                 235                 240

Gln Ala Val Leu Asn Asp Glu Arg Tyr Gln Ala Phe Lys Leu Phe Thr
                245                 250                 255

Ser Val Phe Gly Val Gly Leu Lys Thr Ala Glu Lys Trp Tyr Arg Met
            260                 265                 270

Gly Phe Arg Thr Leu Ser Lys Ile Gln Ser Asp Lys Ser Leu Lys Phe
        275                 280                 285
```

```
Thr Lys Met Gln Lys Ala Gly Phe Leu Tyr Tyr Glu Asp Leu Ile Ser
    290                 295                 300

Cys Val Ser Lys Ala Glu Ala Asp Ala Val Ser Leu Ile Val Lys Glu
305                 310                 315                 320

Ala Val Trp Thr Phe Leu Pro Asp Ala Leu Ile Thr Ile Thr Gly Gly
                325                 330                 335

Phe Arg Arg Gly Lys Glu Phe Gly His Asp Val Asp Phe Leu Ile Thr
                340                 345                 350

Ser Pro Gly Gly Glu Lys Glu Gln Val Asp Gln Leu Leu Gln Lys Val
                355                 360                 365

Thr Asn Leu Trp Glu Lys Gln Gly Leu Leu Tyr Tyr Asp Leu Met
370                 375                 380

Glu Ser Thr Phe Glu Asp Leu Lys Leu Pro Ser Arg Lys Val Asp Ala
385                 390                 395                 400

Leu Asp His Phe Gln Lys Cys Phe Leu Ile Leu Lys Leu Tyr Cys Gln
                405                 410                 415

Arg Gly Asp Arg Ser Lys Trp Glu Gly Pro Glu Gly Ser Asn Gly Leu
                420                 425                 430

Gln Thr Lys Asn Trp Lys Ala Ile Arg Val Asp Leu Val Val Cys Pro
                435                 440                 445

Tyr Asp Arg Tyr Ala Tyr Ala Leu Leu Gly Trp Ser Gly Ser Arg Gln
450                 455                 460

Phe Glu Arg Asp Leu Arg Arg Tyr Ala Thr His Glu Lys Lys Met Met
465                 470                 475                 480

Leu Asp Asn His Ala Leu Tyr Asp Lys Thr Lys Arg Thr Phe Leu Lys
                485                 490                 495

Ala Glu Ser Glu Glu Glu Ile Phe Ser His Leu Gly Leu Glu Tyr Ile
                500                 505                 510

Glu Pro Trp Glu Arg Asn Ala
                515

<210> SEQ ID NO 49
<211> LENGTH: 525
<212> TYPE: PRT
<213> ORGANISM: Raja eglanteria

<400> SEQUENCE: 49

Met Ser Ser Val Glu Lys Leu Ala Ser Leu Gly Ile Thr Pro Lys Arg
1               5                   10                  15

Arg Lys Gln Lys Glu Glu Gly Leu Cys Gly Ser His Ser Gln Tyr Glu
                20                  25                  30

Val Arg Phe Arg Asp Leu Leu Ile Tyr Val Val Glu Arg Lys Met Gly
            35                  40                  45

Ser Ser Arg Arg Met Phe Leu Met Asp Leu Ala Arg Lys Lys Gly Phe
    50                  55                  60

Arg Val Ala Asp Ile Met Ser Asp Ser Val Thr His Ile Val Thr Glu
65                  70                  75                  80

Asn Asn Ser Trp Asn Glu Ile Trp Asp Trp Ile Gln Thr Gln Lys Met
                85                  90                  95

Ser Asp Ala Asp Lys Leu Asn Leu Leu Asp Ile Ser Trp Phe Thr Asp
            100                 105                 110

Ser Met Gly Ala Gly Lys Pro Val Asp Ile Lys Glu His His Arg Leu
        115                 120                 125

Gln Met Gln Lys Ile Gln Pro Leu Gln Ser Asp Val Ser Thr Ser
    130                 135                 140
```

Ser Val Thr His Val Ser Gln Tyr Ala Cys Gln Arg Lys Ser Thr Leu
145                 150                 155                 160

Asp Asn Lys Asn Lys Ile Phe Thr Asp Thr Leu Glu Leu Leu Ala Glu
                165                 170                 175

Asn Cys Glu Phe Asp Glu Asn Ala Gly Ser Phe Val Ala Tyr Ser Arg
            180                 185                 190

Ala Thr Ser Val Leu Lys Ser Leu Pro Tyr Pro Ile Thr Gly Met Asn
        195                 200                 205

Asp Leu Glu Gly Leu Pro Cys Ile Gly Asp Gln Thr Arg Val Ile Ile
    210                 215                 220

Glu Glu Leu Leu Glu Gly Val Cys Ser Lys Val Glu Ser Leu Leu
225                 230                 235                 240

Cys Asp Glu Lys Tyr Lys Ala Arg Lys Leu Phe Thr Ser Val Phe Gly
                245                 250                 255

Val Gly Val Lys Thr Ala Asp Lys Trp Tyr Gly Leu Gly Phe Arg Thr
            260                 265                 270

Leu Glu Glu Ile Lys Ala Arg Lys Asp Ile Thr Phe Thr Lys Met Gln
        275                 280                 285

Lys Ala Gly Phe Leu Tyr Tyr Glu Asp Ile Leu Gln Ala Val Lys Lys
    290                 295                 300

Ser Glu Ala Glu Ala Val Ile Gln Ile Ile Gly Asp Ile Val Gly Gln
305                 310                 315                 320

Cys Ala Pro Asp Ala Lys Val Thr Leu Thr Gly Gly Phe Arg Arg Gly
                325                 330                 335

Lys Glu Val Gly His Asp Val Asp Leu Leu Ile Thr Cys Leu Glu Glu
            340                 345                 350

Gly Asn Glu Glu Gly Val Leu His Lys Ala Ile Ser Lys Leu Asp Arg
        355                 360                 365

His Gly Leu Leu Leu Phe Cys Asp Val Val Glu Ala Thr Met Glu Lys
    370                 375                 380

Arg Gln Leu Pro Ser Arg Lys Tyr Asp Ala Met Asp His Phe Gln Lys
385                 390                 395                 400

Cys Phe Leu Ile Leu Lys Leu Asp Lys Arg Leu Val Asn Lys Arg Asp
                405                 410                 415

Tyr Gly Leu Ala Ser Gly Ser Ala Val Arg Leu Thr Asp Lys Arg Thr
            420                 425                 430

Glu Asp Glu Asn Lys Thr Met Ile Lys Gly Trp Lys Ala Ile Arg Val
        435                 440                 445

Asp Leu Val Ile Val Pro Ser Gln Gln Phe Ala Tyr Ala Leu Leu Gly
    450                 455                 460

Trp Ser Gly Ser Arg Gln Phe Glu Arg Asp Leu Arg Arg Tyr Cys Ser
465                 470                 475                 480

Gln Glu Lys Arg Met Leu Leu Asp Asn His Gly Leu Tyr Asp Lys Asn
                485                 490                 495

Thr Gln Glu Phe Leu Lys Ala Glu Thr Glu Glu Ile Phe Ala His
            500                 505                 510

Leu Gly Leu Glu Tyr Ile Glu Pro Gln Glu Arg Asn Ala
        515                 520                 525

<210> SEQ ID NO 50
<211> LENGTH: 530
<212> TYPE: PRT
<213> ORGANISM: Mus musculus

```
<400> SEQUENCE: 50

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Gly Ser Cys Leu Ala Phe Met
            180                 185                 190

Arg Ala Ser Ser Val Leu Lys Ser Leu Pro Phe Pro Ile Thr Ser Met
    195                 200                 205

Lys Asp Thr Glu Gly Ile Pro Cys Leu Gly Asp Lys Val Lys Ser Ile
210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415
```

```
Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
            450                 455                 460

Thr His Glu Arg Lys Met Met Leu Asp Asn His Ala Leu Tyr Asp Arg
465                 470                 475                 480

Thr Lys Gly Lys Thr Val Thr Ile Ser Pro Leu Asp Gly Lys Val Ser
                485                 490                 495

Lys Leu Gln Lys Ala Leu Arg Val Phe Leu Glu Ala Glu Ser Glu Glu
            500                 505                 510

Glu Ile Phe Ala His Leu Gly Leu Asp Tyr Ile Glu Pro Trp Glu Arg
            515                 520                 525

Asn Ala
    530

<210> SEQ ID NO 51
<211> LENGTH: 487
<212> TYPE: PRT
<213> ORGANISM: Latimeria chalumnae

<400> SEQUENCE: 51

Met Glu Lys Phe Ile Phe Pro Ser Leu Ser Pro His Lys Lys Lys Gln
1               5                   10                  15

Lys Val Thr Glu Pro Leu Lys Ser Phe Gly Asn Tyr Glu Ile Lys Phe
            20                  25                  30

Lys Asp Ile Val Ile Phe Ile Met Glu Arg Lys Met Gly Ser Ser Arg
            35                  40                  45

Arg Met Phe Leu Thr Glu Leu Ala Arg Lys Lys Gly Phe Gln Val Glu
        50                  55                  60

Ser Val Leu Ser Asp Ser Val Asn His Ile Val Ala Glu Asn Asn Ser
65                  70                  75                  80

Cys Ala Glu Val Leu Glu Trp Ile His Lys Gln Asn Leu Arg Asn Asn
                85                  90                  95

Pro Lys Met Glu Val Leu Asp Ile Thr Trp Phe Thr Glu Ser Met Gly
            100                 105                 110

Ala Gly Lys Pro Val Glu Ile Glu Lys Arg His Arg Leu Met Val Arg
        115                 120                 125

Leu Asn Cys Asn Ile Pro Arg Ser Asn Ser Asn Thr Pro Pro Glu
    130                 135                 140

Ser Ser Val Val Ala Ile Ser Pro Tyr Ala Cys Gln Arg Arg Thr
145                 150                 155                 160

Ser Leu Asn Asn Tyr Asn Lys Leu Phe Thr Asp Ala Phe Glu Val Leu
                165                 170                 175

Ala Glu Asn Tyr Glu Met Asn Glu Asn Lys Gly Pro Tyr Leu Gly Phe
            180                 185                 190

Met Arg Ala Ala Ser Met Ile Lys Ser Leu Pro Tyr Ala Ile Ser Ser
        195                 200                 205

Met Lys Asp Leu Glu Gly Leu Pro Cys Leu Gly Asp Gln Thr Lys Ala
    210                 215                 220

Val Ile Glu Gln Cys Cys Gln Asp Thr Glu Lys Ser Thr Ile Lys Ser
225                 230                 235                 240

Cys Ile Asn Phe Ala Arg Ser Gln Ser Ile Ile Leu Phe Thr Ser Val
```

-continued

```
                245                 250                 255
Phe Gly Val Gly Gln Lys Thr Ala Glu Lys Trp Phe Arg Lys Gly Leu
                260                 265                 270
Arg Thr Phe Glu Glu Val Gln Val His Lys Glu Thr Lys Leu Thr Lys
            275                 280                 285
Met Gln Ile Ala Gly Phe Leu Tyr Tyr Glu Asp Leu Ser Ser Phe Val
    290                 295                 300
Thr Lys Pro Glu Ala Asp Ala Ile Gly Gln Ile Ile Glu Asp Thr Val
305                 310                 315                 320
Arg Leu Phe Met Pro Asp Ala Leu Val Thr Leu Thr Gly Gly Phe Arg
                325                 330                 335
Arg Glu Lys Lys Ile Gly His Asp Val Asp Phe Leu Ile Thr Thr Pro
            340                 345                 350
Val Pro Gly Asn Glu Asn Gly Leu Leu Glu Lys Val Ile Asp Val Leu
    355                 360                 365
His Gln Gln Gly Ile Leu Leu Tyr Cys Asp Val Val Glu Ser Thr Phe
370                 375                 380
Asp Lys Ser Arg Leu Pro Ser Arg Lys Val Asp Ala Leu Asp His Phe
385                 390                 395                 400
Gln Lys Cys Phe Ala Ile Leu Lys Leu Leu Lys Gln Lys Val Ile Thr
                405                 410                 415
Ser Asn Cys Glu Glu Ala Glu Glu Pro Ser Asn Thr Ser Thr Lys Glu
            420                 425                 430
Trp Lys Ala Ile Arg Val Asp Leu Val Ile Thr Pro Phe Asp Gln Tyr
    435                 440                 445
Ala Phe Ala Leu Leu Gly Trp Thr Gly Ser Arg Gln Phe Glu Arg Asp
    450                 455                 460
Leu Arg Arg Phe Ala Thr His Glu Arg Lys Met Met Leu Asp Asn His
465                 470                 475                 480
Ala Leu Phe Asp Lys Asn Lys
                485

<210> SEQ ID NO 52
<211> LENGTH: 492
<212> TYPE: PRT
<213> ORGANISM: Oryctolagus cuniculus

<400> SEQUENCE: 52

Met Gly Ala Ser Arg Thr Ser Leu Pro Gln Asp Val Lys Phe Arg Asp
1               5                   10                  15
Leu Val Leu Phe Ile Leu Glu Lys Lys Met Gly Thr Thr Arg Arg Ala
                20                  25                  30
Phe Leu Met Glu Leu Ala Arg Arg Lys Gly Phe Arg Val Glu Asn Glu
            35                  40                  45
Leu Ser Asp Ser Val Thr His Ile Val Ala Glu Asn Asn Ser Gly Ser
        50                  55                  60
Asp Val Leu Glu Trp Leu Gln Val Gln Lys Val Lys Asp Ser Ser Gln
65                  70                  75                  80
Leu Glu Leu Leu Asp Val Ser Trp Leu Ile Glu Cys Met Gly Ala Gly
                85                  90                  95
Arg Pro Val Glu Met Thr Gly Lys His Gln Leu Val Val Arg Gln Asp
            100                 105                 110
Tyr Pro Ala Ser Pro Asn Pro Gly Ser Gln Glu Ala Pro Ala Leu Ala
        115                 120                 125
```

```
Val His Arg Ile Ser Glu Tyr Ala Cys Lys Arg Arg Thr Thr Leu Asn
    130                 135                 140

Asn Cys Asn Arg Ile Phe Thr Asp Ala Phe Glu Ile Leu Ala Glu Asn
145                 150                 155                 160

Ser Glu Phe Arg Glu Asn Glu Asp Ser Tyr Val Thr Phe Ile Arg Ala
                165                 170                 175

Ala Ser Val Leu Lys Ser Leu Pro Phe Pro Ile Val Ser Met Lys Asp
            180                 185                 190

Thr Glu Gly Ile Pro Cys Leu Gly Asp Lys Val Lys Gly Ile Ile Glu
        195                 200                 205

Glu Ile Ile Glu Glu Gly Glu Ser Ser Glu Val Lys Ala Val Leu Asn
    210                 215                 220

Asp Glu Arg Tyr Gln Cys Phe Lys Leu Phe Thr Ala Val Phe Gly Val
225                 230                 235                 240

Gly Leu Lys Thr Ser Glu Lys Trp Phe Arg Met Gly Phe Arg Thr Leu
                245                 250                 255

Ser Lys Ile Arg Glu Asp Lys Ser Leu Lys Phe Thr Arg Met Gln Gln
                260                 265                 270

Ala Gly Phe Arg Tyr Tyr Glu Asp Leu Val Ser Cys Val Thr Arg Ala
            275                 280                 285

Glu Ala Glu Ala Val Asp Val Leu Val Lys Glu Ala Val Arg Ala Tyr
        290                 295                 300

Leu Pro Gly Ala Phe Ile Thr Met Thr Gly Gly Phe Arg Arg Gly Lys
305                 310                 315                 320

Lys Ile Gly His Asp Val Asp Phe Leu Ile Thr Ser Pro Glu Ser Thr
                325                 330                 335

Glu Glu Asp Glu Gln Gln Leu Leu His Lys Val Val Asn Leu Trp Glu
                340                 345                 350

Lys Lys Gly Leu Leu Leu Tyr His Asp Phe Met Glu Ser Thr Phe Glu
            355                 360                 365

Lys Leu Lys Gln Pro Ser Arg Lys Val Asp Ala Leu Asp His Phe Gln
        370                 375                 380

Lys Cys Phe Leu Ile Leu Lys Leu Pro His Glu Arg Val Asp Ser Asp
385                 390                 395                 400

Arg Pro Ser Gln Gln Glu Gly Lys Asn Trp Lys Ala Ile Arg Val Asp
                405                 410                 415

Leu Val Met Cys Pro Tyr Glu Cys His Ala Phe Ala Leu Leu Gly Trp
                420                 425                 430

Thr Gly Ser Arg Gln Phe Glu Arg Asp Leu Arg Arg Tyr Ala Thr His
            435                 440                 445

Glu Arg Arg Met Ile Leu Asp Asn His Ala Leu Tyr Asp Lys Thr Lys
        450                 455                 460

Arg Met Phe Leu Gln Ala Glu Ser Glu Glu Ile Phe Ala His Leu
465                 470                 475                 480

Gly Leu Asp Tyr Ile Glu Pro Trp Glu Arg Asn Ala
                485                 490
```

<210> SEQ ID NO 53
<211> LENGTH: 504
<212> TYPE: PRT
<213> ORGANISM: Balearica regulorum gibbericeps

<400> SEQUENCE: 53

```
Met Asp Arg Ile Arg Ala Pro Ala Val Phe Ser Gln Lys Arg Gln
1               5                   10                  15
```

-continued

```
Lys Gly Thr His Ser Pro Asn Leu Ser Cys Ser Tyr Glu Ile Lys Phe
             20                  25                  30

Asn Lys Phe Val Ile Phe Ile Met Gln Arg Lys Met Gly Met Thr Arg
         35                  40                  45

Arg Thr Phe Leu Met Glu Leu Ala Arg Arg Lys Gly Phe Arg Val Glu
     50                  55                  60

Asn Glu Leu Ser Asp Ser Val Thr His Ile Val Ala Glu Asn Asn Ser
 65                  70                  75                  80

Tyr Leu Glu Val Gln Asp Trp Leu Arg Gly Gln Ala Val Gly Asp Ser
                 85                  90                  95

Ser Arg Phe Glu Leu Leu Asp Ile Ser Trp Phe Thr Ala Cys Met Glu
             100                 105                 110

Ala Gly Arg Pro Val Asp Ser Glu Leu Lys Tyr Arg Leu Met Glu Gln
         115                 120                 125

Asp Gln Ser Pro Pro Leu Asn Ala Pro Glu Ser Glu Val Pro Ser Phe
    130                 135                 140

Ile Ala Ser Lys Val Ser Gln Tyr Ser Cys Gln Arg Lys Thr Thr Leu
145                 150                 155                 160

Asn Asn Tyr Asn Gln Lys Phe Thr Asp Ala Phe Glu Ile Met Ala Glu
                165                 170                 175

Asn Tyr Glu Phe Lys Glu Asn Glu Ile Phe Cys Leu Glu Phe Leu Arg
            180                 185                 190

Ala Ala Ser Val Leu Lys Phe Leu Pro Phe Pro Val Thr Thr Met Lys
        195                 200                 205

Asp Ile Gln Gly Leu Pro Cys Met Gly Asp Arg Val Arg Asp Val Ile
    210                 215                 220

Glu Glu Ile Ile Glu Glu Gly Glu Ser Ser Arg Ala Lys Glu Val Leu
225                 230                 235                 240

Ser Asp Glu Arg Tyr Gln Ser Phe Lys Gln Phe Thr Ser Val Phe Gly
                245                 250                 255

Val Gly Val Lys Thr Ser Glu Lys Trp Tyr Arg Met Gly Leu Arg Thr
            260                 265                 270

Leu Glu Glu Val Lys Ala Asp Arg Thr Leu Lys Leu Ser Lys Met Gln
        275                 280                 285

Lys Ala Gly Phe Leu Tyr Tyr Glu Asp Leu Val Ser Cys Val Ser Lys
    290                 295                 300

Ala Glu Ala Asp Ala Val Ser Leu Ile Val Lys Asn Thr Val Cys Arg
305                 310                 315                 320

Phe Leu Pro Asp Ala Leu Val Thr Ile Thr Gly Gly Phe Arg Arg Gly
                325                 330                 335

Lys Glu Ile Gly His Asp Ile Asp Phe Leu Ile Thr Asn Pro Gly Pro
            340                 345                 350

Arg Glu Asp Asp Glu Leu Leu His Lys Gly Leu Leu Leu Tyr Cys Asp
        355                 360                 365

Met Ile Glu Ser Thr Phe Val Lys Glu Gln Leu Pro Ser Arg Lys Val
    370                 375                 380

Asp Ala Met Asp Asn Phe Gln Lys Cys Phe Ala Ile Leu Lys Leu Tyr
385                 390                 395                 400

Gln Pro Arg Val Asp Asn Ser Ser Tyr Asn Met Ser Lys Lys Phe His
                405                 410                 415

Ile Glu Val Lys Asp Trp Lys Ala Ile Arg Val Asp Leu Val Ile Thr
            420                 425                 430
```

```
Pro Phe Glu Gln Tyr Ala Tyr Ala Leu Leu Gly Trp Thr Gly Ser Arg
            435                 440                 445

Gln Phe Gly Arg Asp Leu Arg Arg Phe Ala Asn His Glu Arg Lys Met
450                 455                 460

Ile Leu Asp Asn His Ala Leu Tyr Asp Arg Arg Lys Arg Ile Phe Leu
465                 470                 475                 480

Lys Ala Gly Ser Glu Glu Ile Phe Ala His Leu Gly Leu Asp Tyr
                485                 490                 495

Val Glu Pro Trp Glu Arg Asn Ala
            500

<210> SEQ ID NO 54
<211> LENGTH: 507
<212> TYPE: PRT
<213> ORGANISM: Xenopus laevis

<400> SEQUENCE: 54

Met Asn Pro Leu Ser Gln Ser Ala Leu Val Pro Leu Arg Lys Lys Ala
1               5                   10                  15

Lys Met Ala Pro Ile Ser Gln Ser Phe Cys Gln His Asn Val Lys Phe
            20                  25                  30

Lys Glu Ile Val Leu Phe Leu Val Glu Arg Lys Met Gly Ser Ser Arg
        35                  40                  45

Arg Thr Phe Leu Met Glu Leu Ala Arg Lys Arg Gly Phe Gln Thr Glu
    50                  55                  60

Ile Glu Leu Ser Asp Ser Val Thr His Ile Val Ala Glu Asn Asn Ser
65                  70                  75                  80

Gly Ala Glu Val Leu Glu Trp Leu Gln Ser Lys Lys Leu Gly Phe Thr
                85                  90                  95

Val Lys Thr His Ile Leu Asp Ile Ser Trp Phe Thr Glu Cys Met Glu
            100                 105                 110

Ala Gly Arg Pro Val Glu Ile Gln Asn Arg His Leu Leu Pro Val Gln
        115                 120                 125

Gln Asp Cys Ser Ala Asn Phe Asn Pro Pro Leu Ser Ser Ser Cys Val
    130                 135                 140

Gln Val Ser Gln Tyr Ala Cys Gln Arg Cys Thr Thr Leu Gln Asp Thr
145                 150                 155                 160

Asn Arg Ile Phe Thr Asp Ala Phe Asp Ile Leu Ala Glu His Phe Glu
                165                 170                 175

Phe Cys Glu Asn Lys Gly Arg Thr Val Ala Phe Leu Arg Ala Ser Ser
            180                 185                 190

Leu Ile Lys Ser Leu Pro Phe Pro Ile Thr Ala Met Lys Glu Leu Glu
        195                 200                 205

Gly Leu Pro Trp Leu Gly Asp Gln Met Lys Gly Ile Ile Glu Glu Ile
    210                 215                 220

Leu Glu Glu Gly Lys Ser Tyr Lys Val Leu Glu Val Met Asn Glu Glu
225                 230                 235                 240

Arg Tyr Lys Ser Phe Lys Gln Phe Thr Ser Val Phe Gly Val Gly Leu
                245                 250                 255

Lys Thr Ser Asp Lys Trp Phe Arg Met Gly Phe Arg Thr Leu Glu Glu
            260                 265                 270

Ile Lys Asn Glu Lys Glu Leu Lys Leu Thr Lys Met Gln Lys Cys Gly
        275                 280                 285

Leu Leu Tyr Tyr Glu Asp Ile Thr Ser Tyr Val Ser Arg Ala Glu Ala
    290                 295                 300
```

```
Glu Thr Thr Glu Gln Leu Ile Lys Ser Ile Val Trp Lys Phe Val Pro
305                 310                 315                 320

Asp Ala Ile Val Thr Leu Thr Gly Gly Phe Arg Arg Gly Lys Lys Lys
                325                 330                 335

Gly His Asp Val Asp Ile Leu Ile Thr Cys Ala Arg Lys Gly Lys Glu
                340                 345                 350

Lys Asn Ile Leu His Asn Thr Met Ser Val Leu Lys Asn Arg Gly Leu
            355                 360                 365

Leu Leu Phe Tyr Asn Ile Ile Glu Ser Thr Phe Asp Glu Thr Lys Leu
370                 375                 380

Pro Ser Arg His Val Asp Ala Leu Asp His Phe Gln Lys Cys Phe Thr
385                 390                 395                 400

Ile Leu Lys Leu Pro Lys Arg Gln Met Asp Ile Gly Asn Ile Ile Asp
                405                 410                 415

Pro His Glu Cys Glu Arg Lys Asn Trp Lys Ala Val Arg Leu Asp Leu
                420                 425                 430

Val Ile Thr Pro Tyr Glu Gln Tyr Pro Tyr Ala Leu Leu Gly Trp Thr
                435                 440                 445

Gly Ser Arg Gln Phe Glu Arg Asp Leu Arg Arg Tyr Ala Thr His Glu
                450                 455                 460

Lys Arg Met Met Leu Asp Asn His Gly Leu Tyr Asp Lys Thr Lys Asn
465                 470                 475                 480

Asn Phe Leu Lys Ala Asn Asn Glu Glu Asp Ile Phe Lys Gln Leu Gly
                485                 490                 495

Leu Asp Tyr Leu Glu Pro Trp Glu Arg Asn Ala
                500                 505

<210> SEQ ID NO 55
<211> LENGTH: 507
<212> TYPE: PRT
<213> ORGANISM: Xenopus laevis

<400> SEQUENCE: 55

Met Asn Pro Leu Ser Gln Ser Ala Leu Val Pro Leu Arg Lys Lys Ala
1               5                   10                  15

Lys Met Ala Pro Ile Ser Gln Ser Phe Cys Gln His Asn Val Lys Phe
                20                  25                  30

Lys Glu Ile Val Leu Phe Leu Val Glu Arg Lys Met Gly Ser Ser Arg
            35                  40                  45

Arg Thr Phe Leu Met Glu Leu Ala Arg Lys Arg Gly Phe Gln Thr Glu
        50                  55                  60

Ile Glu Leu Ser Asp Ser Val Thr His Ile Val Ala Glu Asn Asn Ser
65                  70                  75                  80

Gly Ala Glu Val Leu Glu Trp Leu Gln Ser Lys Lys Leu Gly Phe Thr
                85                  90                  95

Val Lys Thr His Ile Leu Asp Ile Ser Trp Phe Thr Glu Cys Met Glu
                100                 105                 110

Ala Gly Arg Pro Val Glu Ile Gln Asn Arg His Leu Leu Pro Val Gln
            115                 120                 125

Gln Asp Cys Ser Ala Asn Phe Asn Pro Leu Ser Ser Cys Val
        130                 135                 140

Gln Val Ser Gln Tyr Ala Cys Gln Arg Cys Thr Thr Leu Gln Asp Thr
145                 150                 155                 160

Asn Arg Ile Phe Thr Asp Ala Phe Asp Ile Leu Ala Glu His Phe Glu
```

```
                165                 170                 175
Phe Cys Glu Asn Lys Gly Arg Thr Val Ala Phe Leu Arg Ala Ser Ser
            180                 185                 190

Leu Ile Lys Ser Leu Pro Phe Pro Ile Thr Ala Met Lys Glu Leu Glu
        195                 200                 205

Gly Leu Pro Trp Leu Gly Asp Gln Met Lys Gly Ile Ile Glu Glu Ile
    210                 215                 220

Leu Glu Glu Gly Lys Ser Tyr Lys Val Leu Glu Val Met Asn Glu Glu
225                 230                 235                 240

Arg Tyr Lys Ser Phe Lys Gln Phe Thr Ser Val Phe Gly Val Gly Leu
                245                 250                 255

Lys Thr Ser Asp Lys Trp Phe Arg Met Gly Phe Arg Thr Leu Glu Glu
            260                 265                 270

Ile Lys Asn Glu Lys Glu Leu Lys Leu Thr Lys Met Gln Lys Cys Gly
        275                 280                 285

Leu Leu Tyr Tyr Glu Asp Ile Thr Ser Tyr Val Ser Arg Ala Glu Ala
    290                 295                 300

Glu Thr Thr Glu Gln Leu Ile Lys Ser Ile Val Trp Lys Phe Val Pro
305                 310                 315                 320

Asp Ala Ile Val Thr Leu Thr Gly Gly Phe Arg Arg Gly Lys Lys Lys
                325                 330                 335

Gly His Asp Val Asp Ile Leu Ile Thr Cys Ala Arg Lys Gly Lys Glu
            340                 345                 350

Lys Asn Ile Leu His Asn Thr Met Ser Val Leu Lys Asn Arg Gly Leu
        355                 360                 365

Leu Leu Phe Tyr Asn Ile Ile Glu Ser Thr Phe Asp Glu Thr Lys Leu
    370                 375                 380

Pro Ser Arg His Val Asp Ala Leu Asp His Phe Gln Lys Cys Phe Thr
385                 390                 395                 400

Ile Leu Lys Leu Pro Lys Arg Gln Met Asp Ile Gly Asn Ile Ile Asp
                405                 410                 415

Pro His Glu Cys Glu Arg Lys Asn Trp Lys Ala Val Arg Leu Asp Leu
            420                 425                 430

Val Ile Thr Pro Tyr Glu Gln Tyr Pro Tyr Ala Leu Leu Gly Trp Thr
        435                 440                 445

Gly Ser Arg Gln Phe Glu Arg Asp Leu Arg Arg Tyr Ala Thr His Glu
    450                 455                 460

Lys Arg Met Met Leu Asp Asn His Gly Leu Tyr Asp Lys Thr Lys Asn
465                 470                 475                 480

Asn Phe Leu Lys Ala Asn Asn Glu Glu Asp Ile Phe Lys Gln Leu Gly
                485                 490                 495

Leu Asp Tyr Leu Glu Pro Trp Glu Arg Asn Ala
            500                 505

<210> SEQ ID NO 56
<211> LENGTH: 498
<212> TYPE: PRT
<213> ORGANISM: Takifugu rubripes

<400> SEQUENCE: 56

Met Phe His Ala Thr Ala Leu Pro Arg Met Arg Lys Arg Pro Arg Pro
1               5                   10                  15

Glu Glu Val Ala Cys Pro Gly Arg Glu Asp Val Lys Phe Arg Asp Val
            20                  25                  30
```

```
Arg Leu Tyr Leu Val Glu Met Lys Met Gly Arg Ser Arg Ser Phe
             35                  40                  45

Leu Thr Gln Leu Ala Arg Ser Lys Gly Phe Met Val Glu Val Leu
 50                  55                  60

Ser Asn Arg Val Thr His Val Val Ser Glu Ser Ser Gln Ala Pro Val
 65                  70                  75                  80

Leu Trp Ala Trp Leu Lys Glu Arg Ala Pro Gln Asp Leu Pro Asn Met
                 85                  90                  95

His Val Val Asn Ile Thr Trp Phe Thr Asp Ser Met Arg Glu Ser Arg
                100                 105                 110

Pro Val Ala Val Glu Thr Arg His Leu Ile Gln Asp Thr Leu Pro Ala
                115                 120                 125

Ile Pro Glu Gly Gly Ala Pro Ala Ala Glu Val Ser Gln Tyr Ala Cys
130                 135                 140

Gln Arg Arg Thr Thr Thr Asp Asn Tyr Asn Val Val Phe Thr Asp Ala
145                 150                 155                 160

Phe Glu Val Leu Ala Glu Cys Tyr Glu Phe Asn Gln Met Asp Gly Arg
                165                 170                 175

Cys Leu Ala Phe Arg Arg Ala Ala Ser Val Leu Lys Ser Leu Pro Arg
                180                 185                 190

Gly Leu Ser Ser Leu Glu Glu Thr His Ser Leu Pro Cys Leu Gly Gly
                195                 200                 205

His Ala Lys Ala Ile Ile Gly Glu Ile Leu Gln His Gly Arg Ala Phe
210                 215                 220

Asp Val Glu Lys Val Leu Ser Asp Glu Arg Tyr Gln Thr Leu Lys Leu
225                 230                 235                 240

Phe Thr Ser Val Tyr Gly Val Gly Pro Lys Thr Ala Glu Lys Trp Tyr
                245                 250                 255

Arg Ser Gly Leu Arg Ser Leu Asp His Ile Leu Ala Asp Gln Ser Ile
                260                 265                 270

Gln Leu Asn His Met Gln Gln Asn Gly Phe Leu His Tyr Gly Asp Ile
                275                 280                 285

Ser Arg Ala Val Ser Lys Ala Glu Ala Arg Ala Leu Thr Lys Ala Ile
290                 295                 300

Gly Glu Thr Val Gln Ala Ile Thr Pro Asp Ala Leu Leu Ala Leu Thr
305                 310                 315                 320

Gly Gly Phe Arg Arg Gly Lys Glu Phe Gly His Asp Val Asp Ile Ile
                325                 330                 335

Phe Thr Thr Leu Glu Leu Gly Met Glu Glu Asn Leu Leu Leu Ala Val
                340                 345                 350

Ile Lys Ser Leu Glu Lys Gln Gly Ile Leu Leu Tyr Cys Asp Tyr Gln
                355                 360                 365

Ala Ser Thr Phe Asp Leu Thr Lys Leu Pro Thr His Ser Phe Glu Ala
                370                 375                 380

Met Asp His Phe Ala Lys Cys Phe Leu Ile Leu Arg Leu Glu Ala Ser
385                 390                 395                 400

Gln Val Glu Glu Gly Leu Asn Ser Pro Val Glu Asp Ile Arg Gly Trp
                405                 410                 415

Arg Ala Val Arg Val Asp Leu Val Ser Pro Val Asp Arg Tyr Ala
                420                 425                 430

Phe Ala Leu Leu Gly Trp Thr Gly Ser Arg Gln Phe Glu Arg Asp Leu
                435                 440                 445

Arg Arg Phe Ala Arg Lys Glu Arg Arg Met Leu Leu Asp Asn His Gly
```

```
                450             455             460
Leu Tyr Asp Lys Thr Lys Glu Glu Phe Leu Ala Ala Gly Thr Glu Lys
465                 470                 475                 480

Asp Ile Phe Asp His Leu Gly Leu Glu Tyr Met Glu Pro Trp Gln Arg
                485                 490                 495

Asn Ala

<210> SEQ ID NO 57
<211> LENGTH: 504
<212> TYPE: PRT
<213> ORGANISM: Gavia stellata

<400> SEQUENCE: 57

Met Asp Arg Ile Arg Ala Pro Ala Val Phe Ser Gln Arg Lys Arg Gln
1               5                   10                  15

Lys Ala Met His Ser Pro Asn Leu Ser Cys Ser Tyr Glu Ile Lys Phe
                20                  25                  30

Asn Lys Phe Val Ile Phe Ile Met Glu Arg Lys Met Gly Val Thr Arg
            35                  40                  45

Arg Ser Phe Leu Met Asp Leu Ala Arg Arg Lys Gly Phe Arg Val Glu
        50                  55                  60

Ser Glu Leu Ser Asp Ser Val Thr His Ile Val Ala Glu Asn Asn Ser
65              70                  75                  80

Tyr Ser Glu Val Leu Asp Trp Leu Lys Gly Gln Ala Val Gly Asp Ser
                85                  90                  95

Ser Arg Phe Glu Leu Leu Asp Ile Ser Trp Phe Thr Ala Cys Met Glu
            100                 105                 110

Ala Gly Arg Pro Val Asp Ser Glu Met Lys Tyr Arg Leu Met Glu Gln
        115                 120                 125

Asp Gln Ser Pro Pro Leu Asn Thr Pro Glu Ser Glu Val Pro Ser Phe
130                 135                 140

Ile Ala Ser Lys Val Ser Gln Tyr Ser Cys Gln Arg Lys Thr Thr Leu
145                 150                 155                 160

Asn Asn Tyr Asn Lys Lys Phe Thr Asp Ala Phe Glu Ile Met Ala Glu
                165                 170                 175

Asn Tyr Glu Phe Lys Glu Asn Glu Ile Phe Cys Leu Glu Phe Leu Arg
            180                 185                 190

Ala Ala Ser Val Leu Lys Phe Leu Pro Phe Pro Val Thr Arg Met Lys
        195                 200                 205

Asp Ile Gln Gly Leu Pro Cys Met Gly Asp Arg Val Arg Asp Val Ile
210                 215                 220

Glu Glu Ile Ile Glu Glu Gly Glu Ser Ser Arg Ala Glu Glu Val Leu
225                 230                 235                 240

Asn Asp Glu Arg Tyr Lys Ser Phe Lys Gln Phe Thr Ser Val Phe Gly
                245                 250                 255

Val Gly Val Lys Thr Ser Glu Lys Trp Tyr Arg Ile Gly Leu Arg Thr
            260                 265                 270

Leu Glu Glu Val Lys Ala Asp Lys Thr Leu Lys Leu Ser Lys Met Gln
        275                 280                 285

Arg Ala Gly Phe Leu Tyr Tyr Glu Asp Leu Val Ser Cys Val Ser Lys
        290                 295                 300

Ala Glu Ala Asp Ala Val Ser Leu Ile Val Lys Asn Thr Val Cys Thr
305                 310                 315                 320

Phe Leu Pro Asp Ala Leu Val Thr Ile Thr Gly Gly Phe Arg Arg Gly
```

```
                    325                 330                 335
Lys Lys Ile Gly His Asp Ile Asp Phe Leu Ile Thr Asn Pro Gly Pro
                340                 345                 350

Arg Glu Asp Asp Glu Leu Leu His Lys Gly Leu Leu Leu Tyr Cys Asp
            355                 360                 365

Ile Ile Glu Ser Thr Phe Val Lys Glu Gln Leu Pro Ser Arg Lys Val
        370                 375                 380

Asp Ala Met Asp Asn Phe Gln Lys Cys Phe Ala Ile Leu Lys Leu Tyr
385                 390                 395                 400

Gln Pro Arg Val Asn Ser Ser Tyr Asn Thr Ser Lys Asn Phe Asp Met
                405                 410                 415

Ala Glu Val Lys Asp Trp Lys Ala Ile Arg Val Asp Leu Val Ile Thr
            420                 425                 430

Pro Phe Glu Gln Tyr Ala Tyr Ala Leu Leu Gly Trp Thr Gly Ser Arg
        435                 440                 445

Gln Phe Gly Arg Asp Leu Arg Arg Tyr Ala Thr His Glu Arg Lys Met
    450                 455                 460

Ile Leu Asp Asn His Ala Leu Tyr Asp Arg Arg Lys Arg Ile Phe Leu
465                 470                 475                 480

Lys Ala Arg Ser Glu Glu Ile Phe Ala His Leu Gly Leu Asp Tyr
                485                 490                 495

Val Glu Pro Trp Glu Arg Asn Ala
            500

<210> SEQ ID NO 58
<211> LENGTH: 509
<212> TYPE: PRT
<213> ORGANISM: Heterocephalus glaber

<400> SEQUENCE: 58

Met Asp Pro Leu Gln Thr Ala His Leu Gly Pro Arg Lys Lys Arg Pro
1               5                   10                  15

Arg Gln Thr Gly Thr Leu Met Ala Ser Gly Pro His Asn Ile Arg Phe
                20                  25                  30

Gly Asp Leu Val Leu Phe Ile Leu Glu Lys Lys Met Gly Thr Thr Arg
            35                  40                  45

Arg Ala Phe Leu Met Glu Leu Ala Arg Lys Lys Gly Phe Arg Val Glu
        50                  55                  60

Asn Glu Leu Ser Asp Ser Val Thr His Ile Val Ala Glu Asn Asn Ser
65                  70                  75                  80

Gly Asn Asp Val Leu Glu Trp Leu Gln Val Gln Asn Ile Gln Ala Ser
                85                  90                  95

Ser Gln Leu Glu Leu Leu Asp Val Ser Trp Leu Ile Glu Cys Met Gly
                100                 105                 110

Ala Gly Lys Pro Val Glu Met Thr Gly Arg His Gln Leu Val Val Arg
            115                 120                 125

Asp Ser Pro Ala Ser Pro Asn Pro Gly Pro Gln Lys Thr Pro Ser Leu
        130                 135                 140

Ala Val Gln Lys Ile Pro Glu Tyr Ala Cys Gln Arg Arg Thr Thr Leu
145                 150                 155                 160

Asp Asn Cys Asn Tyr Ile Phe Thr Asn Ala Phe Glu Ile Leu Ala Glu
                165                 170                 175

Asp Cys Glu Phe Arg Glu Asn Glu Gly Phe Tyr Val Thr Tyr Met Arg
                180                 185                 190
```

Ala Ala Ser Val Leu Lys Ser Leu Pro Phe Thr Ile Ile Ser Met Lys
            195                 200                 205

Asp Thr Glu Gly Ile Pro Cys Leu Gly Gly Arg Val Lys Cys Ile Ile
210                 215                 220

Glu Glu Ile Ile Glu Asp Gly Glu Ser Ser Glu Val Lys Ala Val Leu
225                 230                 235                 240

Asn Asn Glu Arg Tyr Lys Ser Phe Lys Leu Phe Thr Ser Val Phe Gly
            245                 250                 255

Val Gly Leu Lys Thr Ser Glu Lys Trp Phe Arg Met Gly Phe Arg Ser
            260                 265                 270

Leu Ser Lys Ile Arg Ser Asp Lys Ser Leu Thr Phe Thr Arg Met Gln
            275                 280                 285

Lys Ala Gly Phe Leu Tyr Tyr Glu Asp Leu Val Ser Cys Val Thr Arg
            290                 295                 300

Ala Glu Ala Glu Ala Val Asn Met Leu Val Lys Glu Ala Val Trp Thr
305                 310                 315                 320

Phe Leu Pro Gly Ala Phe Ile Ser Met Thr Gly Gly Phe Arg Arg Gly
                    325                 330                 335

Lys Glu Ile Gly His Asp Val Asp Phe Leu Ile Thr Ser Pro Glu Val
                340                 345                 350

Thr Glu Asp Glu Glu Gln Gln Leu Leu His Lys Val Ile Asn Leu Trp
            355                 360                 365

Glu Lys Lys Gly Leu Leu Leu Tyr Ser Asp Leu Val Glu Ser Thr Phe
            370                 375                 380

Glu Lys Leu Lys Leu Pro Ser Arg Lys Val Asp Ala Leu Asp His Phe
385                 390                 395                 400

Gln Lys Cys Phe Leu Ile Leu Lys Leu His His Gln Arg Val Asp Asn
                    405                 410                 415

Asp Lys Ser Pro Gln Gln Gly Gly Lys Thr Trp Lys Ala Ile Arg Val
                420                 425                 430

Asp Leu Val Met Cys Pro Tyr Glu Arg Arg Ala Phe Ala Leu Leu Gly
            435                 440                 445

Trp Thr Gly Ser Arg Gln Phe Glu Arg Asp Leu Arg Arg Tyr Ala Thr
450                 455                 460

His Glu Arg Lys Met Ile Leu Asp Asn His Ala Leu Tyr Asp Lys Thr
465                 470                 475                 480

Lys Lys Thr Phe Leu Lys Ala Glu Ser Glu Glu Ile Phe Thr His
                    485                 490                 495

Leu Gly Leu Asp Tyr Ile Glu Pro Trp Glu Arg Asn Ala
            500                 505

<210> SEQ ID NO 59
<211> LENGTH: 500
<212> TYPE: PRT
<213> ORGANISM: Xenopus laevis

<400> SEQUENCE: 59

Ala Leu Val Pro Leu Arg Lys Lys Ala Lys Met Ala Pro Ile Ser Gln
1               5                   10                  15

Ser Phe Cys Gln His Asn Val Lys Phe Lys Glu Ile Val Leu Phe Leu
                20                  25                  30

Leu Glu Arg Lys Met Gly Ser Ser Arg Arg Thr Phe Leu Met Glu Leu
            35                  40                  45

Ala Arg Lys Arg Gly Phe Gln Thr Glu Ile Glu Leu Ser Asp Ser Val
50                  55                  60

```
Thr His Ile Val Ala Glu Asn Asn Ser Gly Ala Glu Val Leu Glu Trp
 65                  70                  75                  80

Leu Gln Ser Lys Lys Leu Gly Phe Thr Val Lys Thr His Ile Leu Asp
             85                  90                  95

Ile Ser Trp Phe Thr Glu Cys Met Glu Ala Gly Arg Pro Val Glu Ile
            100                 105                 110

Gln Asn Arg His Leu Leu Pro Val Gln Gln Asp Cys Ser Ala Asn Phe
            115                 120                 125

Asn Pro Pro Leu Ser Ser Ser Cys Val Gln Val Ser Gln Tyr Ala Cys
        130                 135                 140

Gln Arg Cys Thr Thr Leu Gln Asp Thr Asn Arg Ile Phe Thr Asp Ala
145                 150                 155                 160

Phe Asp Ile Leu Ala Glu His Phe Glu Phe Cys Glu Asn Lys Gly Arg
                165                 170                 175

Thr Val Ala Phe Leu Arg Ala Ser Ser Leu Ile Lys Ser Leu Pro Phe
            180                 185                 190

Pro Ile Thr Ala Met Lys Glu Leu Glu Gly Leu Pro Trp Leu Gly Asp
        195                 200                 205

Gln Met Lys Gly Ile Ile Glu Glu Ile Leu Glu Glu Gly Lys Ser Tyr
    210                 215                 220

Lys Val Leu Glu Val Met Asn Glu Glu Arg Tyr Lys Ser Phe Lys Gln
225                 230                 235                 240

Phe Thr Ser Val Phe Gly Val Gly Leu Lys Thr Ser Asp Lys Trp Phe
                245                 250                 255

Arg Met Gly Phe Arg Thr Leu Glu Glu Ile Lys Asn Glu Lys Glu Leu
            260                 265                 270

Lys Leu Thr Lys Met Gln Lys Cys Gly Leu Leu Tyr Tyr Glu Asp Ile
        275                 280                 285

Thr Ser Tyr Val Ser Arg Ala Glu Ala Glu Thr Thr Glu Gln Leu Ile
    290                 295                 300

Lys Ser Ile Val Trp Lys Phe Val Pro Asp Ala Ile Val Thr Leu Thr
305                 310                 315                 320

Gly Gly Phe Arg Arg Gly Lys Lys Lys Gly His Asp Val Asp Ile Leu
                325                 330                 335

Ile Thr Cys Ala Arg Lys Gly Lys Glu Lys Asn Ile Leu His Asn Thr
            340                 345                 350

Met Ser Val Leu Lys Asn Arg Gly Leu Leu Leu Phe Tyr Asn Ile Ile
        355                 360                 365

Glu Ser Thr Phe Asp Glu Thr Lys Leu Pro Ser Arg His Val Asp Ala
    370                 375                 380

Leu Asp His Phe Gln Lys Cys Phe Thr Ile Leu Lys Leu Pro Lys Arg
385                 390                 395                 400

Gln Met Asp Ile Gly Asn Ile Ile Asp Pro His Glu Cys Glu Arg Lys
                405                 410                 415

Asn Trp Lys Ala Val Arg Leu Asp Leu Val Ile Thr Pro Tyr Glu Gln
            420                 425                 430

Tyr Pro Tyr Ala Leu Leu Gly Trp Thr Gly Ser Arg Gln Phe Glu Arg
        435                 440                 445

Asp Leu Arg Arg Tyr Ala Thr His Glu Lys Arg Met Met Leu Asp Asn
    450                 455                 460

His Gly Leu Tyr Asp Lys Thr Lys Asn Asn Phe Leu Lys Ala Asn Asn
465                 470                 475                 480
```

Glu Glu Asp Ile Phe Lys Gln Leu Gly Leu Asp Tyr Leu Glu Pro Trp
                485                 490                 495

Glu Arg Asn Ala
            500

<210> SEQ ID NO 60
<211> LENGTH: 473
<212> TYPE: PRT
<213> ORGANISM: Poecilia formosa

<400> SEQUENCE: 60

Met Phe His Ala Pro Ala Ala Pro Arg Pro Arg Lys Arg Ser Lys Pro
1               5                   10                  15

Gly Glu Asp Ser Val Ser Arg Arg Glu Glu Ala Thr Phe Gln Asp Val
                20                  25                  30

Arg Ile Phe Leu Val Glu Arg Lys Met Gly Arg Ser Arg Ser Arg Phe
            35                  40                  45

Leu Thr Gln Leu Ala Arg Ser Lys Gly Phe Val Val Glu Asp Ile Leu
        50                  55                  60

Ser Asp Ala Val Thr His Val Val Ser Glu Asp Ser Gln Ser Ser Ser
65                  70                  75                  80

Leu Trp Pro Trp Leu Lys Ser Arg Ser Leu Ser Asp Leu Ser Thr Val
                85                  90                  95

Asn Val Leu Asp Ile Ser Trp Phe Thr Asp Ser Met Lys Glu Gly Arg
            100                 105                 110

Pro Val Pro Val Glu Thr Lys His Leu Ile Gln Asp Ile Leu Pro Glu
        115                 120                 125

Ala Pro Lys Ala Ala Pro Val Asn Lys Val Ser Gln Tyr Ala Cys Gln
    130                 135                 140

Arg Arg Thr Thr Ile Glu Asn Asn Asn Arg Ile Phe Thr Asp Ala Phe
145                 150                 155                 160

Glu Val Leu Ala Glu Asn Tyr Glu Phe Asn Glu Ile Glu Gly Arg Cys
                165                 170                 175

Leu Ala Phe Arg Arg Ala Ala Ser Val Leu Lys Ser Leu Pro Trp Ala
            180                 185                 190

Val Arg Ser Val Gly Ala Thr Gln Asp Leu Pro Cys Leu Gly Glu His
        195                 200                 205

Thr Lys Ala Val Met Lys Glu Ile Leu Gln Tyr Gly Arg Ser Phe Glu
    210                 215                 220

Val Glu Lys Ile Leu Ser Asp Glu Arg Cys Gln Thr Leu Lys Leu Phe
225                 230                 235                 240

Thr Ser Val Phe Gly Val Gly Pro Lys Thr Ala Glu Lys Trp Tyr Arg
                245                 250                 255

Arg Gly Leu Arg Ser Phe Ser Asp Val Leu Ala Gln Pro Asp Ile His
            260                 265                 270

Leu Asn Arg Met Gln Gln Ser Gly Phe Leu His Tyr Gly Asp Ile Ser
        275                 280                 285

Arg Ala Val Ser Lys Ala Glu Ala Arg Ala Val Gly Asn Ile Ile Asp
    290                 295                 300

Glu Ala Val His Val Ile Thr Pro Asn Ala Ile Leu Ala Leu Thr Gly
305                 310                 315                 320

Gly Phe Arg Arg Gly Lys Asp Phe Gly His Asp Val Asp Tyr Val Val
                325                 330                 335

Thr Thr Thr Glu Leu Gly Lys Glu Glu Asn Leu Leu Ile Ser Ile Ile
            340                 345                 350

```
Glu Ser Leu Lys Lys Gln Gly Leu Leu Phe Ser Asp Tyr Gln Ala
            355                 360                 365

Ser Thr Phe Asp Leu Ser Lys Leu Pro Ser His Arg Phe Glu Ala Met
    370                 375                 380

Asp His Phe Ala Lys Cys Phe Leu Ile Leu Arg Leu Glu Gly Ser Arg
385                 390                 395                 400

Val Glu Gly Gly Leu Gln Arg Ala Gln Gly Asp Gly Arg Gly Trp Arg
                405                 410                 415

Ala Val Arg Val Asp Leu Val Ser Pro Pro Ala Asp Arg Phe Ala Phe
                420                 425                 430

Thr Met Leu Gly Trp Thr Gly Ser Arg Met Phe Glu Arg Asp Leu Arg
            435                 440                 445

Arg Phe Ala Arg Leu Glu Arg Gln Met Leu Leu Asp Asn His Ala Leu
    450                 455                 460

Phe Asp Lys Thr Lys Val Leu Phe Ile
465                 470

<210> SEQ ID NO 61
<211> LENGTH: 518
<212> TYPE: PRT
<213> ORGANISM: Monodelphis domestica

<400> SEQUENCE: 61

Met His Arg Ile Arg Thr Ile Asp Ser Asp Phe Gly Lys Lys Arg Gln
1               5                   10                  15

Lys Lys Met Asp Asn His Ile Ser Ser Met Ile Tyr Glu Ile Lys Phe
                20                  25                  30

His Glu Phe Val Leu Phe Ile Leu Glu Lys Lys Met Gly Ala Thr Arg
            35                  40                  45

Arg Thr Phe Leu Thr Asp Leu Ala Arg Lys Lys Gly Phe Arg Val Glu
        50                  55                  60

Asn Glu Leu Ser Asn Ser Val Thr His Ile Val Ala Glu Asn Asn Ser
65                  70                  75                  80

Gly Ser Asp Val Leu Ala Trp Leu Lys Thr His Lys Met Glu Lys Thr
                85                  90                  95

Thr Gln Phe Glu Leu Leu Asp Ile Ser Trp Leu Ile Glu Cys Met Lys
            100                 105                 110

Val Gly Lys Pro Val Asp Thr Lys Gly Lys Tyr Gln Leu Met Glu Ser
        115                 120                 125

Arg Val Asp Ser Ala Asn Pro Asp Pro Thr Ala Gly Thr Leu Asn Ile
130                 135                 140

Leu Pro Pro Thr Thr Lys Thr Ile Ser Gln Tyr Ala Cys Gln Arg Arg
145                 150                 155                 160

Thr Thr Ile Asn Asn His Asn Gln Arg Phe Thr Asp Ala Phe Glu Ile
                165                 170                 175

Leu Ala Lys Asn Tyr Glu Phe Lys Glu Asn Asp Asp Thr Cys Leu Thr
            180                 185                 190

Phe Met Arg Ala Ile Ser Val Leu Lys Cys Leu Pro Phe Glu Val Val
        195                 200                 205

Ser Leu Lys Asp Thr Glu Gly Leu Pro Trp Ile Gly Asp Glu Val Lys
        210                 215                 220

Gly Ile Met Glu Glu Ile Ile Glu Asp Gly Glu Ser Leu Glu Val Gln
225                 230                 235                 240

Ala Val Leu Asn Asp Glu Arg Tyr Gln Ser Phe Lys Leu Phe Thr Ser
```

```
            245                 250                 255
Val Phe Gly Val Gly Leu Lys Thr Ala Asp Lys Trp Tyr Arg Met Gly
            260                 265                 270

Phe Arg Thr Leu Asn Lys Ile Arg Ser Asp Lys Thr Leu Lys Leu Thr
            275                 280                 285

Lys Met Gln Lys Ala Gly Leu Cys Tyr Tyr Glu Asp Leu Ile Asp Cys
        290                 295                 300

Val Ser Lys Ala Glu Ala Asp Ala Val Ser Leu Leu Val Gln Asp Ala
305                 310                 315                 320

Val Trp Thr Phe Leu Pro Asp Ala Leu Val Thr Ile Thr Gly Gly Phe
                325                 330                 335

Arg Arg Gly Lys Glu Phe Gly His Asp Val Asp Phe Leu Ile Thr Ser
                340                 345                 350

Pro Gly Ala Glu Lys Glu Gln Glu Asp Gln Leu Leu Gln Lys Val Thr
            355                 360                 365

Asn Leu Trp Lys Lys Gln Gly Leu Leu Leu Tyr Cys Asp Leu Ile Glu
        370                 375                 380

Ser Thr Phe Glu Asp Leu Lys Leu Pro Ser Arg Lys Ile Asp Ala Leu
385                 390                 395                 400

Asp His Phe Gln Lys Cys Phe Leu Ile Leu Lys Leu Tyr His His Lys
                405                 410                 415

Glu Asp Lys Arg Lys Trp Glu Met Pro Thr Gly Ser Asn Glu Ser Glu
                420                 425                 430

Ala Lys Ser Trp Lys Ala Ile Arg Val Asp Leu Val Val Cys Pro Tyr
            435                 440                 445

Asp Arg Tyr Ala Phe Ala Leu Leu Gly Trp Ser Gly Ser Arg Gln Phe
        450                 455                 460

Glu Arg Asp Leu Arg Arg Tyr Ala Thr His Glu Lys Lys Met Met Leu
465                 470                 475                 480

Asp Asn His Ala Leu Tyr Asp Lys Thr Lys Lys Ile Phe Leu Lys Ala
                485                 490                 495

Lys Ser Glu Glu Glu Ile Phe Ala His Leu Gly Leu Glu Tyr Ile Gln
            500                 505                 510

Pro Ser Glu Arg Asn Ala
            515

<210> SEQ ID NO 62
<211> LENGTH: 531
<212> TYPE: PRT
<213> ORGANISM: Loxodonta africana

<400> SEQUENCE: 62

Met Asp Pro Leu Gln Met Ala His Thr Gly Pro Arg Lys Lys Arg Ala
1               5                   10                  15

Arg Pro Met Gly Ala Ser Met Ala Thr Thr Pro Gln Asp Ile Lys Phe
            20                  25                  30

Gln Asp Leu Val Leu Phe Ile Leu Glu Lys Lys Met Gly Thr Ser Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Ile Lys Ala Ser
                85                  90                  95
```

```
Ser Gln Leu Glu Leu Leu Asp Val Ser Trp Leu Ile Glu Cys Met Gly
                100                 105                 110

Ala Gly Lys Pro Val Glu Met Thr Gly Lys His Gln Leu Val Val Arg
        115                 120                 125

Gly Asp Tyr Ser Ala Ser Ser Asn Pro Ser Pro Gln Lys Thr Pro Pro
    130                 135                 140

Pro Ala Val Lys Lys Ile Ser Gln Tyr Ala Cys Gln Arg Arg Thr Thr
145                 150                 155                 160

Leu Asn Asn His Asn Asn Ile Phe Thr Asp Ala Phe Glu Ile Leu Ala
                165                 170                 175

Glu Asn Cys Glu Phe Arg Glu Asn Glu Gly Ser Tyr Val Val Phe Met
            180                 185                 190

Arg Ala Ala Ser Val Leu Lys Ser Leu Pro Phe Thr Ile Ile Ser Met
        195                 200                 205

Lys Asp Thr Gln Gly Ile Pro Cys Leu Glu Asp Lys Ala Lys Cys Val
210                 215                 220

Ile Glu Asp Ile Ile Glu Asp Gly Glu Ser Ser Glu Val Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Ser Leu Ser Lys Ile Arg Thr Asp Lys Thr Leu Lys Phe Thr Glu Met
        275                 280                 285

Gln Glu Ala Gly Phe Leu Tyr Tyr Glu Asp Leu Val Ser Cys Val Thr
290                 295                 300

Lys Ala Glu Ala Asp Ala Val Ser Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Val Gly His Asp Val Asp Phe Leu Ile Thr Ser Gln Gly
            340                 345                 350

Ser Thr Glu Glu Glu Gln Gln Gln Leu Leu His Lys Val Leu Asn Leu
        355                 360                 365

Trp Lys Lys Glu Gly Leu Leu Leu Tyr Ser Asp Leu Ile Glu Ser Thr
370                 375                 380

Phe Glu Lys Leu Lys Leu Pro Ser Arg Lys Val Asp Ala Leu Asp His
385                 390                 395                 400

Phe Gln Lys Cys Phe Leu Ile Leu Lys Leu His His Gln Arg Ile Asp
                405                 410                 415

Asn Ser Lys Ser Ser Gln Leu Gln Gly Lys Thr Trp Lys Ala Ile Arg
            420                 425                 430

Val Asp Leu Val Met Cys Pro Tyr Glu Cys His Ala Phe Ala Leu Leu
        435                 440                 445

Gly Trp Thr Gly Ser Arg Gln Phe Glu Arg Asp Ile Arg Arg Tyr Ala
450                 455                 460

Ser His Glu Arg Lys Met Ile Leu Asp Asn His Ala Leu Tyr Asp Lys
465                 470                 475                 480

Thr Lys Arg Trp Ala Thr Leu Leu Asn Pro Lys Ala Gly Ser Leu
                485                 490                 495

Ser Thr Leu Gln Glu Phe Ile Arg Ile Phe Leu Lys Ala Gly Ser Glu
            500                 505                 510

Glu Glu Ile Phe Ala His Leu Gly Leu Asp Tyr Ile Glu Pro Trp Glu
```

Arg Asn Ala
    530

<210> SEQ ID NO 63
<211> LENGTH: 505
<212> TYPE: PRT
<213> ORGANISM: Taeniopygia guttata

<400> SEQUENCE: 63

Met Asp Arg Phe Lys Ala Pro Ala Val Ile Ser Gln Arg Lys Arg Gln
1               5                   10                  15

Lys Gly Leu His Ser Pro Lys Leu Ser Cys Ser Tyr Glu Ile Lys Phe
            20                  25                  30

Ser Asn Phe Val Ile Phe Ile Met Gln Arg Lys Met Gly Met Thr Arg
        35                  40                  45

Arg Met Phe Leu Met Glu Leu Gly Arg Arg Lys Gly Phe Arg Ile Glu
    50                  55                  60

Ser Glu Leu Ser Glu Ser Val Thr His Ile Val Ala Glu Asn Asn Ser
65                  70                  75                  80

Tyr Leu Glu Val Leu Asp Trp Leu Lys Gln Gln Ala Val Gly Asp Ser
                85                  90                  95

Ser Arg Phe Glu Leu Leu Asp Ile Ser Trp Phe Thr Ala Cys Met Glu
            100                 105                 110

Ala Gly Arg Pro Val Asp Ser Glu Met Lys Tyr Arg Leu Met Glu Gln
        115                 120                 125

Ser Pro Ser Pro Pro Leu Asn Thr Pro Glu Leu Glu Met Pro Ala Leu
    130                 135                 140

Ile Ala Thr Lys Val Ser Gln Tyr Ser Cys Gln Arg Lys Thr Thr Leu
145                 150                 155                 160

Asn Asn Tyr Asn Lys Lys Phe Thr Asp Ala Phe Glu Val Met Ala Glu
                165                 170                 175

Asn Tyr Glu Phe Lys Glu Asn Glu Ile Phe Ser Leu Glu Phe Leu Arg
            180                 185                 190

Ala Ala Ser Leu Leu Lys Ser Leu Pro Phe Ser Val Thr Ser Met Lys
        195                 200                 205

Asp Ile Gln Gly Leu Pro Cys Val Gly Asp Gln Val Arg Asp Ile Ile
    210                 215                 220

Glu Glu Ile Ile Glu Glu Gly Glu Ser Ser Arg Val Lys Glu Val Leu
225                 230                 235                 240

Asn Asp Glu Arg Tyr Lys Ala Phe Lys Gln Phe Thr Ser Val Phe Gly
                245                 250                 255

Val Gly Val Lys Thr Ser Glu Lys Trp Tyr Arg Met Gly Leu Arg Thr
            260                 265                 270

Val Glu Glu Val Lys Ala Glu Lys Thr Leu Lys Leu Ser Lys Met Gln
        275                 280                 285

Lys Ala Gly Ile Leu Tyr Tyr Glu Asp Leu Val Ser Cys Val Ser Lys
    290                 295                 300

Ala Glu Ala Asp Ala Val Ser Leu Ile Val Lys Asn Thr Val Cys Thr
305                 310                 315                 320

Phe Leu Pro Asp Ala Leu Val Thr Ile Thr Gly Gly Phe Arg Arg Gly
                325                 330                 335

Lys Asn Ile Gly His Asp Ile Asp Phe Leu Ile Thr Asn Pro Gly Pro
            340                 345                 350

```
Arg Glu Asp Asp Glu Leu Leu His Lys Gly Leu Leu Tyr Cys Asp
            355                 360                 365
Ile Ile Glu Ser Thr Phe Val Lys Glu Lys Leu Pro Ser Arg Lys Val
370                 375                 380
Asp Ala Met Asp His Phe Gln Lys Cys Phe Ala Ile Leu Lys Leu Tyr
385                 390                 395                 400
Gln Pro Arg Val Asp Asn Ser Thr Cys Asn Thr Ser Lys Lys Leu Glu
                405                 410                 415
Met Ala Glu Val Lys Asp Trp Lys Ala Ile Arg Val Asp Leu Val Ile
                420                 425                 430
Thr Pro Phe Glu Gln Tyr Ser Tyr Ala Leu Leu Gly Trp Thr Gly Ser
            435                 440                 445
Arg Gln Phe Gly Arg Asp Leu Arg Arg Tyr Ala Ala His Glu Arg Lys
        450                 455                 460
Met Ile Leu Asp Asn His Ala Leu Tyr Asp Arg Arg Lys Arg Ile Phe
465                 470                 475                 480
Leu Lys Ala Gly Ser Glu Glu Ile Phe Ala His Leu Gly Leu Asp
                485                 490                 495
Tyr Val Glu Pro Trp Glu Arg Asn Ala
            500                 505

<210> SEQ ID NO 64
<211> LENGTH: 497
<212> TYPE: PRT
<213> ORGANISM: Xiphophorus maculatus

<400> SEQUENCE: 64

Leu Ile Ser Lys Glu Met Phe His Ala Pro Ala Thr Pro Arg Pro Lys
1               5                   10                  15
Lys Arg Ser Lys Pro Ala Gln Asp Ser Phe Cys Arg Arg Glu Glu Ala
            20                  25                  30
Thr Phe Gln Asp Val Arg Ile Phe Leu Val Glu Arg Lys Met Gly Arg
        35                  40                  45
Ser Arg Arg Ser Phe Leu Thr Gln Leu Ala Arg Ser Lys Gly Phe Val
    50                  55                  60
Val Glu Asp Ile Leu Ser Asp Ala Val Thr His Val Val Ser Glu Asp
65                  70                  75                  80
Ser Gln Ser Ser Ser Leu Trp Ala Trp Leu Lys Gly Arg Ser Leu Ser
                85                  90                  95
Asp Leu Ser Thr Val Asn Val Leu Asp Ile Ser Trp Phe Thr Asp Ser
                100                 105                 110
Met Arg Glu Gly Arg Pro Val Pro Val Glu Thr Lys His Leu Ile Gln
        115                 120                 125
Val Asn Met Asn Glu Lys Met Asn Pro Thr Ala Gly Lys Arg Glu Ala
    130                 135                 140
Pro Lys Ala Ala Pro Val Asn Thr Val Ser Gln Tyr Ala Cys Gln Arg
145                 150                 155                 160
Arg Thr Thr Thr Glu Asn Asn Arg Ile Phe Thr Asp Ala Phe Glu
                165                 170                 175
Val Leu Ala Glu Asn Tyr Glu Phe Asn Asp Ile Glu Gly Arg Cys Leu
                180                 185                 190
Ala Phe Arg Arg Ala Ala Ser Val Leu Lys Ser Leu Pro Trp Ala Val
        195                 200                 205
Arg Cys Val Gly Ala Thr Gln Asp Leu Pro Cys Leu Gly Glu His Thr
    210                 215                 220
```

```
Lys Ala Val Met Lys Glu Ile Leu Gln Tyr Gly Arg Ser Phe Glu Val
225                 230                 235                 240

Glu Lys Ile Leu Ser Asp Glu Arg Cys Gln Thr Leu Lys Leu Phe Thr
            245                 250                 255

Ser Val Phe Gly Val Gly Pro Lys Thr Ala Glu Lys Trp Tyr Arg Arg
        260                 265                 270

Gly Leu Arg Ser Phe Ser Glu Val Leu Ala Gln Pro Gly Ile His Leu
        275                 280                 285

Asn Arg Met Gln Gln Ser Gly Phe Leu His Tyr Gly Asp Ile Ser Arg
        290                 295                 300

Ala Val Ser Lys Ala Glu Ala Arg Ala Val Gly Asn Ile Ile Asp Glu
305                 310                 315                 320

Ala Val His Val Ile Thr Pro Asn Ala Ile Leu Ala Leu Thr Gly Gly
                325                 330                 335

Phe Arg Arg Gly Lys Asp Phe Gly His Asp Val Asp Phe Ile Leu Thr
            340                 345                 350

Thr Thr Glu Leu Gly Lys Glu Glu Asn Leu Leu Ile Ser Ile Ile Glu
        355                 360                 365

Ser Leu Lys Lys Gln Gly Leu Leu Leu Phe Ser Asp Tyr Gln Ala Ser
370                 375                 380

Thr Phe Asp Ile Ser Lys Leu Pro Ser His Arg Phe Glu Ala Met Asp
385                 390                 395                 400

His Phe Ala Lys Cys Phe Leu Ile Leu Arg Leu Glu Gly Ser Leu Val
                405                 410                 415

Glu Gly Gly Leu Gln Arg Ala Gln Gly Asp Gly Arg Glu Trp Arg Ala
            420                 425                 430

Val Arg Val Asp Leu Val Ser Pro Pro Val Asp Arg Tyr Ala Tyr Thr
        435                 440                 445

Met Leu Gly Trp Thr Gly Ser Arg Met Phe Glu Arg Asp Leu Arg Arg
450                 455                 460

Phe Ala Arg Leu Glu Arg Gln Met Leu Leu Asp Asn His Ala Leu Tyr
465                 470                 475                 480

Asp Lys Thr Lys Phe Ser Phe Glu Glu Lys Asn Ala Asp Glu His Ser
            485                 490                 495

Phe

<210> SEQ ID NO 65
<211> LENGTH: 518
<212> TYPE: PRT
<213> ORGANISM: Monodelphis domestica

<400> SEQUENCE: 65

Met His Arg Ile Arg Thr Ile Asp Ser Asp Phe Gly Lys Lys Arg Gln
1               5                   10                  15

Lys Lys Met Asp Asn His Ile Ser Ser Met Ile Tyr Glu Ile Lys Phe
            20                  25                  30

His Glu Phe Val Leu Phe Ile Leu Glu Lys Lys Met Gly Ala Thr Arg
        35                  40                  45

Arg Thr Phe Leu Thr Asp Leu Ala Arg Lys Lys Gly Phe Arg Val Glu
        50                  55                  60

Asn Glu Leu Ser Asn Ser Val Thr His Ile Val Ala Glu Asn Asn Ser
65                  70                  75                  80

Gly Ser Asp Val Leu Ala Trp Leu Lys Thr His Lys Met Glu Lys Thr
            85                  90                  95
```

```
Thr Gln Phe Glu Leu Leu Asp Ile Ser Trp Leu Ile Glu Cys Met Lys
            100                 105                 110

Val Gly Lys Pro Val Asp Thr Lys Gly Lys Tyr Gln Leu Met Glu Ser
            115                 120                 125

Arg Val Asp Ser Ala Asn Pro Asp Pro Thr Ala Gly Thr Leu Asn Ile
            130                 135                 140

Leu Pro Pro Thr Thr Lys Thr Ile Ser Gln Tyr Ala Cys Gln Arg Arg
145                 150                 155                 160

Thr Thr Ile Asn Asn His Asn Gln Arg Phe Thr Asp Ala Phe Glu Ile
                165                 170                 175

Leu Ala Lys Asn Tyr Glu Phe Lys Glu Asn Asp Thr Cys Leu Thr
            180                 185                 190

Phe Met Arg Ala Ile Ser Val Leu Lys Cys Leu Pro Phe Glu Val Val
            195                 200                 205

Ser Leu Lys Asp Thr Glu Gly Leu Pro Trp Ile Gly Asp Glu Val Lys
            210                 215                 220

Gly Ile Met Glu Glu Ile Ile Glu Asp Gly Glu Ser Leu Glu Val Gln
225                 230                 235                 240

Ala Val Leu Asn Asp Glu Arg Tyr Gln Ser Phe Lys Leu Phe Thr Ser
                245                 250                 255

Val Phe Gly Val Gly Leu Lys Thr Ala Asp Lys Trp Tyr Arg Met Gly
            260                 265                 270

Phe Arg Thr Leu Asn Lys Ile Arg Ser Asp Lys Thr Leu Lys Leu Thr
            275                 280                 285

Lys Met Gln Lys Ala Gly Leu Cys Tyr Tyr Glu Asp Leu Ile Asp Cys
290                 295                 300

Val Ser Lys Ala Glu Ala Asp Ala Val Ser Leu Leu Val Gln Asp Ala
305                 310                 315                 320

Val Trp Thr Phe Leu Pro Asp Ala Leu Val Thr Ile Thr Gly Gly Phe
            325                 330                 335

Arg Arg Gly Lys Glu Phe Gly His Asp Val Asp Phe Leu Ile Thr Ser
            340                 345                 350

Pro Gly Ala Glu Lys Glu Gln Glu Asp Gln Leu Leu Gln Lys Val Thr
            355                 360                 365

Asn Leu Trp Lys Lys Gln Gly Leu Leu Leu Tyr Cys Asp Leu Ile Glu
            370                 375                 380

Ser Thr Phe Glu Asp Leu Lys Leu Pro Ser Arg Lys Ile Asp Ala Leu
385                 390                 395                 400

Asp His Phe Gln Lys Cys Phe Leu Ile Leu Lys Leu Tyr His His Lys
                405                 410                 415

Glu Asp Lys Arg Lys Trp Glu Met Pro Thr Gly Ser Asn Glu Ser Glu
            420                 425                 430

Ala Lys Ser Trp Lys Ala Ile Arg Val Asp Leu Val Val Cys Pro Tyr
            435                 440                 445

Asp Arg Tyr Ala Phe Ala Leu Leu Gly Trp Ser Gly Ser Arg Gln Phe
            450                 455                 460

Glu Arg Asp Leu Arg Arg Tyr Ala Ile His Glu Lys Lys Met Met Leu
465                 470                 475                 480

Asp Asn His Ala Leu Tyr Asp Lys Thr Lys Lys Ile Phe Leu Lys Ala
                485                 490                 495

Lys Ser Glu Glu Glu Ile Phe Ala His Leu Gly Leu Tyr Ile Gln
            500                 505                 510
```

```
Pro Ser Glu Arg Asn Ala
        515

<210> SEQ ID NO 66
<211> LENGTH: 505
<212> TYPE: PRT
<213> ORGANISM: Buceros rhinoceros silvestris

<400> SEQUENCE: 66

Met Asp Arg Ile Arg Ala Pro Ala Ile Ser Ser Gln Arg Lys Arg Gln
1               5                   10                  15

Lys Thr Met His Ser Pro Asn Leu Ser Cys Ser Tyr Glu Ile Lys Phe
            20                  25                  30

Ser Lys Phe Val Ile Phe Ile Met Gln Arg Lys Met Gly Met Thr Arg
        35                  40                  45

Arg Thr Phe Leu Met Glu Leu Gly Arg Arg Lys Gly Phe Arg Val Glu
    50                  55                  60

Ser Glu Leu Ser Asp Cys Val Thr His Ile Val Ala Glu Asn Asn Ser
65                  70                  75                  80

Tyr Pro Glu Val Leu Asp Trp Leu Arg Gly Gln Ala Val Gly Asp Ser
                85                  90                  95

Ser Arg Phe Glu Leu Leu Asp Ile Ser Trp Phe Thr Ala Cys Met Glu
            100                 105                 110

Ala Gly Arg Pro Val Asp Ser Glu Thr Lys Tyr Arg Leu Val Glu Gln
        115                 120                 125

Asp Gln Pro Leu Pro Leu Asn Thr Ser Glu Ser Glu Val Pro Ser Phe
    130                 135                 140

Ile Ala Ser Lys Val Ser Gln Tyr Ser Cys Gln Arg Lys Thr Thr Leu
145                 150                 155                 160

Asn Asn Tyr Asn Met Lys Phe Thr Asp Ala Phe Glu Ile Met Ala Glu
                165                 170                 175

Asn Tyr Glu Tyr Lys Glu Ser Glu Ile Leu Cys Leu Glu Phe Leu Arg
            180                 185                 190

Ala Ala Ser Val Leu Lys Phe Leu Pro Phe Pro Val Thr Arg Met Lys
        195                 200                 205

Asp Ile Gln Gly Leu Pro Cys Met Gly Asp Arg Val Arg Asp Val Ile
    210                 215                 220

Glu Glu Ile Val Glu Gly Glu Ser Ser Arg Ala Lys Glu Val Leu
225                 230                 235                 240

Asn Asp Glu Arg Tyr Lys Ser Phe Lys Gln Phe Thr Ser Val Phe Gly
                245                 250                 255

Val Gly Val Lys Thr Ser Glu Lys Trp Tyr Arg Lys Gly Leu Arg Thr
            260                 265                 270

Leu Glu Asp Val Lys Ala Asp Lys Thr Leu Lys Leu Ser Lys Met Gln
    275                 280                 285

Lys Ala Gly Phe Leu Tyr Tyr Glu Asp Leu Val Ser Cys Val Ser Lys
        290                 295                 300

Ala Glu Ala Asp Ala Val Ser Leu Ile Val Lys Asn Thr Val Cys Thr
305                 310                 315                 320

Phe Leu Pro Asp Ala Leu Val Thr Ile Thr Gly Gly Phe Arg Arg Gly
                325                 330                 335

Lys Lys Ile Gly His Asp Ile Asp Phe Leu Ile Thr Asn Pro Gly Pro
            340                 345                 350

Arg Glu Asp Asp Glu Leu Leu His Lys Gly Leu Leu Leu Tyr Cys Asp
        355                 360                 365
```

```
Ile Ile Glu Ser Thr Phe Ala Lys Glu Gln Ile Pro Ser Arg Asn Ile
    370                 375                 380

Asp Ala Met Asp Asn Tyr Gln Lys Cys Phe Ala Ile Leu Lys Leu His
385                 390                 395                 400

Gln Pro Arg Ala Asp Asn Ser Ser Tyr Asn Thr Ser Lys Lys Phe Asp
                405                 410                 415

Thr Ala Glu Val Lys Asp Trp Lys Ala Ile Arg Val Asp Leu Val Ile
                420                 425                 430

Thr Pro Phe Glu Gln Tyr Ala Tyr Ala Leu Leu Gly Trp Thr Gly Ser
            435                 440                 445

Arg Gln Phe Gly Arg Asp Leu Arg Tyr Ala Ser His Glu Arg Lys
    450                 455                 460

Met Met Leu Asp Asn His Gly Leu Tyr Asp Arg Arg Lys Arg Ile Phe
465                 470                 475                 480

Leu Lys Ala Gly Ser Glu Glu Ile Phe Ala His Leu Gly Leu Asp
                485                 490                 495

Tyr Val Glu Pro Trp Glu Arg Asn Ala
                500                 505

<210> SEQ ID NO 67
<211> LENGTH: 496
<212> TYPE: PRT
<213> ORGANISM: Chinchilla lanigera

<400> SEQUENCE: 67

Met Leu Pro Lys Arg Arg Arg Ala Arg Ala Arg Ser Pro Gly Gly Ala
1               5                   10                  15

Ala Ala Ser Ser Ala Leu Ser Ser Val Leu Phe Pro Gly Val Ala Ile
                20                  25                  30

Tyr Leu Ala Glu Pro Arg Met Gly Arg Ser Arg Arg Ala Phe Leu Thr
            35                  40                  45

Arg Leu Ala Leu Ser Lys Gly Phe Arg Val Leu Asp Ala Tyr Ser Ser
    50                  55                  60

Glu Val Thr His Val Val Met Glu Arg Thr Ser Ala Glu Glu Ala Val
65                  70                  75                  80

Cys Trp Gln Glu Gln Lys Ala Ala Pro Pro Gly Arg Pro Arg Pro
                85                  90                  95

Ala Leu Leu Asp Ile Ser Trp Phe Thr Glu Ser Met Ala Ala Gly Gln
            100                 105                 110

Pro Val Pro Val Glu Gly Arg His Arg Leu Glu Val Ala Lys Pro Arg
        115                 120                 125

Lys Gly Pro Pro Asn Pro Ala Ala Ala Ala Met Pro Ala Tyr Ala
    130                 135                 140

Cys Gln Arg Ser Thr Pro Leu Met His His Asn Ser Ser Leu Ser Glu
145                 150                 155                 160

Ala Leu Glu Thr Leu Ala Glu Ala Ala Gly Phe Glu Gly Ser Glu Gly
                165                 170                 175

Arg Leu Leu Ser Phe His Arg Ala Ala Ser Val Leu Lys Ala Leu Pro
            180                 185                 190

Trp Pro Val Thr Ala Leu Ser Gln Leu Gln Gly Leu Pro His Phe Gly
        195                 200                 205

Glu His Ser Ser Val Ile Gln Glu Leu Leu Glu Arg Gly Val Cys
    210                 215                 220

Glu Glu Val Glu Arg Val Arg Cys Ser Glu Arg Tyr Arg Thr Met Lys
```

```
                225                 230                 235                 240
Leu Phe Thr Gln Ile Phe Gly Val Gly Val Lys Thr Ala Asn Gln Trp
                    245                 250                 255

Tyr Gln Glu Gly Leu Arg Thr Leu Asp Glu Leu Arg Glu Gln Pro Gln
                    260                 265                 270

Arg Leu Thr Arg Arg Gln Ala Gly Leu Gln His His Leu Asp Leu
                    275                 280                 285

Cys Thr Pro Val Gly Arg Pro Asp Ala Glu Ala Leu Gln Gln Leu Val
                    290                 295                 300

Glu Ala Thr Val Gly Gln Ala Leu Pro Gly Ala Thr Val Thr Leu Thr
305                 310                 315                 320

Gly Gly Phe Arg Arg Gly Lys Leu Gln Gly His Asp Val Asp Phe Leu
                    325                 330                 335

Ile Thr His Pro Glu Glu Gly Arg Glu Val Gly Leu Leu Pro Ser Val
                    340                 345                 350

Met Ser Gln Leu Gln Ser Gln Gly Leu Val Leu Tyr His Gln His Gln
                    355                 360                 365

Pro Ser His Leu Gly Asp Pro Gly His Leu Ala Arg Gln Ser His Thr
                    370                 375                 380

Met Asp Ala Phe Glu Arg Ser Leu Cys Ile Leu Arg Leu Pro Lys Pro
385                 390                 395                 400

Ser Gly Ala Ala Lys Gly Ala Asp Ser Glu Pro Arg Ser Thr Trp Lys
                    405                 410                 415

Ala Val Arg Val Asp Leu Val Val Ala Pro Trp Ser Gln Phe Pro Phe
                    420                 425                 430

Ala Leu Leu Gly Trp Thr Gly Ser Lys Leu Phe Glu Arg Glu Leu Arg
                    435                 440                 445

Arg Phe Ser Arg Lys Glu Lys Gly Leu Cys Leu Asn Ser His Gly Leu
                    450                 455                 460

Phe Asp Pro Glu Gln Ala Cys Phe Pro Val Ala Ser Glu Glu Asp Ile
465                 470                 475                 480

Phe Arg His Leu Gly Leu Glu Tyr Leu Pro Pro Glu Gln Arg Asn Ala
                    485                 490                 495

<210> SEQ ID NO 68
<211> LENGTH: 510
<212> TYPE: PRT
<213> ORGANISM: Dasypus novemcinctus

<400> SEQUENCE: 68

Met Asp Trp Leu Arg Ile Ala Arg Ser Gly Pro Arg Lys Lys Arg Pro
1               5                   10                  15

Arg Gln Met Asp Ala Ser Ala Val Ser Ser Pro His Asn Ile Lys Phe
                20                  25                  30

Gln Asp Leu Val Leu Phe Ile Leu Glu Lys Lys Met Gly Ser Thr Arg
            35                  40                  45

Arg Thr Phe Leu Thr Glu Leu Ala Arg Arg Lys Gly Phe Arg Val Glu
        50                  55                  60

Asn Glu Leu Ser Glu Ser Val Thr His Ile Val Ala Glu Asn Asn Ser
65              70                  75                  80

Gly Ser Asp Val Leu Glu Trp Leu Gln Leu Gln Lys Ile Glu Ala Ser
                85                  90                  95

Ser Gln Phe Glu Leu Leu Asp Val Ser Trp Leu Ile Glu Cys Met Gly
            100                 105                 110
```

Ala Gly Lys Pro Val Glu Thr Thr Gly Lys His Gln Leu Val Val Lys
            115                 120                 125

Gln Asp Cys Ser Ala Ser Pro Asp Pro Gly His Gln Lys Thr Leu Pro
130                 135                 140

Leu Ala Ile Lys Lys Ile Ser Pro Tyr Ala Cys Gln Arg Arg Thr Thr
145                 150                 155                 160

Leu Asn Gln Asn Gln Ile Phe Thr Asp Ala Phe Asp Ile Leu Ala
                165                 170                 175

Glu Asn Cys Glu Leu Arg Glu Asn Glu Ser Tyr Leu Val Phe Ala
            180                 185                 190

Arg Ala Ala Ser Val Leu Lys Ser Leu Pro Phe Thr Ile Ile Ser Met
            195                 200                 205

Lys Asp Thr Glu Gly Ile Pro Cys Leu Gly Asp Lys Ala Lys Cys Val
210                 215                 220

Ile Glu Glu Ile Ile Glu Asp Gly Glu Ser Ser Glu Val Lys Ala Val
225                 230                 235                 240

Leu Asn Asp Glu Arg Tyr Ser Ser Phe Lys Leu Phe Thr Ser Val Phe
            245                 250                 255

Gly Val Gly Leu Lys Thr Ser Glu Lys Trp Phe Arg Met Gly Phe Arg
            260                 265                 270

Thr Leu Ser Gln Ile Arg Ser Asn Glu Ser Leu Lys Leu Thr Arg Met
            275                 280                 285

Gln Lys Ala Gly Phe Leu Tyr Tyr Glu Asp Leu Val Ser Cys Val Ser
            290                 295                 300

Arg Ala Glu Ala Glu Ala Val Ser Val Leu Val Gln Glu Ala Val Trp
305                 310                 315                 320

Ala Phe Leu Pro Asp Ala Phe Val Thr Met Thr Gly Gly Phe Arg Arg
            325                 330                 335

Gly Lys Lys Ser Gly His Asp Val Asp Phe Leu Ile Thr Ser Pro Gly
            340                 345                 350

Ala Thr Glu Glu Glu Glu Glu Leu Leu Gln Lys Val Ile Asn Leu
            355                 360                 365

Trp Gly Lys Glu Gly Leu Leu Leu Tyr Tyr Asp Leu Val Glu Ser Thr
370                 375                 380

Phe Glu Lys Leu Lys Leu Pro Ser Arg Lys Val Asp Ala Leu Asp His
385                 390                 395                 400

Phe Gln Lys Cys Phe Leu Ile Leu Lys Leu Pro Tyr Gln Arg Val Asp
            405                 410                 415

Ser Gly Lys Ser Ser Trp Gln Glu Gly Lys Ala Trp Lys Ala Ile Arg
            420                 425                 430

Val Asp Leu Val Met Cys Pro Tyr Glu Arg Arg Ala Phe Ala Leu Leu
            435                 440                 445

Gly Trp Thr Gly Ser Arg Gln Phe Glu Arg Asp Leu Arg Arg Tyr Ala
            450                 455                 460

Thr His Glu Gln Lys Met Ile Leu Asp Asn His Ala Leu Tyr Asp Lys
465                 470                 475                 480

Thr Lys Arg Ile Phe Leu Pro Ala Glu Ser Glu Glu Ile Phe Ala
            485                 490                 495

His Leu Gly Leu Asp Tyr Ile Glu Pro Cys Glu Arg Asn Ala
            500                 505                 510

<210> SEQ ID NO 69
<211> LENGTH: 478
<212> TYPE: PRT

<213> ORGANISM: Pundamilia nyererei

<400> SEQUENCE: 69

```
Met Phe His Thr Pro Ile Val Pro Arg Ala Arg Lys Arg Ser Arg Pro
1               5                   10                  15

Ala Glu Ala Ser Ala Pro Arg Arg Glu Arg Val Lys Phe Glu Asp Val
            20                  25                  30

Arg Leu Tyr Leu Val Glu Arg Lys Met Gly Arg Ser Arg Arg Ser Phe
        35                  40                  45

Leu Thr Glu Leu Ala Arg Ser Lys Gly Phe Ile Val Glu Asp Val Leu
    50                  55                  60

Ser Asp Val Val Thr His Val Val Ser Glu Asp Ser Gln Ala Ser Ser
65                  70                  75                  80

Leu Trp Ala Trp Leu Lys Gly Gly Pro Val Lys Asn Leu Pro Val Met
                85                  90                  95

His Val Leu Asp Ile Asp Thr Leu Ala Ala Ser Pro Glu Ala Thr Thr
            100                 105                 110

Pro Thr Pro Met Ser Thr Val Ser Gln Tyr Ala Cys Gln Arg Arg Thr
        115                 120                 125

Thr Thr Lys Asn Asn Asn Lys Ile Phe Thr Asp Ala Phe Glu Val Leu
130                 135                 140

Ala Glu Ser His Glu Phe Asn Asp Met Glu Gly Pro Cys Leu Ala Phe
145                 150                 155                 160

Arg Arg Ala Ala Ser Val Leu Lys Ser Leu Pro Trp Thr Val Gln Asn
                165                 170                 175

Leu Arg Val Thr Glu Asp Leu Pro Cys Leu Gly Glu His Ser Met Cys
            180                 185                 190

Val Ile Glu Glu Ile Leu Gln His Gly His Ser Phe Glu Val Glu Lys
        195                 200                 205

Ile Leu Ser Asp Glu Arg Tyr Gln Ile Leu Lys Leu Phe Thr Ser Val
    210                 215                 220

Phe Gly Val Gly Pro Lys Thr Ala Glu Lys Trp Tyr Arg Arg Gly Leu
225                 230                 235                 240

Arg Ser Phe Ser Asp Val Leu Ala Glu Pro Asp Ile His Leu Asn Arg
                245                 250                 255

Met Gln Gln Ser Gly Phe Leu His Tyr Gly Asp Ile Ser Arg Ala Val
            260                 265                 270

Ser Lys Ala Glu Ala Gln Ala Leu Gly Asn Ile Ile Asp Glu Ala Val
        275                 280                 285

Arg Ala Ile Thr Pro Asp Ala Ile Leu Thr Leu Thr Gly Gly Phe Arg
    290                 295                 300

Arg Gly Lys Asp Phe Gly His Asp Val Asp Phe Ile Val Thr Thr Pro
305                 310                 315                 320

Gln Leu Gly Lys Glu Glu Arg Leu Leu Thr Ser Val Ile Asp Arg Leu
                325                 330                 335

Lys Gln Gln Gly Ile Leu Leu Tyr Cys Glu Tyr Gln Ala Ser Thr Phe
            340                 345                 350

Asp Glu Ser Lys Leu Pro Ser His Arg Phe Glu Ala Met Asp His Phe
        355                 360                 365

Ala Lys Cys Phe Leu Ile Leu Arg Leu Glu Asp Ser Gln Val Glu Gly
    370                 375                 380

Gly Leu Gln Thr Ala Glu Glu Asp Arg Arg Gly Trp Arg Ala Val Arg
385                 390                 395                 400
```

Val Asp Leu Val Ser Pro Val Asp Arg Tyr Ala Phe Thr Leu Leu
                405                 410                 415

Gly Trp Ser Gly Ser Arg Gln Phe Glu Arg Asp Leu Arg Arg Phe Ala
        420                 425                 430

Arg Met Glu Arg Arg Met Leu Leu Asp Asn His Ala Leu Tyr Asp Lys
    435                 440                 445

Thr Lys Lys Glu Phe Leu Ala Ala Thr Thr Glu Lys Asp Ile Phe Ala
450                 455                 460

His Leu Gly Leu Glu Tyr Ile Glu Pro Trp Gln Arg Asn Ala
465                 470                 475

<210> SEQ ID NO 70
<211> LENGTH: 573
<212> TYPE: PRT
<213> ORGANISM: Myotis brandtii

<400> SEQUENCE: 70

Met Asp Pro Arg Gly Ile Leu Lys Ala Phe Pro Lys Arg Lys Lys Ile
1               5                   10                  15

Leu Ala Asn Pro Ser Ser Lys Val Leu Ala Lys Ile Pro Lys Arg Glu
            20                  25                  30

Asp Glu Glu Ala Arg Glu Trp Leu Ser Ser Leu Arg Ala His Val
        35                  40                  45

Val Pro Ala Gly Ile Gly Arg Ala Arg Ala Glu Leu Phe Glu Lys Gln
    50                  55                  60

Ile Val Gln His Gly Gly Gln Ile Tyr Ser Ala Gln Ala Pro Gly Val
65                  70                  75                  80

Thr His Ile Val Val Asp Gly Met Asp Cys Glu Arg Ala Leu Arg
                85                  90                  95

Leu Leu Arg Leu Pro Arg Leu Pro Pro Gly Ala Gln Leu Val Lys Ser
            100                 105                 110

Ala Trp Leu Ser Leu Cys Leu Gln Glu Arg Arg Leu Val Asp Thr Ala
        115                 120                 125

Gly Phe Ser Ile Phe Ile Pro Asn Arg Tyr Leu Asp Gln Pro Gln Leu
    130                 135                 140

Ser Lys Ala Asp Gln Asp Ser Ser Pro Gly Ala Cys Glu Ala Leu Leu
145                 150                 155                 160

Arg Thr Val Pro Ser Ser Pro Pro Thr Pro Pro Arg Pro Val Ser Pro
                165                 170                 175

Pro Gln Arg Ile Glu Glu Ala Pro Asn Thr Gln Ala Gln Pro Val Ser
            180                 185                 190

Asp Asp Asp Thr Ser Asp Gly Glu Glu Thr Pro Val Ser Ala Ala Asp
        195                 200                 205

Leu Glu Ala Leu Ile Ser Gly Arg Tyr Pro Ile Pro Pro Glu Gly Asp
    210                 215                 220

Gly Glu Pro Ser Pro Ala Pro Glu Gly Leu Asn Lys Trp Val Cys Ala
225                 230                 235                 240

Gln Pro Ser Ser Gln Lys Ala Thr Asn His Asn Thr His Ile Thr Glu
                245                 250                 255

Lys Leu Glu Val Leu Ala Lys Ala Tyr Ser Val Gln Gly Asp Lys Trp
            260                 265                 270

Arg Ala Leu Gly Tyr Asp Lys Ala Ile Asn Ala Leu Lys Ser Phe His
        275                 280                 285

Lys Pro Val Thr Ser Tyr Gln Glu Ala Cys Ser Ile Pro Gly Ile Gly
    290                 295                 300

Lys Arg Met Ala Glu Lys Ile Val Glu Ile Leu Ser Gly His Leu
305                 310                 315                 320

Arg Lys Leu Asp His Ile Ser Asp Ser Val Pro Val Leu Glu Leu Phe
                325                 330                 335

Ser Asn Ile Trp Gly Ala Gly Thr Lys Thr Ala Gln Met Trp Tyr Gln
            340                 345                 350

Gln Gly Phe Arg Ser Leu Glu Asp Ile Arg Asn Gln Ala Ser Leu Thr
        355                 360                 365

Thr Gln Gln Ala Ile Gly Leu Lys His Tyr Asp Asp Phe Leu Glu Arg
370                 375                 380

Met Pro Arg Glu Glu Ala Ala Glu Ile Glu Gln Thr Val Arg Glu Ser
385                 390                 395                 400

Ala Gln Ala Phe Asn Pro Gly Leu Leu Cys Val Ala Cys Gly Ser Tyr
                405                 410                 415

Arg Arg Gly Lys Ala Thr Cys Gly Asp Val Asp Val Leu Leu Thr His
            420                 425                 430

Pro Asp Gly Arg Ser His Gln Gly Ile Phe Ser Arg Leu Leu Asp Ser
        435                 440                 445

Leu Arg Gln Arg Gly Phe Leu Thr Asp Asp Leu Val Ser Gln Glu Glu
    450                 455                 460

Asn Gly Gln Gln Gln Lys Tyr Leu Gly Val Cys Gln Leu Pro Gly Pro
465                 470                 475                 480

Gly Arg Arg His Arg Arg Leu Asp Ile Ile Val Pro Tyr Ser Glu
                485                 490                 495

Phe Ala Cys Ala Leu Leu Tyr Phe Thr Gly Ser Ala His Phe Asn Arg
                500                 505                 510

Ser Met Arg Ala Leu Ala Lys Thr Lys Gly Met Ser Leu Ser Glu His
            515                 520                 525

Ala Leu Ser Ala Ala Val Val Arg Asp Thr Arg Gly Leu Lys Val Gly
        530                 535                 540

Ser Gly Arg Val Leu Pro Thr Pro Thr Glu Lys Asp Val Phe Arg Leu
545                 550                 555                 560

Leu Gly Leu Pro Tyr Arg Glu Pro Ala Glu Arg Asp Trp
                565                 570

<210> SEQ ID NO 71
<211> LENGTH: 314
<212> TYPE: PRT
<213> ORGANISM: Myotis brandtii

<400> SEQUENCE: 71

Leu Ala Asn Phe Glu Lys Asn Val Asn Gln Ala Ile His Lys Tyr Asn
1               5                   10                  15

Ala Tyr Arg Lys Ala Ala Ser Val Ile Ala Lys Tyr Pro His Lys Ile
            20                  25                  30

Lys Ser Gly Ala Glu Ala Lys Lys Leu Pro Gly Val Gly Thr Lys Ile
        35                  40                  45

Ala Glu Lys Ile Asp Glu Phe Leu Ala Thr Gly Lys Leu Arg Lys Leu
    50                  55                  60

Glu Lys Ile Arg Gln Asp Asp Thr Ser Ser Ser Ile Asn Phe Leu Thr
65                  70                  75                  80

Arg Val Thr Gly Ile Gly Pro Ser Ala Ala Arg Lys Phe Val Asp Glu
                85                  90                  95

Gly Ile Lys Thr Leu Glu Asp Leu Arg Lys Asn Glu Asp Lys Leu Asn

```
                100             105             110
His His Gln Arg Ile Gly Leu Lys Tyr Phe Glu Asp Phe Glu Lys Arg
            115                 120                 125

Ile Pro Arg Glu Glu Met Leu Gln Met Gln Asp Ile Val Leu Asn Glu
130                 135                 140

Val Lys Lys Val Asp Ser Glu Tyr Ile Ala Thr Val Cys Gly Ser Phe
145                 150                 155                 160

Arg Arg Gly Ala Glu Ser Ser Gly Asp Met Asp Val Leu Leu Thr His
                165                 170                 175

Pro Ser Phe Thr Ser Glu Ser Asn Lys Gln Pro Lys Leu Leu His Arg
            180                 185                 190

Val Val Glu Gln Leu Gln Lys Val Cys Phe Ile Thr Asp Thr Leu Ser
            195                 200                 205

Lys Gly Glu Thr Lys Phe Met Gly Val Cys Gln Leu Pro Ser Lys Asn
210                 215                 220

Asp Gly Lys Glu Tyr Pro His Arg Arg Ile Asp Ile Arg Leu Ile Pro
225                 230                 235                 240

Lys Asp Gln Tyr Tyr Cys Gly Val Leu Tyr Phe Thr Gly Ser Asp Ile
                245                 250                 255

Phe Asn Lys Asn Met Arg Thr His Ala Leu Glu Lys Gly Phe Thr Ile
            260                 265                 270

Asn Glu Tyr Thr Ile Arg Pro Leu Gly Val Thr Gly Val Ala Gly Glu
            275                 280                 285

Pro Leu Pro Val Asp Ser Glu Lys Asp Ile Phe Asp Tyr Ile Gln Trp
290                 295                 300

Lys Tyr Arg Glu Pro Lys Asp Arg Ser Glu
305                 310

<210> SEQ ID NO 72
<211> LENGTH: 764
<212> TYPE: PRT
<213> ORGANISM: Lepisosteus oculatus

<400> SEQUENCE: 72

Met Val Pro Leu Lys Arg Arg Lys Thr Val Arg Asn Asp Val Asn Cys
1               5                   10                  15

Glu Arg Asn Glu Val Ile Lys Phe Pro Asp Val Val Ile Phe Leu Leu
            20                  25                  30

Glu Arg Arg Met Gly Ala Ser Arg Arg Ala Phe Leu Thr Arg Leu Gly
        35                  40                  45

Arg Asn Lys Gly Phe Arg Val Glu Asp Cys Tyr Ser Asp Ala Val Thr
50                  55                  60

His Val Val Ser Glu Asn Asn Thr Gly Glu Glu Val Val Asp Trp Leu
65                  70                  75                  80

Asp Arg Gln Ile Pro Gly Gly Trp Thr Pro Arg Pro Val His Leu Leu
                85                  90                  95

Asp Ile Ser Trp Phe Thr Glu Ser Met Gly Ala Ala Arg Pro Leu Asp
            100                 105                 110

Val Gln Asp Ala His Arg Leu Lys Val Lys Ala Val Ser Gln Ala Gly
            115                 120                 125

Gly Gly Thr Arg Thr Val Ser Pro Tyr Ala Cys Gly Arg Arg Thr Pro
        130                 135                 140

Leu Gln His His Asn Arg Ala Leu Thr Asp Ala Leu Glu Val Leu Ala
145                 150                 155                 160
```

-continued

```
Glu Asn Glu Arg Phe Arg Lys Pro Pro Gly Ser Ser Val Ala Thr Gly
            165                 170                 175

Arg Pro Asp Val Leu Tyr Arg Pro Leu Gly Phe Lys Leu Gly Cys Thr
        180                 185                 190

Pro Pro Pro Arg Cys Gly Lys His Ser Gln Gln Asn Arg Val Leu Trp
            195                 200                 205

Ile Ala Leu Gln Ser Ser Gln Arg Arg Leu Ser Leu Tyr Thr Asp Tyr
    210                 215                 220

Thr Glu Ala Phe Gln Leu Leu Arg Leu Pro Phe His Phe Ser Leu
225                 230                 235                 240

Ile Lys Cys Thr Thr Asp Asn Leu Thr Gln Arg Gly Leu Gln Val Leu
                245                 250                 255

Ala Leu Arg Thr Arg Ser Gln Arg Glu Phe Ser Ser Gly Gln Gly Thr
            260                 265                 270

Gly Val Arg His Tyr Glu Asp Leu Ser Thr Pro Ile Thr Lys Glu Glu
            275                 280                 285

Ala His Ala Ile Gly Gln Ile Val Glu Glu Ala Val His Thr Val Leu
    290                 295                 300

Pro Gly Ala Glu Leu Thr Ile Thr Gly Gly Phe Arg Arg Gly Lys Lys
305                 310                 315                 320

Thr Gly His Asp Val Asp Phe Leu Ile Thr His Pro Glu Glu Gly Lys
                325                 330                 335

Glu Val Gly Leu Leu Pro Lys Val Ile Ser Trp Leu Asp Ser Gln Asp
            340                 345                 350

Leu Leu Leu Tyr His Arg Val Lys Asp Asn Thr Tyr Ser Glu Ser Lys
            355                 360                 365

Val Gln Leu Ala Arg Ser Gln Ser Ser Met Asp His Phe Glu Arg Cys
    370                 375                 380

Phe Ser Ile Phe Arg Leu Asn Arg Pro Leu Ala Arg Pro Glu Pro
385                 390                 395                 400

Gly Ala Ser Ser Gly Thr Ala Gln Glu Ser Ala Ala Ser Gly Gly
                405                 410                 415

His Cys Ser Gly Glu Pro Arg Ser Trp Lys Ala Val Arg Val Asp Leu
            420                 425                 430

Val Val Thr Pro Val Ser Gln Phe Ala Phe Gly Leu Leu Gly Trp Thr
    435                 440                 445

Gly Ser Gln His Phe Glu Arg Glu Leu Arg Arg Trp Ala Gly Gln Glu
    450                 455                 460

Lys His Met Thr Leu Asn Ser His Ala Leu Tyr Asp Arg Thr Gln Gly
465                 470                 475                 480

Ser His Arg Ala Lys Asp His His Gln Thr Ile Ala Thr Ser Met Ala
                485                 490                 495

Ser Ser Pro Pro Leu Ser Leu Ser Arg Trp Leu Ser Pro Leu His His
            500                 505                 510

Arg Ala His Thr Arg Glu Arg Tyr Cys Glu Pro Ser Ala Pro Pro Thr
        515                 520                 525

Glu Ser Met Ala Ile Ala Ser His Glu Lys Gly Glu Ile Gln Ala His
    530                 535                 540

Met Pro Val Glu Tyr Ser Arg Gly Gly Lys Arg Ile Ser Leu His Thr
545                 550                 555                 560

Leu Glu Pro Glu Ile Ala Ser Gly Thr Glu Glu Glu Thr Ser Gly
                565                 570                 575

Tyr Glu Ser Glu Gly Gly Gln Ser Ala Ser Pro Ala Asp Pro Pro Gly
```

```
                580             585             590
Gly Ser Ser Ser Pro Pro Thr Pro Pro Gly Arg Arg Pro Arg Thr
            595             600             605
Ala Phe Thr Ser Glu Gln Ile Ser Arg Leu Glu Arg Thr Phe Lys Lys
            610             615             620
His Ala Tyr Leu Gly Thr Arg Glu Lys Glu Leu Cys Arg Lys Leu
625             630             635             640
Asn Leu Ser Glu Lys Gln Ile Lys Asn Trp Phe Gln Asn Arg Arg Met
                645             650             655
Lys Leu Lys Arg Thr Leu Gln Asp Ala Leu Ala Gln Ala Cys His Val
            660             665             670
Lys Val Ala Ser Gln Leu Leu His Tyr Pro Glu Leu Gln Ala Phe Gly
            675             680             685
Pro Ser Ala Tyr Ser Gly Tyr Tyr Pro Asn Gln Asp Ser Thr Ala Ala
            690             695             700
Tyr Leu Pro Leu Pro Gly Leu Pro Tyr Ala Pro Ser Gln Ala Leu Gly
705             710             715             720
His Leu Ser Ala Leu Pro Leu Glu Ala Gln Val His Pro Tyr Ser Val
                725             730             735
Pro Pro Phe Val Met Pro Pro His Ser Ala Gly Thr Gly Ser Pro Pro
            740             745             750
Val Met Ala Arg Tyr His Pro Tyr Ala Pro Arg Tyr
            755             760

<210> SEQ ID NO 73
<211> LENGTH: 560
<212> TYPE: PRT
<213> ORGANISM: Lepisosteus oculatus

<400> SEQUENCE: 73

Met Glu Ala Arg Gly Ile Val Lys Ala Phe Arg Lys Val Lys Arg Ile
1               5                   10                  15
Gly His Gln Leu Glu Lys Glu Glu Pro Gln Asn Lys Lys Gln Gln
            20                  25                  30
Lys Glu Leu Val Thr Gly Thr Trp Leu Asn Gly Ile Cys Ala Tyr Ile
            35                  40                  45
Ile Gln Thr Gly Ile Gly Asn Ala Arg Ala Thr Ile Phe Gln Thr Gln
        50                  55                  60
Ile Val Gln Asn Gly Gly Gln Val Val Asp Thr Phe Ser Pro Cys Val
65                  70                  75                  80
Thr His Val Ile Val Asp Asp Ser Met Asn Tyr Asp Arg Ala Leu Arg
                85                  90                  95
Leu Leu Lys Val Asp Lys Leu Pro Pro Ala Val Gln Leu Val Lys Cys
            100                 105                 110
Ser Trp Leu Ser Leu Cys Ile Thr Glu Lys Lys Leu Leu Asn Thr Ala
            115                 120                 125
Gly Tyr Ser Val Phe Ile Pro Asp Arg Asn Leu Asp Ser Asn His Glu
        130                 135                 140
Gln Thr Asn Asn Lys Gln Lys Thr Glu Lys Glu Ala Thr Val Ser Lys
145                 150                 155                 160
Thr Val Gln Ile Glu Glu Ser Ala Ser Leu Asn Thr Ile Ile Ser Ser
                165                 170                 175
His Arg Ala Gln Thr Ser Asp Asp Asp Gly Ser Asp Thr Glu Glu Ala
            180                 185                 190
```

```
Gly Val Ser Gln Lys Asp Leu Glu Ala Leu Leu Thr Gly Cys Tyr Pro
            195                 200                 205

Thr Thr Glu Glu Pro Ser Pro Ala Gln Pro Asp Pro Val Thr Gly Lys
        210                 215                 220

Trp Val Cys Ala Gln Ser Ser Lys Ala Lys Asn Asp Asn His Asn Gln
225                 230                 235                 240

His Ile Thr Asp Lys Leu Glu Val Leu Ala Lys Ala Tyr Thr His Gln
                245                 250                 255

Gly Asp Lys Trp Arg Ala Leu Gly Tyr Ser Lys Ala Ile Asn Ala Leu
            260                 265                 270

Lys Ser Tyr His Lys Pro Val Ser Ser Tyr Glu Glu Ala Cys Lys Ile
        275                 280                 285

Arg Gly Ile Gly Lys Arg Met Ala Glu Lys Ile Lys Glu Ile Leu Glu
290                 295                 300

Ser Gly Asn Leu Arg Lys Leu Asp His Ile Gly Glu Ser Val Pro Val
305                 310                 315                 320

Leu Glu Leu Phe Thr Asn Ile Trp Gly Val Gly Ser Lys Thr Ala Gln
                325                 330                 335

Met Trp Tyr Gln Gln Gly Phe Arg Thr Leu Glu Asp Ile Arg Thr Lys
            340                 345                 350

Ala Thr Leu Thr Ser Gln Gln Val Ile Gly Leu Lys His Tyr Asp Asp
        355                 360                 365

Phe Leu Asp Arg Met Pro Arg Glu Glu Ala Ala Glu Ile Glu Lys Thr
370                 375                 380

Val Lys Glu Ala Ala Leu Ser Leu Asn Pro Gly Leu Leu Ala Val Ala
385                 390                 395                 400

Cys Gly Ser Tyr Arg Arg Gly Lys Pro Thr Cys Gly Asp Val Asp Ile
                405                 410                 415

Leu Ile Thr His Pro Asp Gly Lys Ser His Lys Gly Ile Phe Ser Lys
            420                 425                 430

Ile Leu His Ile Leu His Gln Ser Gly Phe Leu Thr Asp Asp Leu Val
        435                 440                 445

Ser His Glu Glu Asn Gly Glu Gln Lys Lys Tyr Leu Gly Val Cys Arg
450                 455                 460

Leu Pro Gly Pro Glu Ser Cys His Arg Arg Leu Asp Ile Ile Val Val
465                 470                 475                 480

Pro Tyr Ser Glu Phe Ala Cys Ala Ile Leu Tyr Phe Thr Gly Ser Ala
                485                 490                 495

His Phe Asn Arg Ser Met Arg Ala Leu Ala Lys Thr Lys Asn Met Ser
            500                 505                 510

Leu Ser Glu His Ser Leu Asn Lys Asp Val Leu Arg Gln Gly Ser Leu
        515                 520                 525

Lys Val Ser Thr Gly Ala Pro Leu Pro Thr Pro Thr Glu Lys Asp Val
530                 535                 540

Phe Arg His Leu Gly Leu Pro Tyr Arg Glu Pro Gln Asp Arg Asp Trp
545                 550                 555                 560

<210> SEQ ID NO 74
<211> LENGTH: 579
<212> TYPE: PRT
<213> ORGANISM: Lepisosteus oculatus

<400> SEQUENCE: 74

Met Glu Ala Arg Gly Ile Val Lys Ala Phe Arg Lys Val Lys Arg Ile
1               5                   10                  15
```

```
Gly His Gln Leu Glu Lys Glu Glu Pro Gln Asn Lys Gln Gln
             20                  25                  30

Lys Glu Leu Val Thr Gly Thr Trp Leu Asn Gly Ile Cys Ala Tyr Ile
             35                  40                  45

Ile Gln Thr Gly Ile Gly Asn Ala Arg Ala Thr Ile Phe Gln Thr Gln
 50                  55                  60

Ile Val Gln Asn Gly Gly Gln Val Val Asp Thr Phe Ser Pro Cys Val
 65                  70                  75                  80

Thr His Val Ile Val Asp Asp Ser Met Asn Tyr Asp Arg Ala Leu Arg
                 85                  90                  95

Leu Leu Lys Val Asp Lys Leu Pro Pro Ala Val Gln Leu Val Lys Cys
                100                 105                 110

Ser Trp Leu Ser Leu Cys Ile Thr Glu Lys Lys Leu Leu Asn Thr Ala
             115                 120                 125

Gly Tyr Ser Val Phe Ile Pro Asp Arg Asn Leu Asp Ser Asn His Glu
             130                 135                 140

Gln Val Lys Val Asn Ser Leu Asn Gly Asn Gly Ser Ala Leu Gly Ile
145                 150                 155                 160

His Val Gln Gln Thr Asn Asn Lys Gln Lys Thr Glu Lys Glu Ala Thr
                165                 170                 175

Val Ser Lys Thr Val Gln Ile Glu Glu Ser Ala Ser Leu Asn Thr Ile
             180                 185                 190

Ile Ser Ser His Arg Ala Gln Thr Ser Asp Asp Gly Ser Asp Thr
             195                 200                 205

Glu Glu Ala Gly Val Ser Gln Lys Asp Leu Glu Leu Leu Thr Gly
             210                 215                 220

Cys Tyr Pro Thr Thr Glu Glu Pro Ser Pro Ala Gln Pro Asp Pro Val
225                 230                 235                 240

Thr Gly Lys Trp Val Cys Ala Gln Ser Ser Lys Ala Lys Asn Asp Asn
                245                 250                 255

His Asn Gln His Ile Thr Asp Lys Leu Glu Val Leu Ala Lys Ala Tyr
             260                 265                 270

Thr His Gln Gly Asp Lys Trp Arg Ala Leu Gly Tyr Ser Lys Ala Ile
             275                 280                 285

Asn Ala Leu Lys Ser Tyr His Lys Pro Val Ser Ser Tyr Glu Glu Ala
290                 295                 300

Cys Lys Ile Arg Gly Ile Gly Lys Arg Met Ala Glu Lys Ile Lys Glu
305                 310                 315                 320

Ile Leu Glu Ser Gly Asn Leu Arg Lys Leu Asp His Ile Gly Glu Ser
                325                 330                 335

Val Pro Val Leu Glu Leu Phe Thr Asn Ile Trp Gly Val Gly Ser Lys
             340                 345                 350

Thr Ala Gln Met Trp Tyr Gln Gln Gly Phe Arg Thr Leu Glu Asp Ile
             355                 360                 365

Arg Thr Lys Ala Thr Leu Thr Ser Gln Gln Val Ile Gly Leu Lys His
             370                 375                 380

Tyr Asp Asp Phe Leu Asp Arg Met Pro Arg Glu Glu Ala Ala Glu Ile
385                 390                 395                 400

Glu Lys Thr Val Lys Glu Ala Ala Leu Ser Leu Asn Pro Gly Leu Leu
                405                 410                 415

Ala Val Ala Cys Gly Ser Tyr Arg Arg Gly Lys Pro Thr Cys Gly Asp
             420                 425                 430
```

-continued

Val Asp Ile Leu Ile Thr His Pro Asp Gly Lys Ser His Lys Gly Ile
          435                 440                 445

Phe Ser Lys Ile Leu His Ile Leu His Gln Ser Gly Phe Leu Thr Asp
      450                 455                 460

Asp Leu Val Ser His Glu Glu Asn Gly Glu Gln Lys Lys Tyr Leu Gly
465                 470                 475                 480

Val Cys Arg Leu Pro Gly Pro Glu Ser Cys His Arg Arg Leu Asp Ile
              485                 490                 495

Ile Val Val Pro Tyr Ser Glu Phe Ala Cys Ala Ile Leu Tyr Phe Thr
                  500                 505                 510

Gly Ser Ala His Phe Asn Arg Ser Met Arg Ala Leu Ala Lys Thr Lys
              515                 520                 525

Asn Met Ser Leu Ser Glu His Ser Leu Asn Lys Asp Val Leu Arg Gln
          530                 535                 540

Gly Ser Leu Lys Val Ser Thr Gly Ala Pro Leu Pro Thr Pro Thr Glu
545                 550                 555                 560

Lys Asp Val Phe Arg His Leu Gly Leu Pro Tyr Arg Glu Pro Gln Asp
              565                 570                 575

Arg Asp Trp

<210> SEQ ID NO 75
<211> LENGTH: 499
<212> TYPE: PRT
<213> ORGANISM: Sarcophilus harrisii

<400> SEQUENCE: 75

Met Ala Leu Val Pro Pro Lys Arg Arg Gly Ala Gly Arg Gly Glu
1               5                   10                  15

Glu Ala Gly Gly Ala Ala Ala Pro Ser Pro Ala Pro Leu Arg Phe Pro
              20                  25                  30

Gly Leu Thr Ile Tyr Leu Ala Glu Arg His Met Gly Arg Ser Arg Arg
          35                  40                  45

Ala Phe Leu Thr Gly Leu Ala Arg Ala Lys Gly Phe Arg Val Asp Gln
      50                  55                  60

Ala Tyr Ser Pro Glu Val Thr His Val Val Met Glu Gly Ser Ser Ala
65                  70                  75                  80

Thr Glu Ala Ser Gly Trp Leu Asp Arg Val Leu Gly Ala Ser Gly Ser
              85                  90                  95

Leu Pro Arg Pro Leu Leu Leu Asp Ile Ser Trp Phe Thr Glu Ser Met
          100                 105                 110

Gly Gln Gly Lys Pro Val Pro Val Glu Gly Arg His Cys Leu Gly Val
      115                 120                 125

Pro Leu Pro Thr Arg Ser Gln Ala Asp Pro Gly Cys Leu Pro Ala Tyr
  130                 135                 140

Ala Cys Gln Arg His Ser Pro Leu Asn His Asn Leu Cys Phe Thr
145                 150                 155                 160

Glu Ala Leu Asp Thr Leu Ala Glu Ala Ala Gly Phe Glu Gly Ser Glu
              165                 170                 175

Gly Arg Phe Leu Ser Phe Arg Arg Ala Ala Ser Val Leu Lys Ala Leu
          180                 185                 190

Pro Gly Pro Ile Thr Ser Ile Ser Gln Leu Arg Gly Leu Pro His Phe
      195                 200                 205

Gly Asp His Ser Ser Arg Ile Val Gln Glu Leu Leu Glu Cys Gly Val
  210                 215                 220

```
Ser Ser Glu Val Glu Arg Ile Lys Gln Ser Glu Arg Tyr Gln Thr Met
225                 230                 235                 240

Lys Leu Phe Thr His Ile Phe Gly Val Gly Val Lys Thr Ala Asp Lys
                245                 250                 255

Trp Tyr Arg Asp Gly Leu Arg Ser Leu Ala Asp Leu Gln Gly Gln Thr
            260                 265                 270

Arg Lys Leu Ser Arg Gln Gln Glu Ala Gly Ile Cys His Phe Glu Asp
        275                 280                 285

Leu Asn Thr Leu Val Trp Arg His Glu Ala Glu Ala Ile Gln Arg Val
    290                 295                 300

Val Glu Lys Ala Val Arg Gln Val Leu Pro Gly Ala Thr Val Thr Leu
305                 310                 315                 320

Thr Gly Gly Phe Arg Arg Gly Lys Leu Gln Gly His Asp Val Asp Phe
                325                 330                 335

Leu Ile Thr His Pro Val Glu Gly Gln Glu Gly Leu Leu Pro Lys
            340                 345                 350

Val Met Asp Leu Leu Glu Ser Gln Gly Phe Val Leu Tyr Arg His Thr
    355                 360                 365

Gln Ser Asn His Tyr Gln Asp Leu Lys Asp Pro Ala Gln Ser Thr Ser
370                 375                 380

Leu Phe Asp Ala Tyr Glu Arg Cys Phe Ser Ile Leu Arg Leu Pro Asp
385                 390                 395                 400

Pro Thr Ala Ala Phe Arg Pro Glu Ala Gly Glu Glu Pro Cys Arg Asp
                405                 410                 415

Gly Lys Ala Val Arg Val Asp Leu Val Val Ala Pro Ser Gln Phe
            420                 425                 430

Ala Phe Ala Leu Leu Gly Trp Thr Gly Ser Gln His Phe Glu Arg Glu
        435                 440                 445

Leu Arg Arg Phe Ser Arg Ala Glu Lys Gln Leu Leu Leu Asn Ser His
    450                 455                 460

Gly Leu Tyr Val Pro Gly Lys Lys Glu Ser Phe Pro Ala Ala Ser Glu
465                 470                 475                 480

Glu Asp Ile Phe Arg His Leu Gly Leu Glu Tyr Ile Ala Pro Glu Tyr
                485                 490                 495

Arg Asn Ala

<210> SEQ ID NO 76
<211> LENGTH: 590
<212> TYPE: PRT
<213> ORGANISM: Sarcophilus harrisii

<400> SEQUENCE: 76

Met Pro Arg Pro Arg Pro Cys His Pro Leu Leu Ala Ala Ala Pro Glu
1               5                   10                  15

Arg Glu Gly Pro Gly Trp Ala Leu Ala Met Glu Pro Arg Gly Val Leu
            20                  25                  30

Lys Ala Phe Pro Arg Arg Lys Lys Arg Ser Ser Gly Ser Asp Arg Ser
        35                  40                  45

Ala Leu Leu Lys Ile Pro Lys Lys Glu Gly Leu Glu Gly Gly Glu Trp
    50                  55                  60

Leu Ser Pro Leu Gln Val His Val Leu Pro Ala Gly Ile Gly Arg Ala
65                  70                  75                  80

Arg Ala Glu Ile Phe Glu Lys Gln Ile Ile Gln His Gly Gly Arg Ile
                85                  90                  95
```

```
Cys Ser Pro Gln Ala Pro Gly Ile Thr His Ile Val Val Asp Glu Ala
                100                 105                 110

Val Asp Cys Glu Arg Ala Leu Arg Leu Leu Lys Leu Ser Gln Leu Pro
            115                 120                 125

Leu Gly Val Gln Ile Val Lys Ser Ala Trp Leu Ser Gln Cys Leu Gln
        130                 135                 140

Glu Gln Lys Leu Val Asp Thr Thr Gly Phe Ser Ile Phe Ile Pro Asp
145                 150                 155                 160

Arg Tyr Leu Asp Glu Thr Asp Asn Gln Val Thr Ser Phe Gln Pro Gly
                165                 170                 175

Cys Ser Gly Thr Ser Ala Gln Ala Gly Leu Pro Ser Ala Ala Ala Phe
            180                 185                 190

Ala Pro Pro Gln Glu Pro His Ser Glu Leu Asn Thr Gln Thr Gln Pro
        195                 200                 205

Asn Ser Tyr Glu Ser Ser Asp Glu Glu Val Gln Val Thr Pro Ala
210                 215                 220

Asp Leu Glu Ala Leu Ile Thr Gly Gln Tyr Pro Ser Thr Pro Glu Gly
225                 230                 235                 240

Asp Ala Met Pro Cys Leu Ala Pro Thr Val Ser Asp Lys Trp Val Cys
                245                 250                 255

Ala Gln Pro Ser Ser Gln Lys Arg Thr Asn His Asn Ser His Ile Thr
            260                 265                 270

Glu Lys Leu Glu Val Leu Ala Lys Ala Tyr Ala Val Gln Gly Asp Arg
        275                 280                 285

Trp Arg Ser Leu Ser Tyr Ser Lys Ala Ile Asn Ala Leu Lys Ser Phe
290                 295                 300

His Lys Pro Val Ser Ser Tyr Gln Glu Ala Cys Gly Ile Pro Gly Ile
305                 310                 315                 320

Gly Lys Arg Met Ala Glu Lys Ile Met Glu Ile Val Glu Ser Gly His
                325                 330                 335

Leu Arg Lys Leu Asp His Ile Ser Asp Ser Val Pro Val Leu Glu Leu
            340                 345                 350

Phe Ser Asn Ile Trp Gly Val Gly Ser Lys Thr Ala Gln Met Trp Tyr
        355                 360                 365

Gln Gln Gly Phe Arg Thr Leu Glu Asp Ile Glu Ser Arg Ala Thr Leu
370                 375                 380

Thr Ser Gln Gln Ala Ile Gly Leu Lys His Tyr Glu Asp Phe Leu Lys
385                 390                 395                 400

Arg Ile Pro Arg Glu Glu Ala Ser Glu Ile Glu Gln Thr Val Arg Glu
                405                 410                 415

Ala Ala His Ala Leu Asn Pro Gly Leu Leu Ser Val Ala Cys Gly Ser
            420                 425                 430

Tyr Arg Arg Gly Lys Ala Thr Cys Gly Asp Val Asp Val Leu Val Thr
        435                 440                 445

His Pro Asp Gly Arg Ser His Gln Gly Ile Phe Gly Gln Leu Leu Asp
450                 455                 460

Thr Leu Arg Gln Gln Gly Phe Leu Thr Asp Asp Leu Val Ser Gln Asp
465                 470                 475                 480

Asp Asn Gly Gln Gln Gln Lys Tyr Leu Gly Val Cys Arg Leu Pro Gly
                485                 490                 495

Pro Gly Arg Leu His Arg Arg Leu Asp Ile Ile Val Val Pro Tyr Ser
            500                 505                 510

Glu Phe Ala Cys Ala Leu Leu Tyr Phe Thr Gly Ser Ala Tyr Phe Asn
```

```
            515                 520                 525
Arg Ser Met Arg Ala Leu Ala Lys Thr Lys Gly Met Ser Leu Ser Glu
    530                 535                 540

Arg Ser Leu Tyr Thr Ala Val Val Arg Asp Gly Arg Gly Leu Lys Val
545                 550                 555                 560

Gly Pro Gly Arg Ala Leu Pro Thr Pro Thr Glu Lys Asp Val Phe Arg
                565                 570                 575

Leu Leu Gly Leu Pro Tyr Arg Glu Pro Ser Glu Arg Asp Trp
            580                 585                 590

<210> SEQ ID NO 77
<211> LENGTH: 319
<212> TYPE: PRT
<213> ORGANISM: Sus scrofa

<400> SEQUENCE: 77

Met Arg Ala Ala Ser Val Leu Lys Ser Leu Pro Phe Thr Ile Ile Ser
1               5                   10                  15

Met Lys Asp Thr Glu Gly Ile Pro Cys Leu Gly Asp Lys Val Lys Cys
            20                  25                  30

Val Ile Glu Glu Ile Ile Glu Asp Gly Glu Ser Ser Glu Val Lys Ala
        35                  40                  45

Val Leu Asn Asp Glu Arg Tyr Gln Ser Phe Lys Leu Phe Thr Ser Val
    50                  55                  60

Phe Gly Val Gly Leu Lys Thr Ser Glu Arg Trp Phe Arg Met Gly Phe
65                  70                  75                  80

Arg Ser Leu Ser Lys Ile Arg Ser Asp Lys Thr Leu Lys Phe Thr Arg
                85                  90                  95

Met Gln Lys Ala Gly Phe Leu Tyr Tyr Glu Asp Leu Val Ser Cys Val
            100                 105                 110

Thr Arg Ala Glu Ala Glu Ala Val Gly Val Leu Val Lys Glu Ala Val
        115                 120                 125

Gln Ala Phe Leu Pro Asp Ala Phe Val Thr Met Thr Gly Gly Phe Arg
    130                 135                 140

Arg Gly Lys Lys Met Gly His Asp Val Asp Phe Leu Ile Thr Ser Pro
145                 150                 155                 160

Gly Ser Thr Asp Glu Glu Gln Gln Leu Leu Pro Lys Val Val Asn
                165                 170                 175

Leu Trp Glu Arg Glu Gly Leu Leu Leu Tyr Cys Asp Leu Val Glu Ser
            180                 185                 190

Thr Leu Glu Lys Ser Lys Leu Pro Ser Arg Asn Val Asp Ala Leu Asp
        195                 200                 205

His Phe Gln Lys Cys Phe Leu Ile Leu Lys Leu His His Gln Arg Val
    210                 215                 220

Asp Ser Gly Met Ser Ser Gln Gln Glu Gly Lys Thr Trp Lys Ala Ile
225                 230                 235                 240

Arg Val Asp Leu Val Met Cys Pro Tyr Glu Leu Arg Ala Phe Ala Leu
                245                 250                 255

Leu Gly Trp Thr Gly Ser Arg Gln Phe Glu Arg Asp Leu Arg Arg Tyr
            260                 265                 270

Ala Thr His Glu Arg Lys Met Ile Leu Asp Asn His Ala Leu Tyr Asp
        275                 280                 285

Lys Thr Lys Arg Ile Phe Leu Lys Ala Glu Ser Glu Glu Glu Ile Phe
    290                 295                 300
```

Ala His Leu Gly Leu Asp Tyr Leu Glu Pro Trp Glu Arg Asn Ala
305                 310                 315

<210> SEQ ID NO 78
<211> LENGTH: 454
<212> TYPE: PRT
<213> ORGANISM: Sus scrofa

<400> SEQUENCE: 78

Met Leu Pro Arg Arg Arg Ala Arg Val Gly Pro Pro Glu Ala Ala
1               5                   10                  15

Pro Ser Ser Ala Ala Arg Phe Pro Gly Val Ala Ile Tyr Leu Ala Glu
                20                  25                  30

Pro Arg Met Gly Arg Ser Arg Arg Ala Phe Leu Thr Arg Leu Ala Leu
                35                  40                  45

Ser Lys Gly Phe Arg Val Leu Asp Ala Tyr Ser Pro Glu Val Thr His
50                  55                  60

Val Val Met Glu Gly Thr Ser Ala Glu Ala Ile Ser Trp Gln Glu
65                  70                  75                  80

His Arg Thr Pro Ser Leu Pro Pro Gly Cys Ser His Pro Ala Leu Leu
                85                  90                  95

Asp Val Ser Trp Phe Thr Glu Ser Met Ala Ala Gly Gln Pro Val Pro
                100                 105                 110

Val Glu Arg Arg His Arg Leu Glu Val Ala Val Pro Arg Glu Glu Leu
                115                 120                 125

Pro Ser Pro Val Trp Met Leu Pro Tyr Ala Cys Gln Arg Pro Thr Pro
130                 135                 140

Leu Thr His His Asn Ala Ser Leu Ser Glu Ala Leu Glu Thr Leu Ala
145                 150                 155                 160

Glu Ala Ala Asp Phe Asp Gly Ser Lys Gly Arg His Val Ser Phe Cys
                165                 170                 175

Arg Ala Ala Ser Val Leu Lys Ala Leu Pro Ser Pro Val Thr Ala Leu
                180                 185                 190

Ser Gln Leu Gln Gly Leu Pro His Phe Gly Glu His Ser Arg Arg Val
                195                 200                 205

Ile Gln Glu Leu Leu Glu His Gly Val Cys Glu Glu Val Glu Arg Val
210                 215                 220

Arg Leu Ser Glu Arg Tyr Gln Thr Met Lys Leu Phe Thr Gln Ile Phe
225                 230                 235                 240

Gly Val Gly Val Arg Thr Ala Asp Gln Trp Tyr Gln Glu Gly Leu Arg
                245                 250                 255

Thr Leu Asp Asp Leu Arg Glu Gln Pro Gln Arg Leu Thr Lys Gln Gln
                260                 265                 270

Lys Ala Leu Pro Gly Pro Glu Arg Pro Asp Pro Ala Val Arg Ser
                275                 280                 285

Gly Gly Pro Ala Ala Gly Gly Gly Ser Cys Gly Ala Gly Pro Ala
                290                 295                 300

Gly Gly His Arg Asn Ala Gly Arg Arg Leu Pro Glu Gly Leu Val Leu
305                 310                 315                 320

Tyr His Gln His Gln Arg Gly Gln Gly Asp Pro Thr His Leu Ala
                325                 330                 335

Gln Lys Pro His Ala Met Asp Ala Phe Glu Met Ser Leu Cys Ile Phe
                340                 345                 350

Arg Leu Pro Arg Pro Pro Glu Ala Ala Val Gly Gly Pro Arg Glu Pro
                355                 360                 365

```
Cys Pro Pro Trp Lys Ala Val Arg Val Asp Leu Val Val Thr Pro Ile
    370                 375                 380

Ser Gln Phe Pro Phe Ala Leu Leu Gly Trp Thr Gly Ser Lys His Phe
385                 390                 395                 400

Glu Arg Glu Leu Arg Arg Phe Ser Arg Lys Glu Arg Gly Leu Trp Leu
                405                 410                 415

Asn Ser His Gly Leu Phe Asp Ser Glu Gln Lys Met Pro Phe His Val
            420                 425                 430

Ala Ser Glu Glu Asp Ile Phe Gly Leu Leu Gly Leu Glu Tyr Leu Pro
        435                 440                 445

Pro Glu Gln Arg Asn Ala
    450

<210> SEQ ID NO 79
<211> LENGTH: 575
<212> TYPE: PRT
<213> ORGANISM: Sus scrofa

<400> SEQUENCE: 79

Met Asp Pro Arg Gly Ile Leu Lys Ala Phe Pro Lys Arg Arg Lys Ile
1               5                   10                  15

His Thr Ser Pro Ser Ser Lys Ala Leu Ala Lys Ile Pro Lys Arg Glu
                20                  25                  30

Asp Gly Glu Glu Ala Gly Glu Trp Leu Ser Ser Val Arg Ala His Val
            35                  40                  45

Val Pro Thr Gly Ile Gly Arg Ala Arg Ala Glu Leu Phe Glu Lys Gln
        50                  55                  60

Ile Val Gln His Gly Gly Gln Leu Cys Pro Ala Gln Ala Pro Gly Val
65                  70                  75                  80

Thr His Ile Val Val Asp Glu Gly Met Asp Cys Glu Arg Ala Leu Arg
                85                  90                  95

Leu Leu Arg Leu Pro Arg Leu Pro Pro Gly Ala Gln Leu Val Lys Ser
                100                 105                 110

Ala Trp Leu Ser Leu Cys Leu Gln Glu Arg Arg Leu Val Asp Thr Ala
            115                 120                 125

Gly Phe Ser Ile Phe Ile Pro Glu Arg Tyr Leu Asp Gln Ala Gln Leu
        130                 135                 140

Ser Lys Ala Gly Asn Asp Ser Ser Thr Ser Pro Gly Ala Arg Glu Thr
145                 150                 155                 160

Pro Leu Arg Thr Ala Leu Ser Pro Pro Ser Pro Pro Thr Arg Pro Val
                165                 170                 175

Ser Pro Ser Glu Arg Thr Glu Glu Phe Ala Ser Ile Gln Ala Gln Pro
            180                 185                 190

Gly Ser Asp Gly Asp Thr Ser Asp Gly Glu Glu Thr Gln Val Ser Ala
        195                 200                 205

Ala Asp Leu Glu Ala Leu Ile Ser Gly Arg Tyr Pro Thr Pro Leu Glu
    210                 215                 220

Glu Asp Gly Glu Pro Ser Pro Ala Pro Lys Gly Leu Asp Lys Trp Val
225                 230                 235                 240

Cys Ala Gln Pro Ser Ser Gln Lys Ala Thr Asn His Asn Pro His Ile
                245                 250                 255

Thr Glu Lys Leu Glu Val Leu Ala Lys Ala Tyr Ser Val Gln Gly Asp
            260                 265                 270

Lys Trp Arg Ala Leu Gly Tyr Ala Lys Ala Ile Asn Ala Leu Lys Ser
```

```
              275                 280                 285
    Phe His Lys Pro Val Thr Ser Tyr Gln Glu Ala Cys Ala Ile Pro Gly
    290                 295                 300

Ile Gly Lys Arg Met Ala Glu Lys Ile Leu Glu Ile Leu Glu Ser Gly
305                 310                 315                 320

His Leu Arg Lys Leu Asp His Ile Ser Glu Ser Val Pro Val Leu Gln
                    325                 330                 335

Leu Phe Ser Asn Ile Trp Gly Ala Gly Thr Lys Thr Ala Gln Leu Trp
                    340                 345                 350

Tyr His Gln Gly Phe Arg Ser Leu Glu Asp Ile Arg Asn Gln Ala Ser
                    355                 360                 365

Leu Thr Thr Gln Gln Ala Ile Gly Leu Lys His Tyr His Asp Phe Leu
                370                 375                 380

Asp Arg Met Pro Arg Glu Glu Ala Ser Glu Ile Glu Gln Thr Val Arg
385                 390                 395                 400

Glu Ala Ala Gln Ala Phe Asn Pro Gly Leu Leu Cys Val Ala Cys Gly
                    405                 410                 415

Ser Tyr Arg Arg Gly Arg Ala Thr Cys Gly Asp Val Asp Val Leu Leu
                    420                 425                 430

Thr His Pro Asp Gly Arg Ser His Gln Gly Ile Phe Ser Arg Leu Leu
                435                 440                 445

Asp Ser Leu Arg Gln Arg Gly Phe Leu Thr Asp Asp Leu Val Ser Gln
    450                 455                 460

Glu Gln His Gly Gln Gln Gln Lys Tyr Leu Gly Val Cys Gln Leu Pro
465                 470                 475                 480

Gly Pro Gly Arg Arg His Arg Arg Leu Asp Ile Ile Val Val Pro Tyr
                    485                 490                 495

Ser Glu Phe Ala Cys Ala Leu Leu Tyr Phe Thr Gly Ser Ala His Phe
                    500                 505                 510

Asn Arg Ser Met Arg Ala Leu Ala Lys Thr Lys Gly Met Ser Leu Ser
                515                 520                 525

Glu His Ala Leu Ser Thr Ala Val Val Arg Asp Ala His Gly Leu Lys
    530                 535                 540

Val Gly Leu Gly Arg Val Leu Pro Thr Pro Thr Glu Lys Asp Val Phe
545                 550                 555                 560

Arg Leu Leu Gly Leu Pro Tyr Arg Glu Pro Ala Glu Arg Asp Trp
                    565                 570                 575

<210> SEQ ID NO 80
<211> LENGTH: 491
<212> TYPE: PRT
<213> ORGANISM: Otolemur garnettii

<400> SEQUENCE: 80

Met Leu Pro Lys Arg Arg Ala Arg Ile Gly Ser Pro Gly Gly Asn
1               5                   10                  15

Ala Ala Ser Ser Glu Arg Pro Ser Thr Arg Phe Pro Gly Ile Thr Ile
                20                  25                  30

Tyr Leu Val Glu Arg Arg Met Gly Arg Ser Arg Arg Ala Phe Leu Thr
                35                  40                  45

Arg Leu Ala Arg Ser Lys Gly Phe Arg Val Leu Asp Ala Cys Ser Ser
            50                  55                  60

Glu Val Thr His Ile Val Met Glu Gln Thr Ser Ala Glu Glu Ala Val
65                  70                  75                  80
```

-continued

```
Cys Trp Gln Glu His Arg Ala Thr Ala Ala Pro Ser Glu Cys Thr Pro
                85                  90                  95
Ala Thr Leu Leu Asp Ile Ser Trp Leu Thr Glu Ser Leu Ala Ala Gly
                100                 105                 110
Gln Pro Val Pro Met Glu Ser Arg His Arg Leu Glu Val Ala Glu Pro
                115                 120                 125
Arg Lys Ala Pro Pro Ser Ser Ile Trp Met Pro Ala Tyr Ala Cys Gln
130                 135                 140
Arg Pro Thr Pro Leu Thr His His Asn Ile Ser Leu Ser Glu Ala Leu
145                 150                 155                 160
Glu Thr Leu Ala Glu Ala Ala Gly Phe Glu Gly Arg Glu Gly His Ser
                165                 170                 175
Leu Thr Phe Leu Arg Ala Ala Ser Val Leu Arg Ala Leu Pro Arg Pro
                180                 185                 190
Val Val Ala Leu Thr Gln Leu Arg Gly Leu Pro His Phe Gly Glu His
                195                 200                 205
Ser Phe Arg Val Val Gln Glu Leu Leu Glu His Gly Val Cys Glu Glu
                210                 215                 220
Val Glu Arg Val Arg His Ser Glu Arg Phe Gln Thr Met Lys Leu Phe
225                 230                 235                 240
Thr Gln Ile Phe Gly Val Gly Val Arg Thr Ala Asp Arg Trp Tyr Gln
                245                 250                 255
Glu Gly Leu Arg Thr Leu Asp Asp Leu Arg Glu Gln Pro Gln Arg Leu
                260                 265                 270
Thr Gln Gln Lys Ala Gly Val Gln Tyr Tyr Gln Asp Leu Ser Thr
                275                 280                 285
Pro Val Leu Gln Pro Asp Ala Glu Ala Leu Gln Gln Leu Val Glu Ala
                290                 295                 300
Ala Val Glu Gln Val Leu Ser Gly Ala Thr Val Thr Leu Thr Gly Gly
305                 310                 315                 320
Phe Arg Arg Gly Lys Leu Gln Gly His Asp Val Asp Phe Leu Ile Thr
                325                 330                 335
His Pro Glu Glu Gly Gln Glu Ala Gly Leu Leu Pro Arg Val Ile Arg
                340                 345                 350
Cys Leu Gln Asp Gln Gly Leu Val Leu Tyr Gln Gln Tyr Gln His Ser
                355                 360                 365
Leu Tyr Gly Ala Pro Gly His His Ser His Thr Met Asp Ala Phe Glu
                370                 375                 380
Arg Ser Phe Cys Ile Phe Arg Leu Pro Gln Pro Pro Gly Ala Ser Val
385                 390                 395                 400
Arg Glu Asp Pro Ser Cys Pro Ala Trp Lys Ala Val Arg Val Asp Leu
                405                 410                 415
Val Val Ala Pro Ile Ser Gln Phe Pro Phe Ala Leu Leu Gly Trp Thr
                420                 425                 430
Gly Ser Lys Leu Phe Gln Arg Glu Leu Arg Arg Phe Ser Arg Lys Glu
                435                 440                 445
Lys Gly Leu Cys Leu Asn Ser His Gly Leu Phe Asn Pro Glu Gln Asn
                450                 455                 460
Thr Val Phe His Val Ala Ser Glu Glu Asp Ile Phe Arg His Leu Gly
465                 470                 475                 480
Leu Glu Tyr Leu Pro Pro Glu Gln Arg Asn Ala
                485                 490
```

<210> SEQ ID NO 81
<211> LENGTH: 571
<212> TYPE: PRT
<213> ORGANISM: Otolemur garnettii

<400> SEQUENCE: 81

```
Met Asp Pro Arg Gly Ile Leu Lys Ala Phe Pro Lys Arg Lys Lys Ile
1               5                   10                  15

His Ala Asn Pro Ser Ser Lys Ala Leu Ala Lys Ile Pro Lys Arg Glu
            20                  25                  30

Glu Gly Glu Glu Ala Gly Glu Trp Leu Ser Ser Leu Arg Ala His Ile
        35                  40                  45

Val Pro Thr Gly Ile Gly Arg Ala Arg Ala Glu Leu Phe Lys Lys Gln
    50                  55                  60

Ile Val Gln His Gly Gly Arg Ile Cys Pro Ala Gln Asp Pro Gly Val
65                  70                  75                  80

Thr His Ile Val Val Asp Glu Gly Met Asp Tyr Glu Arg Ala Leu Arg
                85                  90                  95

Leu Leu Arg Leu Pro Gln Leu Pro Leu Gly Ala His Leu Val Lys Ser
            100                 105                 110

Ala Trp Leu Ser Leu Cys Leu Gln Glu Arg Arg Leu Val Asp Val Ala
        115                 120                 125

Gly Phe Ser Ile Phe Ile Pro Asn Arg Tyr Leu Asp Gln Pro Gln Pro
    130                 135                 140

Asn Lys Thr Glu Gln Asp Ser Thr Pro Ser Val His Glu Ala Val Leu
145                 150                 155                 160

Met Thr Ala Leu Ser Pro Pro Ser Thr Arg Pro Val Ser Pro Pro Gln
                165                 170                 175

Lys Ala Glu Glu Ala Pro Ser Ala Gln Pro Gln Pro Ile Ser Asp Asp
            180                 185                 190

Glu Thr Ser Asp Ser Glu Glu Met Arg Val Ser Thr Ala Asp Leu Glu
        195                 200                 205

Ala Leu Ile Ser Gly His Tyr Pro Thr Pro Leu Glu Gly Asp Arg Glu
    210                 215                 220

Pro Thr Leu Ala Pro Asp His Leu Asp Lys Trp Val Cys Ala Gln Ser
225                 230                 235                 240

Ser Ser Gln Lys Ala Thr Asn His Asn Leu His Ile Thr Glu Lys Leu
                245                 250                 255

Glu Val Leu Ala Lys Ala Tyr Arg Val Gln Gly Asp Lys Trp Arg Ala
            260                 265                 270

Leu Gly Tyr Ala Lys Ala Ile Asn Ala Leu Lys Ser Phe His Lys Pro
        275                 280                 285

Val Thr Ser Tyr Gln Glu Ala Cys Ser Ile Pro Gly Ile Gly Lys Arg
    290                 295                 300

Met Ala Glu Lys Ile Ile Glu Ile Leu Glu Ser Gly His Leu Arg Lys
305                 310                 315                 320

Leu Asp His Ile Ser Glu Ser Val Pro Val Leu Glu Leu Phe Ser Asn
                325                 330                 335

Ile Trp Gly Ala Gly Thr Lys Thr Ala Leu Met Trp Tyr His Gln Gly
            340                 345                 350

Phe Arg Ser Leu Glu Asp Ile Arg Ser Gln Ala Ser Leu Thr Ile Gln
        355                 360                 365

Gln Ala Ile Gly Leu Lys His Tyr Asp Asp Phe Leu Glu Arg Met Pro
    370                 375                 380
```

```
Arg Glu Glu Ala Ala Glu Ile Glu Gln Thr Val Arg Glu Ala Ala His
385                 390                 395                 400

Ala Phe Asn Pro Gly Leu Leu Cys Val Ala Cys Gly Ser Phe Arg Arg
            405                 410                 415

Gly Lys Val Thr Cys Gly Asp Val Asp Val Leu Ile Thr His Pro Asp
            420                 425                 430

Gly Gln Ser His Gln Gly Ile Phe Thr Leu Leu Leu Asp Thr Leu Arg
            435                 440                 445

His Gln Gly Phe Leu Thr Asp Asp Leu Val Ser Gln Glu Glu Asn Gly
        450                 455                 460

Gln Gln Lys Lys Tyr Leu Gly Val Cys Gln Leu Pro Gly Pro Gly Arg
465                 470                 475                 480

Arg His Arg Arg Leu Asp Ile Ile Ile Val Pro Tyr Ser Glu Phe Ala
            485                 490                 495

Cys Ala Leu Leu Tyr Phe Thr Gly Ser Ala His Phe Asn Arg Ser Met
            500                 505                 510

Arg Ala Leu Ala Lys Thr Lys Gly Met Ser Leu Ser Glu His Ala Leu
            515                 520                 525

Ser Thr Asp Val Val Arg Asn Thr Gln Gly Phe Lys Val Gly Pro Gly
530                 535                 540

Arg Val Leu Pro Thr Pro Thr Glu Lys Asp Val Phe Arg Leu Leu Gly
545                 550                 555                 560

Leu Pro Tyr Arg Glu Pro Ala Glu Arg Asp Trp
            565                 570

<210> SEQ ID NO 82
<211> LENGTH: 335
<212> TYPE: PRT
<213> ORGANISM: Otolemur garnettii

<400> SEQUENCE: 82

Met Ser Lys Arg Lys Ala Pro Gln Glu Thr Leu Asn Gly Gly Ile Thr
1               5                   10                  15

Asp Met Leu Thr Glu Leu Ala Asn Phe Glu Lys Asn Val Asn Gln Ala
            20                  25                  30

Ile His Lys Tyr Asn Ala Tyr Arg Lys Ala Ala Ser Val Ile Ala Lys
        35                  40                  45

Tyr Pro His Lys Ile Lys Ser Gly Ala Glu Ala Lys Lys Leu Pro Gly
    50                  55                  60

Val Gly Thr Lys Ile Ala Glu Lys Ile Asp Glu Phe Leu Ala Thr Gly
65                  70                  75                  80

Lys Leu Arg Lys Leu Glu Lys Ile Arg Gln Asp Asp Thr Ser Ser Ser
                85                  90                  95

Ile Asn Phe Leu Thr Arg Val Thr Gly Ile Gly Pro Ser Ala Ala Arg
            100                 105                 110

Lys Phe Val Asp Glu Gly Ile Lys Thr Leu Glu Asp Leu Arg Lys Asn
            115                 120                 125

Glu Asp Lys Leu Asn His His Gln Arg Ile Gly Leu Lys Tyr Phe Glu
        130                 135                 140

Asp Phe Glu Lys Arg Ile Pro Arg Glu Glu Met Leu Gln Met Gln Asp
145                 150                 155                 160

Ile Val Leu Asn Glu Val Lys Lys Val Asp Ser Glu Tyr Ile Ala Thr
                165                 170                 175

Val Cys Gly Ser Phe Arg Arg Gly Ala Glu Ser Ser Gly Asp Met Asp
            180                 185                 190
```

-continued

```
Val Leu Leu Thr His Pro Ser Phe Thr Ser Glu Ser Pro Lys Gln Pro
            195                 200                 205

Lys Leu Leu His Arg Val Val Glu Gln Leu Gln Lys Val Leu Phe Ile
        210                 215                 220

Thr Asp Thr Leu Ser Lys Gly Glu Thr Lys Phe Met Gly Val Cys Gln
225                 230                 235                 240

Leu Pro Arg Asn Ser Asp Glu Arg Glu Tyr Pro His Arg Arg Ile Asp
                245                 250                 255

Ile Arg Leu Ile Pro Lys Asp Gln Tyr Tyr Cys Gly Val Leu Tyr Phe
            260                 265                 270

Thr Gly Ser Asp Ile Phe Asn Lys Asn Met Arg Ala His Ala Leu Glu
        275                 280                 285

Lys Gly Phe Thr Ile Asn Glu Tyr Thr Ile Arg Pro Leu Gly Val Thr
    290                 295                 300

Gly Val Ala Gly Glu Pro Leu Pro Val Asp Ser Glu Arg Asp Ile Phe
305                 310                 315                 320

Glu Tyr Ile Gln Trp Lys Tyr Arg Glu Pro Lys Asp Arg Ser Glu
                325                 330                 335

<210> SEQ ID NO 83
<211> LENGTH: 460
<212> TYPE: PRT
<213> ORGANISM: Monodelphis domestica

<400> SEQUENCE: 83

Met Ala Ser Val Pro Leu Lys Arg Arg Gly Arg Ser Phe Gly Glu
1               5                   10                  15

Glu Ala Gln Gly Ala Ala Ala Pro Ser Pro Leu Ser Arg Phe Pro
            20                  25                  30

Glu Phe Thr Leu Tyr Leu Ala Glu Arg Arg Met Gly Arg Met Arg Arg
        35                  40                  45

Ala Phe Leu Thr Glu Leu Ala Arg Gly Lys Gly Phe Arg Val Asp Glu
    50                  55                  60

Val Tyr Ser Pro Gln Val Thr His Val Leu Met Glu Asp Ala Ser Gly
65                  70                  75                  80

Ala Glu Ala Ser Asp Tyr Leu Asp Arg Val Leu Gly Ala Ser Gln Ser
                85                  90                  95

Leu Gln Lys Pro Leu Leu Leu Asp Ile Ser Trp Leu Thr Glu Ser Ile
            100                 105                 110

Gly Arg Gly Lys Pro Val Pro Val Glu Ala Lys Tyr Cys Leu Gly Ile
        115                 120                 125

Pro Glu Leu Leu Lys Asn Gln Val Pro Pro Val Ser Met Pro Ala Tyr
    130                 135                 140

Ala Cys Gln Arg His Thr Pro Leu Asn His Asn Phe His Leu Thr
145                 150                 155                 160

Glu Ala Leu Glu Thr Leu Ala Glu Ala Asp Phe Glu Gly Ser Gln
                165                 170                 175

Gly Arg Phe Ile Ser Phe His Arg Ala Ala Ser Val Leu Lys Ala Leu
            180                 185                 190

Pro Asp Pro Ile Thr Asn Met Ser Gln Leu His Gly Leu Pro His Ile
        195                 200                 205

Gly Asp His Ser Ser Arg Ile Ile Gln Glu Leu Leu Glu His Gly Val
    210                 215                 220

Ser Asn Glu Val Glu Thr Ile Lys Leu Ser Lys Arg Tyr Gln Thr Met
```

```
            225                 230                 235                 240
Lys Leu Phe Thr Gln Ile Phe Gly Val Gly Val Lys Thr Ala Asp Arg
                245                 250                 255

Trp Tyr Gln Glu Gly Leu Arg Thr Leu Asp Asp Leu Gln Lys His Ser
                260                 265                 270

Arg Lys Leu Thr Arg Gln Glu Ala Gly Ile His His Phe Glu Asp
                275                 280                 285

Leu Asn Thr Pro Val Tyr Arg His Glu Ala Asp Ala Ile Gln Gln Ile
                290                 295                 300

Val Glu Glu Val Val Gln Gln Met Leu Pro Gly Ala Arg Val Ile Leu
305                 310                 315                 320

Ala Gly Gly Phe Arg Arg Gly Lys Pro His Gly His Asp Val Asp Phe
                325                 330                 335

Leu Ile Thr His Pro Val Glu Gly Leu Glu Ala Gly Leu Leu Ser Lys
                340                 345                 350

Val Met Gly Arg Leu Glu Ser Gln Gly Leu Val Leu Tyr Arg His Thr
                355                 360                 365

Gln Ser Pro Lys Asn Pro Asp Asn Thr Ala Phe Gln Ser Thr Ala Met
                370                 375                 380

Asp Asp Tyr Glu Lys Cys Phe Ser Ile Leu Trp Phe Pro Lys Ser Pro
385                 390                 395                 400

Thr Thr Ser Ser His Leu Glu Ala Gly Glu Ser Ser Arg Asp Gly Lys
                405                 410                 415

Ala Val Arg Val Asp Phe Val Val Thr Pro Ile Ser Gln Phe Ala Phe
                420                 425                 430

Ala Leu Leu Gly Trp Thr Gly Ser Gln Tyr Phe Glu Arg Glu Leu Arg
                435                 440                 445

Arg Phe Ser Leu Asn Arg Glu Glu Ala Ala Ala Glu
                450                 455                 460

<210> SEQ ID NO 84
<211> LENGTH: 545
<212> TYPE: PRT
<213> ORGANISM: Monodelphis domestica

<400> SEQUENCE: 84

Met Glu Pro Arg Gly Ile Leu Lys Ala Phe Pro Lys Arg Lys Lys Met
1               5                   10                  15

Arg Thr Ala Ser Asp Gly Ser Gly Leu Leu Lys Ile Pro Lys Lys Glu
                20                  25                  30

Lys Ala Glu Ala Gly Glu Trp Leu Ser Pro Leu Gln Val His Val Leu
                35                  40                  45

Pro Val Gly Ile Gly Arg Ala Arg Ala Glu Ile Phe Glu Lys Gln Ile
                50                  55                  60

Ile Gln His Gly Gly Gln Ile Cys Ser Pro Gln Ala Pro Gly Ile Thr
65                  70                  75                  80

His Ile Val Val Asp Glu Thr Val Asp Gly Glu Arg Ala Leu Arg Leu
                85                  90                  95

Leu Lys Leu Pro Gln Leu Pro Leu Gly Ala Gln Leu Val Lys Ser Ala
                100                 105                 110

Trp Leu Ser Gln Cys Leu Lys Glu Gln Lys Leu Val Asp Thr Asp Gly
                115                 120                 125

Phe His Val Val Phe Ile Pro Asn Arg Tyr Leu Asp Lys Ala Asp Ile
                130                 135                 140
```

```
Ser Phe Gln Pro Gly Pro Ser Gly Thr Ser Ala Gln Ala Gly Leu Ser
145                 150                 155                 160

Ser Val Ala Pro Leu Ala Pro Pro Gln Glu Pro His Ser Arg Leu Gly
            165                 170                 175

Ile Gln Ala Gln Ala Asn Ser Asp Asp Glu Asp Ser Asp Glu Glu Glu
            180                 185                 190

Val Arg Val Thr Pro Asp Asp Leu Glu Ala Leu Ile Thr Gly Arg Tyr
            195                 200                 205

Pro Ser Thr Pro Glu Gly Asp Thr Glu Pro Ser Leu Ala Pro Asn Leu
        210                 215                 220

Ser Glu Lys Trp Val Cys Ala Gln Pro Ser Ser Gln Lys Met Thr Asn
225                 230                 235                 240

His Asn Leu His Ile Thr Glu Lys Leu Glu Val Leu Ala Lys Ala Tyr
                245                 250                 255

Ala Val Gln Gly Asp Arg Trp Arg Thr Leu Gly Tyr Ser Lys Ala Ile
            260                 265                 270

Asn Ala Leu Lys Ser Phe Pro Lys Pro Val Ser Tyr Gln Glu Ala
            275                 280                 285

Cys Gly Ile Pro Gly Ile Gly Lys Arg Met Ala Glu Lys Ile Met Glu
        290                 295                 300

Ile Val Glu Ser Gly His Leu Arg Lys Leu Asp His Ile Ser Asp Ser
305                 310                 315                 320

Val Pro Ile Leu Glu Leu Phe Ser Asn Ile Trp Gly Val Gly Ala Lys
                325                 330                 335

Thr Ala Gln Met Trp Tyr Gln Gln Gly Phe Arg Thr Leu Glu Asp Ile
            340                 345                 350

Gln Ser Gln Ala Thr Leu Ser Thr Gln Ala Ile Gly Leu Lys His
            355                 360                 365

Tyr Glu Asp Phe Leu Lys Arg Ile Pro Arg Glu Glu Ala Ala Glu Ile
        370                 375                 380

Glu Lys Thr Val Arg Glu Thr Ala His Thr Leu Asn Pro Gly Leu Leu
385                 390                 395                 400

Ser Val Ala Cys Gly Ser Tyr Arg Arg Gly Lys Ala Thr Cys Gly Asp
            405                 410                 415

Val Asp Val Leu Val Thr His Pro Asp Gly Arg Ser His Gln Gly Ile
            420                 425                 430

Phe Ser Gln Leu Leu Asp Ala Leu Arg Lys Arg Gly Phe Leu Thr Asp
        435                 440                 445

Asp Leu Val Ser Gln Asp Asp Asn Gly Gln Gln Gln Lys Tyr Leu Gly
    450                 455                 460

Val Cys Gln Leu Pro Gly Pro Gly Arg His His Arg Arg Leu Asp Ile
465                 470                 475                 480

Ile Val Val Pro Tyr Arg Ser Leu Val Lys Ile Gln Ser Val Val Thr
                485                 490                 495

Ile Leu Asn Trp Thr Gly Asn Ser Asp Cys Glu Ser Leu Leu Ser Pro
            500                 505                 510

Ile Cys Leu Ala Ile Gly Ala Gly His Ile His Val Ser Leu Leu His
        515                 520                 525

Tyr Ala Gly Phe Trp Phe Leu Leu Trp Phe Ala Pro Pro Leu Val Pro
    530                 535                 540

Val
545
```

```
<210> SEQ ID NO 85
<211> LENGTH: 467
<212> TYPE: PRT
<213> ORGANISM: Myotis brandtii

<400> SEQUENCE: 85

Met Asp Ser Leu Gln Met Ala His Ser Gly Pro Arg Lys Lys Arg Pro
1               5                   10                  15

Arg Gln Met Gly Ala Ser Met Ala Ser Pro Pro Gln Asp Ile Lys Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Val Arg Ala Ser
                85                  90                  95

Ser Gln Pro Glu Leu Leu Asp Val Ser Trp Leu Ile Glu Cys Met Ser
            100                 105                 110

Ala Gly Lys Pro Val Ala Thr Thr Gly Gln His Gln Leu Val Asp Ala
        115                 120                 125

Phe Glu Val Leu Ala Glu Asn Cys Glu Phe Arg Glu Asn Glu Gly Ser
    130                 135                 140

Cys Leu Ala Phe Met Arg Ala Ala Ser Val Leu Lys Ser Leu Pro Phe
145                 150                 155                 160

Thr Ile Ile Ser Met Lys Asp Thr Glu Gly Ile Pro Cys Leu Gly Asp
                165                 170                 175

Lys Val Lys Ser Ile Ile Glu Glu Ile Ile Glu Asp Gly Glu Ser Ser
            180                 185                 190

Glu Val Lys Ala Val Leu Asn Asp Glu Arg Tyr Gln Ser Phe Lys Leu
        195                 200                 205

Phe Thr Ser Val Phe Gly Val Gly Leu Lys Thr Ser Glu Lys Trp Phe
    210                 215                 220

Arg Met Gly Phe Arg Thr Leu Ser Lys Ile Arg Ser Asp Lys Thr Leu
225                 230                 235                 240

Lys Phe Thr Arg Met Gln Lys Ala Gly Phe Leu Tyr Tyr Glu Asp Leu
                245                 250                 255

Val Ser Cys Val Thr Lys Ala Glu Ala Glu Ala Val Gly Val Leu Val
            260                 265                 270

Lys Glu Ala Val Trp Ala Phe Leu Pro Asp Ala Phe Val Thr Val Thr
        275                 280                 285

Gly Gly Phe Arg Arg Gly Lys Lys Ile Gly His Asp Val Asp Phe Leu
    290                 295                 300

Ile Thr Ser Pro Gly Ser Thr Glu Glu Glu Gln Gln Leu Leu Pro Lys
305                 310                 315                 320

Lys Val Ile Asn Leu Trp Glu Arg Lys Gly Leu Leu Leu Tyr Tyr Asp
                325                 330                 335

Leu Val Glu Ser Thr Phe Glu Lys Phe Lys Leu Pro Ser Arg Lys Val
            340                 345                 350

Asp Ala Leu Asp His Phe Gln Lys Cys Phe Leu Ile Leu Lys Leu His
        355                 360                 365

His Gln Arg Val Asp Gly Gly Lys Ser Ser Gln Gln Glu Gly Lys Thr
    370                 375                 380
```

```
Trp Lys Ala Ile Arg Val Asp Leu Val Met Cys Pro Tyr Glu Arg Arg
385                 390                 395                 400

Ala Phe Ala Leu Leu Gly Trp Thr Gly Ser Arg Gln Phe Glu Arg Asp
                405                 410                 415

Leu Arg Arg Tyr Ala Thr His Glu Arg Lys Met Met Leu Asp Asn His
                420                 425                 430

Ala Leu Tyr Asp Lys Thr Lys Val Glu Glu Met Arg Phe Phe Tyr Lys
                435                 440                 445

Glu Thr Glu Phe Arg Asn Ser Gly Glu Val Ser Val Met Tyr Pro Arg
450                 455                 460

Asp Leu Pro
465

<210> SEQ ID NO 86
<211> LENGTH: 467
<212> TYPE: PRT
<213> ORGANISM: Myotis brandtii

<400> SEQUENCE: 86

Met Asn Ser Ala Pro Leu Ala Glu Pro Arg Leu Ala Gly Ala Glu Trp
1               5                   10                  15

Ser Arg Arg Val Ala Gly Leu Gly Thr Gly Ser Phe Pro Leu Pro Ser
                20                  25                  30

Ser Glu Val Thr His Val Val Met Glu Gln Thr Ser Ala Glu Ala
                35                  40                  45

Val Arg Trp Gln Glu Ser Arg Pro Ala Pro Pro Gly Gly Thr His
    50                  55                  60

Pro Ala Leu Leu Asp Ile Ser Trp Phe Thr Glu Ser Met Ala Ala Gly
65                  70                  75                  80

Gln Pro Val Pro Val Glu Gly Arg His Cys Leu Gln Val Ala Val Ser
                85                  90                  95

Arg Glu Val Leu Pro Asn Pro Val Trp Met Pro Pro Tyr Ala Cys Gln
                100                 105                 110

Arg Pro Thr Pro Leu Thr His His Asn Thr Ser Leu Ser Glu Ala Leu
                115                 120                 125

Glu Met Leu Ala Glu Ala Ala Gly Phe Ala Gly Ser Glu Gly Arg Leu
    130                 135                 140

Leu Ser Phe Ser Arg Ala Ala Ser Val Leu Lys Ala Leu Pro Cys Pro
145                 150                 155                 160

Val Thr Ala Leu Ser Gln Leu Gln Gly Leu Pro His Phe Gly His
                165                 170                 175

Ser Cys Arg Val Ile Gln Glu Leu Leu Glu His Gly Val Cys Glu Glu
                180                 185                 190

Val Glu Arg Val Gln Arg Ser Glu Arg Tyr Gln Ser Met Lys Leu Phe
    195                 200                 205

Thr Arg Ile Phe Gly Val Gly Val Arg Thr Ala Asp Gln Trp Tyr Arg
    210                 215                 220

Glu Gly Leu Arg Thr Leu Asp Asp Val Trp Lys Gln Val Gln Arg Leu
225                 230                 235                 240

Thr Gln Gln Gln Lys Ala Gly Leu Gln His Tyr Gln Asp Leu Ser Ser
                245                 250                 255

Pro Val Gln Arg Pro Asp Ala Glu Ala Leu Arg Gln Val Val Glu Ala
                260                 265                 270

Ala Val Gly Trp Ala Leu Pro Arg Ala Thr Val Thr Leu Ala Gly Gly
                275                 280                 285
```

-continued

```
Phe Arg Arg Pro Thr Leu Arg Gly Lys Leu Gln Gly His Asp Val Asp
    290                 295                 300

Phe Leu Ile Thr His Pro Glu Glu Gly Gln Glu Val Gly Leu Leu Pro
305                 310                 315                 320

Arg Val Met His Tyr Leu Glu Gln Gln Gly Leu Val Leu Tyr Gln Gln
                325                 330                 335

His Gln Arg Ser Pro Ser Gly Asp Pro Ala Arg Leu Ala Pro Lys Gly
            340                 345                 350

His Ser Met Asp Thr Phe Glu Gln Ser Phe Cys Ile Phe Arg Leu Pro
        355                 360                 365

Arg Pro Pro Arg Thr Ala Glu Gly Gly Thr Trp Ser Pro His Pro Ser
    370                 375                 380

Trp Lys Ala Val Arg Val Asp Leu Val Val Ala Pro Ile Ser Gln Phe
385                 390                 395                 400

Pro Phe Ala Leu Leu Gly Trp Thr Gly Ser Lys His Phe Glu Arg Glu
                405                 410                 415

Leu Arg Arg Phe Ser Arg Lys Glu Arg Gly Leu Trp Leu Asn Ser His
            420                 425                 430

Gly Leu Phe Asp Pro Glu Gln Lys Thr Phe Phe Gln Ala Ala Thr Glu
        435                 440                 445

Glu Asp Ile Phe Arg His Leu Gly Leu Ala Tyr Leu Pro Pro Glu Gln
    450                 455                 460

Arg Asn Ala
465

<210> SEQ ID NO 87
<211> LENGTH: 307
<212> TYPE: PRT
<213> ORGANISM: Artificial Sequence
<220> FEATURE:
<223> OTHER INFORMATION: Synthetic Sequence

<400> SEQUENCE: 87

Gln Glu Ile Ala Asp Ile Leu Glu Glu Leu Ala Asp Leu Leu Glu Leu
1               5                   10                  15

Leu Gly Gly Asn Pro Phe Arg Val Arg Ala Tyr Arg Lys Ala Ala Arg
            20                  25                  30

Ala Leu Glu Ser Leu Pro Glu Pro Ile Glu Ser Leu Glu Glu Ala Lys
        35                  40                  45

Lys Leu Pro Gly Ile Gly Lys Lys Ile Ala Glu Lys Ile Glu Glu Ile
    50                  55                  60

Leu Glu Thr Gly Lys Leu Arg Lys Leu Glu Glu Leu Arg Glu Asp Val
65                  70                  75                  80

Pro Pro Gly Leu Leu Leu Leu Arg Val Pro Gly Val Gly Pro Lys
                85                  90                  95

Thr Ala Arg Lys Leu Tyr Glu Leu Gly Ile Arg Thr Leu Glu Asp Leu
                100                 105                 110

Arg Lys Ala Ala Gly Ala Lys Leu Glu Gln Asn Ile Leu Ile Gly Leu
            115                 120                 125

Glu Tyr Tyr Glu Asp Phe Gln Gln Arg Ile Pro Arg Glu Glu Ala Leu
        130                 135                 140

Ala Ile Ala Glu Ile Ile Lys Glu Ala Leu Arg Glu Val Asp Pro Val
145                 150                 155                 160

Leu Gln Val Glu Ile Ala Gly Ser Tyr Arg Arg Gly Lys Glu Thr Val
                165                 170                 175
```

```
Gly Asp Ile Asp Ile Leu Val Thr His Pro Asp Ala Thr Ser Arg Gly
            180                 185                 190

Leu Leu Glu Lys Val Val Asp Ala Leu Val Glu Leu Gly Phe Val Thr
        195                 200                 205

Glu Val Leu Ser Lys Gly Asp Thr Lys Ala Ser Gly Ile Leu Lys Leu
    210                 215                 220

Pro Gly Gly Trp Lys Gly Arg Arg Val Asp Leu Arg Val Val Pro Pro
225                 230                 235                 240

Glu Glu Phe Gly Ala Ala Leu Leu Tyr Phe Thr Gly Ser Lys Gln Phe
                245                 250                 255

Asn Arg Ala Leu Arg Arg Leu Ala Lys Glu Lys Gly Leu Lys Leu Asn
            260                 265                 270

Glu Tyr Gly Leu Phe Asp Gly Val Asp Gly Glu Arg Leu Pro Gly Glu
        275                 280                 285

Thr Glu Glu Glu Ile Phe Glu Ala Leu Gly Leu Pro Tyr Ile Glu Pro
    290                 295                 300

Glu Leu Arg
305

<210> SEQ ID NO 88
<211> LENGTH: 72
<212> TYPE: PRT
<213> ORGANISM: Artificial Sequence
<220> FEATURE:
<223> OTHER INFORMATION: Synthetic Sequence

<400> SEQUENCE: 88

Gly Leu Thr Phe Val Ile Thr Gly Asp Leu Pro Ser Glu Glu Arg Asp
1               5                   10                  15

Glu Leu Lys Glu Leu Ile Glu Lys Leu Gly Gly Lys Val Thr Ser Ser
            20                  25                  30

Val Ser Lys Lys Thr Thr His Val Ile Val Gly Ser Asp Ala Gly Pro
        35                  40                  45

Lys Lys Leu Leu Lys Ala Ile Lys Leu Gly Ile Pro Ile Val Thr Pro
    50                  55                  60

Glu Trp Leu Leu Asp Cys Leu Lys
65                  70
```